(12) United States Patent
Eichner et al.

(10) Patent No.: US 8,840,879 B2
(45) Date of Patent: Sep. 23, 2014

(54) CONJUGATES OF HYDROXYALKYL STARCH AND A PROTEIN

(75) Inventors: Wolfram Eichner, Butzbach (DE); Martin Schimmel, Woellstadt (DE); Frank Hacket, Rappweiler (DE); Elmar Kraus, Bad Nauheim (DE); Norbert Zander, Meine (DE); Ronald Frank, Meine-Grassel (DE); Harald Conradt, Braunschweig (DE); Klaus Langer, Erlangen (DE); Michele Orlando, The Hague (NL); Klaus Sommermeyer, Rosbach v.d.H (DE)

(73) Assignee: Fresenius Kabi Deutschland GmbH, Bad Homburg v.d.H. (DE)

( * ) Notice: Subject to any disclaimer, the term of this patent is extended or adjusted under 35 U.S.C. 154(b) by 0 days.

(21) Appl. No.: 13/018,648

(22) Filed: Feb. 1, 2011

(65) Prior Publication Data
US 2011/0200555 A1 Aug. 18, 2011

Related U.S. Application Data

(60) Division of application No. 11/518,558, filed on Sep. 8, 2006, now Pat. No. 8,017,739, which is a continuation-in-part of application No. PCT/EP2005/002637, filed on Mar. 11, 2005.

(60) Provisional application No. 60/552,174, filed on Mar. 11, 2004.

(30) Foreign Application Priority Data

Mar. 11, 2004 (EP) .................................. 04005849
Aug. 6, 2004 (WO) ................. PCT/EP2004/008821
Aug. 9, 2004 (AR) ............................... P040102853

(51) Int. Cl.
*A61K 38/21* (2006.01)
*A61K 38/49* (2006.01)
*C07K 17/10* (2006.01)
*A61K 31/718* (2006.01)
*A61K 38/18* (2006.01)
*A61K 38/36* (2006.01)
*A61K 38/37* (2006.01)

(52) U.S. Cl.
USPC ............. 424/85.6; 514/1.8; 514/7.6; 514/7.7; 514/7.9; 514/14.1; 514/14.2; 514/14.3; 514/20.9; 514/60; 530/402; 424/94.64

(58) Field of Classification Search
None
See application file for complete search history.

(56) References Cited

U.S. PATENT DOCUMENTS

| | | |
|---|---|---|
| 3,191,291 A | 6/1965 | Maier |
| 3,226,395 A | 12/1965 | Schimmelschmidt et al. |
| 4,001,200 A | 1/1977 | Bonsen et al. |
| 4,001,401 A | 1/1977 | Bonsen et al. |
| 4,053,590 A | 10/1977 | Bonsen et al. |
| 4,061,736 A | 12/1977 | Morris et al. |
| 4,064,118 A | 12/1977 | Wong |
| 4,068,321 A | 1/1978 | Chayer |
| 4,125,492 A | 11/1978 | Cuatrecasas et al. |
| 4,179,337 A | 12/1979 | Davis et al. |
| 4,261,973 A | 4/1981 | Lee et al. |
| 4,412,989 A | 11/1983 | Iwashita et al. |
| 4,454,161 A | 6/1984 | Okada et al. |
| 4,496,689 A | 1/1985 | Mitra |
| 4,667,016 A | 5/1987 | Lai et al. |
| 4,703,008 A | 10/1987 | Lin |
| 4,766,106 A | 8/1988 | Katre et al. |
| 4,836,964 A | 6/1989 | Tsai |
| 4,847,325 A | 7/1989 | Shadle et al. |
| 4,900,780 A | 2/1990 | Cerny |
| 4,904,584 A | 2/1990 | Shaw |
| 4,925,677 A | 5/1990 | Feijen |
| 4,939,239 A | 7/1990 | Matsuhashi et al. |
| 4,952,496 A | 8/1990 | Studier et al. |
| 5,073,628 A | 12/1991 | Matsuhashi et al. |
| 5,079,337 A | 1/1992 | Leonard et al. |
| 5,110,909 A | 5/1992 | Dellacherie et al. |
| 5,214,132 A | 5/1993 | Kuga et al. |
| 5,217,998 A | 6/1993 | Hedlund et al. |
| 5,218,092 A | 6/1993 | Sasaki |
| 5,218,108 A | 6/1993 | Sommermeyer et al. |
| 5,281,698 A | 1/1994 | Nitecki |
| 5,342,770 A | 8/1994 | Yamasaki |
| 5,362,853 A | 11/1994 | Kuga |
| 5,420,105 A | 5/1995 | Gustavson et al. |
| 5,470,843 A | 11/1995 | Stahl et al. |
| 5,484,903 A | 1/1996 | Szablikowski et al. |
| 5,543,332 A | 8/1996 | Lihme et al. |

(Continued)

FOREIGN PATENT DOCUMENTS

AU 5238393 9/1993
CA 2 110 543 2/1993

(Continued)

OTHER PUBLICATIONS

Bayer et al., "The avidin-biotin complex in affinity cytochemistry," *Meth. Enzymol.*, 1979, 62: 308-315.
Boyer et al., "Reaction in biphasic water/organic solvent system in the presence of surfactant: inverse phase transfer catalysis versus interfacial catalysis," *Tetrahedron*, 2000, 56:303-307.

(Continued)

*Primary Examiner* — Marianne P Allen
(74) *Attorney, Agent, or Firm* — Fish & Richardson P.C.

(57) ABSTRACT

Conjugates of hydroxyalkyl starch and a protein are provided herein. The conjugates are formed by a covalent linkage between the hydroxyalkyl starch or a derivative of the hydroxyalkyl starch and the protein. Methods of producing the conjugates and the use of the conjugates also are provided herein.

29 Claims, 44 Drawing Sheets

(56) References Cited

U.S. PATENT DOCUMENTS

| | | |
|---|---|---|
| 5,581,476 A | 12/1996 | Osslund |
| 5,622,718 A | 4/1997 | Al-Shamkhani et al. |
| 5,723,589 A | 3/1998 | Miljkovic et al. |
| 5,736,533 A | 4/1998 | Simon et al. |
| 5,770,645 A | 6/1998 | Stamler |
| 5,824,778 A | 10/1998 | Ishikawa et al. |
| 5,840,900 A | 11/1998 | Greenwald |
| 5,847,110 A | 12/1998 | Dragsten et al. |
| 5,851,984 A | 12/1998 | Matthews et al. |
| 5,876,980 A | 3/1999 | DeFrees |
| 5,880,270 A | 3/1999 | Berninger et al. |
| 5,952,347 A | 9/1999 | Arison et al. |
| 5,977,163 A | 11/1999 | Li et al. |
| 5,981,507 A | 11/1999 | Josephson et al. |
| 5,990,237 A | 11/1999 | Bentley et al. |
| 6,011,008 A | 1/2000 | Domb et al. |
| 6,083,909 A | 7/2000 | Sommermeyer et al. |
| 6,172,208 B1 | 1/2001 | Cook |
| 6,261,800 B1 | 7/2001 | Nikolics et al. |
| 6,299,881 B1 | 10/2001 | Lees et al. |
| 6,340,746 B1 | 1/2002 | Roberts et al. |
| 6,375,846 B1 | 4/2002 | Jarrett et al. |
| 6,395,266 B1 | 5/2002 | Martinez et al. |
| 6,417,347 B1 | 7/2002 | Herrmann |
| 6,451,337 B1 | 9/2002 | Smith et al. |
| 6,500,930 B2 | 12/2002 | Adamson |
| 6,544,503 B1 | 4/2003 | Vanderhoff |
| 6,555,660 B2 | 4/2003 | Nissen |
| 6,586,398 B1 | 7/2003 | Kinstler |
| 6,596,135 B1 | 7/2003 | Mitsui |
| 6,596,861 B1 | 7/2003 | Moreau |
| 6,624,142 B2 | 9/2003 | Greenwald |
| 6,660,843 B1 | 12/2003 | Feige et al. |
| 6,875,594 B2 | 4/2005 | Muir et al. |
| 6,916,962 B2 | 7/2005 | Rosen et al. |
| 7,115,576 B2 | 10/2006 | Sommermeyer |
| 7,125,843 B2 | 10/2006 | DeFrees et al. |
| 7,157,546 B2 | 1/2007 | Kozlowski |
| 7,179,617 B2 | 2/2007 | DeFrees et al. |
| 7,279,176 B1 | 10/2007 | West et al. |
| 7,285,661 B2 | 10/2007 | Sommermeyer et al. |
| 7,538,092 B2 | 5/2009 | Orlando et al. |
| 7,541,328 B2 | 6/2009 | Hemberger |
| 7,629,456 B2 | 12/2009 | Lange et al. |
| 7,815,893 B2 | 10/2010 | Zander et al. |
| 7,816,516 B2 | 10/2010 | Hemberger et al. |
| 8,017,739 B2 | 9/2011 | Eichner et al. |
| 2002/0065410 A1 | 5/2002 | Antrim |
| 2003/0087877 A1 | 5/2003 | Calias et al. |
| 2003/0191291 A1 | 10/2003 | Kochendoerfer et al. |
| 2004/0023306 A1 | 2/2004 | Aebersold et al. |
| 2004/0043446 A1 | 3/2004 | DeFrees et al. |
| 2004/0180858 A1 | 9/2004 | Sommermeyer |
| 2005/0063943 A1 | 3/2005 | Sommermeyer et al. |
| 2005/0238723 A1 | 10/2005 | Zander et al. |
| 2006/0019877 A1 | 1/2006 | Conradt et al. |
| 2006/0121062 A1 | 6/2006 | Eichner et al. |
| 2006/0188472 A1 | 8/2006 | Sommermeyer et al. |
| 2006/0194940 A1 | 8/2006 | Kozlowski |
| 2006/0217293 A1 | 9/2006 | Orlando et al. |
| 2007/0087961 A1 | 4/2007 | Eichner et al. |
| 2007/0134197 A1 | 6/2007 | Eichner et al. |
| 2008/0206182 A1 | 8/2008 | Sommermeyer et al. |
| 2008/0207562 A1 | 8/2008 | Zander et al. |
| 2008/0274948 A1 | 11/2008 | Eichner et al. |
| 2009/0091549 A1 | 4/2009 | Matsumoto et al. |
| 2009/0233847 A1 | 9/2009 | Hemberger et al. |
| 2010/0062973 A1 | 3/2010 | Frank et al. |
| 2010/0297078 A1 | 11/2010 | Hacket et al. |
| 2010/0305033 A1 | 12/2010 | Hacket et al. |
| 2010/0311670 A1 | 12/2010 | Zander et al. |
| 2010/0317609 A1 | 12/2010 | Zander et al. |
| 2011/0054152 A1 | 3/2011 | Zander et al. |

FOREIGN PATENT DOCUMENTS

| | | |
|---|---|---|
| CA | 2 233 725 | 9/1999 |
| CA | 2 441 442 | 10/2002 |
| CA | 2 478 478 | 9/2003 |
| CA | 2 478 480 | 9/2003 |
| DE | 2 233 977 | 2/1973 |
| DE | 2 616 086 | 11/1977 |
| DE | 3 501 616 | 7/1986 |
| DE | 3 029 307 | 12/1989 |
| DE | 3 836 600 | 5/1990 |
| DE | 279 486 | 6/1990 |
| DE | 4 130 807 | 3/1993 |
| DE | 2 607 706 | 5/1993 |
| DE | 69025920 | 8/1996 |
| DE | 196 28 705 | 1/1998 |
| DE | 198 08 079 | 8/1999 |
| DE | 100 41 541 | 3/2002 |
| DE | 101 12 825 | 10/2002 |
| DE | 101 26 158 | 12/2002 |
| DE | 101 35 694 | 2/2003 |
| DE | 101 29 369 | 3/2003 |
| DE | 101 55 098 | 5/2003 |
| DE | 102 09 821 | 9/2003 |
| DE | 102 17 994 | 11/2003 |
| DE | 102 54 745 | 6/2004 |
| DE | 102 56 558 | 9/2004 |
| EP | 0 019 403 | 7/1985 |
| EP | 0 218 825 | 4/1987 |
| EP | 0 609 968 | 6/1987 |
| EP | 0 307 827 | 3/1989 |
| EP | 0 331 471 | 9/1989 |
| EP | 0 138 572 | 7/1990 |
| EP | 0 127 839 | 7/1992 |
| EP | 0 338 916 | 7/1992 |
| EP | 0 315 349 | 2/1993 |
| EP | 0 549 721 | 4/1994 |
| EP | 0 304 183 | 6/1994 |
| EP | 0 605 963 | 7/1994 |
| EP | 0 342 557 | 11/1994 |
| EP | 0 661 294 | 12/1994 |
| EP | 0 418 523 | 6/1995 |
| EP | 0 243 929 | 9/1995 |
| EP | 0 402 724 | 2/1996 |
| EP | 0 646 130 | 12/1996 |
| EP | 0 806 140 | 11/1997 |
| EP | 0 148 605 | 12/1998 |
| EP | 0 668 351 | 9/1999 |
| EP | 0 411 678 | 1/2000 |
| EP | 0 205 564 | 6/2000 |
| EP | 0 809 996 | 4/2003 |
| EP | 1 398 327 | 3/2004 |
| EP | 1 398 328 | 3/2004 |
| EP | 1 400 533 | 3/2004 |
| EP | 1 424 086 | 6/2004 |
| EP | 0 428 267 | 12/2004 |
| EP | 1 496 076 | 1/2005 |
| EP | 0 640 619 | 3/2005 |
| EP | 1 230 935 | 8/2005 |
| EP | 1 591 467 | 11/2005 |
| EP | 1 398 322 | 4/2006 |
| EP | 1 064 951 | 8/2007 |
| EP | 2 070 950 | 6/2009 |
| EP | 2 143 736 | 1/2010 |
| EP | 2 154 160 | 2/2010 |
| EP | 1 660 134 | 12/2010 |
| EP | 1372735 | 10/2011 |
| FR | 2 378 094 | 8/1978 |
| GB | 1 419 080 | 12/1975 |
| GB | 1 549 246 | 7/1979 |
| IL | 1 665 06 | 2/2010 |
| JP | 10-287554 | 10/1998 |
| JP | 2001-294601 | 10/2001 |
| WO | WO 80/02374 | 11/1980 |
| WO | WO 90/07939 | 7/1990 |
| WO | WO 90/12874 | 11/1990 |
| WO | WO 90/15628 | 12/1990 |
| WO | WO 92/11037 | 7/1992 |
| WO | WO 93/23062 | 11/1993 |

(56) References Cited

FOREIGN PATENT DOCUMENTS

| | | |
|---|---|---|
| WO | WO 93/24476 | 12/1993 |
| WO | WO 94/01483 | 1/1994 |
| WO | WO 94/05332 | 3/1994 |
| WO | WO 94/07536 | 4/1994 |
| WO | WO 94/13697 | 6/1994 |
| WO | WO 94/28024 | 12/1994 |
| WO | WO 94/29370 | 12/1994 |
| WO | WO 95/06058 | 3/1995 |
| WO | WO 95/13090 | 5/1995 |
| WO | WO 96/11953 | 4/1996 |
| WO | WO 96/19242 | 6/1996 |
| WO | WO 96/40662 | 12/1996 |
| WO | WO 96/41813 | 12/1996 |
| WO | WO 97/21452 | 6/1997 |
| WO | WO 97/30148 | 8/1997 |
| WO | WO 97/33552 | 9/1997 |
| WO | WO 97/38727 | 10/1997 |
| WO | WO 97/42225 | 11/1997 |
| WO | WO 98/01158 | 1/1998 |
| WO | WO 98/05689 | 2/1998 |
| WO | WO 98/07713 | 2/1998 |
| WO | WO 98/08856 | 3/1998 |
| WO | WO 98/14212 | 4/1998 |
| WO | WO 98/14215 | 4/1998 |
| WO | WO 98/20905 | 5/1998 |
| WO | WO 98/32466 | 7/1998 |
| WO | WO 98/56424 | 12/1998 |
| WO | WO 99/07719 | 2/1999 |
| WO | WO 99/17783 | 4/1999 |
| WO | WO 99/49897 | 10/1999 |
| WO | WO 00/07738 | 2/2000 |
| WO | WO 00/18893 | 4/2000 |
| WO | WO0055210 | 9/2000 |
| WO | WO 00/66633 | 11/2000 |
| WO | WO 00/78355 | 12/2000 |
| WO | WO 01/70272 | 9/2001 |
| WO | WO 01/78682 | 10/2001 |
| WO | WO 01/83522 | 11/2001 |
| WO | WO01/85799 | 11/2001 |
| WO | WO 01/93862 | 12/2001 |
| WO | WO 02/09766 | 2/2002 |
| WO | WO 02/20033 | 3/2002 |
| WO | WO 02/28841 | 4/2002 |
| WO | WO 02/40057 | 5/2002 |
| WO | WO 02/080979 | 10/2002 |
| WO | WO 03/000738 | 1/2003 |
| WO | WO 03/031464 | 4/2003 |
| WO | WO 03/031581 | 4/2003 |
| WO | WO 03/049699 | 6/2003 |
| WO | WO 03/059246 | 7/2003 |
| WO | WO 03/070772 | 8/2003 |
| WO | WO 03/074087 | 9/2003 |
| WO | WO 03/074088 | 9/2003 |
| WO | WO 2004/009082 | 1/2004 |
| WO | WO 2004/022630 | 3/2004 |
| WO | WO 2004/024761 | 3/2004 |
| WO | WO 2004/024776 | 3/2004 |
| WO | WO 2004/024777 | 3/2004 |
| WO | WO 2004/030701 | 4/2004 |
| WO | WO 2004/033651 | 4/2004 |
| WO | WO 2004/050710 | 6/2004 |
| WO | WO 2004/065425 | 8/2004 |
| WO | WO 2005/014024 | 2/2005 |
| WO | WO 2005/014035 | 2/2005 |
| WO | WO 2005/014050 | 2/2005 |
| WO | WO 2005/014655 | 2/2005 |
| WO | WO 2005/072778 | 8/2005 |
| WO | WO 2005/074993 | 8/2005 |
| WO | WO 2005/083103 | 9/2005 |
| WO | WO 2005/092369 | 10/2005 |
| WO | WO 2005/092390 | 10/2005 |
| WO | WO 2005/112954 | 12/2005 |
| WO | WO 2006/108052 | 10/2006 |
| WO | WO 2007/053292 | 5/2007 |
| WO | WO 2010/042638 | 4/2010 |

OTHER PUBLICATIONS

Caliceti et al., ""Immunological properties of uricase conjugated to neutral soluble polymers,"" *Bioconjugate Chem.*, 2001, 12:515-522.

Carey and Sundberg, "Organische Chemie," VCH Verlagsgesellschaft mbH, Weinheim (DE), 1995, 432-436, *with English translation*.

Cervigni et al., "Synthesis of glycopeptides and lipopeptides by chemoselective ligation," Angewandte Chemie, International Edition in English, 1996, 35(11):1230-1232.

Dorwald, "Side Reactions in Organic Synthesis, A Guide to Successful Synthesis Design," Wiley-VCH Verlag GmbH & Co., 2005, Preface p. IX-X.

Grieco et al., "Aryl selenocyanates and aryl thiocyanates: reagents for the preparation of activated esters," *J. Org. Chem.*, 1978, 43(6):1283-1285.

Heitzmann and Richards, "Use of the avidin-biotin complex for specific staining of biological membranes in electron microscopy," *Proc. Natl. Acad. Sci. USA*, 1974, 71(9):3537-3541.

Heterobifunctional Crosslinkers by Molecular Biosciences, retrieved Jun. 6, 2011 from http://www.molbio.com/Heterobi.htm, 2000, 13 pages.

Lewis and Wähälä, "Regiospecific 4'-O-β-glucosidation of isoflavones," *Tetrahedron Letters*, 1998, 39:9559-9562.

Lewis et al., "The phase transfer catalysed synthesis of isoflavone-O-glucosides," *J. Chem. Soc.*, Perkins Trans. 1, 1998, pp. 2481-2484.

Lund et al., "Assessment of methods for covalent binding of nucleic acids to magnetic beads, Dynabeads, and the characteristics of the bound nucleic acids in hybridization reactions," *Nucl. Acids Res.*, 1988, 16(22): 10861-10880.

Organikum, Organisch-chemisches Grundpraktikum, 1984, VEB Deutscher Verlag der Wissenschaften, p. 472 (with verified English translation).

"Oxime," In AccessScience, McGraw-Hill Companies, 2008, retrieved from http://www.accessscience.com., 7 pages.

Pierce Company, Crosslinking Reagents, retrieved on Aug. 25, 2011 from http://www.piercenet.com/browse.cfm?fldID=0203, 2011, 2 pages.

Reischl (ed)., "Molecular Diagnosis of Infectious Diseases," 1997, vol. 13, Totowa NJ, Humana Press Inc. (table of contents only).

Riess, "Oxygen carriers ('blood substitutes')—raison d'etre, chemistry, and some physiology," Chem. Rev., 2001,101:2797-2919.

Svenson et al., "Oligosaccharide-protein conjugate: a novel approach for making salmonella O-antigen immunogens," *FEMS Microbiology Letters*, 1977, 1: 145-148.

Wang et al., "Delivery of antisense oligonucleotides using HPMA polymer: synthesis of a thiol polymer and its conjugation to water-soluble molecules," *Bioconj. Chem.*, 1998, 9:749-757.

Blackburn and Gait, Eds., "DNA and RNA Structure," in *Nucleic Acids in Chemistry and Biology*, 2nd Edition, 1996, Oxford University Press, pp. 15-81.

Englisch and Gauss, "Chemically modified oligonucleotides as probes and inhibitors," *Angew. Chem. Int. Ed. Engl.*, 1991, 30:613-629.

Ersdal-Badju et al., "Identification of the antithrombin III heparin binding site," *J. Biol. Chem.*, 1997, 272(31):19393-19400.

Lonngren et al., "Aldonate coupling, a simple procedure for the preparation of carbohydrate-protein conjugates for studies of carbohydrate-binding proteins," *Arch. BioChem. BioPhys.*, 1976, 175:661-669.

Ng et al., "Pegaptanib, a targeted anti-VEGF aptamer for ocular vascular disease," *Nature Reivews*, 2005, 5:123-126.

Nielsen et al., "Sequence-selective recognition of DNA by strand displacement with a thymidine-substituted polyamide," *Science*, 1991, 254:1497-1500.

Pieve et al., "Modification of thiol functionalized aptamers by conjugation of synthetic polymers," *Bioconjugate Chemistry*, 2012, 21:169-174.

Pierce Chemical Technical Library, "Cross-linking," printed Mar. 6, 2009, 45 pages.

Chu et al., "Iodine-catalysed Michael addition of mercaptans to α,β-unsaturated ketones under solvent-free conditions," *Tetrahedron Lett*, 2005, 46(30):4971-4974.

(56) References Cited

OTHER PUBLICATIONS

Faith, "Aldehyde-phenol reaction products and derivatives," *J Amer Chem Soc*, 1950, 72(2):837-839.
Iranpoor et al., "Easily prepared azopyridines as potent and recyclable reagents for facile esterification reactions. AN efficient modified mitsunobu reaction," *J Org Chem*, 2008, 73(13):4882-4887.
Nakazawa et al., "An efficient synthesis of naphthyl alkyl and aryl sulfides by the reaction of naphthols with alkane- and arenethiols," *Synthesis*, 1989, 1989(12):955-957.
Anno et al., "Basic of Sugar chemistry," 1994-1995, Kodansha Limited, Otowa, Bunkyo-ku, Tokyo, 30-31, (w/ English translation) 5 pages.
Bronzino, The Biomedical Engineering Handbook, CRC Press, USA, Salem, 1995, Table of Contents only, 13 pages.
Hermanson, Bioconjugate Techniques, 1996, Table of Contents only, 3 pages.
Klemm et al., "Esterification of Cellulose," Comprehensive Cellulose Chemistry, 1998, vol. 2, Wiley-VCH, Weinheim, New York, pp. 99-207.
Nouaimi et al., "Immobilization of trypsin on polyester fleece via different spacers," Enzyme and Microbial Technology, 2001, 29:567-574.
Abuchowski and Davis, "Soluble Polymer-Enzyme Adducts," *Enzymes as Drugs*, 1981, Holcenberg and Rubberts (eds.), Chapter 13, pp. 367-383, John Wiley & Sons N.Y.
Adamczyk and Fishpaugh, "A Solid Supported Synthesis of Thiol Esters," *Tetrahedron Lett.*, 1996, 37(25):4305-8.
Alagon et al., "Activation of Polysaccharides with 2-Iminothiolane and its uses," *Biochem.*, 1980 19:4341-4345.
Alayash and Cahson, "Hemoglobin and free radicals: implications for the development of a safe blood substitute," *Molec. Med. Today*, 1995, 1(3):122-7.
Aly et al., "Hemophilia A due to mutations that create new N-glycosylation sites," *Proc. Natl. Acad. Sci. USA*, 1992, 89(11):4933-7.
Anderson and Meister, "Inhibition of γ-glutamyl transpeptidase and induction of glutathionuria by γ-glutamyl amino acids," *Proc. Natl. Acad. Sci. USA*, 1986, 86: 5029-5032.
Andersson et al., "Isolation and characterization commercial factor VIII: molecular forms in commercial factor VIII concentrate, cryoprecipitate, and plasma," *Proc. Natl. Acad. Sci. USA*, 1986, 83(9):2979-83.
Armitage, "Emerging applications of recombinant human granulocyte-macrophage colony-stimulating factor," *Blood*, 1998, 92(12):4491-4508.
Ashwell, "Carbohydrate Antigens: Coupling of Carbohydrates to Proteins by a Mixed Anhydride Reaction," *Methods Enzymol.*, 1972, 28:219-22.
Avigad, "A simple spectrophotometric determination of formaldehyde and other aldehydes: application to periodate-oxidized glycol systems," *Anal. Biochem.*, 1983, 134(2):499-504.
Axén et al., "Chemical Coupling of Peptides and Proteins to Polysaccharides by Means of Cyanogen Halides," *Nature*, 1967, 214:1302-1304.
Balazy et al., "S-Nitroglutathione, a Product of the Reaction between Peroxynitrite and Glutathione that Generates Nitric Oxide," *J. Biol. Chem.*, 1998 273(48): 32009-32015.
Baldwin et al., "Synthesis of Polymer-Bound Hemoglobin Samples," *Tetrahedron*, 1981, 37:1723-1726.
Balland et al., "Characterisation of two differently processed forms of human recombinant factor IX synthesised in CHO cells transformed with a polycistronic vector," *Eur. J. Biochem.*, 1988, 172(3):565-72.
Balland et al., "Intracellular distribution of ampicillin in murine macrophages infected with *Salmonella typhimurium* and treated with ($^3$H)ampicillin-loaded nanoparticles," *J. Antimicrob. Chemother.*, 1996, 37:105-115.
Barbone et al., "Reticulocyte measurements as a bioassay for erythropoietin," *J. Pharm. Biomed. Anal.*, 1994, 12(4):515-522.

Bårström et al., "New derivatives of reducing oligosaccharides and their use in enzymatic reactions: efficient synthesis of sialyl Lewis a and sialyl dimeric Lewis x glycoconjugates," *Carbohydr. Res.*, 2000, 328:525-531.
Bauer and Rosenberg, "Role of antithrombin III as a regulator of in vivo coagulation," *Semin. Hematol.*, 1991, 28(1):10-18.
Bauer and Suresh, "S-[$w$-(Aminoöxy)alkyl]isothiuronium Salts, $w,w'$-Bis(aminoöxy)alkanes and Related Compounds," *J. Org. Chem.*, 1963, 28:1604-1608.
Bauer et al., "Synthesis of $w$—(Aminooxy)alkanethiols," *J. Org. Chem.*, 1965, 30:949-951.
Bendele et al., "Short Communication: Renal Tubular Vacuolation in Animals Treated with Polyethylene-Glycol-Conjugated Proteins," *Toxicol. Sci.*, 1998, 42:152-157.
Benesch, "Bis(pyridoxal) Polyphosphates as Specific Intramolecular Cross-Linking Agents for Hemoglobin," *Meth. Enzymol.*, 1994, 231:267-274.
Bepperling et al., "HES 130/0.4, a new HES specification: tissue storage after multiple infusions in rats," *Crit. Care*, 1999, 3(suppl 1):P153.
Berg et. al., "Engineering the proteolytic specificity of activated protein C improves its pharmacological properties," *Proc. Natl. Acad. Sci. USA*, 2003, 100(8):4423-4428.
Berger et al., "Galactosyltransferase-dependent sialylation of complex and endo-*N*-acetylglucosaminidase H-treated core *N*-glycans in vitro," *FEBS Lett.*, 1986, 203(1):64-68.
Bernardes et al. "The Direct Formation of GlycosylThiols from Reducing Sugars Allows One-Pot Protein Glycoconjugation," *Angew Chem.*, 2006 118: 4111-4115.
Besheer et al., "Enzymatically Catalyzed HES Conjugation Using Microbial Transglutaminase: Proof of Feasibility," *J. Pharm. Sci.*, 2009, 98 (11):4420-4428.
Bhattacharyya et al., "Recombinant Factor VIII for Haemophilia," *CRIPS*, 2003, 4(3):2-8.
Bjork and Danielsson, "Antithrombin and related inhibitors of coagulation proteinases," *Proteinase Inhibitors*, Barrett and Salvesen (eds.), 1986, Chapter 17, Amsterdam, The Netherlands, Elsevier Science Publishers (Biomedical Devision), pp. 489-513.
Black et al., "*N*-Bromoacetyl-glycopyranosylamines as affinity labels for a β-glucosidase and a cellulase," *Carbohydr. Res.*, 1993, 250:195-202.
Blum et al., "Improved silver staining of plant proteins, RNA and DNA in polyacrylamide gels," *Electrophoresis*, 1987, 8:93-99.
Bobbitt, "Periodate Oxidation of Carbohydrates," *Carbohydr. Chem.*, 1956, 11:1-41.
Boissel et al., "Erythropoietin Structure-Function Relationships. Mutant proteins that test a model of tertiary structure," *J. Biol. Chem.*, 1993, 268(21):15983-15993.
Boorsma et al., "Bioprocess applications of a Sindbis virus-based temperature-inducible expression system," *Biotechnol. Bioeng.*, 2002, 79(6): 602-609.
Boturyn et al., "Synthesis of Fluorescent Probes for the Detection of Abasic Sites in DNA," *Tetrahedron*, 1997, 53(15):5485-5492.
Bowen et al., "Estimation of Effective and Total Erythropoiesis in Myelodysplasia Using Serum Transferrin Receptor and Erythropoietin Concentrations, with Automated Reticulocyte Parameters," *Leukemia*, 1994, 8(1):151-155.
Bronzino, *The Biomedical Engineering Handbook*, CRC Press, USA, Salem, 1995, table of contents.
Bunn & Jandl, "The Renal Handling of Hemoglobin. II. Catabolism," *J. Exp. Med.*, 1967, 129:925-934.
Burgess et al., "Stimulation by Human Placental Conditioned Medium of Hemopoietic Colony Formation by Human Marrow Cells," *Blood*, 1977, 49(4):573-583.
Bystrický et al., "Determination of the cross-linking effect of adipic acid dihydrazide on glycoconjugate preparation," *Glycoconj. J.*, 1999, 16:691-695.
Cabacungan et al., "Amine Boranes as Alternative Reducing Agents for Reductive Alkylation of Proteins," *Anal. Biochem.*, 1982, 124:272-278.
Carlsson et al., "Protein Thiolation and Reversible Protein-Protein Conjugation," *Biochem J.*, 1978, 173:723-737.

(56) References Cited

OTHER PUBLICATIONS

Carrell et al., "Human alpha 1-antitrypsin: carbohydrate attachment and sequence homology," *FEBS Lett.*, 1981, 135(2):301-3.
Carrell et al., "Structural mobility of antithrombin and its modulation by heparin," *Thromb. Haemost.*, 1997, 78(1):516-9.
Carver et al., "Expression of human alpha 1 antitrypsin in transgenic sheep," *Cytotechnology*, 1992, 9(1-3):77-84.
Castillo et al., "Sensitive substrates for human leukocyte and porcine pancreatic elastase: a study of the merits of various chromophoric and fluorogenic leaving groups in assays for serine proteases," *Anal. Biochem.*, 1979, 99(1):53-64.
Cavallaro et al., "Folate-mediated targeting of polymeric conjugates of gemcitabine," *Int. J. Pharmaceutics*, 2006, 307:258-269.
Cebon et al., "Granulocyte-macrophage colony stimulating factor from human lymphocytes. The effect of glycosylation on receptor binding and biological activity," *J. Biol. Chem.*, 1990, 265(8):4483-4491.
Cera et al., "Water-soluble polysaccharide-anthracycline conjugates: biological activity," *Anti-Cancer Drug Design*, 1992, 7(2):143-151.
Cerami, "Beyond Erythropoiesis: Novel Applications for Recombinant Human Erythropoietin," *Semin. Hematol.*, 2001, 38:(3 Suppl 7):33-39.
Cerny et al., "A Hydroxyethyl Starch-Hemoglobin Polymer as a Blood Substitute," *Clinical Hemorheology*, 1982, 2(4):355-365.
Chagnon et al., "Murine renal cell carcinoma: evaluation of a dendritic-cell tumour vaccine," *BJU Int.*, 2001, 88:418-424.
Chamow and Ashkenazi(eds.), "Antibody Fusion Proteins," 1999, 312 pages, John Wiley & Sons, Inc., (TOC).
Chamow et al., "Conjugation of Soluble CD4 without Loss of Biological Activity via a Novel Carbohydrate-directed Cross-linking Reagent," *J. Biol. Chem.*, 1992, 267(22):15916-15922.
Chan et al., "Preparation of O-esters from the corresponding thiol esters: *tert*-butyl cyclohexanecarboxylate," *Organic Syntheses, Coll.*, 1990, 7:87-93.
Chang, "Blood Substitutes Based on Modified Hemoglobin Prepared by Encapsulation or Crosslinking: An Overview," *Biomat., Art. Cells & Immob. Biotech.*, 1992, 20:159-179.
Chaplin and Kennedy (eds.), 1996, "Carbohydrate Analysis: A Practical Approach," Montreuill, *Glycoproteins*, pp. 175-177; IRL Press Practical Approach Series.
Chaplin and Kennedy (eds.), *Carbohydrate Analysis: A Practical Approach*, 1994, 2nd Edition, Chapter 1 "Monosaccharides," pp. 1-41, Chapter 2 "Oligosaccharides" pp. 42-72, Chapter 3 "Neutral Polysaccharides" pp. 73-124, Chapter 5 "Glycoproteins" pp. 181-293, IRL Press.
Chaplin, "A Rapid and Sensitive Method for the Analysis of Carbohydrate Components in Glycoproteins Using Gas-Liquid Chromatography," *Anal. Biochem.*, 1982, 123:336-341.
Chaplin, "Monosaccharides," *Carbohydrate analysis: a practical approach*, 1996, Chaplin and Kennedy (eds.), Chapter 1, "Oligosaccharides," pp. 37-54.
Chapman et al., "Therapeutic antibody fragments with prolonged in vivo half-lives," *Nature Biotech.*, 1999, 17:780-783.
Chen et al., "Purification of alpha 1 proteinase inhibitor from human plasma fraction IV-1 by ion exchange chromatography," *VoxSanguinis*, 1998, 74(4):232-241.
Choay et al., "Structural studies on a biologically active hexasaccharide obtained from heparin," *Ann. NY Acad. Sci.*, 1981, 370:644-9.
Choay et al., "Structure-activity relationship in heparin: a synthetic pentasaccharide with high affinity for antithrombin III and eliciting high anti-factor Xa activity," *Biochem. Biophys. Res. Commun.*, 1983, 116(2):492-9.
Chow et al., "In vitro Induction of apoptosis of neoplastic cells in low-grade non-Hodgkin's lymphomas using combinations of established cytotoxic drugs with bendamustine," *Haematologica*, 2001, 86:485-493.
Chu et al., "Further Studies on the Immunogenicity of *Haemophilus influenzae* Type b and Pneumococcal Type 6A Polysaccharide-Protein Conjugates," *Infect. Immun.*, 1983, 40:245-256.
Colman, "Production of therapeutic proteins in the milk of transgenic livestock," *Biochem. Soc. Symp.*, 1998, 63:141-147.
Conradt et al., "Expression of human interleukin-2 in recombinant baby hamster kidney, Ltk-, and Chinese hamster ovary cells. Structure of O-linked carbohydrate chains and their location within the polypeptide," *J. Biol. Chem.*, 1989, 264:17368-17373.
Corey and Clark, "A New Method for the Synthesis of 2-Pyridinethiol Carboxylic Esters," *Tetrahedron Lett.*, 1979, 2875-8.
Cumber et al., "Preparation of Antibody-Toxin Conjugates," *Meth. Enzymol.*, 1985, 112:207-225.
Davis and Flitsch, "A Novel Method for the Specific Glycosylation of Proteins," *Tetrahedron Lett.*, 1991, 32(46):6793-6.
De Koning et al., "An approach to the synthesis of peptide-PNA-peptide conjugates via native ligation," *Tetrahedron Lett.*, 2002, 43(45):8173-8176.
De Velasco et al., "Synthetic Peptides Representing T-Cell Epitopes Act as Carriers in Pneumococcal Polysaccharide Conjugate Vaccines," *Infect. Immun.*, 1995, 36(3):961-968.
Delgado et al., "The Uses and Properties of PEG-Linked Proteins," *Crit. Rev. Ther. Drug Carrier Syst.*, 1992, 9(3,4):249-304.
Delorme et al., "Role of Glycosylation on the Secretion and Biological Activity of Erythropoietin," *Biochemistry*, 1992, 31(41):9871-9876.
Denzlinger et al., "Differential activation of the endogenous leukotriene biosynthesis by two different preparations of Granulocyte-Macrophage Colony-Stimulating Factor in healthy volunteers," *Blood*, 1993, 81(8):2007-2013.
Dieterich et al., "Hydroxyethyl Starch Antibodies in Humans: Incidence and Clinical Relevance," *Anesth. Analg.*, 1998, 86:1123-1126.
Dittmar et al., "Human Glycoproteins and Derived Variants from Recombinant Mammalian Cell Lines," *Advances in Protein Design*, 1989, 12:145-156.
Donahue et al., "Effects of N-linked carbohydrates on the in vivo properties of human GM-CSF," *Cold Spring Harbor Symp. Quant. Biol.*, 1986, 51, pp. 685-692.
Dorner et al., "Increased Synthesis of Proteins Induces Expression of Glucose-regulated Proteins in Butyrate-treated Chinese Hamster Ovary Cells," *J. Biol. Chem.*, 1989, 264(34):20602-20607.
Dowling and Russell, "Pharmacokinetics of a long-acting oxytetracycline-polyethylene glycol formulation in horses," *J. Vet. Pharmacol. Therap.*, 2000, 23:107-110.
Dreborg and Åkerblom, "Immunotherapy with Monomethoxypolyethylene Glycol Modified Allergens," *Crit. Rev. Ther. Drug Carrier Syst.*, 1990, 6(4):315-365.
Edmunds et al., "Transgenically Produced Human Antithrombin: Structural and Functional Comparison to Human Plasma-Derived Antithrombin," *Blood*, 1998, 91, 12:4561-4671.
Elliott et al., "Mapping of the Active Site of Recombinant Human Erythropoietin," *Blood*, 1997, 89(2):493-502.
*European Pharmacopeia*, 2001, 911-918.
*European Pharmacopoeia*, 1996, Erythropoietin concentrated solution, Pharmaeuropa., 8, 371-377.
Ernst, Hart and Sinay eds., *Carbohydrates in Chemistry and Biology*, part I, vols. 1 and 2, 2000, Whiley-VCH Weinheim-New York-Chichester-Brisbane-Toronto, ISBN 3-527-29511-9, table of contents.
Etrych et al., "New HPMA Copolymers containing doxorubicin bound via pH-sensitive linkage: synthesis and preliminary in vitro and in vivo biological properties," *Journal of Controlled Release*, 2001, 73: 89-102.
*European Pharmacopoeia*, "Erythropoietin Concentrated Solution," 3rd Edition, 2000, Monography, pp. 655-660.
*European Pharmacopoeia*, "Erythropoietin Concentrated Solution," 4th Edition, 2002, Monography, pp. 1123-1128.
Fernández-Santana et al., "Conjugation of 5-azido-3-oxapentyl glycosides with thiolated proteins through the use of thiophilic derivatives," *Glycoconj. J.*, 1998, 15:549-553.
Fibi et al., "Evidence for the Location of the Receptor-Binding Site of Human Erythropoietin at the Carboxyl-Terminal Domain," *Blood*, 1991, 77(6):1203-1210.
Fibi et al., "N- and O-Glycosylation Muteins of Recombinant Human Erythropoietin Secreted From BHK-21 Cells," *Blood*, 1995, 85(5):1229-1236.

(56) References Cited

OTHER PUBLICATIONS

Fissekis et al., "*N*-Pantyol-(substituted)amines, Pantothenic Acid Analogues," *J. Med. Pharm. Chem.*, 1960, 2:47-56.

Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271:907-919.

Franzen et al., "Structural studies on the carbohydrate portion of human antithrombin III," *J. Biol. Chem.*, 1980, 255(1):5090-3.

Frie, "Evaluating a Novel Method for Coupling of Low Molecular Hydroxyethylstarch with Model Compounds and Application of this Method to further Selected Proteins," Diploma Thesis dated Feb. 2, 1998, Diplomarbeit, Fachhochschule, Hamburg, Germany, 82 pages including English-language Abstract.

Fujiki et al., "Studies on the disulfide bonds in human pituitary follicle-stimulating hormone." *Biochim. Biophys. Acta*, 1980, 624:428-435.

Gaertner and Offord, "Site-Specific Attachment of Functionalized Poly(ethylene glycol) to the Amino Terminus of Proteins," *Bioconjugate Chemistry*, 1996, 7(1):38-44.

Ganson et al., "Control of Hyperuricemia in Subjects with refractory gout, and induction of antibody against poly (ethylene glycol) (PEG), in a phase 1 trial of subcutaneous PEGylated urate oxidase," *Arthritis Res. Ther.*, 8: R12 (2005).

Gaucher et al., "Stereospecific Synthesis and Characterization of Aminoglycoside Ligands from Diethylenetriamine," *J. Organic Chemistry*, 1999, 64:1402-4015.

Gerwech et al., "Tumor pH controls the in vivo efficacy of weak acid and base chemotherapeutics," *Mol. Cancer Ther.*, 2006, 5(5): 1275-2179.

Gervais et al., "NMR investigations of the role of the sugar moiety in glycosylated recombinant human granulocyte-colony-stimulating factor," *Eur. J. Biochem.*, 1997, 247:386-395.

Gillis et al., "T Cell Growth Factor: Parameters of Production and a Quantitative Microassay for Activity," *J. Immunol.*, 1978, 120(6):2027-2032.

Glederblom et al., "Cremophor E1: the drawbacks and advantages of vehicle selection for drug formulation," *Eur. J. Cancer*, 2001, 37: 1590-1598.

Goldstein and Gelb, "An alternate preparation of thioester resin linkers for solid-phase synthesis of peptide C-terminal thioacids," *Tetrahedron Lett.*, 2000, 41(16):2797-2800.

Gonzales, Lio and Thiem, "Chemoenzymatic synthesis of spacer-linked oligosaccharides for the preparation of neoglycoproteins," *Carbohydr. Res.*, 1999, 317:180-190.

Goronzy et al., "T-Cell Derived Lymphokines as Regulators of Chronic Inflammation: Potential Targets for Immunomodulation," *Am. J. Therap*, 1996, 3(2):109-114.

Gould et al., "The Development of Hemoglobin Solutions as Red Cell Substitutes: Hemoglobin Solutions," *Transfus. Sci.*, 1995, 16:5-17.

Grabenhorst and Conradt, "The Cytoplasmic, Transmembrane, and Stem Regions of Glycosyltransferases Specify Their in vivo Functional Sublocalization and Stability in the Golgi," *J. Biol. Chem.*, 1999, 274(51):36107-36116.

Grabenhorst et al., "Biosynthesis and secretion of human interleukin 2 glycoprotein variants from baculovirus-infected Sf21 cells. Characterization of polypeptides and posttranslational modifications," *Eur. J. Biochem.*, 1993, 215:189-197.

Grabenhorst et al., "Construction of stable BHK-21 cells coexpressing human secretory glycoproteins and human Gal(β1-4)GlcNAc-R α2,6-sialyltransferase: α2,6-Linked NeuAc is preferentially attached to the Gal(β1-4)GlcNAc(β1-2)Man(α1-3)-branch of diantennary oligosaccharides from secreted recombinant β$-trace protein," *Eur. J. Biochem.*, 1995, 232:718-725.

Grabenhorst et al., "Genetic engineering of recombinant glycoproteins and the glycosylation pathway in mammalian host cells," *Glycoconj J.*, 1999, 16(2):81-97.

Grabenhorst et al., "In Vivo Specificity of Human α1,3/4-Fucosyltransferases III-VII in the Biosynthesis of Lewis$^x$ and Sialyl Lewis$^x$ Motifs on Complex-type *N*-Glycans. Coexpression studies from BHK-21 cells together with human β-trace protein," *J. Biol. Chem.*, 1998 273(47):30985-30994.

Gray, "The Direct Coupling of Oligosaccharides to Proteins and Derivatized Gels," *Arch. Biochem. Biophys.*, 1974, 163:426-428 (Fig. 2.1a).

Greenfield et al., "Evaluation in Vitro of Adriamycin Immunoconjugates Synthesized Using an Acid-sensitive Hydrazone Linker," *Cancer Research*, 1990, 50:6600-6607.

Greenwald et al., Drug Delivery Systems: Water Soluble Taxol 2'-Poly (ethylene glycol) Ester Prodrugs—Design and in Vivo Effectiveness *J. Med. Chem.*, 1996, 39: 424-431.

Gribben et al., "Development of antibodies to unprotected glycosylation sites on recombinant GM-CSF," *Lancet*, 1990, 335:434-437.

Grieco et al., "Favored Reduction of α-Chlorosilanes vs. α-Chloroalkanes with Tri-n-butyltin Hydride," *J.Org.Chem*, 1978, 43(6):1285.

Grimmecke and Brade, "Studies on the reductive amination of 3-deoxy-D-*manno*-octulosonic acid (Kdo)," *Glycoconj. J.*, 1998, 15:555-562.

Guillaumie et al., "Immobilization of pectin fragments on solid supports: Novel coupling by thiazolidine formation," *Bioconjugate Chem.*, 2002, 13:285-294.

Habeeb, "Determination of Free Amino Groups in Proteins by Trinitrobenzenesulfonic Acid," *Anal. Biochem.*, 1966, 14:328-336.

Hai et al., "Diaspirin Crosslinked Hemoglobin (DCLHb™) Polymerization," *Art. Cells, Blood Subs., and Immob Biotech.*, 1994, 22(3):923-931.

Hallaway et al., "Modulation of Deferoxamine Toxicity and Clearance by Covalent Attachment to Biocompatible Polymers," *Proc. Natl. Acad. Sci. USA*, 1989, 86:10108-10112.

Hamma and Miller et al., "4-(2-Aminooxyethoxy)-2-(ethylureido)quinoline-Oligonucleotide Conjugates: Synthesis, Binding Interactions, and Derivatization with Peptides," *Bioconj. Chem.*, 2003, 14:320-330.

Hamilton et al., Characterization of Human Ovarian Carcinoma Cell Line (NIH: OVCAR-3) with Androgen and Estrogen Receptors, *Cancer Res.*, 1983, 43: 5379-5389.

Harada, et al. "Carrier and dose effects on the pharmacokinetics of T-0128, a camptothecin analogue-carboxymethyl dextran conjugate, in non-tumor-and tumor-bearing rats," *J. Controlled Release*, 2001, 71:71-86.

Harada, et al., "Determinants for the drug release from T-0128, camptothecin analogue-carboxymethyl dextran conjugate," *J. Controlled Release*, 2000, 69: 399-412.

Harris et al., "Pegylation. A novel process for modifying pharmacokinetics," *Clin. Pharmacokinet.* 2001, 40(7): 539-551.

Hartman and Wold, "Cross-Linking of Bovine Pancreative Ribonuclease A with Dimethyl Adipimidate," *Biochemistry*, 1967, 6(8):2439-2448.

Hashimoto et al., "Chemical Modification of the Reducing Chain End in Dextrans and Trimethylsilylations of Its Hydroxyl Groups," *J. Polymer Science: Part A: Polymer Chemistry*, 1991, 29:1271-1279.

Hattori et al., "Reduced Immunogenicity of β-Lactoglobulin by Conjugation with Carboxymethyl Dextran," *Bioconjug. Chem.*, 2000, 11:84-93.

He et al., "A simplified system for generating recombinant adenoviruses," *Proc. Natl. Acad. Sci. USA*, 1998, 95(5):2509-2514.

Heindel, Ned D. et al, "Hydrazide Pharmaceuticals as Conjugates to Polyaldehyde Dextran" *Bioconjugate Chem.*, 1990, 1: 77-82.

Herman et al., "Characterization, Formulation, and Stability of Neupogen® (Filgrastim), a Recombinant Human Granulocyte-Colony Stimulating Factor," *Formulation, Characterization, and Stability of Protein Drugs*, Pearlman and Wang (eds.), Plenum Press, Chapter 7, 1996, pp. 308-328.

Hermanson, *Bioconjugate Techniques*, 1996, table of contents only.

Hermentin et al., "A Strategy for the Mapping of *N*-Glycans by High-pH Anion-Exchange Chromatography with Pulsed Amperometric Detection," *Anal. Biochem.*, 1992, 203(2):281-289.

Higuchi et al., "Role of Sugar Chains in the Expression of the Biological Activity of Human Erythropoietin," *J. Biol. Chem.*, 1992, 267(11):7703-7709.

(56) References Cited

OTHER PUBLICATIONS

Hodges and Chan, "Locations of oligosaccharide chains in human alpha 1-protease inhibitor and oligosaccharide structures at each site," *Biochemistry*, 1982, 21(11):2805-10.
Hodges et al., "Structure of the oligosaccharide chains in human alpha 1-protease inhibitor," *J. Biol. Chem.*, 1979, 254(17):8208-12.
Hovgaard et al., "Clinical pharmacokinetic studies of a human haemopoietic growth factor, GM-CSF," *Eur. J. Clin. Inv.*, 1992, 22:45-49.
Hovinen et al., "Ethyl[2-deoxy-5-0-(4,4'-dimethoxytrityl)-α-and β-D-*erythro*-pentofuranosyl] acetates as versatile intermediates in nucleic acid chemistry," *Nucleosides Nucleotides*, 1999, 18:1263-1264.
Iakovenko et al., "Semi-synthetic Rab proteins as tools for studying intermolecular interactions," *FEBS Lett.*, 2000, 468:155-158.
Ingenito et al., "Solid Phase Synthesis of Peptide C-Terminal Thioesters by Fmoc/*t*-Bu Chemistry," *J. Am. Chem. Soc.*, 1999, 121:11369-11374.
Inoue et al., "An Improved Method for the Purification of Human Erythropoietin with High in Vivo Activity from the Urine of Anemic Patients," *Biol. Pharm. Bull.*, 1994, 17(2):180-184.
Iwamoto et al., "Polysaccharide-Coated Oil Droplets in Oil-in-Water Emulsions as Targetable Carriers for Lipophilic Drugs," *J. Pharm. Sci.*, 1991, 80(3):219-224.
Jaques et al., "N.M.R. spectroscopy and calcium binding of sialic acids: *N*-glycolylneuraminic acid and periodate-oxidized *N*-acetylneuraminic acid," *Carb. Res.*, 1980, 83:21-32.
Jia et al., "S-nitrosohaemoglobin: a dynamic activity of blood involved in vascular control," *Nature*, 1996, 380:221-226.
Jones et al., "Multivalent poly (ethylene glycol)-containing conjugates for in vivo antibody suppression" *Bioconjugate Chemistry*, 2003, 14(6):1067-1076.
Jones et al., "A convenient synthesis of *N*-(*tert*-butyloxycarbonyl)aminooxy ethers," *Tetrahedron Lett.*, 2000, 41(10):1531-1533.
Jungheinrich et al., "Pharmacokinetics of Hydroxyethyl Starch," *Clin. Pharmacokinet.*, 2005, 44 (7):681-699.
Kallin, "Coupling of Oligosaccharides to Proteins Using *p*-Trifluoroacetamidoaniline," *Meth. Enzymol.*, 1994, 242:119-123.
Karpusas et al., "Commercial preparations of interferon beta are Betaseron (IFN beta 1b), Avonex and Rebif (IFN beta 1a)," *Proc. Natl. Acad. Sci. USA*, 1997, 94:11813-11818.
Katsumi et al., "Development of Polyethylene Glycol-Conjugated Poly-S Nitrosated Serum Albumin, a Novel S-Nitrosothiol for Prolonged Delivery of Nitric Oxide in the Blood Circulation in Vivo," *J. Pharmacol. Exp. Ther.*, 2005, 314(3): 1117-1124.
Kaufman et al., "Synthesis, processing, and secretion of recombinant human factor VIII expressed in mammalian cells," *J. Biol. Chem.*, 1988, 263(13):6352-62.
Kaushansky et al., "Role of carbohydrate in the function of human Granulocyte-Macrophage Colony-Stimulating Factor," *Biochemistry*, 1987, 26:4861-4867.
Keaney, Jr. et al., "NO Forms an Adduct with Serum Albumin that Has Endothelium-derived Relaxing Factor-like Properties," *J. Clin. Invest.*, 1993, 91:1582-1589.
Keene et al., "Expression of biologically active human follitropin in Chinese hamster ovary cells," *J. Biol. Chem.*, 1989, 264:4769-4775.
Keipert et al., "Functional properties of a new crosslinked hemoglobin designed for use as a red cell substitute," *Transfusion*, 1989, 29:768-773.
Kinstler et al., "Characterization and Stablility of N-terminally PEGylated rhG-CSF," *Pharm. Res.*, 1996, 13(7):996-1002.
Kitamura et al., "Chemical Engineering of the Monoclonal Antibody A7 by Polyethylene Glycol for Targeting Cancer Chemotherapy," *Cancer Res.*, 1991, 51:4310-4315.
Kitamura et al., "Establishment and Characterization of a Unique Human Cell Line That Proliferates Dependently on GM-CSF, IL-3, or Erythropoietin," *J. Cell. Phys.*, 1989, 140:323-334.

Kleine-Tebbe et al., "Allergen Immunotherapy—A Position Paper of the German Society for Allergology and Clinical Immunology," *Pneumologie*, 2001, 55:438-444 (w/English summary).
Klimek et al., "Specific Immunotherapy (Hyposensibilisation)," *Allergologie und Umweltmedizin*, Chapter 15, pp. 157-195.
Kobayashi et al., "Reduced Immunogenicity of β-Lactoglobulin by Conjugation with Carboxymethyl Dextra Differing in Molecular Weight," *J. Agric. Food Chem.*, 2001, 49(2):823-831.
Kochendoerfer et al., "Design and chemical synthesis of a homogeneous polymer-modified erythropoiesis protein," *Science*, 2003, 299(5608):884-887.
Kojima et al., "Mitomycin C-dextran conjugate: a novel high molecular weight pro-drug of mitomycin C," *J. Pharm. Pharmacol.*, 1980, 32:30-34.
Komatsu et al., "Cloning of granulocyte colony-stimulating factor cDNA from human macrophages and its expression in *Escherichia coli*," *Jpn. J. Cancer Res.*, 1987, 78(11):1179-1181.
Kraehenbuhl et al, "Preparation and Characterization of an Immuno Electron Microscope Tracer consisting of a Heme Octa Peptide coupled to FAB," *J. Exp. Med.*, 1974, 139(1):208-223.
Krantz, "Erythropoietin," *Blood*, 1991, 77(3):419-434.
Krystal et al., "Purification of Human Erythropoietin to Homogeneity by a Rapid Five-Step Procedure," *Blood*, 1986, 67(1):71-79.
Krystal, "A Simple Microassay for Erythropoietin Based on $^3$H-Thymidine Incorporation into Spleen Cells from Phenylhydrazine Treated Mice," *Exp. Hematol.*, 1983, 11(7):649-660.
Krystal, "Physical and Biological Characterization of Erythroblast Enhancing Factor (EEF), a Late Acting Erythropoietic Stimulator in Serum Distinct from Erythropoietin," *Exp. Hematol.*, 1983, 11(1):18-31.
Kuberan et al., "Preparation and isolation of neoglycoconjugates using biotin-streptavidin complexes," *Glycoconj. J.*, 1999, 16:271-281.
Kulicke et al., "Measurements of the Refractive Index Increment on Hydroxyethyl Starch as a Basis for Absolute Molecular Weight Determinations," *Starch*, 1991, 43(10): 392-396.
Kurtz and Eckardt, "Assays for Erythropoietin," *Nephron*, 1989, 51(suppl 1):11-14 (w/English summary).
Lahiri et al., "Antithrombin-heparin cofactor: an inhibitor of plasma kallikrein," *Arch. Biophys.*, 1976, 175:737-47.
Laine et al., "Polyethylene Glycol Nephrotoxicity Secondary to Prolonged High-Dose Intravenous Lorazepam," *Annals Pharmacother.*, 1995, 29:1110-1114.
Lapthorn et al., "Crystal structure of human chorionic gonadotropin," *Nature*, 1994, 369:455-461.
Larionova et al., "Conjugation of the Bowman-Birk Soybean Proteinase Inhibitor with Hydroxyethylstarch," *Appl. Biochem. Biotech.*, 1997, 62:175-182.
Lee (ed.), "Synthesis of Peptides and Proteins," *Peptide and Protein Drug Delivery*, 1991, p. 65.
Lee and Lee, "Neoglycoproteins," *Glycoproteins II*, 1997, Chapter 17, Elsevier Science B.V., pp. 601-620.
Lee et al., "Functional Polymers for Layer-by-Layer Construction of Multilayer via Chemoselective Immobilization," *Macrocolecules*, 2004, 37:1849-1856.
Lee et al. "Conjugation of trypsin by temperature-sensitve polymers containing a carbohydrate moiety: thermal modulation of enzyme activity," *Biotechnol. Prog.*, 1998, 14(3):508-516.
Lee, Ed., *Peptide and Protein Drug Delivery*, Marcel Dekker, 1991, p. 65.
Leenders et al., "β-Glucuronyl Carbamate Based Pro-moieties Designed for Prodrugs in ADEPT," *Tetrahedron Lett.*, 1995, 36(10):1701-1704.
Lees et al., "Activation of soluble polysaccharides with 1-cyano-4-dimethylaminopyridinium tetrafluoroborate for use in protein-polysaccharide conjugate vaccines and immunological reagents," *Vaccine*, 1996, 14(3):190-198.
Lesnefsky et al., "High-Dose Iron-Chelator Therapy During Reperfusion with Deferoxamine-Hydroxyethyl Starch Conjugate Fails to Reduce Canine Infarct Size," *J. Cardiovasc. Pharmacol.*, 1990, 16(4):523-528.

(56) References Cited

OTHER PUBLICATIONS

Levy et al., "Recombinant Antithrombin: Production and Role in Cardiovascular Disorder," *Sem. Thromb. Hem.*, 2001, 27(4):405-416.
Li et al., "Direct preparation of peptide thioesters using an Fmoc solid-phase method," *Tetrahedron Lett.*, 1998, 39(47):8669-8672.
Lieber et al., "A Continuous Tumor-Cell Line From a Human Lung Carcinoma with Properties of Type II Alveolar Epithelial Cells," *Int. J. Cancer*, 1976 17:62-70.
Lin et al., "L-Cysteine as a water-soluble cation scavenger in the removal of the 2,4,6-trimethoxybenzyl group from thiols," *Tetrahedron Lett.*, 2002, 43:4531-4533.
Lin et al., "Cloning and expression of the human erythropoietin gene," *Proc. Natl. Acad. Sci. USA*, 1985, 82:7580-7584.
Lindsey at al., "Porphyrin Building Blocks for Modular Construction of Bioorganic Model Systems," *Tetrahedron*, 1994, 50(30):8941-8968, especially p. 8956.
Lipke et al., Localized Delivery of Nitric Oxide from Hydrogels Inhibits Neointima Formation in Rat Cartoid Ballon Injury Model, *Acta Biomaterialia*, 2005, 1:597-606.
Liu et al., "Characterization of the structural and functional changes of hemoglobin in dimethyl sulfoxide by spectroscopic techniques," *Biochim. Biophys. Acta*, 1998, 138:53-60.
Lomant and Fairbanks, "Chemical Probes of Extended Biological Structures: Synthesis and Properties of the Cleavable Protein Cross-linking Reagent [$^{35}$S]Dithiobis(succinimidyl propionate)," *J. Mol. Biol.*, 1976, 104:243-261.
Lönngren and Goldstein, "Coupling of Aldobionic Acids to Proteins Using Water-Soluble Carbodiimide," *Meth. Enzymol.*, 1994, 242:116-118.
Luo et al., "Controlled DNA delivery systems," *Pharm. Res.*, 1999, 16(8):1300-1308.
Manger et al., "1-*N*-Glycyl β-Oligosaccharide Derivatives as Stable Intermediates for the Formation of Glycoconjugate Probes," *Biochemistry*, 1992, 31:10724-10732.
Manger et al., "Synthesis of 1-*N*-Glycyl β-Oligosaccharide Derivatives. Reactivity of *Lens culinaris* Lectin with a Fluorescent Labeled Streptavidin Pseudoglycoprotein and Immobilized Neoglycolipid," *Biochemistry*, 1992, 31:10733-10740.
Maout et al., "Hydroxyethylstarch Conjugated to Human Hemoglobin for use in Blood Transfusion: Comparsion with Dextran Conjugates," *Carbohydrates and Carbohydrate Polymers—Analysis, Biotechnology, Modification, Antiviral and Other Applications*, 1993, Chapter 12, pp. 132-140.
March, *Advanced Organic Chemistry*, 4th edition, John Wiley and Sons, New York (1992) 409.
Masamune et al., "A General, Selective Synthesis of Thiol Esters," *Can. J. Chem.*, 1975, 53:3693-5.
Masamune et al., "Tylonolide hemiacetal, the aglycone of tylosin, and its partial synthesis," *J. Am. Chem. Soc.*, 1976, 98(24):7874-5.
Masuda et al., "Synthesis and anti-influenza evaluation of orally active bicyclic ether derivatives related to zanamivir," *Bioorganic & Medicinal Chemistry Letters*, 2003, 13(4):669-673.
McMahon et al., "Pharmacokinetics and Effects of Recombinant Human Erythropoietin After Intravenous and Subcutaneous Injections in Healthy Volunteers," *Blood*, 1990, 76(9):1718-1722.
Mega et al., "Studies on the oligosaccharide chains of human alpha 1-protease inhibitor. I. Isolation of glycopeptides," *J. Biol. Chem.*, 1980, 255(9):4053-6.
Mega et al., "Studies on the Oligosaccharide Chains of Human α$_1$-Protease Inhibitor. II. Structure of oligosaccharides," *J. Biol. Chem.*, 1980, 255(9):4057-4061.
Megson et al., "Inhibition of Human Platelet Aggregation by a Novel S-Nitrosothiol is Abolished by Hemoglobin and Red Blood Cell in vitro: Implications for Anti-Thrombotic Therapy," *Brit. J. Pharmacol.*, 2000, 131: 1391-1398.
Meinjohanns et al., "Novel sequential solid-phase synthesis of N-linked glycopeptides from natural sources," *J. Chem. Soc., Perkin Trans.*, 1998, 1:549-560.
Menache et al., "Antithrombin III: physiology, deficiency, and replacement therapy," *Transfusion*, 1992, 32(6):580-8.
Menache, "Antithrombin III: introduction," *Semin. Hematol.*, 1991, 28(1):1-2.
Merck Index 2006, Definition of Dimethyl Sulfoxide, Merck & Co., 14th Edition, accessed online: http//themerckindex.cambridgesoft.com/themerckindex/index.asp on Sep. 4, 2007.
Mikola and Hänninen, "Introduction of Aliphatic Amino and Hydroxy Groups to Keto Steroids Using O-Substituted Hydroxylamines," *Bioconj. Chem.*, 1992, 3(2):182-186.
Ming et al., "Interleukin 6 is the principal cytolytic T lymphocyte differentiation factor for thymocytes in human leukocyte conditioned medium," *J. Mol. Cell. Immunol.*, 1989, 4:203-211.
Minnema et al., "Recombinant human antithrombin III improves survival and attenuates inflammatory responses in baboons lethally challenged with *Escherichia coli*", *Blood*, 2000, 95(4):1117-1123.
Miyake et al., "Purification of Human Erythropoietin," *J. Biol. Chem.*, 1977, 252(15):5558-5564.
Montreuil et al., "Hexuronic acids," *Carbohydrate analysis: a practical approach*, 1996, Chaplin and Kennedy (eds.), Chapter 5, pp. 175-204.
Moonen et al., "Increased biological activity of deglycosylated recombinant human granulocyte-macrophage colony-stimulating factor produced by yeast or animal cells," *Proc. Natl. Acad. Sci. USA*, 1987, 84(13):4428-4431.
Mori et.al., "The activation of type 1 and type 2 plasminogen by type I and type II tissue plasminogen activator," *J. Biol. Chem.*, 1995, 270(7):3261-3267.
Mosbech et al., "Hyposensitization in asthmatics with mPEG-modified and unmodified house dust mite extract," *Allergy*, 1990, 45(2):130-141.
Mosmann, "Rapid Colorimetric Assay for Cellular Growth and Survival: Application to Proliferation and Cytotoxicity Assays," *J. Immunol. Meth.*, 1983, 65:55-63.
Mueller et al., "Recombinant Glycoprotein Product Quality in Proliferation-Controlled BHK-21 Cells," *Biotechnol. Bioeng.*, 1999, 65(5):529-536.
Muir et al., "Expressed protein ligation: a general method for protein engineering," *Proc. Natl. Acad. Sci. USA*, 1998, 95(12):6705-6710.
Mukaiyama et al., "Peptide Synthesis via Oxidation-Reduction Condensation by the Use of Non-metallic Compound as a Mercaptan Scavenger," *Bull. Chem. Soc. Jpn.*, 1970, 43:1271.
Mumberg et al., "Regulatable promoters of *Saccharomyces cerevisiae*: comparison of transcriptional activity and their use for heterologous expression," *Nucl. Acids Res.*, 1994, 22(25):5767-5768.
Murano et al., "Some properties of antithrombin-III and its concentration in human plasma," *Thromb. Res.*, 1980, 18(1-2):259-62.
Nagata et al., "Molecular cloning and expression of cDNA for human granulocyte colony-stimulating factor," *Nature*, 1986, 319:415-418.
Nagata et al., "The chromosomal gene structure and two mRNAs for human granulocyte colony-stimulating factor," *EMBO J.*, 1986, 5(3):575-581.
Nakane et al., "The Accumulation Mechanism of Cationic Mitomycin C-dextran Conjugates in the Liver: In-vivo Cellular Localization and In-vitro Interaction with Hepatocytes," *J. Pharm. Pharmacol.*, 1988, 40:1-6.
Nathan et al., "Strategies for Covalent Attachment of Doxorubicin to Ply (PEG-Lys), a New Water Soluble Poly (etherurethane)," *J. Bioactive Compatible Polymers*, 1994, 9:239-251.
Naundorf et al., "Characterization of two human mammary carcinomas, MT-1 and MT-3, suitable for in vivo testing of either lipids and their derivatives," *Breast Cancer Res. Treatment*, 1992, 23: 87-95.
Nedospasov and Khomutov, "Synthesis and some properties of aminooxyalkylcelluloses," *Bulletin of the Academy of Sciences of the USSR*, 1976, Division of Chemical Science, Consultants Bureau, New York, 25:1105-1110.
Nimtz et al., "Carbohydrate structures of a human tissue plasminogen activator variant expressed in recombinant Chinese hamster ovary cells," *FEBS Lett.*, 1990, 271:14-18.
Nimtz et al., "Structural characterization of the oligosaccharide chains of native and crystallized boar seminal plasma spermadhesin PSP-I and PSP-II glycoforms," *Eur. J. Biochem.*, 1999, 265:703-718.

(56) References Cited

OTHER PUBLICATIONS

Nimtz et al., "Structures of sialylated oligosaccharides of human erythropoietin expressed in recombinant BHK-21 cells," *Eur. J. Biochem.*, 1993, 213:39-56.

Nohynek et al., "Comparison of the potency of glycosylated and nonglycosylated recombinant human granulocyte colony-stimulating factors in neutropenic and nonneutropenic CD rates," *Cancer Chemother Pharmacol.*, 1997, 39:259-266.

Nomura et al., "Pharmacokinetic characteristics and therapeutic effects of mitomycin C-dextran conjugates after intratumoural injection," *J. Controlled Release*, 1998, 52:239-252.

O'Shannessy and Wilchek, "Immobilization of Glycoconjugates by Their Oligosaccharides: Use of Hydrazido-Derivatized Matrices," *Analytical Biochemistry*, 1990, 191:1.

Ohta et al., "Usefulness of Glycopeptide Mapping by Liquid Chromatography/Mass Spectrometry in Comparability Assessment of Glycoprotein Products," *Biologicals*, 2002, 30(3):235-244.

Okamoto et al., "Purification and characterization of three forms of differently glycosylated recombinant human Granulocyte-Macrophage Colony-Stimulating Factor," *Arch. Biochem. Biophys.*, 1991, 286(2):562-568.

Okamoto et al., "A facile incorporation of the aldehyde function into DNA: 3-formylindole nucleoside as an aldehyde-containing universal nucleoside," *Tetrahedron Lett.*, 2002, 43:4581-4583.

Olson and Bjork, "Predominant contribution of surface approximation to the mechanism of heparin acceleration of the antithrombin-thrombin reaction. Elucidation from salt concentration effects," *J. Biol. Chem.*, 1991, 266(10):6353-64.

Olson et al., "Role of the antithrombin-binding pentasaccharide in heparin acceleration of antithrombin-proteinase reactions. Resolution of the antithrombin conformational change contribution to heparin rate enhancement," *J. Biol. Chem.*, 1992, 267(18):12528-38.

Opal et al., "Antithrombin, heparin, and heparan sulfate," *Crit. Care Med.*, 2002, 30(5):S325-S331.

Pasut et al., "Antitumoral activity of PEG-gemcitabine prodrugs targeted by folic acid," *J. Controlled Release*, 2008, 127(3):239-248.

Pawlowski et al., "A new method of non-cross-linking conjugates of polysaccharides to protein via thioether bonds for the preparation of saccharide-protein conjugate vaccines," *Vaccine*, 1999, 17:1474-1483.

Pazur, "Neutral polysaccharides," *Carbohydrate analysis: a practical approach*, 1996, Chaplin and Kennedy (eds.), Chapter 3, pp. 55-96.

Pedley et al., "The potential for enhanced tumour localization by poly)ethylene glycol) modification of anti-CEA antibody," *Br. J. Cancer*, 1994, 70:1126-1130.

Peeters et al., "Comparison of four bifunctional reagents for coupling peptides to proteins and the effect of the three moieties on the immunogenicity of the conjugates," *J. Immunol. Meth.*, 1989, 120:133-143.

Pelter et al., "Synthesis of Thioesters by Reactions of Carboxylic Acids with Tris-(ethylthio)borane," *J. Am. Chem. Soc., Perkin Trans I*, 1977, 1672-674.

Peluso et al., "Asparagine surrogates for the assembly of N-linked glycopeptide mimetics by chemoselective ligation," *Tetrahedron Lett.*, 2001, 42:2085-2087.

Peri, F. et al, "Chemo- and Stereoselective Glycosylation of Hydroxylamino Derivatives: A Versatile Approach to Glycoconjugates," *Tetrahedron*, 1998, 54: 12269-12278.

Peron et al., "Hydroxyethyl starch-induced renal insufficiency after plasma exchange in a patient with polymyositis and liver cirrhosis," *Clin. Nephrol.*, 2001, 55(5):408-411.

Peterson, *The Physiological Inhibitions of Blood Coagulation and Fibrinolysis*, Elsevier/ North-Holland Biomedical Press 1979, p. 43.
*Pharma Business*, Jul./Aug. 2000, pp. 45-60.

Ph. Eur. Nachtrag., "Erythropoietini solutio concentrata," pp. 780, (2000).

Pike et al., "Heparin-dependent Modification of the Reactive Center Arginine of Antithrombin and Consequent Increase in Heparin Binding Affinity," *J. Biol. Chem.*, 1997, 272_32:19652-19655.

Quelle et al., "High-Level Expression and Purification of a Recombinant Human Erythropoietin Produced Using a Baculovirus Vector," *Blood*, 1989, 74(2):652-657.

Rabiner et al., "Evaluation of a stroma-free hemoglobin solution for use as a plasma expander," *J. Exp. Med.*, 1967, 126:1127-1142.

Radomsky and Temeriusz, "Thiazolidine-4(R)-carboxylic acids derived from sugars: part I, C-2-epimerisation in aqueous solutions," *Carb. Res.*, 1989, 187:223-237.

Ragnhammar et al., "Induction of anti-recombinant human Granulocyte-Macrophage Colony-Stimulating Factor (*Escherichia coli*-derived) antibodies and clinical effects in nonimmunocompromised patients," *Blood*, 1994, 84:4078-4087.

Ragupathi et al., "A novel and efficient method for synthetic carbohydrate vaccine preparation: synthesis of sialyl Tn-KLH conjugate using a 4-(4-N-maleimidomethyl) cyclohexane-1-carboxyl hydrazide (MMCCH) linker arm," *Glycoconj. J.*, 1998, 15:217-221.

Ramos et al., "Enzymatic Synthesis of Neoglycopeptide Building Blocks," *Angew. Chem. Int. Ed.*, 2000, 39(2):396-398.

Rapoport et al., "Protein transport across the eukaryotic endoplasmic reticulum and bacterial inner membranes," *Annu Rev Biochem.*, 1996, 65:271-303.

Reddy et al., "Use of peginterferon alfa-2a (40 KD) (Pegasys) for the treatment of hepatitis C," *Advanced Drug Delivery Reviews*, 2002, 54:571-586.

Reidhaar-Olson et al., "Identification of Residues Critical to the Activity of Human Granulocyte Colony-Stimulating Factor," *Biochemistry*, 1996, 35:9034-9041.

Relihan et al., "Clearance Rate and Effect on Renal Function of Stroma-Free Hemoglobin Following Renal Ischemia," *Ann. Surg.*, 1972, 176(6):700-704.

Reynolds et al., "S-nitrosohemoglobin deficiency: A mechanism for loss of physiological activity in banked blood," *Proc. Natl. Acad. Sci. USA*, 2007, 104(43): 17058-17062.

Revoltella et al., "Natural and therapy-induced anti-GM-CSF and anti-G-CSF antibodies in human serum," *Leukemia and Lymphoma*, 1997, 26:29-34.

Richter and de Belder, "Antibodies against Hydroxyethylstarch Produced in Rabbits by Immunization with a Protein-Hydroxyethylstarch Conjugate," *Int. Arch. Allergy Appl. Immun.*, 1976, 52:307-314.

Rodrigues et al., "Correlation of the acid-sensitivity of polyethylene glycol daunorubicin conjugates with their in vitro anti proliferative activity," *Bioorganic Med. Chem.*, 2006, 14: 4110-4117.

Roemisch et al., "Antithrombin: a new look at the actions of a serine protease inhibitor," *Blood Coagul Fibrinolysism*, 2002, 13(8):657-70.

Rogers et al., "Effects of polymerization on the oxygen carrying and redox properties of diaspirin cross-linked hemoglobin," *Biochim. Biophys. Acta*, 1995, 1248:135-142.

Rohrling et al., "Synthesis and testing of a novel fluorescene label for carbonyls in carbohydrates and cellulosics," *Synlett*, 2001, 5:682-684.

Römpp Chemielexikon, Thieme Verlag Stuttgart, Germany, 9th edition, 1990, vol. 9, pp. 2281-2285.

Rose, "Facile Synthesis of Homogeneous Artificial Proteins," *J. Am. Chem. Soc.*, 1994, 116:30-33.

Rosenberg et al., "Antithrombin-III," *Rev. Hematol.*, 1986, 2:351-416.

Rosenberg, "Role of heparin and heparinlike molecules in thrombosis and atherosclerosis," *Fed. Proc.*, 1985, 44:404-9.

Rotondaro et al., "Purification and Characterization of Two Recombinant Human Granulocyte Colony-Stimulating Factor Glycoforms." *Molecular Biotechnology*, 1999, 11:117-128.

Rudolph et al., "Circulation persistence and biodistribution of lyophilized liposome-encapsulated hemoglobin: An oxygen-carrying resuscitative fluid," *Crit. Care Med.*, 1994, 22:142-150.

Rudolph, "The Freeze-Dried Preservation of Liposome Encapsulated Hemoglobin: A Potential Blood Substitute," *Cryobiology*, 1988, 25:277-284.

Rush et al., "Microheterogeneity of Erythropoietin Carbohydrate Structure," *Anal. Chem.*, 1995, 67(8):1442-1452.

(56) References Cited

OTHER PUBLICATIONS

Ruttmann et al., "In vivo investigation into the effects of haemodilution with hydroxyethylstarch (200/0.5) and normal saline on coagulation," *Br. J. Anaesthesia*, 1998, 80(5):612-616.

Sadamoto et al., "Control of Bacteria Adhesion by Cell-Wall Engineering," *J. Am. Chem. Soc.*, 2004, 126:3755-3761.

Sadrzadeh et al., "The Long-Acting Parenteral Iron Chelator, Hydroxyethyl Starch-Deferoxamine, Fails to Protect Against Alcohol-Induced Liver Injury in Rats," *J. Pharmacol. Exp. Ther.*, 1997, 280(2):1038-1042.

Sakai et al., "Synthesis and Physicochemical Characterization of a Series of Hemoglobin-Based Oxygen Carriers: Objective Comparison between Cellular and Acellular Types," *Bioconj. Chem.*, 2000, 11:56-64.

Salo, et al., "Aminooxy Functionalized Oligonucleotides: Preparation, On-Support Derivitization and PostsyntheticAttachment to Polymer Support," *Bioconjugate Chem.*, 1999, 10:815-823.

Sato et al., "Disposition of a Polymeric Prodrug of Mitomycin C, Mitomycin C-Dextran Conjugate, in the Perfused Rat Liver," *J. Pharm. Sci.*, 1989, 78:11-16.

Sawaikar et al., "Products active on mosquitoes. Part VII, Synthesis and biological activity of longifolene derivatives," *Indian J. Chem.*, 1995, 34B:832-835.

Scaglione et al., "A New Model Examining Intracellular and Extracellular Activity of Amoxicillin, Azithromycin, and Clarithromycin in Infected Cells," *Chemotherapie*, 1993, 39:416-423.

Schäfer et al., "Two-year double-blind trial of a monomethoxy polyethylene glycol (mPEG) modified grass pollen extract at different dose levels," *Ann. Allergy*, 1992, 68(4):334-339.

Schlenke et al., "Construction and characterization of stably transfected BHK-21 cells with human-type sialylation characteristic," *Cytotechnology*, 1999, 30:17-25.

Schlesinger, "Alphaviruses—vectors for the expression of heterologous genes," *Trends Biotechnol.*, 1993, 11(1):18-22.

Schmoll et al. (eds.), "Summary of Basics of Oncology and Current Therapeutic Approaches," *Compendium for Internistic Oncology*, 1996, Table of Contents with English Summary.

Schneerson et al., "Preparation, characterization and immunogenicity of haemophilus influenzae type b polysaccharide-protein conjugates," *J. Exp. Med.*, 1980, 152:361-376.

Schottelius et al., "Improvement of Pharmacokinetics of Radioiodinated Tyr$^3$-Octreotide by Conjugation with Carbohydrates," *Bioconjugate Chem.*, 2002, 13:1021-1030.

Schroeter et al., "Male-specific Modification of Human CD52," *J. Biol. Chem.*, 1999, 274(42):29862-29873.

Seymour et al., "A phase 1 study of BAY 38/3441 given as a short infusion daily for five days every 3 weeks. A National Cancer Institute of Canada Clinical Trials Group Study," *Eur. J. Cancer*, 37(1):73, 2001.

Shafer et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides," *Vaccine*, 2000, 18:1273-1281.

Shah et al., "Characterization of Colony-stimulating Activity Produced by Human Monocytes and Phytohemagglutinin-stimulated Lymphocytes," *Blood*, 1977, 50(5):811-821.

Shao and Tam, "Unprotected peptides as building blocks for the synthesis of peptide dendrimers with oxime, hydrazone and thiazolidine linkages," *J. Am. Chem. Soc.*, 1995, 117(14):3893-3899.

Sharaf et al., "Studies on Aroyl- and Aryl-Hydrazide Derivatives from D-glycero-D-gulo-Heptono-1,4-Lactone," *Carb. Res.*, 1981, 91:39-48.

Shin et al., "Fmoc-Based Synthesis of Synthesis of Peptide-$^\alpha$Thioesters: Application to the Total Chemical Synthesis of a Glycoprotein by Native CHemical Ligation," *J. Am. Chem. Soc.*, 1999, 121:11684-11689.

Shirafuji et al., "A new bioassay for human granulocyte colony-stimulating factor (hG-CSF) using murine myeloblastic NFS-60 cells as targets and estimation of its levels in sera from normal healthy persons and patients with infectious and hematological disorders," *Exp. Hematol.*, 1989, 17:116-119.

Shu, "Somogyi Micro Copper Method," *Meth. Carb. Chem.*, 1962, 1:383-388.

Simmons G., et al; Potent inhibition of HIV-1 infectivity in macrophages and lymphocytes by a novel CCr5 antagonist; *Science*, 1997, 276:276-279.

Skopp et al., "Fingerprinting of proteins cleaved in solution by cyanogen bromide," *Appl. Theoret. Electrophoresis*, 1989, 1:61-64.

Skwarczynski et al., "Paclitaxel Prodrugs Toward Smarter Delivery of Anticancer Agents," *J. Med. Chem.*, 2006, 49 (25):7253-7269.

Snyder et al., "HbXL99α: A hemoglobin derivative that is cross-linked between the α subunits is useful as a blood substitute," *Proc. Natl. Acad. Sci. USA*, 1987, 84:7280-4.

Sommermeyer et al., "Hydroxyethylstarch for Clinical Application: Physical and Chemical Characterisation," *Krankenhauspharmazie*, 1987, 8:271-278.

Somogyi, "Determination of reducing sugars," *Meth. Carb. Chem.*, 1962, 1:384-386.

Song et al., "Toxicity and Antitumor Activity of the Conjugate of Mitomycin C with Carboxymethyl-chitin," *Arch. Pract. Pharm.*, 1993, 53(3):141-147.

Souza et al., "Recombinant human granulocyte colony-stimulating factor: effects on normal and leukemic myeloid cells," *Science*, 1986, 232:61-65.

Soyez et al., "Biological evaluation of mitomycin C bound to a biodegradable polymeric carrier," *J. Controlled Release*, 1997, 47:71-80.

Spellman et al., "Carbohydrate structures of human tissue plasminogen activator expressed in Chinese hamster ovary cells," *J. Biol. Chem.*, 1989, 264:14100-11.

Spivak and Hogans, "The In Vivo Metabolism of Recombinant Human Erythropoietin in the Rat," *Blood*, 1989, 73:90-99.

Staab, "New Methods in Preparatory Organic Chemistry IV. Synthesis using heterocyclic amides (azolides)," *Angew. Chemie*, 1962, 74(12):407-22.

Staros, "*N*-Hydroxysulfosuccinimide Active Esters: Bis(*N*-hydroxysulfosuccinimide) Esters of Two Dicarboxylic Acids Are Hydrophilic, Membrane-Impermeant, Protein Cross-Linkers," *Biochemistry*, 1982, 21:3950-3955.

Stetsenko et al, "Efficient conjugation of peptides to oligonucleotides by native ligation," *J. Org. Chem.*, 2000, 65(16):4900-4908.

Stewart et.al., "Identification of the mechanism responsible for the increased fibrin specificity of TNK-tissue plasminogen activator relative to tissue plasminogen activator," *J. Biol. Chem.*, 2000, 275(14):10112-10120.

Stien et al., "Development and characterisation of novel human multidrug resistant mammary carcinoma lines in vitro and in vivo," *Int. J. Cancer*, 1997, 72:885-891.

Stille et al., "Atherosclerosis as Consequence of Chronic Infection by *Chlamydia pneumoniae*," *Herz*, 1998, 23:185-192 (w/English summary).

Sunamoto and Iwamoto, "Protein-Coated and Polysaccharide-Coated Liposomes as Drug Carriers," *CRC Critical Review in Therapeutic Drug Carrier Systems*, 1986, 2:117-136.

Svenson and Lindberg, "Coupling of Acid Labile *Salmonella* Specific Oligosaccharides to Macromolecular Carriers," *J. Immunolog. Meth.*, 1979, 25:323-335.

Svenson, "Immunochemistry of *Salmonella* O-Antigens: Preparation of an Octasaccharide-Bovine Serum Albumin Immunogen Representative of *Salmonella* Serogroup B O-Antigen and Characterization of the Antibody Response," *J. Immunol.*, 1978, 120(5): 1750-1757.

Sytkowski et al., "An Erythropoietin Fusion Protein Comprised of Identical Repeating Domains Exhibits Enhanced Biological Properties," *J. Biol. Chem.*, 1999, 274(35):24773-24778.

Sytkowski et al., "Human erythropoietin dimers with markedly enhanced in vivo activity," *Proc. Natl. Acad. Sci. USA*, 1998, 95(3):1184-1188.

Takeuchi and Kobata, "Structures and functional roles of the sugar chains of human erythropoietins," *Glycobiology*, 1991, 1(4):337-346.

(56) References Cited

OTHER PUBLICATIONS

Takeuchi et al., "Relationship between sugar chain structure and biological activity of recombinant human erythropoietin produced in Chinese hamster ovary cells," *Proc. Natl. Acad. Sci. USA*, 1989, 86:7819-7822.

Tam et al., "Peptide Synthesis Using Unprotected Peptides Through Orthogonal Coupling Methods," *Proc. Natl. Acad. Sci. USA*, 1995, 92: 12485-12489.

Tam et al., "Soluble Dextran-Hemoglobin Complex as a Potential Blood Substitute," *Proc. Natl. Acad. Sci. USA*, 1976, 73(6):2128-2131.

Tanaka et al., "Pharmacokinetics of recombinant human granulocyte colony-stimulating factor conjugated to polyethylene glycol in rats," *Cancer Research*, 1991, 51:3710-3714.

Tebbutt, "Technology evaluation: transgenic alpha-1-antitrypsin (AAT), PPL therapeutics," *Curr. Opin. Mol. Ther.*, 2000, 2(2):199-204.

Thermo Scientific Pierce "Crosslinking Technical Handbook," 48pgs. (2009).

Thim et al., "Amino acid sequence and posttranslational modifications of human factor VIIa from plasma and transfected baby hamster kidney cells," *Biochemistry*, 1988, 27:7785-7793.

Thomas et al., "Measuring blood volume with fluorescent-labeled hydroxyethyl starch," *Crit. Care Med.*, 2000, 28(3):627-631.

Thomas, "Carbohydrate Binding Sites," *Meth. Enzymol.*, 1977, 46:362-368.

Thorpe et al., "Blockade of the galactose-binding sites of ricin by its linkage to antibody," *Eur. J. Biochem.*, 1984, 140:63-71.

Tomasik et al., "Chemical Modification of Starch," *Adv. Carbohydrate Chem. Biochem.*, 2004, 59:179-403.

Toole et al., "Molecular cloning of a cDNA encoding human antihaemophilic factor," *Nature*, 1984, 312(5992):342-7.

Toyama et al., "Surface design of SPR-based immunosensor for the effective binding of antigen or mixed antibody in the evanescent field using mixed polymer matrix," *Sensors and Actuators B*, 1998, 52:65-71.

Travis and Salvesen, "Human plasma proteinase inhibitors," *Ann. Rev. Biochem.*, 1983, 52:655-709.

Ubeda and Habener, "The large subunit of the DNA replication complex C (DSEB/RF-C140) cleaved and inactivated by caspase-3 (CPP32/YAMA) during Fas-induced apoptosis," *J. Biol. Chem.*, 1997, 272(31):19562-8.

Van Patten et al., "Oxidation of Methionine Residues in Antithrombin," *J. Biol. Chem.*, 1999, 274(15):10268-10276.

Vasey et al., "Phase I Clinical and Pharmacokinetic Study of PKI [N-(2-Hydroxypropyl) methacrylamide Copolymer Doxorubicin]: First Member of a New Class of Chemotherapeutic Agents-Drug-Polymer Conjugates," *Clin. Cancer Res.*, 1999, 5:83-94.

Velasco et al., "Synthetic Peptides Representing T-Cell Epitopes Act as Carriers in Pneumococcal Polysaccharide Conjugate Vaccines," *Infection and Immunity*, 1995, 63(3):961-968.

Veronese et al., "Surface Modification of Proteins. Activation of Monomethoxy-Polyethylene Glycols by Phenylchloroformates and Modification of Ribonuclease and Superoxide Dismutase," *Appl. Biochem. Biotech.*, 1985, 11:141-152.

Veronese, "Peptide and protein PEGylation: a review of problems and solutions," *Biomaterials*, 2001, 22(5):405-417.

Vilaseca et al., "Protein conjugates of defined structure: Synthesis and use of a new carrier molecule," *Bioconjugate Chemistry*, 1993, 4(6):515-520.

Wadhwa et al., "Immunogenicity of Granulocyte-Macrophage Colony-Stimulating Factor (GM-CSF) products in patients undergoing combination therapy with GM-CSF," *Clin. Cancer Res.*, 1999, 5:1351-1361.

Waltzinger et al., "Pharmacokinetics and Tolerability of a New Hydroxyethyl Starch (HES) Specification [HE (130/0.4)] after Single-Dose Infusion of 6% or 10% Solutions in Healthy Volunteers," *Pharmacokinetics*, 16(2):151-160 (1998).

Wasley et al., "The Importance of N- and O-Linked Oligosaccharides for the Biosynthesis and In Vitro and In Vivo Biologic Activities of Erythropoietin," *Blood*, 1991, 77(12):2624-2632.

Watanabe et al., "A facile synthesis of carboxylic thiol esters from carboxylic acids and thiols," *Chem. Lett.*, 1976, 741-742.

Webb II and Kaneko, "Synthesis of 1-(Aminooxy)-4-[(3-nitro-2-pyridyl)dithio]butane and 1-(Aminooxy)-4-[(3-nitro-2-pyridyl)dithio]but-2-ene, Novel Heterobifunctional Cross-Linking Reagents," *Bioconjugate Chem.*, 1990, 1:96-99.

Weidler et al., "Pharmakokinetische Merkmale als Kriterien für den klinischen Einsatz von Hydroxyethylstärke," *Arzneim.-Forsch./Drug Res.*, 1991, 41:494-498 (w/English summary).

Weisshaar et al., "NMR investigations of the N-linked oligosaccharides at individual glycosylation sites of human lutropin," *Eur. J. Biochem.*, 1991, 195:257-268.

Whitesides et al., "Rates of Thiol-Disulfide Interchange Reactions between Mono- and Dithiols and Ellman's Reagent," *J. Org. Chem.*, 1977, 42(2):332-338.

Wilchek, M., Bayer, E.A., Labeling "Glycoconjugates with Hydrazide Reagents," *Meth. Enzymol.*, 1987, 138:429-442.

Wong et al., "Analysis of carbohydrate-protein interactions with synthetic N-linked neoglycoconjugate probes," *Biochem. J.*, 1993, 296:817-825.

Wong et al., "Synthetic glycosylation of proteins using N(β-saccharide) iodoacetamides: applications in site-specific glycosylation and solid-phase enzymic oligosaccharide synthesis," *Biochem. J.*, 1994, 300:843-850.

Wong, Chemical Dictionary Entry Concerning Carbohydrates, *Chemistry of Protein Conjugation and Cross-Linking*, 1993, CRCS, Inc., 6 pages including English-language Abstract.

Wong, *Chemistry of protein conjugation and cross-linking*, 1993, CRCS, Inc. (TOC only).

Wright et al., "High level expression of active human alpha-1-antitrypsin in the milk of transgenic sheep," *Biotechnology NY*, 1991, 9:830-4.

Xue and Wong; "Preparation of Conjugated Hemoglobins," *Meth. Enzymol.*, 1994, 231:308-322.

Yalpani et al., "Selective Chemical Modifications of Dextran," *J. Polymer Science: Polymer Chemistry Edition*, 1985, 23:1395-1405.

Yamaguchi et al., "Effects of site-directed removal of N-glycosylation sites in human erythropoietin on its production and biological properties," *J. Biol. Chem.*, 1991, 266(30):20434-20439.

Yang et al., "Functional changes of carboxymethyl potato starch by conjugation with amino acids," *Biosci. Biotechnol. Biochem.*, 1995, 59(12):2203-2206.

Yoshida, "Glycamine Formation via Reductive Amination of Oligosaccharides with Benzylamine," *Meth. Enzymol.*, 1994, 247:55-64.

Yoshitake et al., "Nucleotide sequence of the gene for human factor IX (antihemophilic factor B)," *Biochemistry*, 1985, 24:3736-3750.

Zalipsky, "Functionalized Poly(ethylene glycol) for Preparation of Biologically Relevant Conjugates," *Bioconjugate Chem.*, 1995, 6:150-165.

Zara et al., "A Carbohydrate-Directed Heterobifunctional Cross-Linking Reagent for the Synthesis of Immunoconjugates," *Anal. Biochem.*, 1991, 194:156-162.

Zettlmeissl et al., "Characterization of Recombinant Human Antithrombin III Synthesized in Chinese Hamster Ovary Cells," *J. Biol. Chem.*, 1989, 264 (35):21153-21159.

Zhang, L. et al. "Thiazolidine formation as a general and site-specific conjugation method . . ." *Anal. Biochem.* (1996) vol. 233, pp. 87-93.

Zhou et al., "Application of capillary electrophoresis, liquid chromatography, electrospray-mass spectrometry and matrix-assisted laserdesorption/ionization—time of flight—mass spectrometry to the characterization of recombinant human erythropoietin,"*Electrophoresis*, 1998, 19(13):2348-2355.

Zou et al., "Allylmalonamide as a bivalent linker: Synthesis of biantennary $Gm_3$-saccharide-Keyhole limpet hemocyanin glycoconjugate and the immune response in mice," *Glycoconj. J.*, 1999, 16:507-515.

Zucali and Sulkowski, "Purification of human urinary erythropoietin on controlled-pore glass and silicic acid," *Exp. Hematol.*, 1985, 13(3):833-837.

A  B   C   D   E   F   G   H   I   J   K

A B C D E F G H I J

A B C D     E F G

A  B  C    D    E  F  G    H    I    J    K

Lane      A   B   C   D   E   F   G   H   K

Lane            A   B   C     D   E

X  A  B  C  D  E  F  G

Lane:            A    B    C    D

X A B a) IFN-alpha starting material b) IFN-alpha-HES

Lane:     A   B   C   D

Lane: 1 2 3 4 5

CONJUGATES OF HYDROXYALKYL STARCH AND A PROTEIN

CROSS-REFERENCE TO RELATED APPLICATIONS

This application is a divisional of U.S. Ser. No. 11/518,558, filed Sep. 8, 2006, now U.S. Pat. No. 8,017,739, which is a continuation-in-part and claims benefit under 35 U.S.C. §120 of International Application No. PCT/EP2005/002637 having an International Filing Date of Mar. 11, 2005, which published in English as International Publication Number WO 2005/092390, and which claims the benefit of priority of U.S. Provisional Application Ser. No. 60/552,174, filed on Mar. 11, 2004, European Application Serial No. 04005849.7, filed on Mar. 11, 2004, Argentinian Application Serial No. P20040102853, filed on Aug. 9, 2004, and International Application No. PCT/EP2004/008821, filed on Aug. 6, 2004.

TECHNICAL FIELD

The present invention relates to conjugates of hydroxyalkyl starch and a protein, wherein the conjugates are formed by a covalent linkage between the hydroxyalkyl starch or a derivative of the hydroxyalkyl starch and the protein. The present invention also relates to the method of producing these conjugates and the use of these conjugates.

BACKGROUND

It is generally accepted that the stability of proteins can be improved and the immune response against these proteins is reduced when these proteins are coupled to polymeric molecules. WO 94/28024 discloses that physiologically active proteins modified with polyethylene glycol (PEG) exhibit reduced immunogenicity and antigenicity and circulate in the bloodstream considerably longer than unconjugated proteins, i.e. have a reduced clearance rate.

WO 02/09766 discloses, among others, biocompatible protein-polymer compounds which are produced by conjugation of biologically active protein with a biocompatible polymer derivative. The biocompatible polymers used are highly reactive branched polymers, and the resulting conjugates contain a long linker between polymer derivative and protein. As biocompatible polymers, polymers of formula (P—OCH$_2$CO—NH—CHR—CO—)$_n$-L-Q$_k$-A are described, wherein P and Q are polymeric residues and k may be 1 or 0. For P and Q, polyethylene glycol, polypropylene glycol, polyoxyethylene, polytrimethylene glycol, polylactic acid and its derivatives, polyacrylic acid and its derivatives, polyamino acid, polyvinyl alcohol, polyurethane, polyphosphazene, poly(L-lysine), polyalkylene oxide, polyacrylamide and water soluble polymers such as dextran or polysaccharide are mentioned. As proteins, among others, alpha, beta and gamma interferons, blood factors, cytokines such as interleukins, G-CSF, GM-CSF are mentioned. In the examples of WO 02/09766, only mono-, di- and tri-polyethyleneglycol derivatives are disclosed which are coupled exclusively to interferon and epidermal growth factor, and human growth hormone.

WO 94/01483 discloses biocompatible polymer conjugates which are formed by covalently binding a biologically inactive polymer or polymer derivative to a pharmaceutically pure, synthetic hydrophilic polymer via specific types of chemical bonds. As naturally occurring polymers and derivatives thereof, polysaccharides such as hyaluronic acid, proteoglycans such as chondroitin sulfates A, B and C, chitin, heparin, heparin sulfate, dextrans such as cyclodextran, hydroxyethyl cellulose, cellulose ether and starch, lipids such as triglycerides and phospholipids are disclosed. As synthetic polymers, among others, polyethylene and derivatives thereof are described having an average molecular weight of from about 100 to about 100,000. As proteins linked to the polymer or the polymer derivative, cytokines and growth factors are described, including interferons, tumor necrosis factors, interleukins, colony stimulating factors, growth factors such as osteogenic factor extract, epidermal growth factor, transforming growth factor, platelet derived growth factor, acidic fibroblast growth factor and others are disclosed. In all working examples of WO 94/01483, polyethylene glycols derivatives are used as polymer.

WO 96/11953 discloses N-terminally chemically modified protein compounds and methods of their production. Specifically, G-CSF compositions are described which result from coupling a water soluble polymer to the N terminus of G-CSF. In the context of WO 96/11953, also consensus interferone N-terminally coupled to water soluble polymers are disclosed. While a wide variety of water polymers are listed in WO 96/11953 (e.g. copolymers of ethylene glycol and propylene glycol, carboxymethyl cellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, polypropylene glycol homopolymers, polypropylene oxide/ethylene oxide copolymers or polyoxyethylated polyols), only PEGylated G-CSF or consensus IFN compositions are described in the working examples of WO 96/11953.

WO 97/30148 relates to polypeptide conjugates with reduced allergenicity comprising a polymeric carrier molecule having two or more polypeptide molecules coupled thereto. These conjugates are preferably part of compositions used in the personal care market. Said conjugates are produced by activating a polymeric carrier molecule, reacting two or more polypeptide molecules with the activated polymeric carrier molecule and blocking of residual active groups on the conjugate. As polymeric carrier molecule, a vast variety is listed in WO 97/30148, including such different groups of compound like natural or synthetic homopolymers such as polyols, polyamines, polycarboxylic acids and heteropolymers comprising at least two different attachment groups. Examples are given, which comprise star PEGs, branched PEGs, polyvinyl alcohols, polycarboxylates, polyvinylpyrrolidones and poly-D,L-amino acids. Among others, also dextrans such as carboxymethyl dextran, celluloses such as hydroxyethyl cellulose or hydroxypropyl cellulose, hydrolysates of chitosan, starches such as hydroxyethyl starches or hydroxypropyl starches, glycogen, agarose, guar gum, inulin, pullulan, xanthan gum, carrageenin, pectin, alginic acid etc. are disclosed. As polypeptides, only some enzymes are explicitly disclosed.

Baldwin, J. E. et al., *Tetrahedron*, vol. 27 (1981), pp. 1723-1726 describe the chemical modification of dextran and hydroxyethyl starch to give aldehyde substituted polymers which are allowed to react with hemoglobin to give soluble polymer-bound hemoglobins. These were shown to be capable of binding oxygen, but heart perfusion experiments clearly indicated that the polymer-bound hemoglobins were not suitable for use as blood substitutes.

WO 99/49897 describes conjugates of hemoglobin formed by reacting polysaccharides such as dextrane or hydroxyethyl starch with amino groups of the hemoglobin. As functional groups of the polysaccharide, aldehyde groups produced by oxidative saccharide ring-opening are used. As preferred reducing agent used, borane dimethylamine is disclosed. Moreover, WO 99/49897 is exclusively limited to hemoglobin.

WO 03/074087 relates to a method of coupling proteins to a starch-derived modified polysaccharide. The binding action between the protein and the polysaccharide, hydroxyalkyl starch, is a covalent linkage which is formed between the terminal aldehyde group or a functional group resulting from chemical modification of said terminal aldehyde group of the hydroxy alkyl starch molecule, and a functional group of the protein. As reactive group of the protein, amino groups, thio groups and carboxyl groups are disclosed, and aldehyde groups of the protein are not mentioned. Moreover, while a vast variety of possibilities of different linkages is given in the form of many lists, including different functional groups, theoretically suitable different linker molecules, and different chemical procedures, the working examples describe only two alternatives: first, an oxidized hydroxyethyl starch is used and coupled directly to proteins using ethyldimethylaminopropyl carbodiimide (EDC) activation, or a non-oxidized hydroxyethyl starch is used and coupled directly to a protein forming a Schiff's base which is subsequently reduced to the respective amine. Thus, the working examples of WO 03/074087 neither disclose a single conjugate coupled via a thio group or a carboxy group of the protein, nor describe a conjugate comprising hydroxyethyl starch, the protein, and one or more linker molecules.

Nearly the complete literature regarding techniques of coupling a polymer to a protein describes PEGylation methods and PEGylated proteins (e.g. interferons alpha, interferons beta). Despite the progress of coupling methods and use of monofunctional PEG-molecules, a general disadvantage of PEGylated drugs is that the metabolization pathway of PEG as a non-natural polymer is not known in detail.

Some of the patents describe the modification of interferon by substitution of amino acids, increased glycosylation or formation of multimers. These methods require high technological efforts (recombinant techniques) and could result in new entities which are markedly different from the natural proteins (e.g. interferon) and could exhibit different properties.

Moreover, it is taught in the art describe to form, e.g., of complexes between IFN-beta and polysaccharides via metal complexation. However, complexes are not as stable as covalent conjugates and contain metal ions (e.g. $Zn^{2+}$), which might have undesired side effects.

SUMMARY

Thus, it was an object of the present invention to overcome the above mentioned drawbacks of these conjugation techniques and to provide interferon beta conjugates based on a well defined, biodegradable, water soluble polymer, which is covalently coupled to the protein.

It was another object of the present invention to overcome the above mentioned drawbacks of these conjugation techniques and to provide interferon alpha conjugates based on a well defined, biodegradable, water soluble polymer, which is covalently coupled to the protein.

It was yet another object of the present invention to overcome the above mentioned drawbacks of these conjugation techniques and to provide AT III conjugates based on a well defined, biodegradable, water soluble polymer, which is covalently coupled to the protein.

It was still another object of the present invention to overcome the above mentioned drawbacks of these conjugation techniques and to provide GM-CSF conjugates based on a well defined, biodegradable, water soluble polymer, which is covalently coupled to the protein.

It was yet a further object of the present invention to overcome the above mentioned drawbacks of these conjugation techniques and to provide A1AT and/or tPA and/or APC and/or and/or Factor VII and/or Factor VIII and/or factor IX conjugates based on a well defined, biodegradable, water soluble polymer, which is covalently coupled to the protein.

It is a further object of the present invention to provide methods of producing these conjugates.

In one aspect, this document features a method for preparing a conjugate comprising a protein and a polymer or a derivative thereof, wherein the polymer is a hydroxyalkyl starch (HAS). The method can include reacting at least one functional group A of the polymer or the derivative thereof with at least one functional group Z of the protein and thereby forming a covalent linkage, wherein Z is selected from the group consisting of an amino group, a thiol group, an aldehyde group and a keto group, and wherein, when Z is an aldehyde group or a keto group, A comprises an amino group forming the linkage with Z, and the protein is selected from the group consisting of IFN beta, GM-CSF, APC, tPA, A1AT, AT III, factor VII, factor VIII, and factor IX, wherein, when Z is an amino group, A is selected from the group consisting of a reactive carboxy group and an aldehyde group, a keto group or a hemiacetal group, and wherein the protein is selected from the group consisting of IFN alpha, IFN beta, GM-CSF, APC, tPA, A1AT, AT III, factor VII, factor VIII, and factor IX, wherein, when A is an aldehyde group, a keto group or a hemiacetal group, the method further comprises introducing A in the polymer to give a polymer derivative by reacting the polymer with an at least bifunctional compound, one functional group of which reacts with the polymer and at least one other functional group of which is an aldehyde group, a keto group or a hemiacetal group, or is a functional group which is further chemically modified to give an aldehyde group, a keto group or a hemiacetal group, or by oxidizing the polymer to give at least one aldehyde group, in particular at least two aldehyde groups, or wherein, when A is a reactive carboxy group, the method further comprises introducing A in the polymer to give a polymer derivative by selectively oxidizing the polymer at its reducing end and activating the resulting carboxy group, or by reacting the polymer at its non-oxidized reducing end with a carbonic diester, or wherein, when Z is a thiol group, the protein is selected from the group consisting of IFN alpha, IFN beta, tPA, A1AT, APC, factor VII and factor IX, and A comprises a maleimido group or a halogenacetyl group forming the linkage with Z.

The hydroxyalkyl starch can be hydroxyethyl starch. The hydroxyethyl starch can have a molecular weight of from 2 to 200 kD, preferably of from 4 to 130 kD, more preferably of from 4 to 70 kD. Z can be an aldehyde group or a keto group and the protein can be selected from the group consisting of IFN beta, GM-CSF, APC, tPA, A1AT, AT III, factor VII, factor VIII, and factor IX. The aldehyde group or the keto group can be located in a carbohydrate side chain of the protein and/or at the N-terminal group of the protein.

The method can further comprise oxidizing the carbohydrate side chain of the protein and/or oxidizing the N-terminal group of the protein to give the aldehyde group or keto group.

The oxidation reaction can be carried out enzymatically or using a periodate, in each case, if necessary, after having removed a terminal sialic acid. The method can further comprise reacting the polymer at its non-oxidized reducing end with an at least bifunctional linking compound comprising a functional group capable of reacting with the non-oxidized reducing end of the polymer and a group A, prior to the reaction of the polymer derivative comprising A and the protein comprising Z. A can be an aminooxy group or a hydrazido group. The at least bifunctional linking compound can be a homobifunctional compound. The homobifunctional compound can comprise two aminooxy groups. The homobifunctional compound can be O-[2-(2-aminooxy-ethoxy)-ethyl]hydroxyl amine. The reaction of the polymer with the at least bifunctional linking compound can be carried out in an aqueous medium. The reaction of the polymer with the at least bifunctional linking compound can lead to an oxime linkage and/or an oxyamino linkage. Z can be an amino group and the protein is selected from the group consisting of IFN alpha, IFN beta, GM-CSF, APC, tPA, A1AT, AT III, factor VII, factor VIII, and factor IX.

The method can further comprise selectively oxidizing the polymer at its reducing end and reacting the oxidized polymer with N,N'-disuccinimidyl carbonate at its oxidized reducing end to give a polymer derivative comprising the reactive carboxy group A. The method can further comprise reacting at least one hydroxy group of the polymer whose reducing end is not oxidized, with a carbonic diester to give the reactive carboxy group A. The carbonic diester can be a symmetrical diester. The alcohol component of the ester can be selected from the group consisting of N-hydroxy succinimide, sulfonated N-hydroxy succinimide, N-hydroxy benzotriazole, and nitro- and halogen-substituted phenols. The halogen-substituted phenol can be selected from the group consisting of nitrophenol, dinitrophenol, trichlorophenol, trifluorophenol, pentachlorophenol, and pentafluorophenol. The reaction of the at least one hydroxy group of the polymer whose reducing end is not oxidized, with the carbonic diester to give a reactive ester group A can be carried out in an anhydrous aprotic polar solvent (e.g., dimethyl acetamide, dimethyl formamide or a mixture thereof).

A can be an aldehyde group, a keto group or a hemiacetal group, and the method can further comprise reacting the polymer with a functional group M of an at least bifunctional compound to give a polymer derivative, the at least bifunctional compound further comprising at least one other functional group Q which is the aldehyde group, keto group or hemiacetal group A. M can comprise an amino group.

A can be an aldehyde group, keto group or hemiacetal group, and the method can further comprise reacting the polymer with a functional group M of an at least bifunctional compound to give a polymer derivative, the at least bifunctional compound further comprising at least one other functional group Q which is not an aldehyde group, keto group or hemiacetal group, and the method further comprising reacting the functional group Q with at least one suitable compound to give the polymer derivative comprising the aldehyde group, keto group or hemiacetal group A. M and Q can comprise an amino group. The at least one suitable compound which is reacted with the functional group Q can comprise a carboxy group and an aldehyde group, keto group or hemiacetal group. The at least one suitable compound which is reacted with the functional group Q can be formylbenzoic acid or 4-(4-formyl-3,5-dimethoxyphenoxy)butyric acid. M can comprise an amino group and Q can comprise a beta hydroxy amino group. The polymer can be reacted at its oxidized reducing end with a functional group M of an at least bifunctional compound.

The method can further comprise oxidizing the beta hydroxyamino group to give the aldehyde group. The oxidation reaction can be carried out using a periodate.

The polymer can be subjected to a ring-opening oxidation reaction using a periodate to give a polymer derivative having at least one aldehyde group A, in particular at least two aldehyde groups A. The reaction of the polymer or the polymer derivative with the protein can be a reductive amination. The reductive amination can be carried out in the presence of NaCNBH$_3$. The reductive amination can be carried out at a pH of 7 or less (e.g., a pH of 6 or less). The reductive amination can be carried out at a temperature of from 0 to 25° C. The reductive amination can be carried out in an aqueous medium.

Z can be a thiol group and the protein can be selected from the group consisting of IFN alpha, IFN beta, tPA, A1AT, APC, factor VII, and factor IX. A can comprise a halogenacetyl group, and the method can further comprise reacting the polymer at its optionally oxidized reducing end with an at least bifunctional compound having at least two functional groups each comprising an amino group to give a polymer derivative having at least one functional group comprising an amino group, the method further comprising reacting the polymer derivative with a monohalogen-substituted acetic acid and/or a reactive monohalogen-substituted acetic acid derivative. The halogen can be Br or I. The at least bifunctional compound can be a diaminoalkane having from 2 to 10 carbon atoms. The at least bifunctional compound can be a diaminopolyethylene glycol having from 1 to 5 alkylene units. The polymer can be reacted with the at least bifunctional compound at its oxidized reducing end. The polymer derivative comprising the halogenacetyl group can be reacted with the protein in the presence of a solvent comprising a mixture of dimethyl formamide and water.

A can comprise a maleimido group, and the method can further comprise reacting the polymer at its optionally oxidized reducing end with an at least bifunctional compound comprising a functional group U capable of reacting with the optionally oxidized reducing end, the at least bifunctional compound further comprising a functional group W capable of being chemically modified to give a maleimido group, the method further comprising chemically modifying the functional group W to give a maleimido group. U can comprise an amino group. W can comprise an amino group. The polymer derivative comprising W can be reacted with an at least bifunctional compound comprising a functional group capable of being reacted with W and further comprising a maleimido group. The at least bifunctional compound can be N-(alpha-maleimidoacetoxy)succinimide ester.

In another aspect, this document features a conjugate as obtainable by a method described herein. A can be a reactive carboxy group, and wherein A was introduced in the polymer whose reducing end was not oxidized, by reacting at least one hydroxy group of the polymer with a carbonic diester, and wherein, the conjugate comprising one polymer molecule and at least one protein molecule, in particular of from 1 to 10 protein molecules linked to the polymer via amide linkages, and wherein the protein is selected from the group consisting of IFN alpha, IFN beta, GM-CSF, APC, tPA, A1AT, AT III, factor VII, factor VIII, and factor IX.

In another aspect, this document features a conjugate comprising a protein and a polymer or a derivative thereof, wherein the polymer is a hydroxyalkyl starch (HAS) and the protein is selected from the group consisting of IFN beta, GM-CSF, APC, tPA, A1AT, AT III, factor VII, factor VIII, and factor IX, the conjugate having a structure according to the formula

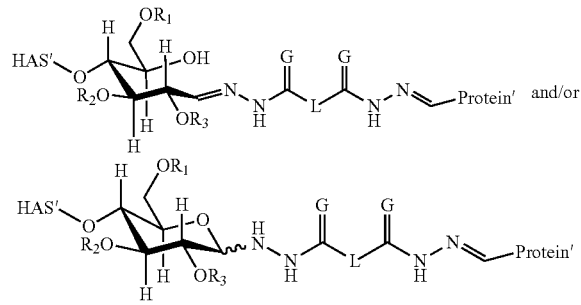

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, wherein G is selected from the group consisting of O and S, preferably O, and wherein L is an optionally suitably substituted, linear, branched and/or cyclic hydrocarbon residue, optionally comprising at least one heteroatom, preferably an alkyl, aryl, aralkyl, heteroaryl, heteroaralkyl residue having from 2 to 60 carbon atoms. -L- can be $-(CH_2)_n-$ with n=2, 3, 4, 5, 6, 7, 8, 9, 10, preferably 2, 3, 4, 5, 6, more preferably 2, 3, 4, and especially preferably 4.

This document also features a conjugate comprising a protein and a polymer or a derivative thereof, wherein the polymer is a hydroxyalkyl starch (HAS) and the protein is selected from the group consisting of IFN beta, GM-CSF, APC, tPA, A1AT, AT III, factor VII, factor VIII, and factor IX, the conjugate having a structure according to the formula

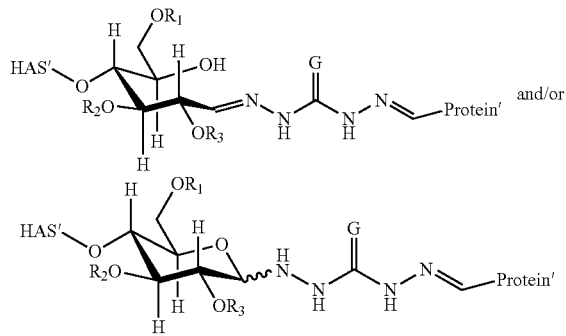

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein G is selected from the group consisting of O and S, preferably O.

In another aspect, this document features a conjugate comprising a protein and a polymer or a derivative thereof, wherein the polymer is a hydroxyalkyl starch (HAS) and the protein is selected from the group consisting of IFN beta, GM-CSF, APC, tPA, A1AT, AT III, factor VII, factor VIII, and factor IX, the conjugate having a structure according to the formula

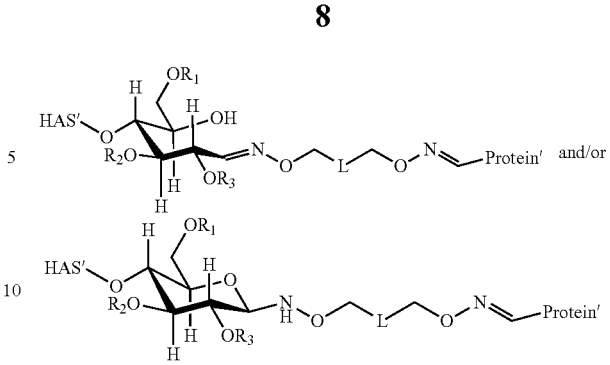

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein L is an optionally suitably substituted, linear, branched and/or or cyclic hydrocarbon residue, optionally comprising at least one heteroatom, preferably an alkyl, aryl, aralkyl, heteroaryl, heteroaralkyl residue having from 2 to 60 carbon atoms. -L- can be $-[(CR_aR_b)_mG]_n[CR_cR_d]_o-$, wherein $R_a$, $R_b$, $R_c$, and $R_d$ are independently hydrogen, alkyl, aryl, preferably hydrogen, wherein G is selected from the group consisting of O and S, preferably O, and wherein m is 1, 2, 3 or 4, wherein the residues $R_a$ and $R_b$ may be the same or different in the m groups $CR_aR_b$; n is 0 to 20, preferably 0 to 10, more preferably 1, 2, 3, 4, 5, most preferably 1 or 2; o is 0 to 20, preferably 0 to 10, more preferably 1, 2, 3, 4, 5, most preferably 1 or 2, wherein the residues $R_c$ and $R_d$ may be the same or different in the o groups $CR_cR_d$; and wherein the integers for n and o are selected in a way that in the formula above, no peroxy moiety results, such as n and o are not 0 at the same time. $R_a$, $R_b$, $R_c$, and $R_d$ can be hydrogen, m=2, n=1, and o=2.

In still another aspect, this document features a conjugate comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, the conjugate having a structure according to the formula

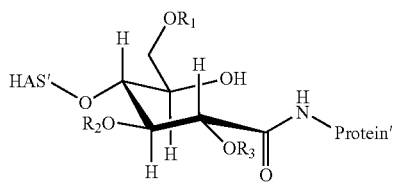

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group.

In another aspect, this document features a conjugate comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, having a structure according to the formula

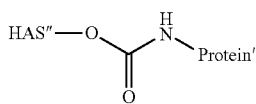

wherein the linkage —O—(C=O)— was formed by a reaction of a carboxy group or a reactive carboxy group with a hydroxy group of the HAS molecule, and wherein HAS" refers to the HAS molecule without the hydroxy group.

In another aspect, this document features a conjugate, comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, the conjugate having a structure according to the formula

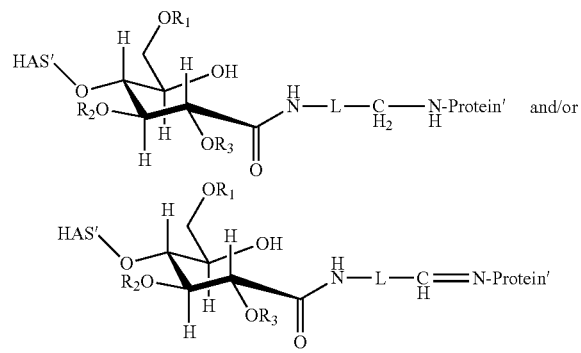

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein L is an optionally substituted, linear, branched and/or or cyclic hydrocarbon residue, optionally comprising at least one heteroatom, having from 1 to 60 carbon atoms preferably from 1 to 40, more preferably from 1 to 20, more preferably from 1 to 10, more preferably from 1 to 6 more preferably from 1 to 2 carbon atoms and especially preferably 1 carbon atom, L being in particular $CH_2$.

In another aspect, this document features a conjugate, comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, the conjugate having a structure according to the formula

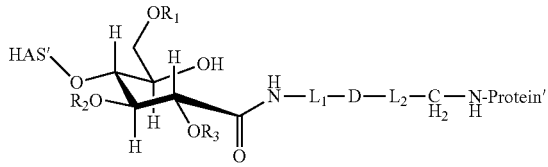

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein $L_1$ and $L_2$ are independently an optionally substituted, linear, branched and/or or cyclic hydrocarbon residue, optionally comprising at least one heteroatom, comprising an alkyl, aryl, aralkyl heteroalkyl, and/or or heteroaralkyl moiety, the residue having from 1 to 60 preferably from 1 to 40, more preferably from 1 to 20, more preferably from 1 to 10 carbon atoms, and wherein D is a linkage, preferably a covalent linkage which was formed by a suitable functional group $F_2$ linked to $L_1$ and a suitable functional group $F_3$ linked to $L_2$ and wherein $F_3$ is capable of forming a chemical linkage with $F_2$. $L_1$ can be —$(CH_2)_n$— with n=2, 3, 4, 5, 6, 7, 8, 9, 10, preferably 2, 3, 4, 5, 6, more preferably 2, 3, 4, and especially preferably 4. $L_2$ can comprise an optionally suitably substituted aryl moiety, preferably an aryl moiety containing 6 carbon atoms, $L_2$ being especially preferably $C_6H_4$. $F_2$ and $F_3$ can be independently selected from the group consisting of a C—C-double bond or a C—C-triple bond or an aromatic C—C-bond;

a thio group or a hydroxy group;

an alkyl sulfonic acid hydrazide, or an aryl sulfonic acid hydrazide;

a 1,2-diol;

a 1,2 amino-thioalcohol;

an azide;

a 1,2-aminoalcohol;

an amino group —$NH_2$ or a derivative of an amino group comprising the structure unit —NH— such as aminoalkyl groups, aminoaryl group, aminoaralkyl groups, or alkarlyamino groups;

a hydroxylamino group —O—$NH_2$, or a derivative of a hydroxylamino group comprising the structure unit —O—NH—, such as hydroxylalkylamino groups, hydroxylarylamino groups, hydroxylaralkylamino groups, or hydroxalalkarylamino groups;

an alkoxyamino group, an aryloxyamino group, an aralkyloxyamino group, or an alkaryloxyamino group, each comprising the structure unit —NH—O—;

a residue having a carbonyl group, -Q-C(=G)-M, wherein G is O or S, and M is, for example, —OH or —SH;

an alkoxy group, an aryloxy group, an aralkyloxy group, or an alkaryloxy group;

an alkylthio group, an arylthio group, an aralkylthio group, or an alkarylthio group;

an alkylcarbonyloxy group, an arylcarbonyloxy group, an aralkylcarbonyloxy group, or an alkarylcarbonyloxy group;

an activated ester such as an ester esters of hydroxylamines having imide imid structure such as N-hydroxysuccinimide or having a structure unit O—N where N is part of a heteroaryl compound or, with G=O and Q absent, such as an aryloxy compound compounds with a substituted aryl residue such as pentafluorophenyl, paranitrophenyl or trichlorophenyl;

wherein Q is absent or NH or a heteroatom such as S or O;

—NH—$NH_2$, or —NH—NH—;

—$NO_2$;

a nitril group;

a carbonyl group such as an aldehyde group or a keto group;

a carboxy group;

a —N=C=O group or a the —N=C=S group;

a vinyl halide group such as vinyl iodide or vinyl bromide or triflate;

—C≡C—H;

—(C=$NH_2Cl$)—OAlkyl;

a group —(C=O)—CH2-Hal wherein Hal is Cl, Br, or I;
—CH=CH—SO₂—;
a disulfide group comprising the structure —S—S—;
the group

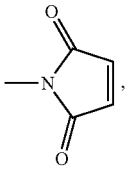

and
the group

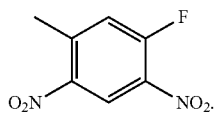

and wherein $F_3$ is a functional group capable of forming a chemical linkage with $F_2$ and is preferably selected from the above-mentioned group, $F_2$ preferably comprising the moiety —NH—, more preferably comprising an amino group, $F_3$ preferably comprising the moiety —(C=G)-, more preferably —(C=O)—, more preferably the moiety —(C=G)-G-, still more preferably —(C=O)-G-, and especially preferably —(C=O)—O, D being particularly preferably an amide linkage.

In still another aspect, this document features a conjugate, comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, the conjugate having a structure according to the formula

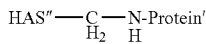

wherein the carbon atom of the moiety —CH₂—NH— is derived from an aldehyde group which was introduced in the polymer by a ring-opening oxidation reaction, and wherein the nitrogen atom is derived from an amino group of the protein, wherein HAS" refers to the HAS molecule without the carbon atom of the aldehyde group involved in the reaction.

This document also features a conjugate, comprising a protein and a polymer or a derivative thereof, wherein the polymer is a hydroxyalkyl starch (HAS) and the protein is selected from the group consisting of IFN alpha, IFN beta, tPA, A1AT, factor VII and factor IX, the conjugate having a structure according to the formula

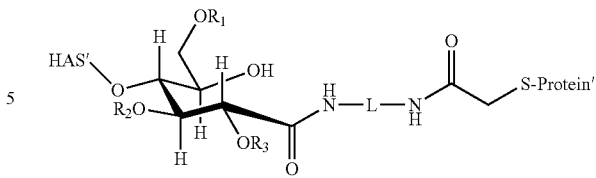

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein L is an optionally substituted, linear, branched and/or cyclic hydrocarbon residue, optionally comprising at least one heteroatom, comprising an alkyl, aryl, aralkyl heteroalkyl, and/or heteroaralkyl moiety, the residue having from 2 to 60 preferably from 2 to 40, more preferably from 2 to 20, more preferably from 2 to 10 carbon atoms, and wherein the sulfur atom is derived from a cysteine residue or a disulfide group of the protein. -L- can be —[(CR$_a$R$_b$)$_m$G]$_n$[CR$_c$R$_d$]$_o$— wherein R$_a$, R$_b$, R$_c$ and R$_d$ are independently hydrogen, alkyl, aryl, preferably hydrogen, wherein G is selected from the group consisting of 0 and S, preferably O, and wherein m 1, 2, 3 or 4, most preferably 2, wherein the residues Ra and Rb may be the same or different in the m groups CR$_a$R$_b$;

n 1 to 20, preferably 1 to 10, most preferably 1, 2, 3, or 4;

o 1 to 20, preferably 1 to 10, more preferably 1, 2, 3, 4, 5, more preferably 1 or 2, most preferably 1, wherein the residues R$_c$ and R$_d$ may be the same or different in the o groups CR$_c$R$_d$;

or wherein n 0, and o 2 to 20, preferably 2 to 10, more preferably 2, 3, 4, 5, 6, 7, or 8, wherein the residues Rc and Rd may be the same or different in the o groups CR$_c$R$_d$.

In another aspect, this document features a conjugate, comprising a protein and a polymer or a derivative thereof, wherein the polymer is a hydroxyalkyl starch (HAS) and the protein is selected from the group consisting of IFN alpha, IFN beta, tPA, A1AT, APC, factor VII and factor IX, the conjugate having a structure according to the formula

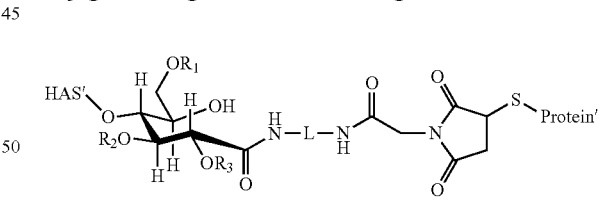

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein L is an optionally substituted, linear, branched and/or cyclic hydrocarbon residue, optionally comprising at least one heteroatom, comprising an alkyl, aryl, aralkyl heteroalkyl, and/or heteroaralkyl moiety, the residue having from 2 to 60 preferably from 2 to 40, more preferably from 2 to 20, more preferably from 2 to 10 carbon atoms, and wherein the sulfur atom is derived from a cysteine residue or a disulfide group of the protein. -L- can be —[(CR$_a$R$_b$)$_m$G]$_n$[CR$_c$R$_d$]$_o$— wherein R$_a$, R$_b$, R$_c$, and R$_d$ are independently hydrogen, alkyl, aryl, preferably hydrogen, wherein G is selected from the group consisting of O and S, preferably O, and wherein m 1, 2, 3 or 4, most preferably 2, wherein the residues Ra and Rb may be the same or different in the m groups $CR_aR_b$;

n 1 to 20, preferably 1 to 10, most preferably 1, 2, 3, or 4;

o 1 to 20, preferably 1 to 10, more preferably 1, 2, 3, 4, 5, more preferably 1 or 2, most preferably 1, wherein the residues Rc and Rd may be the same or different in the o groups $CR_cR_d$;

or wherein n 0, and o 2 to 20, preferably 2 to 10, more preferably 2, 3, 4, 5, 6, 7, or 8, wherein the residues Rc and Rd may be the same or different in the o groups $CR_cR_d$.

In yet another aspect, this document features a method for the treatment of a human or animal body, comprising administering a conjugate as described herein to a human or animal in need of treatment.

In another aspect, this document features a pharmaceutical composition comprising in a therapeutically effective amount a conjugate as described herein. The pharmaceutical composition can further comprise at least one pharmaceutically acceptable diluent, adjuvant, or carrier.

In another aspect, this document features a composition for the treatment of leukaemia e.g. hairy cell leukaemia, chronic myelogeneous leukaemia, multiple myeloma, follicular lymphoma, cancer, e.g. carcinoid tumour, malignant melanoma and hepatitis, e.g., chronic hepatitis B and chronic hepatitis C, comprising a HAS-protein conjugate as described herein, wherein the protein is IFN alpha.

This document also features a composition for the treatment of multiple sclerosis, preferably relapsing forms of multiple sclerosis, comprising a HAS-protein conjugate as described herein, wherein the protein is IFN beta.

In another aspect, this document features a composition for myeloid reconstitution following bone marrow transplant or induction chemotherapy in older adults with acute myelogenous leukaemia, bone marrow transplant engraftment failure or delay, mobilization and following transplantation of autologous peripheral blood progenitor cells, comprising a HAS protein conjugate as described herein, wherein the protein is GM-CSF beta.

In another aspect, this document features a composition for the treatment of severe sepsis, thrombosis, thromboembolism or occlusive diseases, especially occlusive arterial diseases, comprising a HAS-protein conjugate as described herein, wherein the protein is APC.

In another aspect, this document features a composition for the treatment of myocardial infarctions (heart attacks), thrombosis, thromboembolism or occlusive diseases, especially occlusive arterial diseases, comprising a HAS-protein conjugate as described herein, wherein the protein is tPA.

In another aspect, this document features a composition for the treatment of emphysema, cystic fibrosis, atopic dermatitis, and/or or bronchitis, comprising a HAS-protein conjugate as described herein, wherein the protein is A1AT.

In still another aspect, this document features a composition for the treatment of hereditary deficiency, veno-occlusive disease, burns and heparin resistance in coronary arterial bypass Graft (CABG) surgery, prevention of micro-clot formation associated with ventilation therapy, treatment of bowel perforation resulting from trauma or gastrointestinal surgery; disseminated intravascular coagulation (DIC) and/or or sepsis, comprising a HAS-protein conjugate as described herein, wherein the protein is AT III.

In yet another aspect, this document features a composition for the treatment of episodes in hemophilia A or B patients with inhibitors to Factor VIII or Factor IX, comprising a HAS-protein conjugate as described herein, wherein the protein is factor VII.

In another aspect, this document features a composition for the treatment of haemophilia A, comprising a HAS-protein conjugate as described herein, wherein the protein is factor VIII.

This document also features a composition for the control and prevention of hemorrhagic episodes in patients with hemophillia B, preferably congenital factor IX deficiency or Christmas disease, including control and prevention of bleeding in surgical settings, comprising a HAS-protein conjugate as described herein, wherein the protein is factor IX.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

Lane A: Protein marker SeeBlue® Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD Lane B: Crude product after conjugation of oxidized IFN beta with HES derivative prepared as described in Example 1.1(a)

Lane C: Crude product after conjugation of oxidized IFN beta with HES derivative prepared as described in Example 1.1(b)

Lane D: Crude product after conjugation of oxidized IFN beta with HES derivative prepared as described in Example 1.1(c)

Lane E: Crude product after conjugation of oxidized IFN beta with HES derivative prepared as described in Example 1.1(d)

Lane F: Crude product after conjugation of oxidized IFN beta with HES derivative prepared as described in Example 1.1(e)

Lane G: Crude product after conjugation of oxidized IFN beta with HES derivative prepared as described in Example 1.1(f)

Lane H: Crude product after conjugation of oxidized IFN beta with HES derivative prepared as described in Example 1.1(g)

Lane I: Crude product after conjugation of oxidized IFN beta with HES derivative prepared as described in Example 1.1(h)

Lane J: Crude product after conjugation of oxidized IFN beta with HES derivative prepared as described in Example 1.1(i)

Lane K: Oxidized IFN beta, prepared as in Example 1.2(a)

Figure 2:
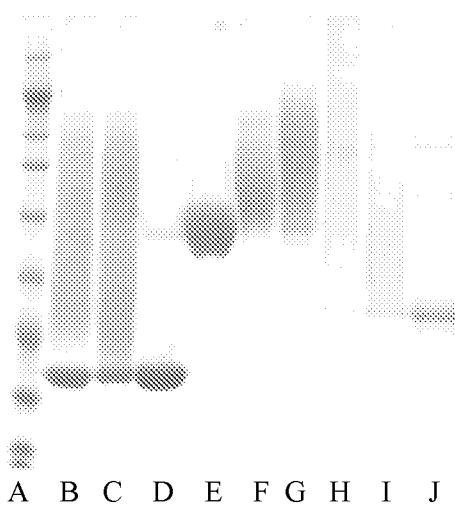

FIG. 2 shows an SDS page analysis of HES-IFN beta conjugates, produced according to Example 1.4. A 12% Bis-Tris gel together with a MOPS SDS running buffer at reducing conditions (both Invitrogen GmbH, Karlsruhe, D) were used according to the manufacture's instruction. Samples with a volume greater then 15 μL were concentrated in vacuo to this volume.

Lane A: Protein marker SeeBlue® Plus2 (Invitrogen GmbH, Karlsruhe, D) Molecular weight marker from top to bottom: 188 kD, 98 kD, 62 kD, 49 kD, 38 kD, 28 kD, 17 kD, 14 kD, 6 kD, 3 kD.

Lane H: Conjugation of IFN-beta with aldehydo-HES synthesized as described in Example 1.3(a).

Lane I: Conjugation of IFN-beta with aldehydo-HES synthesized as described in Example 1.3(b).

Lane J: Control: IFN-beta, treated with sodium borohydride without aldehydo-HES.

Figure 3:
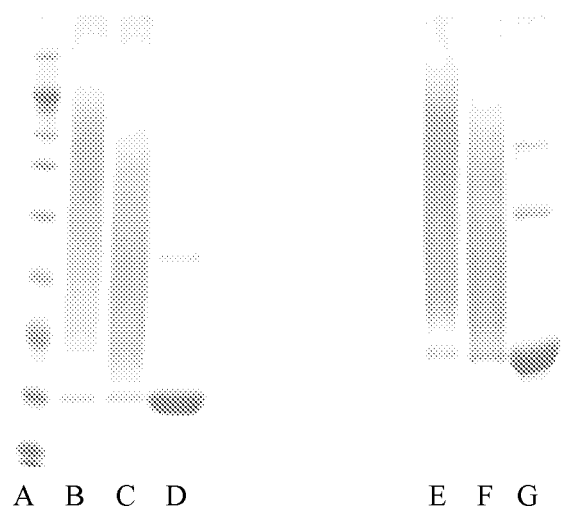

FIG. 3 shows an SDS page analysis of HES-IFN alpha conjugates, produced according to Example 2.2. A 12% Bis-Tris gel together with a MOPS SDS running buffer at reducing conditions (both Invitrogen GmbH, Karlsruhe, D) were used according to the manufacture's instruction. Samples with a volume greater then 15 μl were concentrated in vacuo to this volume.

Lane A: Protein marker SeeBlue® Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.

Lane E: Conjugation of IFN-alpha with aldehydo-HES synthesized as described in Example 2.1(a).

Lane F: Conjugation of IFN-alpha with aldehydo-HES synthesized as described in Example 2.1(b).

Lane G: Control: IFN-alpha according to Example 2.2, treated with sodium borohydride without aldehydo-HES.

Figure 4:
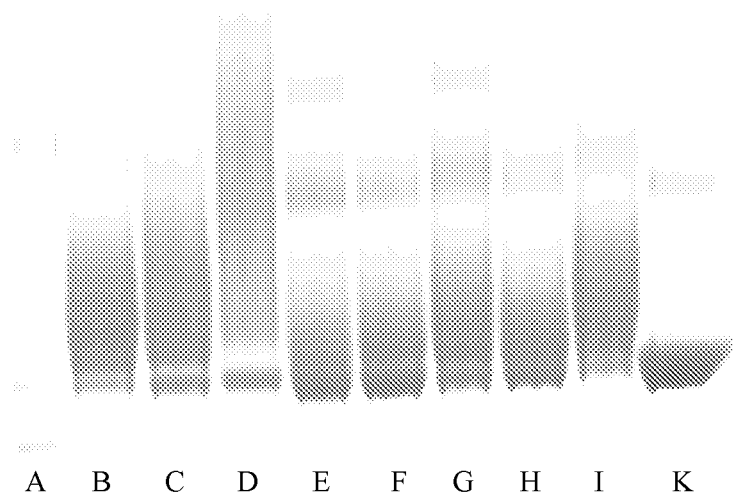

FIG. 4 shows an SDS page analysis of HES-AT III conjugates, produced according to Example 3.2. A NuPage 3-8% Tris-Acetate gel together with a Tris-Acetate SDS running buffer at reducing conditions (both Invitrogen GmbH, Karlsruhe, D) were used according to the manufactures instruction.

Lane A: Protein marker SeeBlue® Plus2 (Invitrogen GmbH, Karlsruhe, D) Molecular weight marker from top to bottom: 188 kD, 98 kD, 62 kD, 49 kD, 38 kD, 28 kD, 17 kD, 14 kD, 6 kD, 3 kD Lane B: Crude product after conjugation of oxidized ATIII with HES derivative prepared as described in Example 3.1(a)

Lane C: Crude product after conjugation of oxidized ATIII with HES derivative prepared as described in Example 3.1(b)

Lane D: Crude product after conjugation of oxidized ATIII with HES derivative prepared as described in Example 3.1(c)

Lane E: Crude product after conjugation of oxidized ATIII with HES derivative prepared as described in Example 3.1(d)

Lane F: Crude product after conjugation of oxidized ATIII with HES derivative prepared as described in Example 3.1(e)

Lane G: Crude product after conjugation of oxidized ATIII with HES derivative prepared as described in Example 3.1(f)

Lane H: Crude product after conjugation of oxidized ATIII with HES derivative prepared as described in Example 3.1(g)

Lane I: Crude product after conjugation of oxidized ATIII with HES derivative prepared as described in Example 3.1(h)

Lane K: Oxidized ATIII GlycoThera, according to Example 3.2

Figure 5:
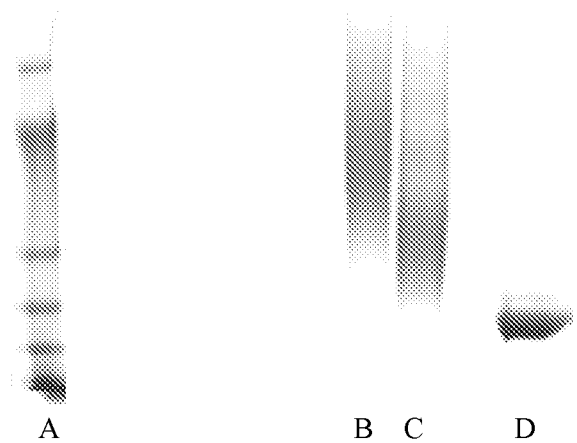

FIG. 5 shows an SDS page analysis of HES-AT III conjugates, produced according to Example 3.4. A 3-8% Tris-Acetate gel together with a Tris-Acetate SDS running buffer at reducing conditions (both Invitrogen GmbH, Karlsruhe, D) were used according to the manufacture's instruction.

Lane A: Protein marker SeeBlue®Plus2 (Invitrogen GmbH, Karlsruhe, D) Molecular weight marker from top to bottom: 188 kD, 98 kD, 62 kD, 49 kD, 38 kD, 28 kD, 17 kD, 14 kD, 6 kD, 3 kD.

Lane B: Conjugation of AT III with aldehydo-HES synthesized as described in Example 3.3(a).

Lane C: Conjugation of AT III with aldehydo-HES synthesized as described in Example 3.3(b).

Lane D: Control: AT III according to Example 3.3, treated with sodium borohydride without aldehydo-HES.

Figure 6:
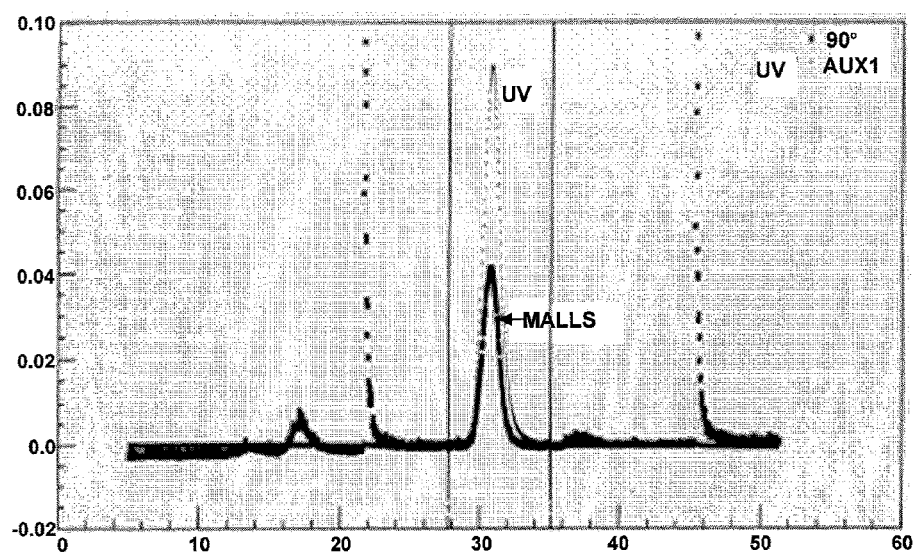

FIG. 6 shows a HPGPC (high-performance gel permeation chromatography) chromatogram with regard to the AT III purified from glycerol according to Example 3.5 (UV and MALLS detector results in a single chromatogram, the x axis relating to time/minutes).

The following parameters were used in the HPGPC analysis:

Column: Superose 12 HR 10/30 300×10 mm I.D. (Pharmacia)

Eluent: 27.38 mM $Na_2HPO_4$; 12.62 mM $NaH_2PO_4$; 0.2 M NaCl; 0.005% $NaN_3$ in 1 l of demineralized water Flux: 0.24 ml/h Detector 1: MALLS detector Detector 2: UV (280 nm)

Detector 3: RI (refractive index detector)

Figure 7:
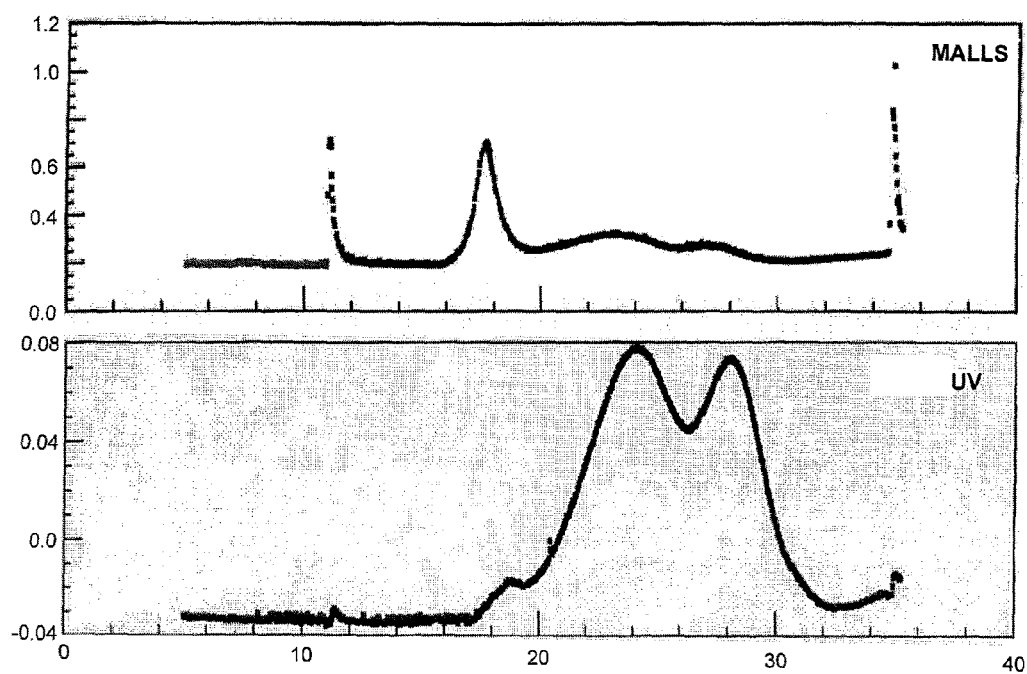

FIG. 7 shows a HPGPC chromatogram with regard to the AT III conjugate according to Example 3.5 (MALLS detector in the upper chromatogram, UV detector in the lower chromatogram, the x axis relating to time/minutes).

The following parameters were used in the HPGPC analysis:

Column: Superose 12 HR 10/30 300×10 mm I.D. (Pharmacia)

Eluent: 27.38 mM $Na_2HPO_4$; 12.62 mM $NaH_2PO_4$; 0.2 M NaCl; 0.005%

$NaN_3$ in 1 l of demineralized water

Flux: 0.24 ml/h

Detector 1: MALLS detector

Detector 2: UV (280 nm)

Detector 3: RI (refractive index detector)

Figure 8:
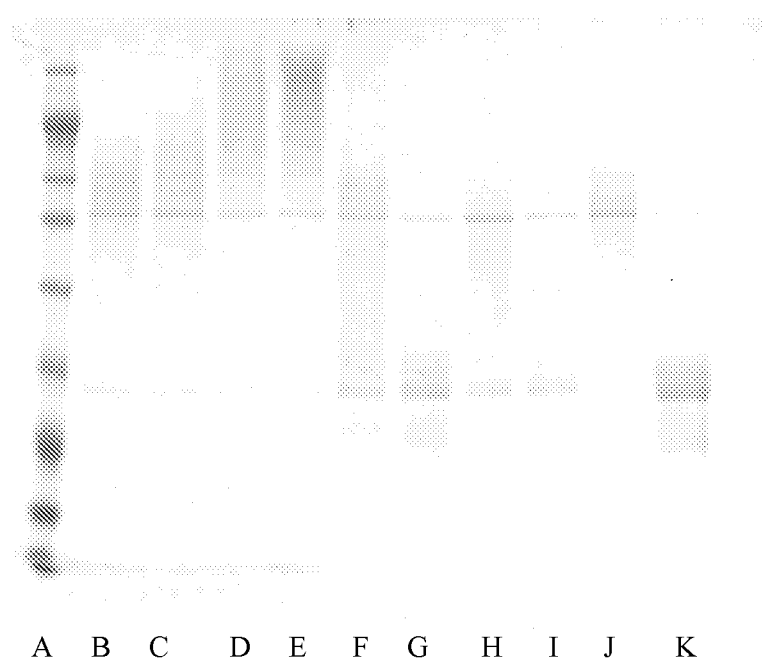

FIG. 8 shows an SDS page analysis of HES-GM-CSF conjugates, produced according to Example 4.2. A 12% Bis-Tris gel together with a MOPS SDS running buffer at reducing conditions (both Invitrogen GmbH, Karlsruhe, D) were used according to the manufacturer's instruction.

Lane A: Protein marker SeeBlue® Plus2 (Invitrogen GmbH, Karlsruhe, D) Molecular weight marker from top to bottom: 188 kD, 98 kD, 62 kD, 49 kD, 38 kD, 28 kD, 17 kD, 14 kD, 6 kD, 3 kD Lane B: Crude product after conjugation of oxidized GM-CSF with HES derivative prepared as described in Example 4.1(a)

Lane C: Crude product after conjugation of oxidized GM-CSF with HES derivative prepared as described in Example 4.1(b)

Lane D: Crude product after conjugation of oxidized GM-CSF with HES derivative prepared as described in Example 4.1(c)

Lane E: Crude product after conjugation of oxidized GM-CSF with HES derivative prepared as described in Example 4.1(d)

Lane F: Crude product after conjugation of oxidized GM-CSF with HES derivative prepared as described in Example 4.1(e)

Lane G: Crude product after conjugation of oxidized GM-CSF with HES derivative prepared as described in Example 4.1(f)

Lane H: Crude product after conjugation of oxidized GM-CSF with HES derivative prepared as described in Example 4.1(g)

Lane I: Crude product after conjugation of oxidized GM-CSF with HES derivative prepared as described in Example 4.1(g)

Lane J: Crude product after conjugation of oxidized GM-CSF with HES derivative prepared as described in Example 4.1(h)

Lane K: Oxidized GM-CSF according to Example 4.2.

Figure 9:
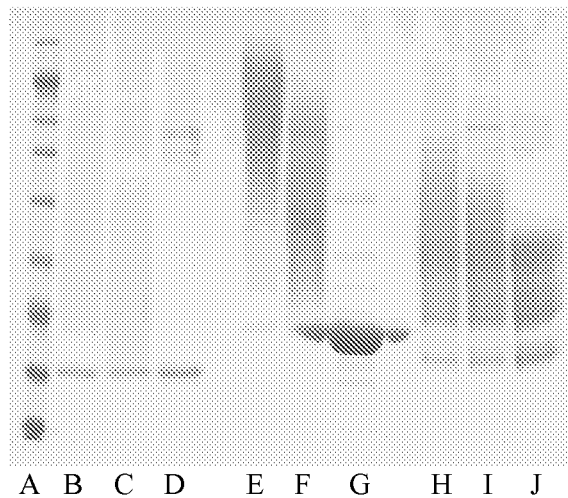

FIG. 9 shows an SDS page analysis of HES-GM-CSF conjugates, produced according to Example 4.4. A 12% Bis-Tris gel together with a MOPS SDS running buffer at reducing conditions (both Invitrogen GmbH, Karlsruhe, D) were used according to the manufacture's instruction. Samples with a volume grater then 15 μL were concentrated in vacuo to this volume.

Lane A: Protein marker SeeBlue® Plus2 (Invitrogen GmbH, Karlsruhe, D) Molecular weight marker from top to bottom: 188 KD, 98 KD, 62 KD, 49 KD, 38 KD, 28 KD, 17 KD, 14 KD, 6 KD, 3 KD Lane H: Conjugation of GM-CSF with aldehydo-HES synthesized as described in Example 4.3(a)

Lane I: Conjugation of GM-CSF with aldehydo-HES synthesized as described in Example 4.3(b)

Figure 10:
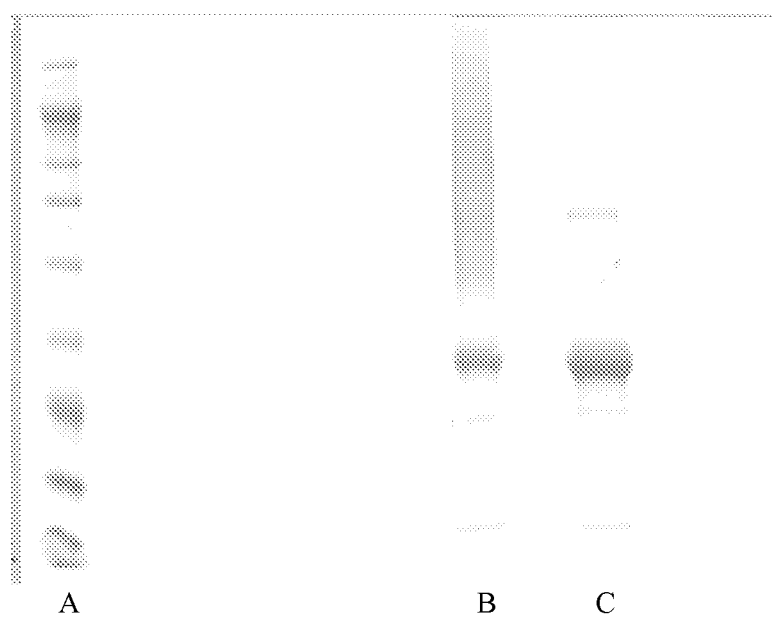

Lane J: Control: GM-CSF according to Example 4.4, treated with sodium borohydride without aldehydoHES FIG. 10 shows an SDS page analysis of IFN beta-conjugates, produced according to Example 5.2. A 12% Bis-Tris gel together with a MOPS SDS running buffer at reducing conditions (both Invitrogen GmbH, Karlsruhe, D) were used according to the manufacture's instruction.

Lane A: Protein marker SeeBlue® Plus2 (Invitrogen GmbH, Karlsruhe, D) Molecular weight marker from top to bottom: 188 kD, 98 kD, 62 kD, 49 kD, 38 kD, 28 kD, 17 kD, 14 kD, 6 kD, 3 kD.

Lane B: Crude product after conjugation of oxidized IFN beta with hydroxylaminoHES derivative prepared as described in Example 1.1(c).

Lane C: Oxidized IFN beta.

Figure 11:
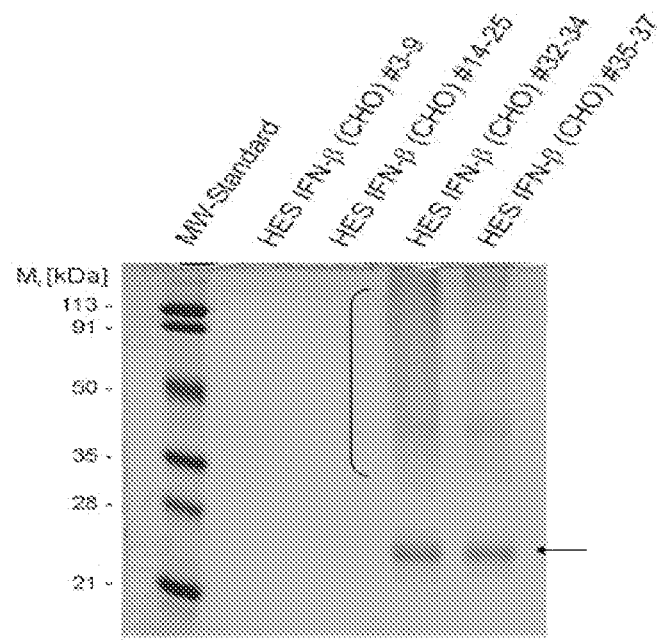

FIG. 11 shows an SDS-PAGE gel of RP-HPLC purified HAS-modified IFN-β (CHO cell). The arrow indicates the migration position of unmodified IFN-β presumably due to forms lacking terminal sialic acid derivatives whereas the HAS modified IFN-β was detected as a broad diffuse Coomassie stained area spanning molecular masses of 35 Kda-120 Kda.

Figure 12:
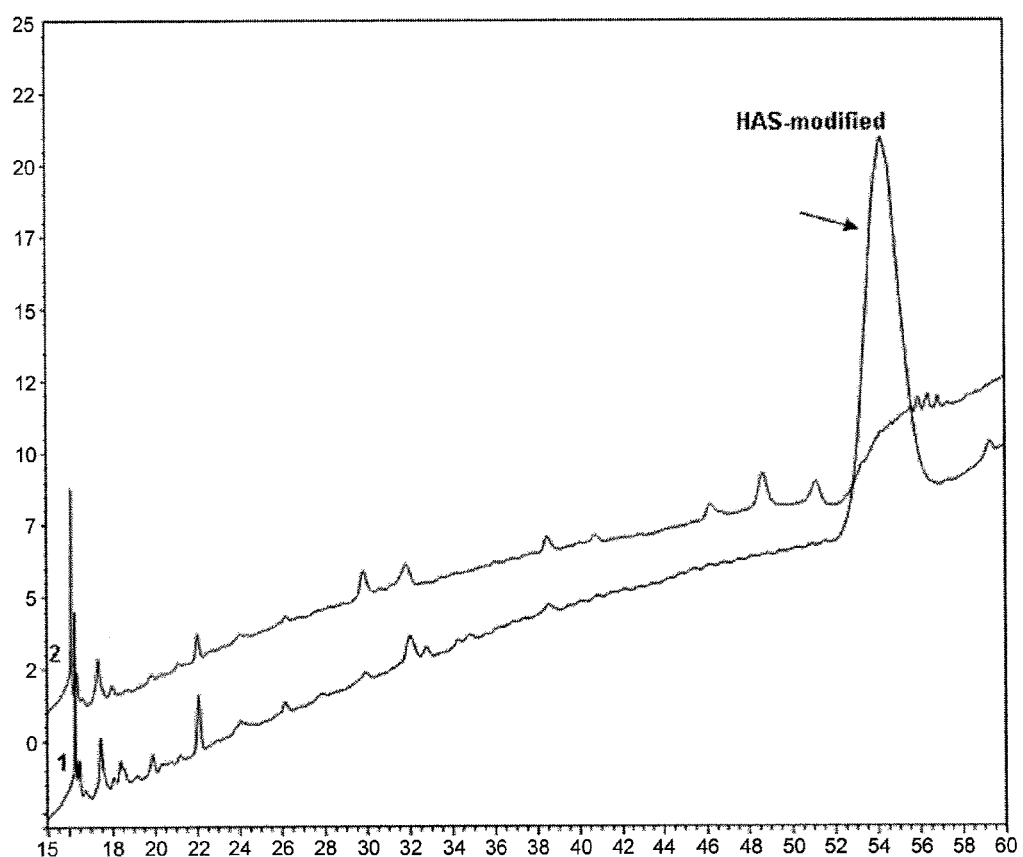

FIG. 12 shows a HPAEC-PAD analysis of N-linked oligosaccharides enzymatically released from HAS modified IFN-β

Figure 13:
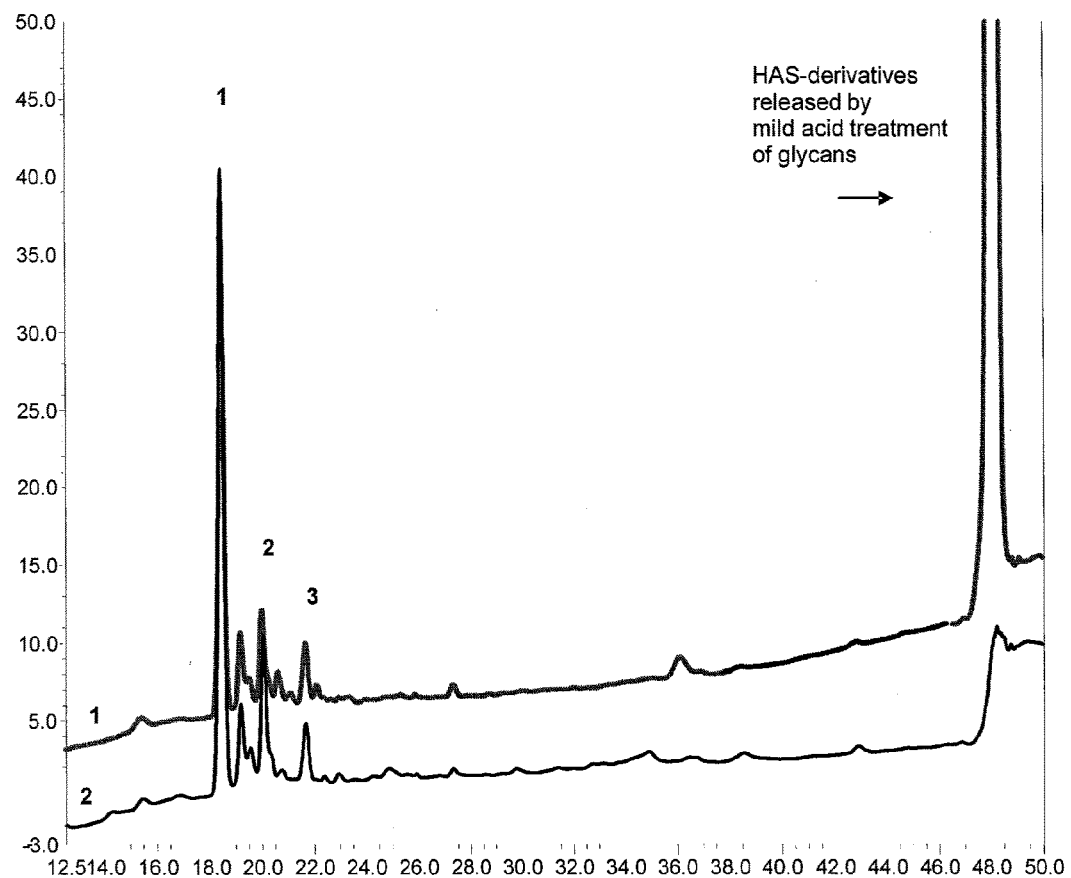

FIG. 13 shows a HPAEC-PAD analysis of N-linked oligosaccharides after mild hydrolysis prepared from HAS modified IFN-β

Figure 14:
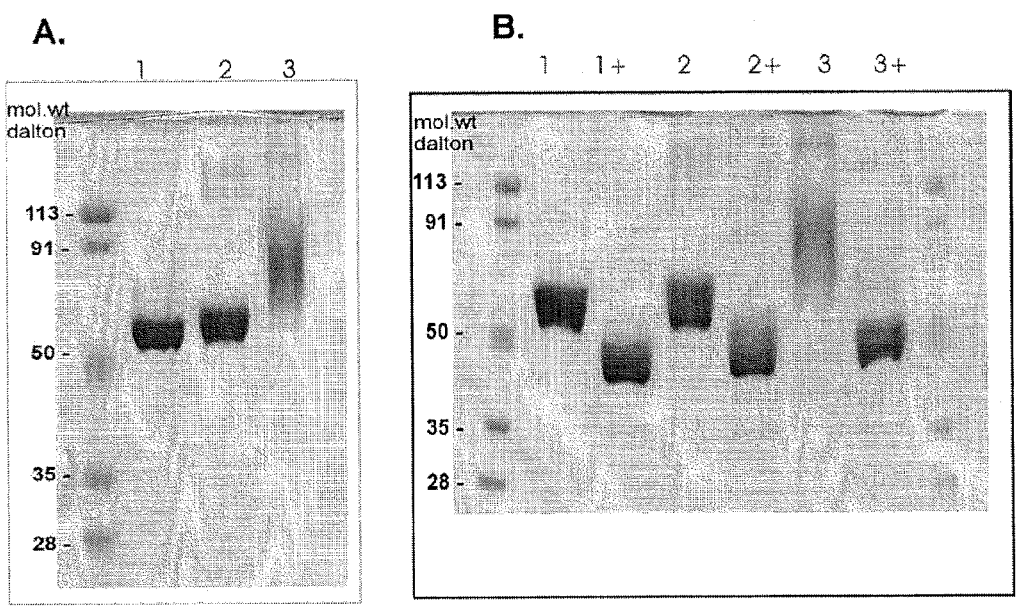

FIG. 14A shows an SDS-PAGE analysis of antithrombin III: 1=untreated AT III; 2=periodate treated AT III; 3=HAS modified AT IIII; 10 μg each were applied onto a 10% polyacrylamide gel FIG. 14B shows an SDS-PAGE analysis of antithrombin III: 1=untreated AT III; 2=periodate treated AT III; 3=HAS modified AT IIII; 10 μg each were applied onto a 10% polyacrylamide gel. 1+, 2+ and 3+ indicates AT III samples after de-N-glycosylation with polypeptide N-glycosidase.

Figure 15:
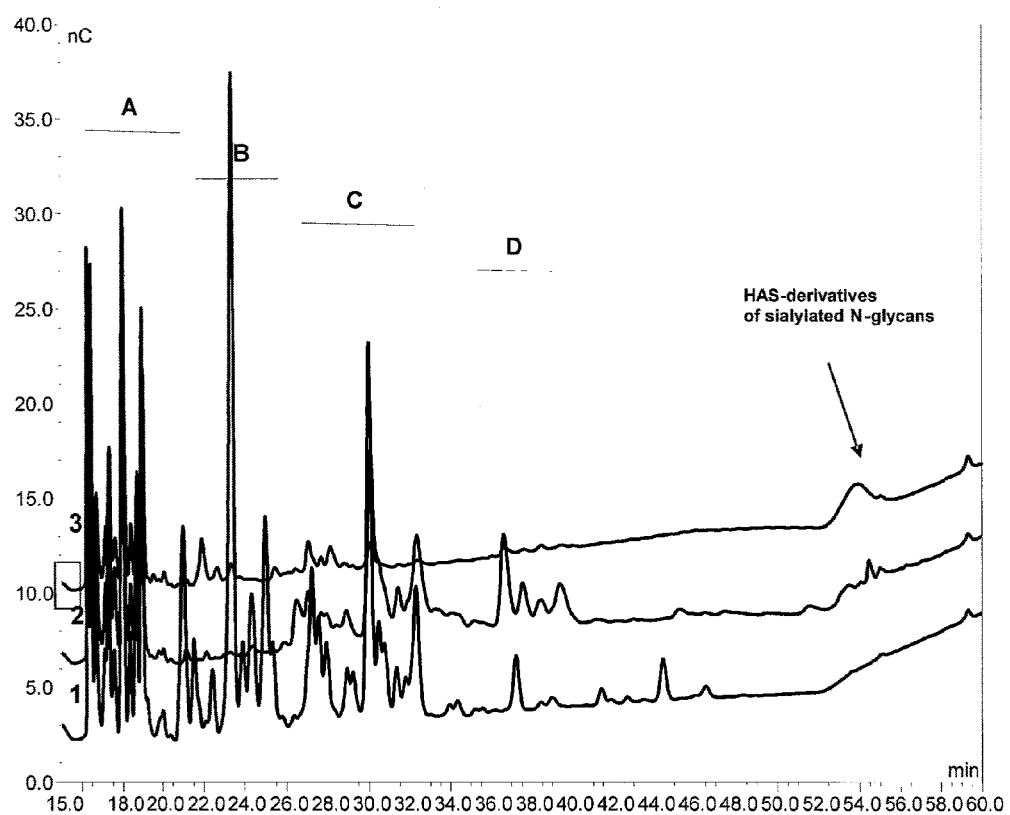

FIG. 15 shows a HPAEC-PAD analysis of N-linked glycans of AT III samples obtained after polypeptide-N-glycosidase treatment as described in Example 8.6.b). 1=N-glycans from untreated AT III; 2=N-glycans from mild periodate treated AT III; 3=N-glycans from HAS-modified AT IIII. A=elution area of neutral oligosaccharides including oligomannosidic glycans (with 6 to 9 mannose residues). B=elution area of monosialylated N-glycans; C=elution area of disialylated N-glycans; D=elution area of trisialylated N-glycans. The elution of HAS-modified N-glycans is indicated in trace no. 3.

Figure 16:
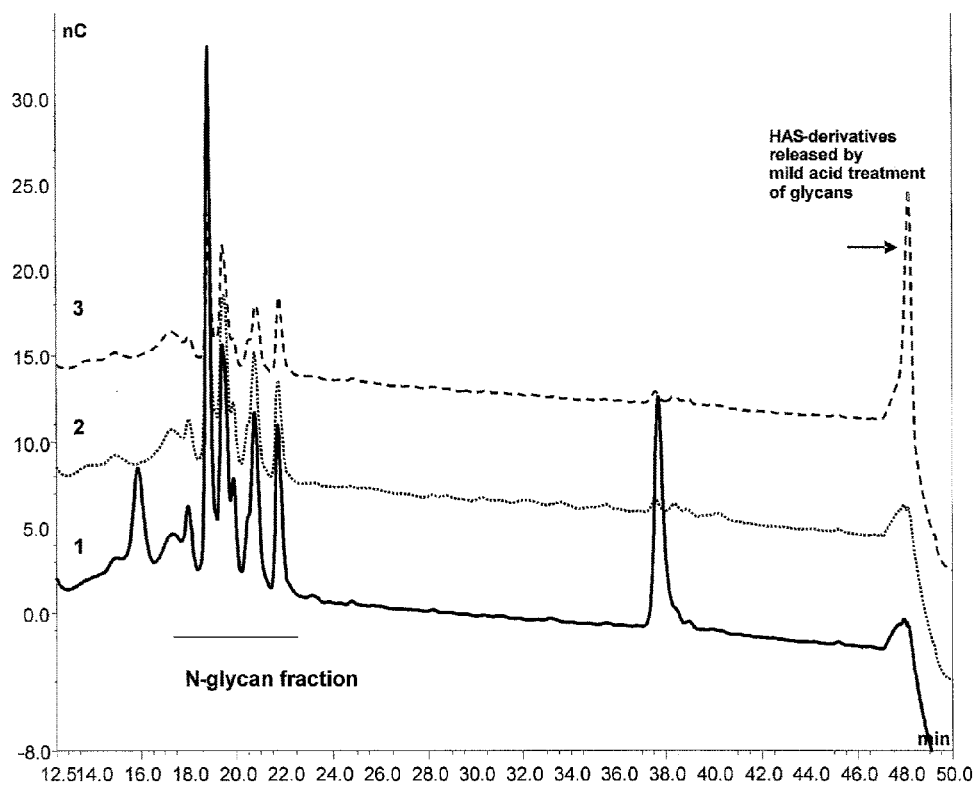

FIG. 16 shows a HPAEC-PAD analysis of desialylated N-glycans (from mild acid treated Example 8.6.c)) obtained from AT III samples after polypeptide-N-treatment (Example 8.6.b)). 1=N-glycans from untreated AT III; 2=N-glycans from mild periodate treated AT III; 3=N-glycans from HAS-modified AT. In trace no. 1 the peak eluting at 16 min represents N-acetylneuraminic acid, the peak at 38 min represents N-glycolylneuraminic acid. The major meak at 19 min represent a diantennary structure with proximal α1-6-linked fucose. The remaining peaks are diantennary without fucose, diantennry minus 1 galactose and oligomannosidic structures with mainly 6-9 mannose residues. The elution position of HAS-modified sialic acid derivatives is indicated in trace no. 3.

Figure 17:
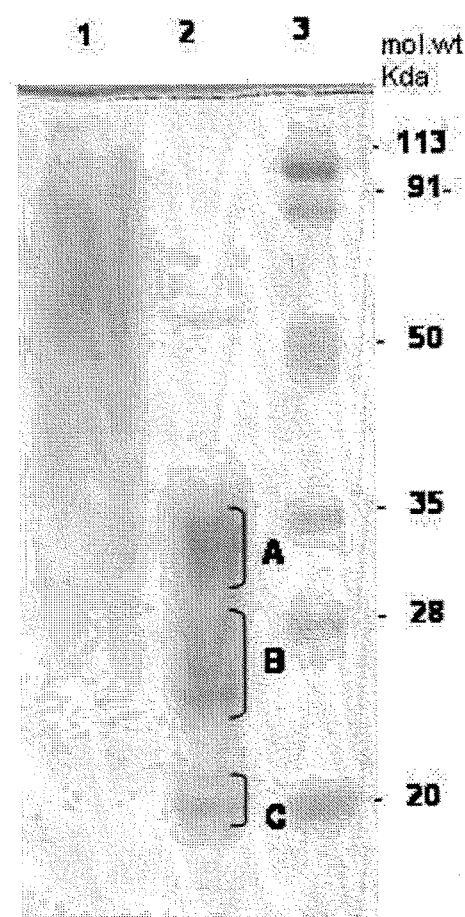

FIG. 17 shows an SDS-PAGE analysis of HAS(10 Kda)-modified GM-CSF. 1=RP-HPLC eluate; 2=recombinant human GM-CSF starting material. The brackets indicate the migration position of C=only O-glycosylated and non-glycosylated forms; B=GM-CSF forms with a single N-glycosylation site occupied; A=GM-CSF with 2 N-glycosylation sites occupied with carbohydrates (cf. Forno et al., 2004).

Figure 18:
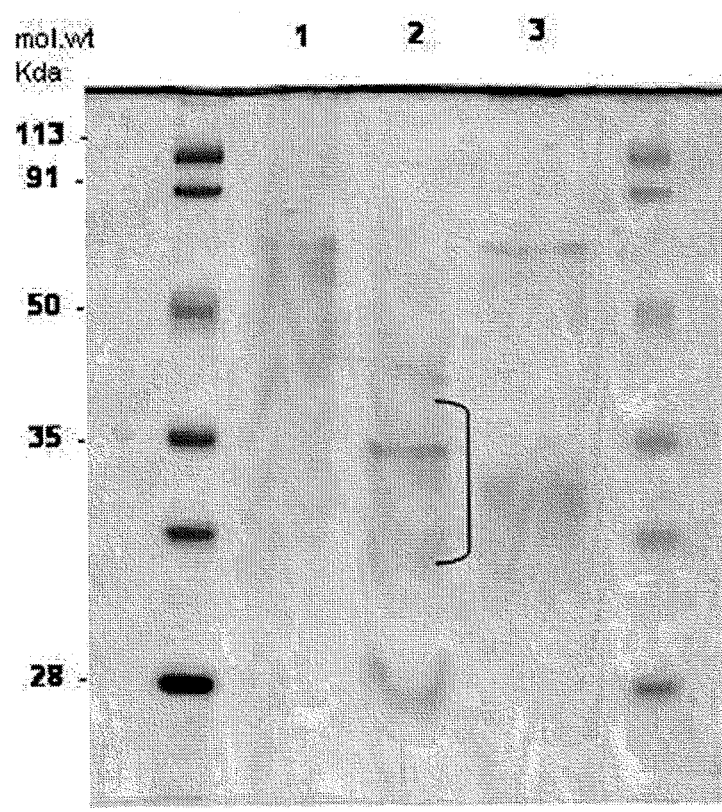

FIG. 18 shows an SDS-PAGE analysis of HAS(10 Kda)-modified (10 Kda) GM-CSF. 1=RP-HPLC eluate; 2=RP-HPLC eluate after digestion with polypeptide N-glycosidase; 3=RP-HPLC eluate after mild acid treatment. The bracket indicates the GM-CSF which is presumably HAS modified at periodate oxidised sialic acid residues attached to O-glycans.

Figure 19:
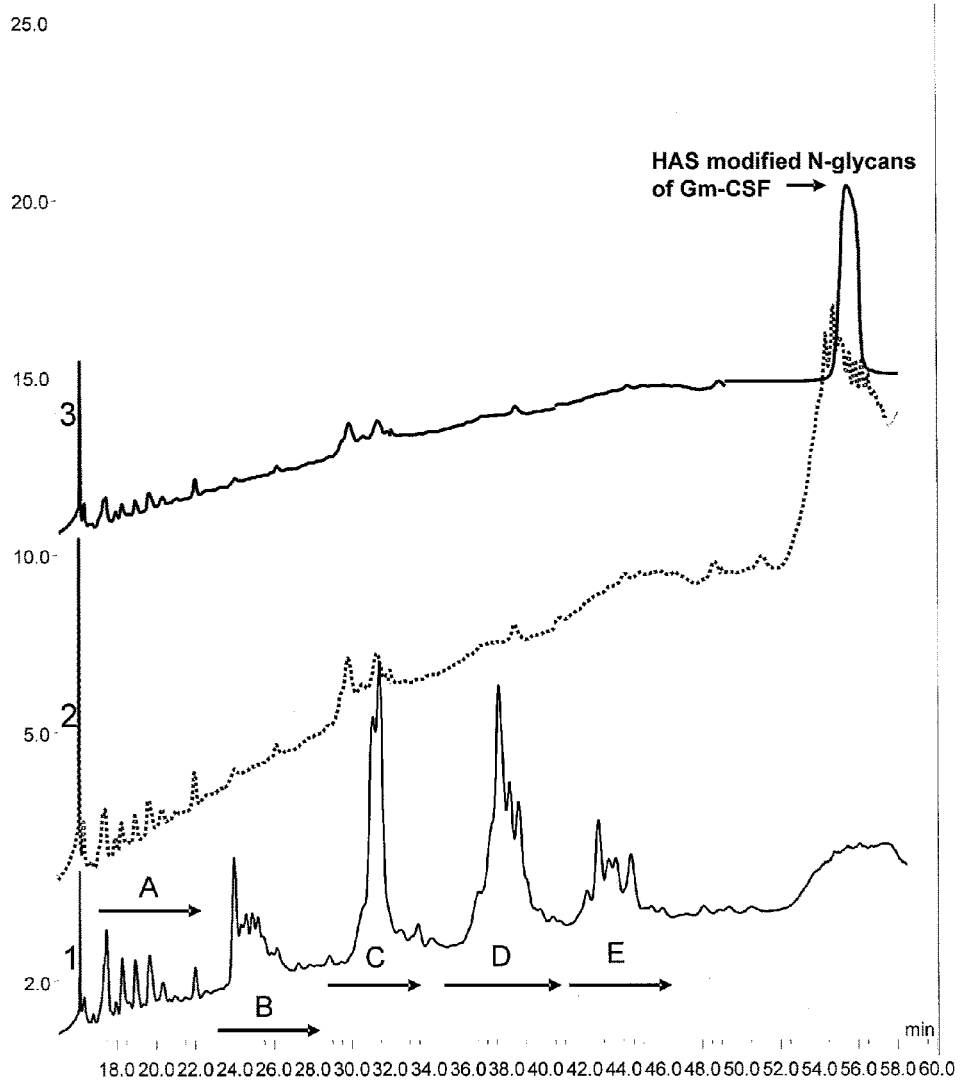

FIG. 19 shows an HPAEC-PAD analysis of N-glycans isolated from GM-CSF. Trace 1=untreated protein; trace 2=mild periodate oxidised GM-CSF; HAS(10 Kda)-modified GM-CSF after purification by RP-HPLC. Arrows A-E indicate the elution positions of asialo, mono-di-, tri- and tetra-sialo oligosaccharides. The oligosaccharide composition of the starting material was essentially the same as described in reference Forno et al., 2004.

Figure 20:
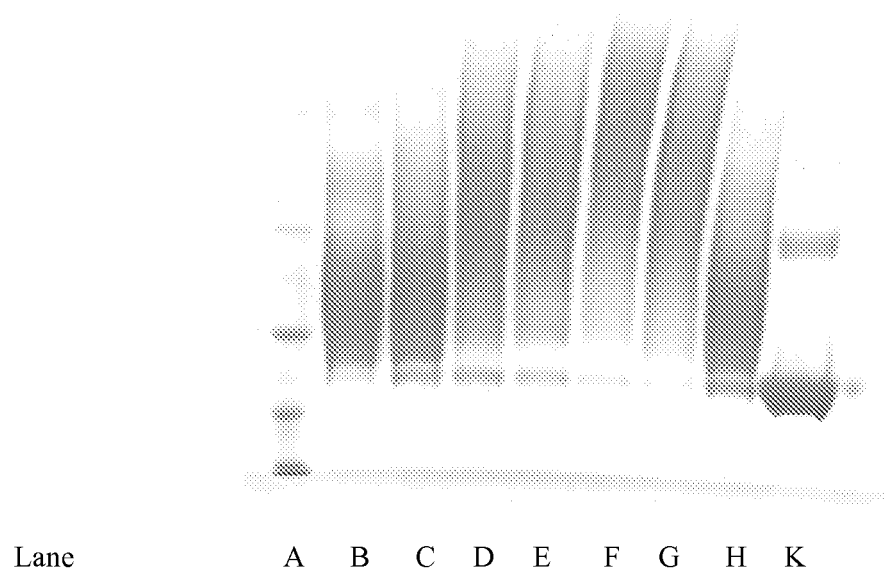

FIG. 20 shows an electrophoresis gel of the crude products after conjugation of oxidized ATIII with HES derivatives according to example 9.3. A NuPage 3-8% Tris-Acetate gel together with a Tris-Acetate SDS running buffer at reducing conditions (both Invitrogen GmbH, Karlsruhe, D) were used according to the manufacturers instruction. The gel was stained with Roti-Blue (Carl Roth GmbH+Co.KG, Karlsruhe, D) according to the manufacturer's instruction.

Lane A: Protein marker Roti-Mark STANDARD (Carl Roth GmbH+Co.KG, Karlsruhe, D) Molecular weight marker from top to bottom: 200 KD, 119 KD, 66 KD, 43 KD, 29 KD, 20 KD, 14.3 KD.

Lane B: Crude product after conjugation of oxidized ATIII with HES derivative prepared as described in Example 9.1(a).

Lane C: Crude product after conjugation of oxidized ATIII with HES derivative prepared as described in Example 9.1(b).

Lane D: Crude product after conjugation of oxidized ATIII with HES derivative prepared as described in Example 9.1(c).

Lane E: Crude product after conjugation of oxidized ATIII with HES derivative prepared as described in Example 9.1(d).

Lane F: Crude product after conjugation of oxidized ATIII with HES derivative prepared as described in Example 9.1(e).

Lane G: Crude product after conjugation of oxidized ATIII with HES derivative prepared as described in Example 9.1(f).

Lane H: Crude product after conjugation of oxidized ATIII with HES derivative prepared as described in Example 9.1(g).

Lane K: Reaction control.

Figure 21:
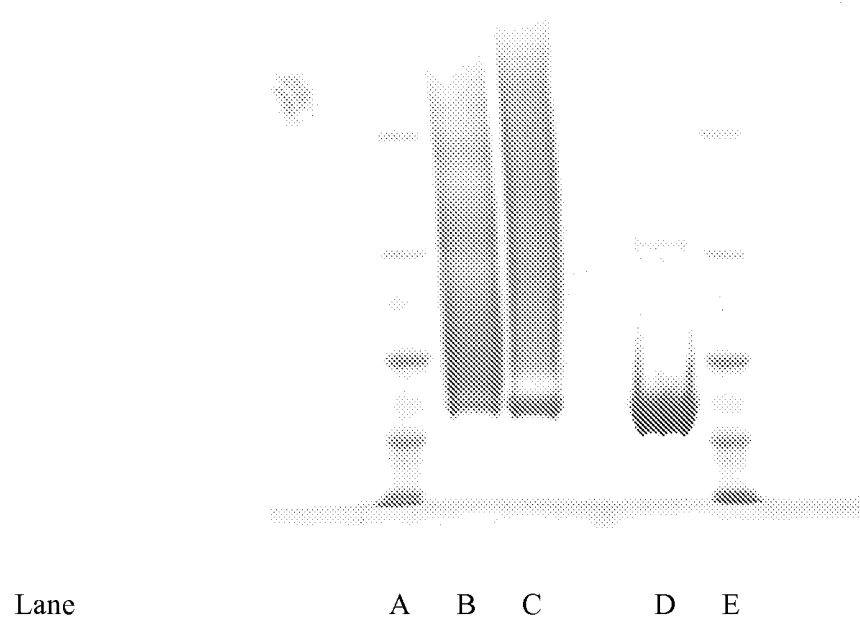

FIG. 21 shows an electrophoresis gel of ATIII conjugates produced according to example 9.4. A NuPage 3-8% Tris-Acetate gel together with a Tris-Acetate SDS running buffer at reducing conditions (both Invitrogen GmbH, Karlsruhe, D) were used according to the manufacturer's instruction. The gel was stained with Roti-Blue (Carl Roth GmbH+Co.KG, Karlsruhe, D) according to the manufacturer's instruction.

Lane A: Protein marker Roti-Mark STANDARD (Carl Roth GmbH+Co.KG, Karlsruhe, D) Molecular weight marker from top to bottom: 200 KD, 119 KD, 66 KD, 43 KD, 29 KD, 20 KD, 14.3 KD.

Lane B: Crude product after conjugation of ATIII with HES derivative prepared as described in Example 9.2(b).

Lane C: Crude product after conjugation of ATIII with HES derivative prepared as described in Example 9.2(d).

Lane D: Reaction control.

Lane E: Protein marker Roti-Mark STANDARD.

Figure 22:
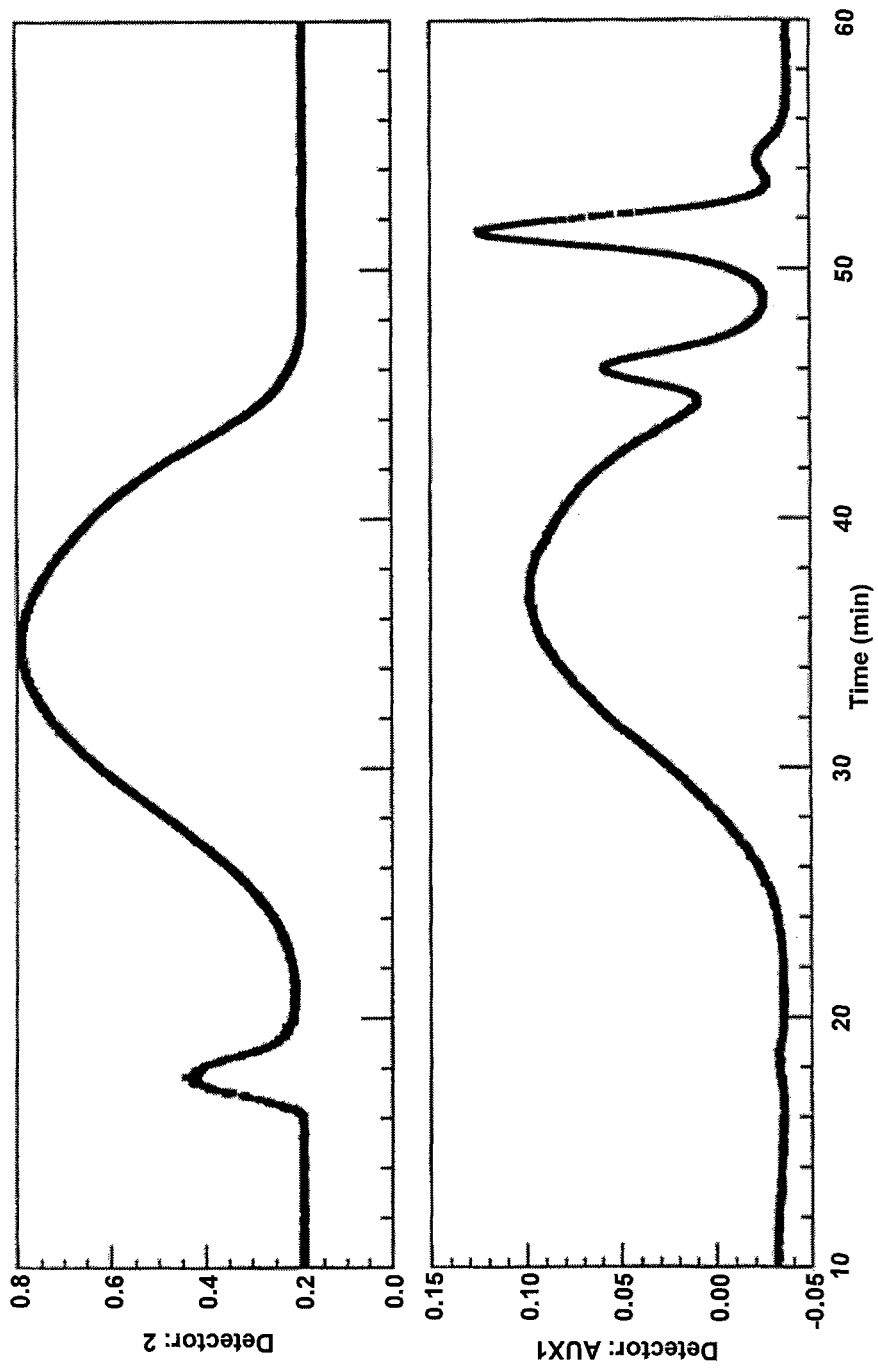

FIG. 22 shows SEC of IFN-alpha-HES coupled via activated aldonic acids according to example 10.3. MALLS and UV-detection proved the high degree of conversion of IFN-alpha in the reaction.

Figure 23:
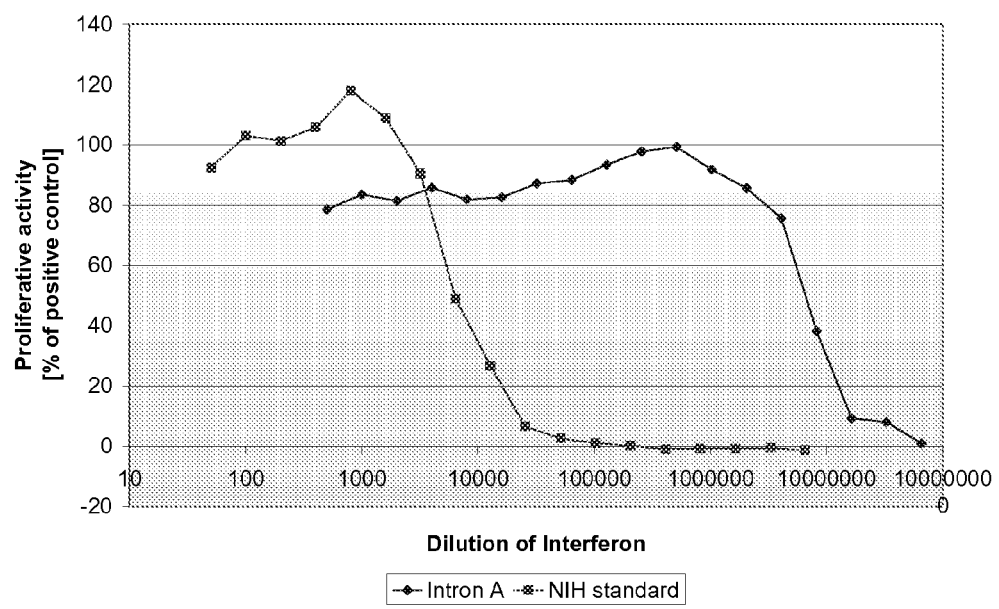

FIG. 23 is a graph showing the activity of Intron® A compared to NIH standard IFN-alpha 2a (see example 11.1)

Figure 24:
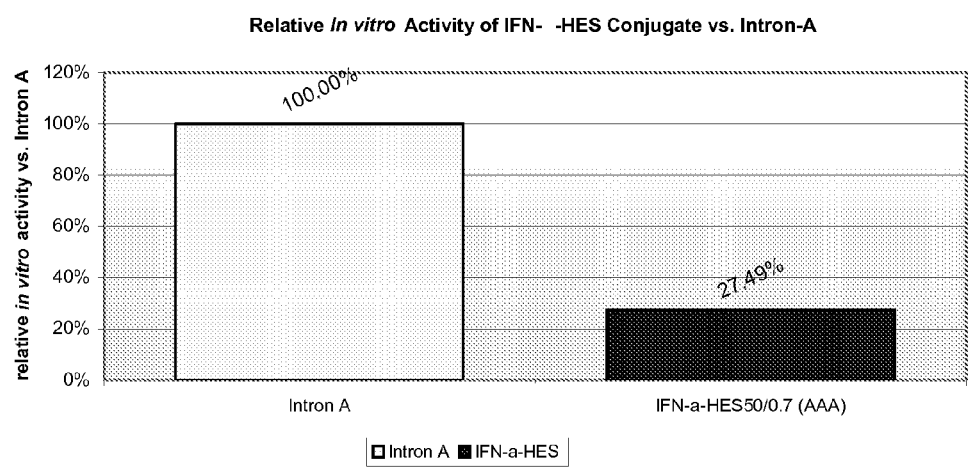

FIG. 24 is a graph showing the relative in vitro activity of IFN-alpha-HES (right column) compared to Intron® A (left column), see example 11.2.

Figure 25:
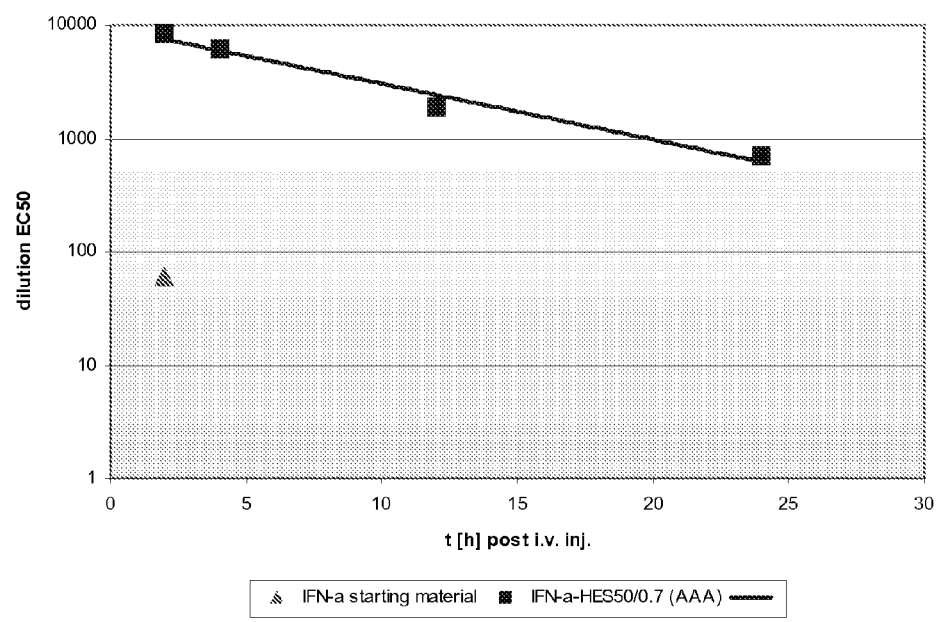

FIG. 25 is a graph showing the result of example 12.2 (the triangle represents IFN-alpha starting material, the squares represent HES-modified IFN alpha; dilution of serum samples required to achieve a 50% protection of MDBK cells against viral infection vs. time post i.v. injection of 30 µg/kg in mice). Serum from mice treated with unmodified starting material has a very low antiviral effect. Modification of IFN-alpha with HES substantially prolongs the antiviral effect of serum.

Figure 26:
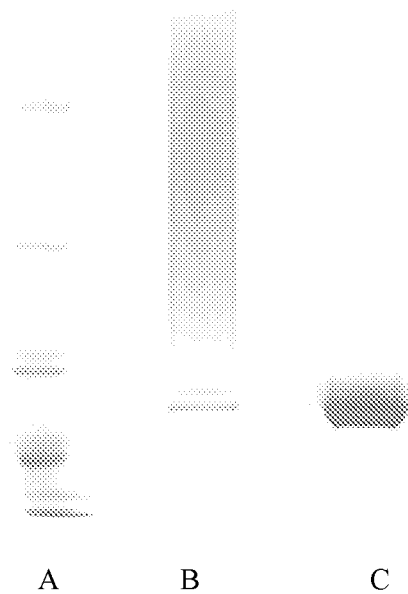

FIG. 26 shows results of example 13 (analysis of the crude α1AT-HES conjugates prepared as described in example 13.5 by gel electrophoresis). A 3-8% Tris-Acetate gel together with a Tris-Acetate SDS running buffer at reducing conditions (both Invitrogen GmbH, Karlsruhe, D) were used according to the manufacturer's instruction.

Lane A: Unstained SDS Page Protein Marker 6.5-200 KDa (SERVA Elektrophoresis GmbH, Heidelberg, D) Molecular weight marker from top to bottom: 200 KD, 116 KD, 67 KD, 45 KD, 29 KD, 21 KD, 14.3 KD, 6.5 KD;

Lane B: Conjugation to aldehydo-HES as described in example 13.5;

Lane C: Conjugation to HES as described in example 13.6.

Figure 27:
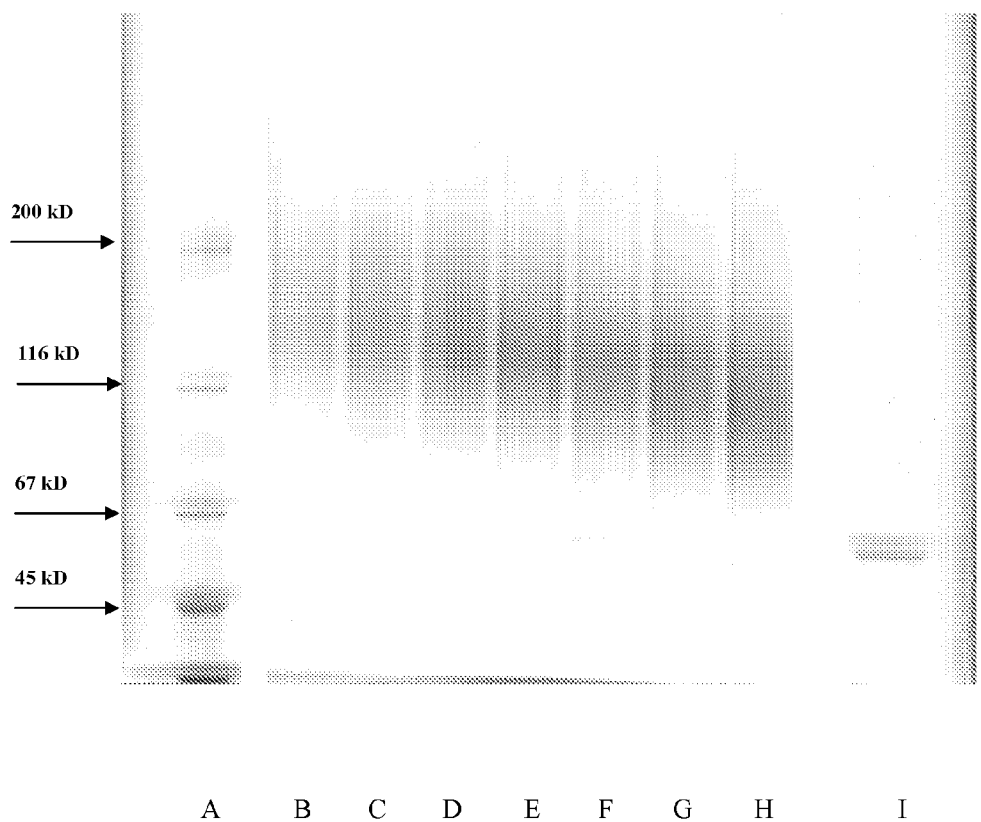

FIG. 27 shows results of example 13 (analysis of the fractions B1-C6 collected after Ion Exchange Chromatography (see example 13.7)

Lane A: Unstained SDS Page Protein Marker 6.5-200 KDa (SERVA Elektrophoresis GmbH, Heidelberg, D) Molecular weight marker from top to bottom: 200 KD, 116 KD, 67 KD, 45 KD, 29 KD, 21 KD, 14.3 KD, 6.5 KD;

Lane B: Fraction B1

Lane C: Fraction C1

Lane D: Fraction C2

Lane E: Fraction C3

Lane F: Fraction C4

Lane G: Fraction C5

Lane H: Fraction C6

Lane I: A1AT (GTC Biotherapeutics Inc., Framingham, Mass., lot No. 080604A)

Figure 28:
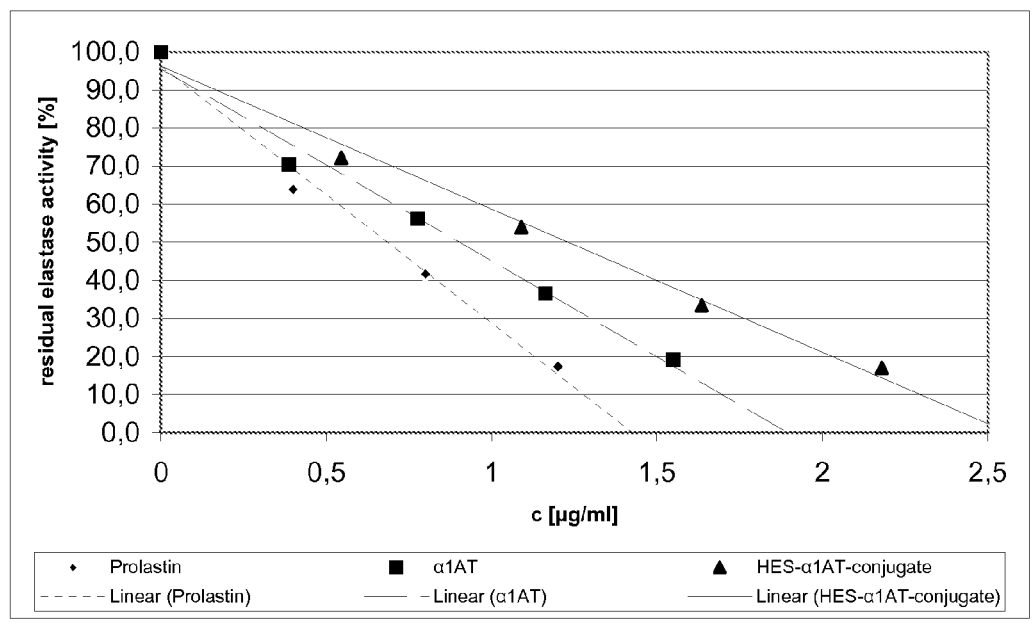

FIG. 28 is a graph showing the residual enzyme activity vs. concentration plot of Prolastin® HS (Bayer Vital GmbH, Leverkusen, Germany, Lot No. PR4HA43), A1AT (GTC Biotherapeutics Inc., Framingham, Mass., lot No. 080604A) and a HES-A1AT-conjugate synthesized as described in example 13.5

Figure 29:
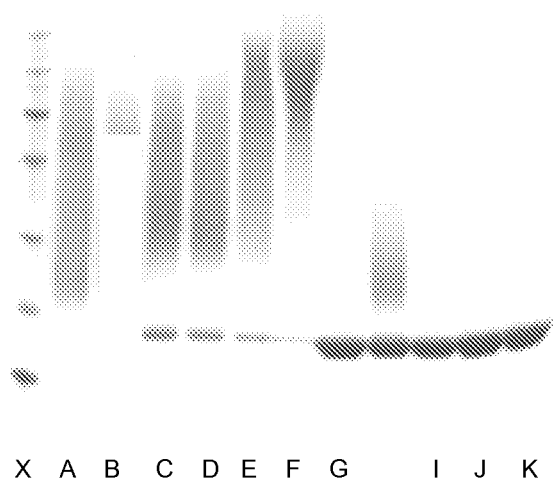

FIG. 29 shows the analysis of IFN-alpha-HES conjugates of example 14.3.1 by gel electrophoresis. A 10% Bis-Tris gel together with a MOPS SDS running buffer at reducing conditions (both Invitrogen GmbH, Karlsruhe, D) were used according to the manufacturer's instruction.

Lane X: Roti®-Mark STANDARD (Carl Roth GmbH+Co. KG, Karlsruhe, D) Molecular weight marker from top to bottom: 200 KD, 119 KD, 88 KD, 43 KD, 29 KD, 20 KD, 14.3 KD;

Lane A: Conjugation to aldehydoHES 10/0.4 as described in ex. 14.3.1, entry A;

Lane B: Conjugation to aldehydoHES 10/0.7 as described in ex. 14.3.1, entry B;

Lane C: Conjugation to aldehydoHES 30/0.4 as described in ex. 14.3.1, entry C;

Lane D: Conjugation to aldehydoHES 30/0.7 as described in ex. 14.3.1, entry D;

Lane E: Conjugation to aldehydoHES 50/0.4 as described in ex. 14.3.1, entry E;

Lane F: Conjugation to aldehydoHES 50/0.7 as described in ex. 14.3.1, entry F;

Lane G: Reaction control, without aldehydoHES as described in ex. 14.3.1, entry G;

Lane I: Reaction control, without aldehydoHES and without NaCNBH3 as described in ex. 14.3.1, entry I;

Lane J: Reaction control, with HES10/0.4 as described in ex. 14.3.1, entry J;

Lane K: Reaction control, with HES10/0.4 but without NaCNBH3 as described in ex. 14.3.1, entry K.

Figure 30:
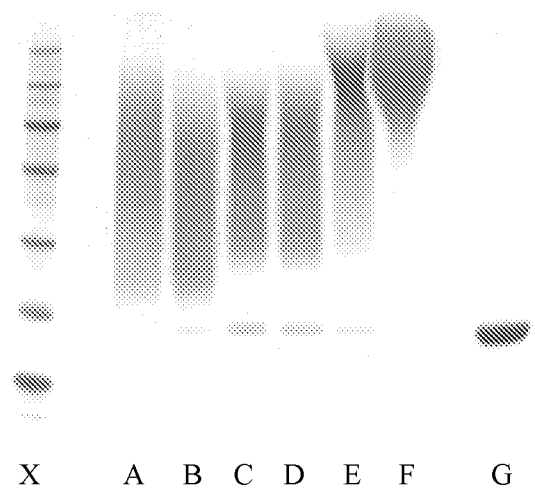

FIG. 30 shows an analysis of IFN-alpha-HES conjugates of example 14.3.2 by gel electrophoresis. A 10% Bis-Tris gel together with a MOPS SDS running buffer at reducing conditions (both Invitrogen GmbH, Karlsruhe, D) were used according to the manufacturer's instruction.

Lane X: Roti®-Mark STANDARD (Carl Roth GmbH+Co. KG, Karlsruhe, D) Molecular weight marker from top to bottom: 200 KD, 119 KD, 88 KD, 43 KD, 29 KD, 20 KD, 14.3 KD;

Lane A: Conjugation to aldehydo-HES as described in example 14.3.2 entry A;

Lane B: Conjugation to aldehydo-HES as described in example 14.3.2 entry B;

Lane C: Conjugation to aldehydo-HES as described in example 14.3.2 entry C;

Lane D: Conjugation to aldehydo-HES as described in example 14.3.2 entry D;

Lane E: Conjugation to aldehydo-HES as described in example 14.3.2 entry E;

Lane F: Conjugation to aldehydo-HES as described in example 14.3.2 entry F;

Lane G: Reaction control, with HES as described in example 14.3.2 entry G.

No reaction was observed for the reaction control G.

Figure 31:
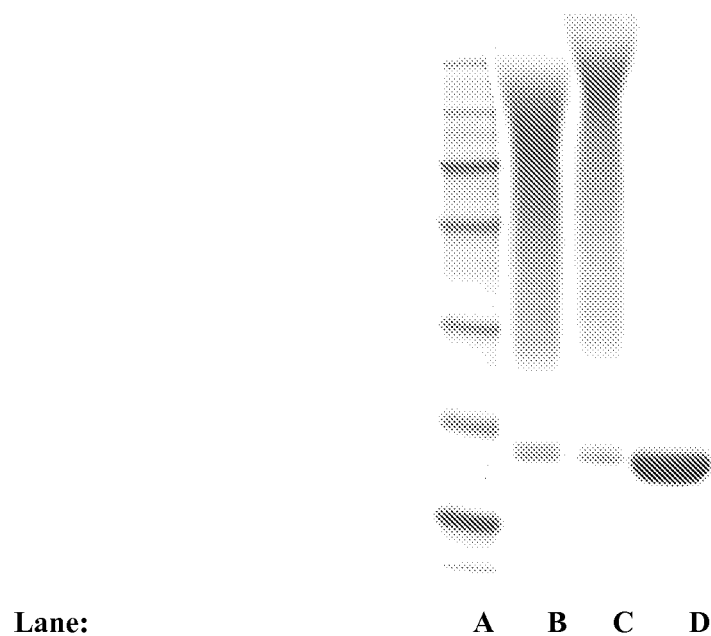

FIG. 31 shows an analysis of IFN-alpha-HES conjugates of example 14.3.3 by gel electrophoresis. A 10% Bis-Tris gel together with a MOPS SDS running buffer at reducing conditions (both Invitrogen GmbH, Karlsruhe, D) were used according to the manufacturer's instruction.

Lane A: Roti®-Mark STANDARD (Carl Roth GmbH+Co. KG, Karlsruhe, D) Molecular weight marker from top to bottom: 200 KD, 119 KD, 66 KD, 43 KD, 29 KD, 20 KD, 14.3 KD;

Lane B: Conjugation of IFNα to AldehydoHES 30/0.8 as described in 14.3.3;

Lane C: Conjugation of IFNα to AldehydoHES 130/0.7 as described in 14.3.3;

Lane D: Conjugation of IFNα to HES 10/0.4 sodium (Reaction Control) as described in 14.3.3

Figure 32:
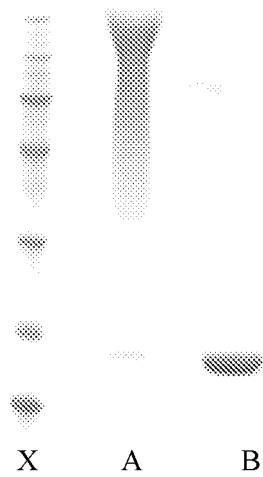

FIG. 32 shows an analysis of IFN-alpha-HES conjugates of example 14.3.4 by gel electrophoresis. A 10% Bis-Tris gel together with a MOPS SDS running buffer at reducing conditions (both Invitrogen GmbH, Karlsruhe, D) were used according to the manufacturer's instruction.

Lane X: Roti®-Mark STANDARD (Carl Roth GmbH+Co. KG, Karlsruhe, D) Molecular weight marker from top to bottom: 200 KD, 119 KD, 88 KD, 43 KD, 29 KD, 20 KD, 14.3 KD Lane A: Conjugation to aldehydo-HES as described in example 14.3.4;

Lane B: Reaction control; conjugation to HES as described in example 14.3.4.

No reaction was observed for the reaction control B.

Figure 33:
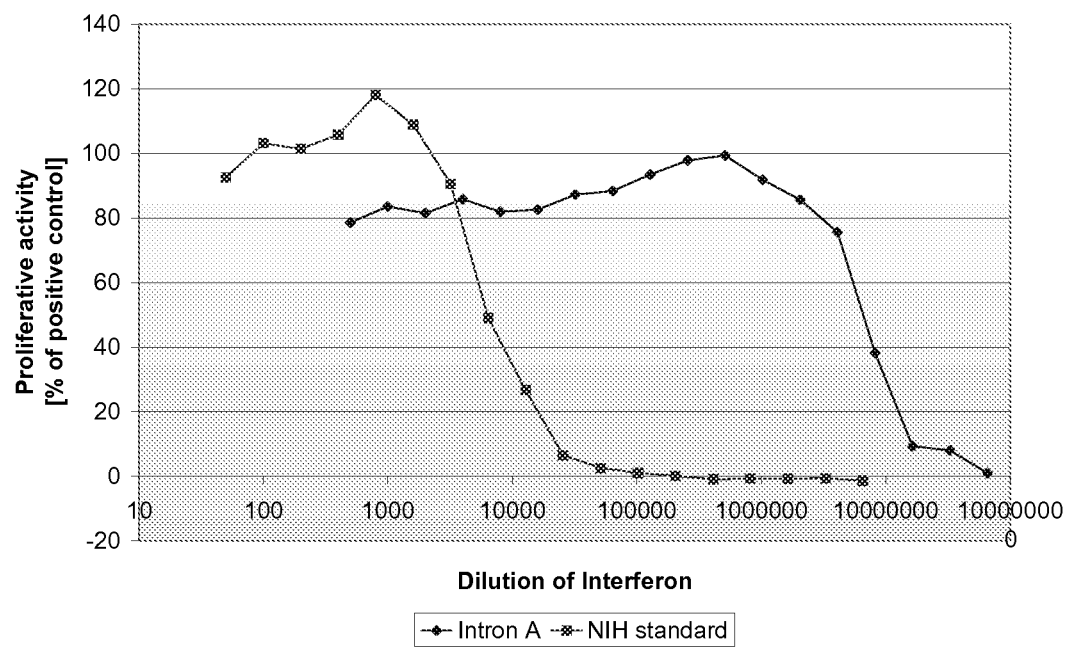

FIG. 33 is a graph showing the proliferative activity of Intron® A compared to NIH standard rhIFN-alpha 2a according to example 15.1.

Figure 34:
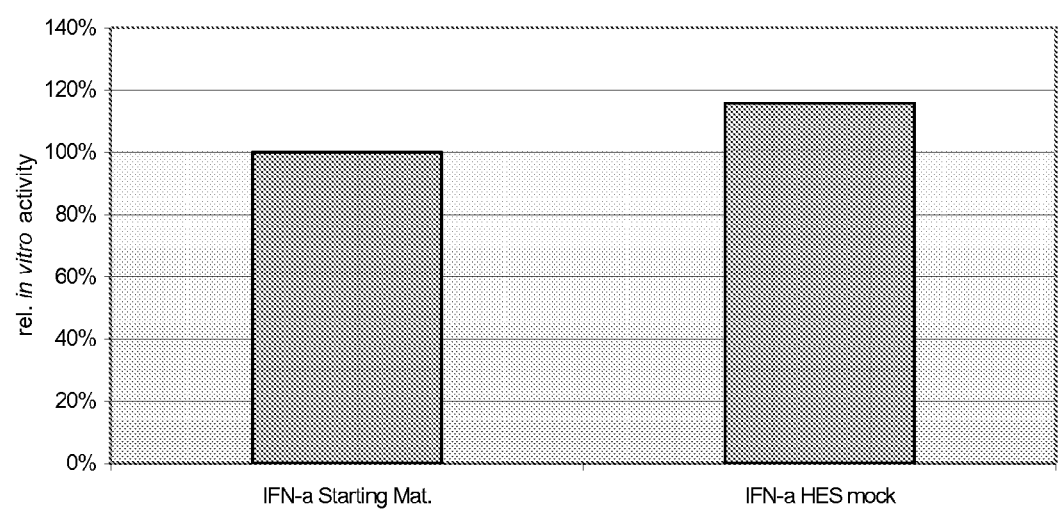

FIG. 34 is a graph showing the relative in vitro activity of mock incubated IFN-alpha-HES compared to unmodified IFN-alpha starting material according to example 15.2.

Figure 35:
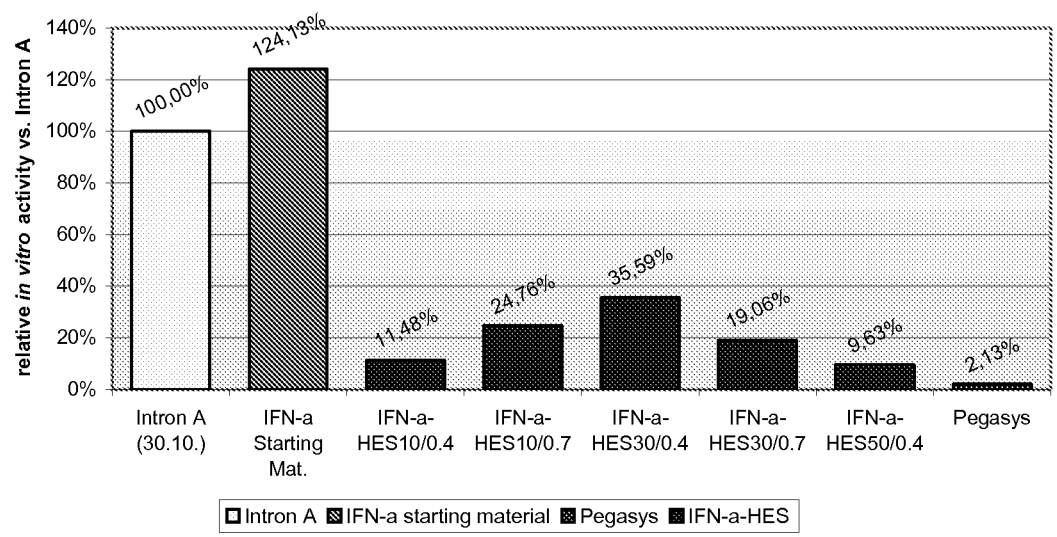

FIG. 35 is a graph showing relative in vitro activity of IFN-alpha-HES conjugates compared to unmodified IFN-alpha starting material, Intron® A and Pegasys, respectively, according to example 15.3.

Figure 36:
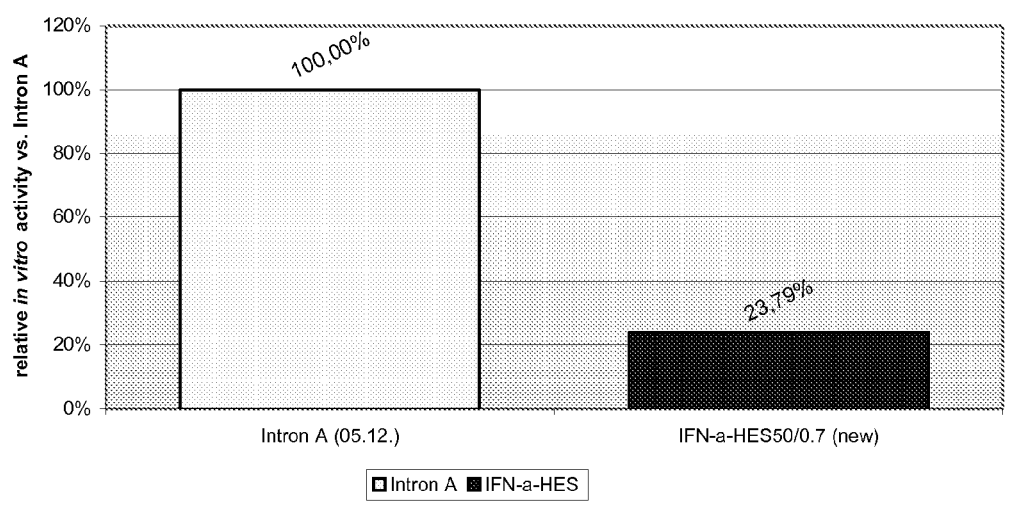

FIG. 36 is a graph showing the relative in vitro activity of IFN-alpha-HES conjugate compared to Intron® A according to example 15.4.

Figure 37:
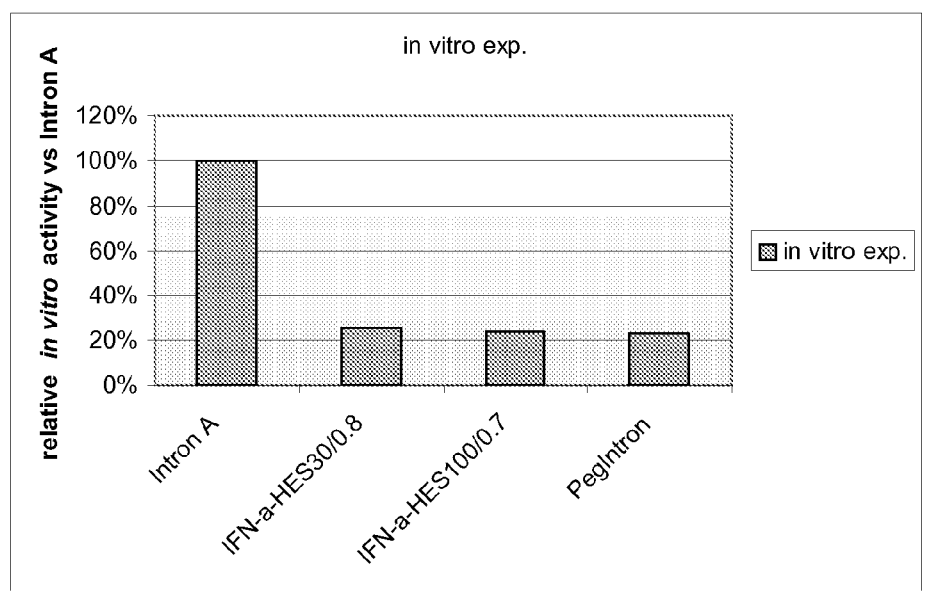

FIG. 37 is a graph showing the results of example 15.5 in a graph (antiviral activity of IFN-alpha-HES conjugates)

Figure 38:
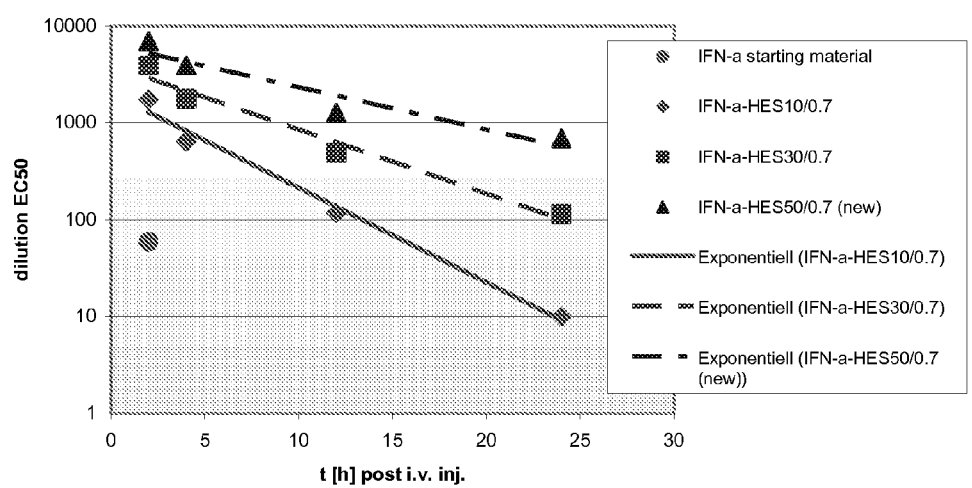

FIG. 38 is a graph showing the dilution of serum samples required to achieve a 50% protection of MDBK cells against viral infection vs. time post i.v. injection of 30 g/kg in mice. Serum from mice treated with unmodified starting material has a very low antiviral effect. Modification of IFN-alpha with HES prolongs the antiviral effect of serum substantially. The half life increases with molecular weight of HES used for modification of IFN-alpha (see example 16).

Figure 39:
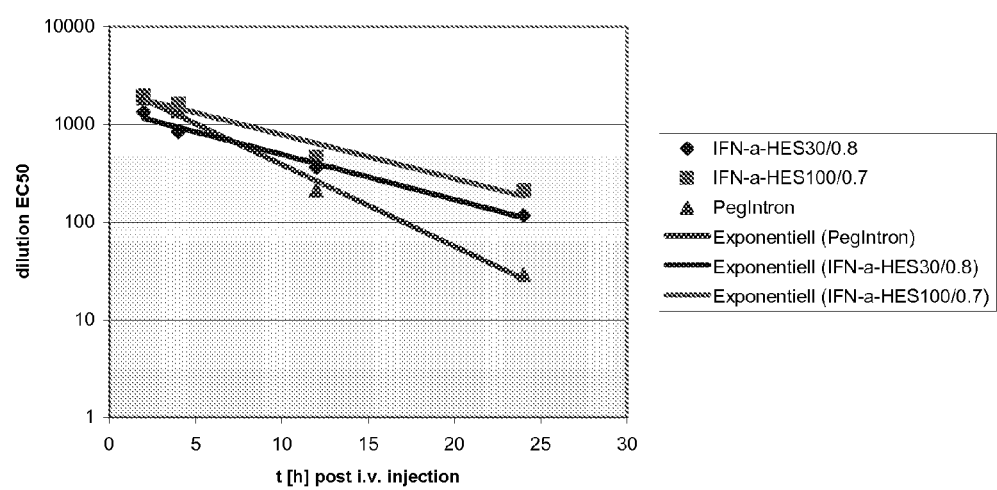

FIG. 39 is a graph showing the results of example 16.3 in a graph (antiviral activity of IFN-alpha-HES conjugates)

Figure 40:
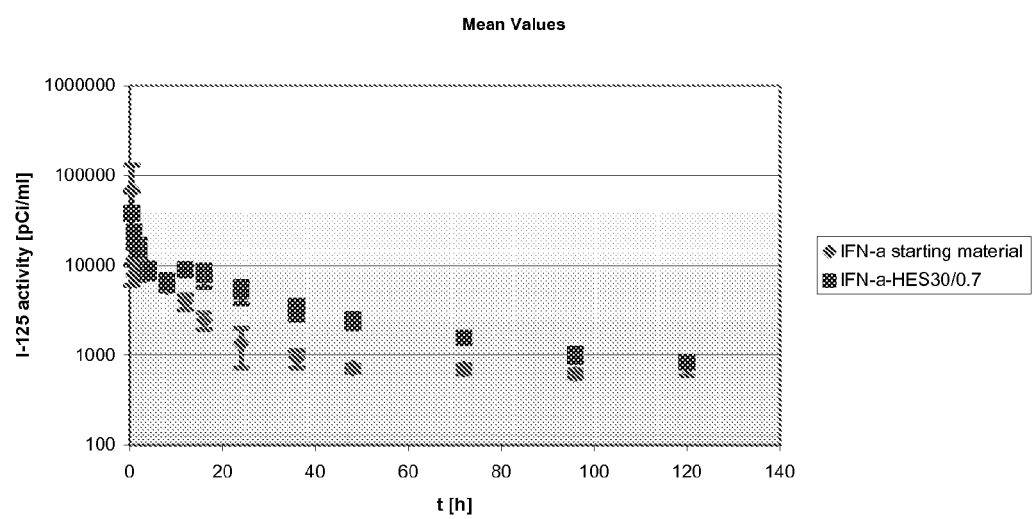
Figure 41:
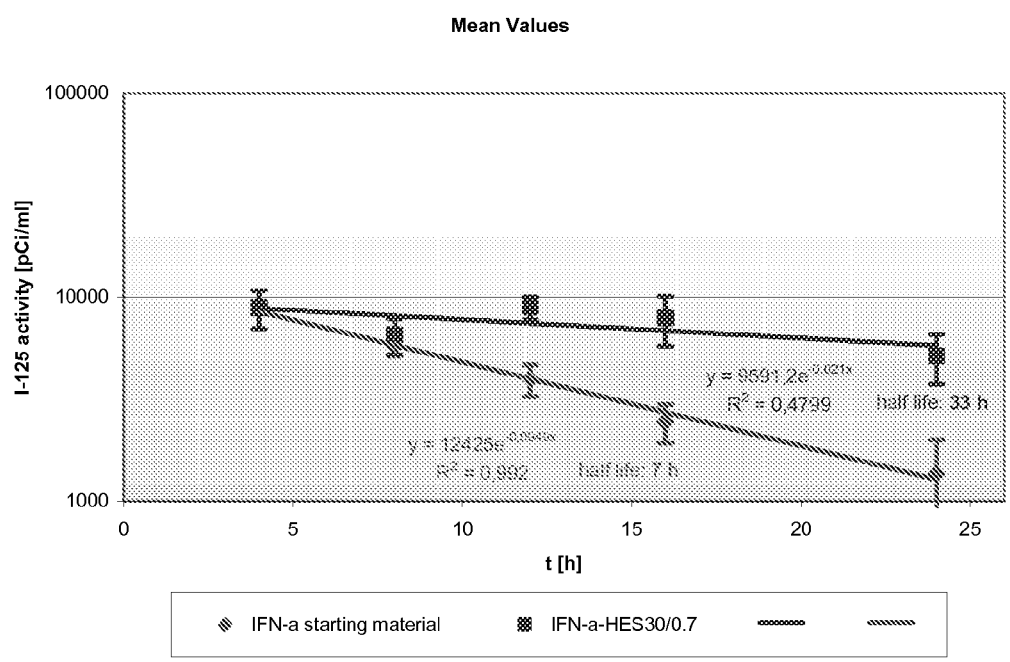

FIG. 40 is a graph showing data from the PK-Study in rabbits according to example 17. IFN-alpha-HES shows a distinct prolongation of half-life compared to the IFN-alpha starting material. For >24 h (approx. <1000 pCi/ml) the curve of the unmodified material levels off and almost no further decrease of activity can be observed FIG. 41 is a graph showing PK-Study in rabbits according to example 17. Data were evaluated in the period between 4 and 24 h. IFN-alpha-HES shows a distinct prolongation of half-life compared to the unmodified IFN-alpha starting material.

Figure 42:
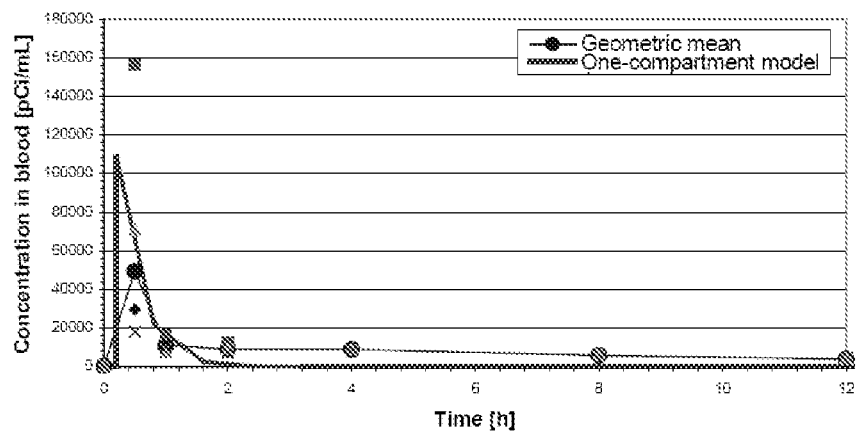
Figure 42:
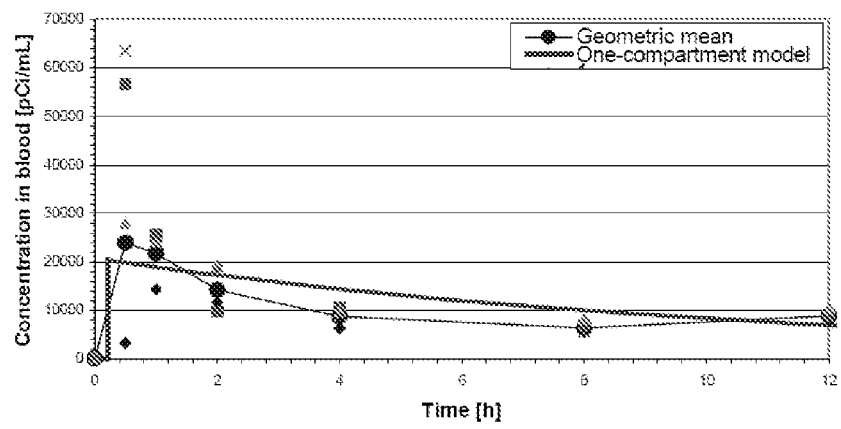

FIG. 42 is a graph showing the statistical evaluation of the PK-Study (shown: period up to 12 h) according to example 17. In the case of the unmodified starting material (see FIG. 42($a$)), the concentration dropped to almost zero during the first two hours, whereas IFNalpha-HES shows a distinctly prolonged half-life (FIG. 42($b$)).

Figure 43:
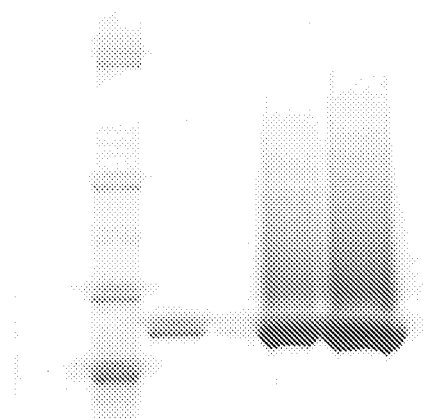

FIG. 43 shows an SDS-PAGE analysis of the crude alpha1AT-HES conjugate prepared as described in example 18.5. A 3-8% Tris-Acetate gel together with a Tris-Acetate SDS running buffer at reducing conditions (both Invitrogen GmbH, Karlsruhe, D) were used according to the manufactures instruction.

Figure 44:
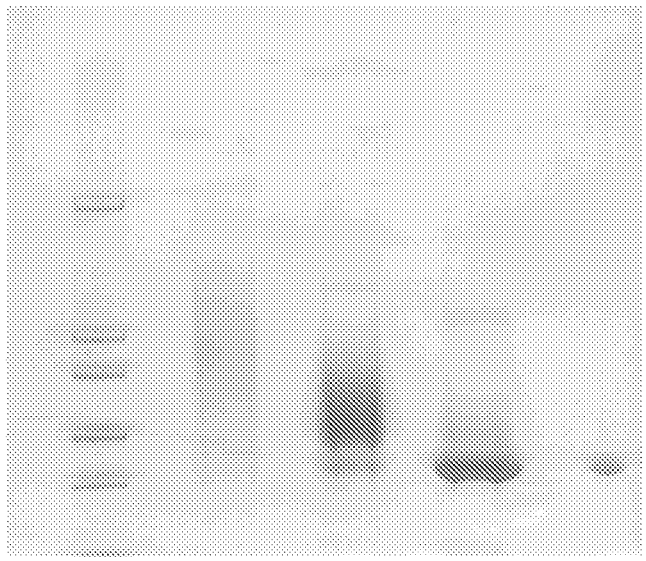

Lane A: Unstained SDS Page Protein Marker 6.5-200 KDa (SERVA Elektrophoresis GmbH, Heidelberg, D) Molecular weight marker from top to bottom: 200 KD, 116 KD, 67 KD, 45 KD, 29 KD, 21 KD, 14.3 KD, 6.5 KD;

Lane B: alpha1AT (GTC Biotherapeutics Inc., Framingham, Mass., lot No. 080604A);

Lane C: Conjugation to MaleimidoHES as described in example 18.5;

Lane D: Conjugation to MaleimidoHES as described in example 18.5 (double concentration);

FIG. 44 shows an analysis of the fractions A, B, and C collected after Ion exchange chromatography (see example 18.7). A 3-8% Tris-Acetate gel together with a Tris-Acetate SDS running buffer at reducing conditions (both Invitrogen GmbH, Karlsruhe, D) were used according to the manufacturer's instruction.

Lane 1: Unstained SDS Page Protein Marker Mark12® 2.5-200 KDa (Invitrogen GmbH, Karlsruhe, D) Molecular weight marker from top to bottom: 200 KD, 116 KD, 97 KD, 66 KD, 55 KD, 36 KD, 31 KD, 21 KD; 14 KD, 4KD Lane 2: Fraction A Lane 3: Fraction B Lane 4: Fraction C Lane 5: alpha1AT (GTC Biotherapeutics Inc., Framingham, Mass., lot No. 080604A).

DETAILED DESCRIPTION

The proteins which can be conjugated according to the invention can be characterized as follows:

Interferons are cytokines that mediate antiviral, anti-proliferative and immuno-modulatory activities in response to viral infection and other biological inducers. In contrast to IFN alpha, IFN beta is highly species-specific. There are two subtypes of IFN beta, IFN beta 1a and IFN beta 1b. When it comes to industrial production then the main difference between IFN beta 1a and IFN beta 1b is the respective cell systems utilized for their production with consequences for glycosylation and number of amino acids. IFN beta 1a is produced by mammalian cells and receives the designation 1a because its amino acid sequence is identical to that of the naturally occurring interferon beta. IFN beta 1b is produced by bacteria. Interferons, like most other mammalian proteins are modified post-translationally by glycosylation. Bacteria, however, lack the ability to glycosylate proteins and thus IFN beta 1b does not include the carbohydrate side chains found in the natural material. IFN beta 1a has 166 amino acids and a molecular weight of about 22,500 D, IFN beta 1b has 165 amino acids and a molecular weight of about 18,500 D, because the N-terminal methionin is missing in IFN beta 1b as well as the glycosylation due to the bacterial production method. The amino acid sequence of human interferon beta is given, e.g., in EP 0 218 825 A1. The crystal structure of interferon beta was reported in: *Proc. Natl. Acad. Sci. USA* 94 (1997) pp 11813-11818, Biochemistry, Karpusas M, Nolte M, Benton C B, Meier W, Lipscomb W N, Goelz S. Commercial preparations of interferon beta are Betaseron (IFN beta 1b), Avonex and Rebif (IFN beta 1a). Interferon beta 1b is manufactured by bacterial fermentation of a strain of *E. coli* that bears a genetically engineered plasmid containing the gene for human interferon beta$_{ser17}$. The native gene was obtained from human fibroblasts and altered in a way that substitutes serine for the cysteine residue found at position 17. Interferon beta 1a is produced by recombinant DNA technology using genetically engineered Chinese Hamster Ovary (CHO) cells into which the human interferon beta gene has been introduced. The amino acid sequence of IFN beta 1a is identical to that of natural fibroblast derived human interferon beta. Natural interferon beta and interferon beta 1a are glycosylated with each containing a single N-linked complex carbohydrate moiety at the Asn80. The interferon beta drugs are indicated for the treatment of relapsing remitting multiple sclerosis. However, there are many serious side effects related to the administration of the interferon beta drug products. Furthermore they are administered by injection (intramuscular or subcutanously), leading to additional risks. Reducing the side effects and easier (e.g. less frequent) administration are the reason, why lot of development work is performed to improve the properties of IFN beta. Polymer modification of proteins is a technique which is applied to improve the properties of the proteins. The mainly used technique is the modification of interferon with polyethylen glycol, known as PEGylation.

IFN alpha forms are naturally produced by monocytes/macrophages, lymphoblastoid cells, fibroblasts and a number of different cell types following induction by viruses, nucleic acids, glucocorticoid hormones, and other inductors. At least 23 different variants of IFN alpha are known. The individual proteins have molecular masses between 19-26 kD and consist of proteins with lengths of 156-166 or 172 amino acids. All IFN alpha subtypes possess a common conserved sequence region between amino acid positions 115-151 while the amino-terminal ends are variable. Many IFN alpha subtypes differ in their sequences only at one or two positions. Disulfide bonds are formed between cysteins at positions 1/98 and 29/138. The disulfide bond 29/138 is essential for biological activity while the 1/98 bond can be reduced without affecting biological activity. All IFN alpha forms contain a potential glycosylation site but most subtypes are not glycosylated. In contrast to IFN gamma, IFN alpha proteins are stable at a pH of 2. Industrial production of IFN alpha is performed using genetically modified *E. coli*. Because bacteria lack the ability to glycosylate proteins, the two variants of IFN alpha (IFN alpha 2a, and IFN alpha 2b), which are used in approved drug products, are both non-glycosylated. A major drawback of conventional IFN alpha are the side effects. A lot of work has been done on improvement of interferon alpha drugs, which are indicated for treatment of Hepatitis C. Polymer modification of proteins is a technique which is applied to improve the properties of the proteins. The mainly used technique is the modification of interferon with polyethylen glycol, known as PEGylation. Two commercially available PEGylated variants of IFN-alpha are PEGIntron (SP) and Pegasys (Roche).

Antithrombin III (AT III) is a serine protease inhibitor that inhibits thrombin and factor Xa (Travis, *Annu. Rev. Biochem.* 52: 655, 1983). To a lesser extent, factor IXa, XIa, XIIa, tPA, urokinase, trypsin, plasmin and kallikrein are also inhibited (Menache, *Semin. Hematol.* 28:1, 1991; Menache, *Transfusion* 32:580, 1992; Lahiri, *Arch. Biochem. Biophys.* 175:737, 1976). Human AT III is synthesized in the liver as a single chain glycoprotein of 432 amino acids with a molecular weight (MW) of approximately 58.000 D. Its normal plasma concentration is within the range of 14-20 mg/dL (Rosenberg, *Rev. Hematol.* 2:351, 1986; Murano, *Thromb. Res.* 18:259, 1980). The protein bears three disulfide bridges (Cys 8-128, Cys 21-95, Cys 247-430) and four N-linked carbohydrate chains (Asn 96, -135, -155, -192) which account for 15% of the total mass (Franzen, *J. Biol. Chem.* 255:5090, 1980; Peterson, *The Physiological Inhibitions of Blood Coagulation and Fibrinolysis*, Elsevier/North-Holland Biomedical Press 1979, p 43). Antithrombin is a serine proteinase inhibitor of the serpin type that is of major importance in the control of blood coagulation. AT III is the most abundant endogenous anticoagulant circulating in human plasma and participates in the regulation of clotting in both physiologic and pathologic states (Opal, *Crit. Care Med.* 2002, 30:325). It circulates in two forms with low thrombin inhibitory capacity (Pike, *J. Biol. Chem.* 272:19562, 1997; Ersdal-Badju, *Fed. Proc.* 44:404, 1985) (85-95% alpha isoform with 4 biantennary, mono- and di-sialylated oligosaccharide chains, 5-15% is the high heparin affinity beta isoform lacking glycosylation at Asn 135, 2-6 terminal sialic acid linkage). A small fraction of the circulating AT III is normally bound to proteoglycans on the surface of vascular endothelial cells. These proteoglycans are predominantly heparan sulfate, a molecule structurally similar to heparin, which is able to catalyze the inhibition of thrombin in the same way as heparin. The AT III binding to well defined pentasaccharide units of heparin causes a conformational change of the protein (Choay, *Ann. NY Acad. Sci.* 370:644, 1981; Choay, *Biochem. Biophys. Res. Commun.* 116:492, 1983; Olson, J. Biol. Chem. 266:6353, 1991; Bauer, *Semin. Hematol.* 28:10, 1991; Carell, *Thromb. Haemost.* 78:516, 1997). This binding catalyzes a 1000 fold increase of AT III inhibitory activity toward thrombin and Factor Xa (Rosenberg, *Fed. Proc.* 44:404, 1985; Bjork, "Antithrombin and related inhibitors of coagulation proteinases," in Barett, Salvesen (eds.): *Proteinase Inhibitors*, vol 17, Amsterdam, The Netherlands Elsevier Science Publishers (Biomedical Devision) 1986 p 489; Olson, *J. Biol. Chem.* 267:12528, 1992). This localization of a fraction of the AT on the endothelial surface, where enzymes of the intrinsic coagulation cascade are commonly generated, enables AT III to rapidly neutralize these hemostatic enzymes and protect natural surfaces against thrombus formation. Thus, the key properties of AT III in prevention of thrombotic events are its ability to bind the catalyst heparin, undergo the conformational change that alters its inhibitory properties, and irreversibly bind thrombin or Factor Xa thereby inhibiting their activities. AT III also has anti-inflammatory properties, several of which result from its actions in the coagulation cascade (Roemisch, *Blood Coagul Fibrinolysis.* 2002, 13:657). Activated coagulation proteases like activated factor X and thrombin contribute to inflammation, for instance by the release of pro-inflammatory mediators. Inhibition of these proteases by AT III prevents their specific interaction with cells and subsequent reactions (Roemisch, *Blood Coagul Fibrinolysis.* 2002, 13:657). Anti-inflammatory properties of AT III independent of coagulation involve direct interactions with cells leading to the release of, for instance, prostacyclin. Binding of AT III to a recently identified cellular receptor, syndecan-4, leads to the interference with the intracellular signal induced by mediators like lipopolysaccharides and, thereby, to a down-modulation of the inflammatory response (Roemisch, *Blood Coagul Fibrinolysis.* 2002, 13:657). Beside the analysis of the free AT III structure, many studies have been conducted evaluating the complexation sites for oligosaccharide units of heparin due to the importance of the heparin-AT III complex for the physiological function of AT III (Choay, *Ann. NY Acad. Sci.* 370: 644, 1981; Choay, *Biochem. Biophys. Res. Commun.* 116: 492, 1983; Olson, J. Biol. Chem. 266:6353, 1991; Bauer, *Semin. Hematol.* 28:10, 1991; Carell, *Thromb. Haemost.* 78:516, 1997). AT III can be produced following classical human plasma fractionating techniques. Affinity chromatography (heparin-sepharose) using the high affinity of heparin for AT III followed by heat treatment for virus inactivation is used for the separation from plasma. More recent alternatives are available for the AT III production are recombinant production techniques that provide a safer access to this therapeutic Protein (Levi, *Semin Thromb Hemost* 27: 405, 2001). ATryn™ is a recombinant human AT III (rh AT III) produced by Genzyme Transgenics Corp. (GTC) in transgenic goats. Detailed investigations have been conducted comparing the structural and functional properties of both plasma derived AT III (ph AT III) and rh AT III (Edmunds, *Blood,* 91:4561, 1998). Based on this experiments rh AT III is structurally identical to ph AT III with the exception of the glycosylation. Oligomannose structures were found on Asn 155 of the transgenically produced material whereas complex structures are detected in the case of the plasma derived protein. Some of the galactose units of the pd AT III are substituted by GalNac units in the rh AT III. A higher degree of fucosylation in rh AT III is another difference. Finally the sialylation pattern of both proteins differs in two ways: The rh AT III is less sialylated and contains N-acetyl- as well as N-glycolylneuramin acids. This structural difference between the two carbohydrate parts of both molecules also results in different biochemical properties. The following AT III drugs are available on the European hospital market. (Source: IMS-ATC group 2001): Kybernin (Aventis Behring), AT III (Baxter, Grifols), Atenativ (Pharmacia), Aclotine (LFB), Grifols (Anbin).

Factor VII participates in the intrinsic blood coagulation cascade of proteinases and promoting hemostatsis by activating the extrinsic pathway of the coagulation cascade. F VII is converted to factor VIIa by factor Xa, factor XIIa, factor IXa, or thrombin by minor proteolysis. In the presence of tissue factor and calcium ions, factor VIIa then converts factor X to factor Xa by limited proteolysis. Factor VIIa will also convert factor IX to factor IXa in the presence of tissue factor and calcium. Factor VII is a vitamin K-dependent glycoprotein consisting of 406 amino acid residues (MW 50 K Dalton). Factor VII is either produced by conventional extraction from donated human plasma or, more recently, using recombinant systems. Novo Nordisk uses Baby hamster kidney (BHK) cells for production of NovoSeven®. Expressed as the single-chain protein of 406 amino acids with a nominal molecular weight of 55 kDa (Thim, L. et al., *Biochemistry* 27:7785-7793 (1988). The molecule bears four carbohydrate side chains. Two O-linked carbohydrate side chains at Ser 52, 60 and two N-linked carbohydrate side chains at Asn 145, 322 (Thim, L. et al., *Biochemistry* 27:7785-7793(1988).

Factor VIII participates in the intrinsic blood coagulation cascade of proteinases and serves as a cofactor in the reaction of factor IXa converting factor X to the active form, factor Xa, which ultimately leads to the formation of a fibrin clot. A lack or instability of factor VIII leads to haemophilia A, a common recessive x-linked coagulation disorder. The frequency of haemophilia A is 1-2 in 10,000 male births in all ethnic groups. Patients either do express levels of factor VIII well below normal or belong to the so-called group of crm (cross-reacting material) positive patients (approximately 5% of patients) that have considerable amount of factor VIII in their plasma (at least 30% of normal), but the protein is non-functional. About 50% of all patients have severe haemophilia a with a factor VIII activity of less than 1% of normal; they have frequent spontaneous bleeding into joints, muscles and internal organs.

Mild haemophilia A, which occurs in 30-40% of patients, is associated with an activity of 5-30% of normal. Bleeding occurs only after significant trauma or surgery. Moderately severe haemophilia a occurs in about 10% of patients; Here, factor VIII activity is 2-5% of normal, and bleeding occurs already after minor trauma.

The human in-vivo half-life of factor VIII is usually 10-15 hours but it has to be noted that the release, stability, and degradation kinetics are also influenced by another factor, the van Willebrand factor.

Factor VIII is either produced by conventional extraction from donated human plasma or, more recently, using recombinant systems. Bayer uses Baby hamster kidney (BHK) cells for production of Kogenate, whereas Baxter uses Chinese Hamster Ovary (CHO) cells for its product Recombinate. as the full single-chain protein of 2351 amino acids with a nominal molecular weight of 267 kDa (Toole et al., 1984, *Nature* 312: 342) or in different versions, where the full B-domain or parts of it are deleted in order to have a product that is more stable and gives a higher yield in production (Bhattacharyya et al. 2003, CRIPS 4/3: 2-8). The precursor product is processed into two polypeptide chains of 200 and 80 kDa in the Golghi and the two chains which are held together by metal ion(s) are expressed in the blood (Kaufman et al., 1988, *J. Biol. Chem.,* 263: 6352).

Procoagulant activity requires further thrombin cleavage to yield 54 kDa and 44 kDa fragments of the heavy chain plus a 72 kDa light-chain fragment (Aly et al., 1992, *Proc. Natl. Acad. Sci. USA:* 4933). In factor VIII concentrates derived from human plasma several fragmented fully active factor VIII forms have thus been described (Anderson et al., 1986, *Proc. Natl. Acad, Sci.* 83: 2979).

A common side effect of the administration of plasmatic or recombinant factor VIII are immunological reactions in quite a high number of patients (up to 30%), that forfeit the therapeutic value. In the past, various attempts to tolerate the patients by oral induction of tolerance were started but results were not all too encouraging. New genetic means of inducing tolerance have been proposed but not yet found widespread application. A hesylated protein is expected to have a lower degree of immunogenicity and could thus reduce this complication.

Factor VIII is very rich in lysine residues (over 220 of the overall 2350 amino acids; see attachment 1), that could be used for the Reductive Amination approach.

Factor IX is a vitamin K-dependent plasma protein that participates in the intrinsic pathway of blood coagulation by converting factor X to its active form in the presence of Ca(2+) ions, phospholipids, and factor VIIIa. Factor IX is a glycoprotein with an approximate molecular mass of 55,000 Da consisting of 415 amino acids in a single chain (Yoshitake S. et al., *Biochemistry* 24:3736-3750(1985)). Factor IX is either produced by conventional extraction from donated human plasma or, more recently, using recombinant systems. Wyeth uses Chinese hamster ovary (CHO) cells for production of BeneFIX®. It has a primary amino acid sequence that is identical to the Ala[148] allelic form of plasma-derived factor IX, and has structural and functional characteristics similar to those of endogenous factor IX. The protein bears eight carbohydrate side chains. Six O-linked carbohydrate side chains at Ser 53, 61 and at Threonine 159, 169, 172, 179 and two N-linked carbohydrate side chains at Asn 157, 167 (Yoshitake S. et al., *Biochemistry* 24:3736-3750(1985); Balland A. et al., *Eur J Biochem.* 1988; 172(3):565-72).

Human granulocyte macrophage colony stimulating factor (hGM-CSF) is an early acting factor essential for regulation and differentiation of haematopoietic progenitor cells as well as for stimulating functional activation of mature cell populations. It has been cloned and expressed in yeast, bacteria, insect, plant and mammalian cells, resulting in a protein that varies in structure, composition, serum half-life and functions in vivo (Donahue, R. E. et al. *Cold Spring Harbor Symp. Quant. Biol.* 1986, 51: 685-692). Natural and mammalian cell-derived hGM-CSF is a 127 amino acid protein and it contains both N- and O-glycans. It is highly heterogeneous due to the different states of occupancy of one or two N-glycosylation sites and the O-glycosylation site(s) (Cebon, J. et al. *J. Biol. Chem.* 1990, 265: 4483-4491; Kaushansky, K. et al. *Biochemistry* 1987, 26: 4861-4867; Armitage, J. O. *Blood* 1998, 92: 4491-4508). This lymphokine is of clinical interest due to its potential the treatment of myeloid leukemia and its ability to stimulate the granulocyte and macrophage production in patients suffering immunodeficiency or being suppressed by disease or radiation and/or chemotherapy (reviewed by Moonen, P. et al. *Proc. Natl. Acad. Sci. USA.* 1987, 84: 4428-4431). Several studies have suggested that hGM-CSF lacking N-linked carbohydrate has a significantly higher specific activity in vitro when compared to the native recombinant cytokine (Armitage, J. O. *Blood* 1998, 92: 4491-4508; Okamoto, M. et al. *Arch. Biochem. Biophys.* 1991, 286: 562-568; Hovgaard, D. et al. *Eur. J. Clin. Inv.* 1992, 22: 45-49). However, there are numerous evidences supporting the key role of carbohydrate chains in hGM-CSF functions, such as pharmacokinetic (Cebon, J. et al. *J. Biol. Chem.* 1990, 265: 4483-4491; Hovgaard, D.; et al. *Eur. J. Clin. Inv.* 1992, 22: 45-49; Denzlinger, C. et al. *Blood* 1993, 81: 2007-2013), toxicity (Denzlinger, C. et al. *Blood* 1993, 81:2007-2013) and immunogenicity (Donahue, R. E. et al. *Cold Spring Harbor Symp. Quant. Biol.* 1986, 51: 685-692; Revoltella, R. et al. *Leukemia and Lymphoma* 1997, 26: 29-34; Ragnhammar, P. et al. *Blood* 1994, 84:4078-4087; Wadhwa, M. et al. *Clinical Cancer Research* 1999, 5:1351-1361; Gribben, J. G. et al. *Lancet* 1990, 335: 434-437). In view of the antigenecity which has been frequently reported for GM-CSF clinical products from *E. coli* and from yeast, the chemical modification strategy is suggested to represent a promising approach for this product including those manufactured from non-mammalian expression systems. GM-CSF preparations are available under the names Leukine (Immunex) and Leucomax (Novartis). GM-CSF is used in myeloid reconstitution following bone marrow transplant, bone marrow transplant engraftment failure or delay, mobilization and following transplantation of autologous peripheral blood progenitor cells, and following induction chemotherapy in older adults with acute myelogenous leukemia.

Alpha1-Antitrypsin (A1AT, also referred to as alpha1-proteinase inhibitor) is a proteinase inhibitor that has been shown to inhibit virtually all mammalian serine proteinases (Travis *Ann. Rev. Biochem.* 52 (1983) p. 655) including neutrophil elastase, thrombin, factors Xa and XIa. A1AT is a single chain glycoprotein synthesized in the liver with 394 amino acids and a molecular weight of 53 kD. The plasma concentration is within a range of 1-1.3 g/l. The presence of only one cysteine in the whole protein does not allow the formation of intramolecular disulfide bridges. The molecule bears three carbohydrate side chains (Asn 46, 83, 247) (Mega *J. Biol. Chem.* 255 (1980) p. 4057; Mega *J. Biol. Chem.* 255 (1980) p. 4053; Caren *FEBS Letters* 135 (1981) p. 301; Hodges *Biochemistry* 21 (1982) p. 2805) that represent 12% of the molecular weight. Two types of carbohydrate chains were discovered having a bi- or triantennary structure, respectively (Hodges *J. Biol. Chem.* 254 (1979) p. 8208). Human A1AT occurs in at least twenty different forms in the general population. This micro-heterogenicity is a result of variable amounts of the two types of carbohydrate chains. The key function is the activity control of neutrophil elastase (Travis *Ann. Rev. Biochem.* 52 (1983) p. 655). An uncontrolled activity of elastase leads to an attack on epithelial tissues with the result of irreparable damage. During the inactivation process A1AT acts as a substrate for elastase binding to the active center of the protease wich is subsequently inactivated by this complex formation. A deficiency of A1AT causes e.g. pulmonary emphysema which is in connected with a damage of the pulmonary epithelium. The distribution of the two types of carbohydrate side chains of A1AT to the three N-glycosylation sites of A1AT is different for each isotype of A1AT. The classical production of A1AT is conducted in human plasma fractionation using different affinity-chromatography steps. However a more recent way of producing A1AT is the use of recombinant techniques. PPL Therapeutics has developed a process that allows to recover recombinant human A1AT (rHA1AT) from the milk of transgenic sheep (Olman *Biochem. Soc. Symp.* 63 (1998) p. 141; Tebbutt *Curr. Opin. Mol. Ther.* 2 (2000) p. 199; Carver *Cytotechnology* 9 (1992) p. 77; Wright *Biotechnology (NY)* 9 (1991) p. 830). With respect to the protein part of the molecule the rhA1AT shows an identical structure compared to pdA1AT. But—as is the case for other recombinant produced human proteins—differences occur in the carbohydrate side chains, especially with regard to the amount of sialic acid residues.

The tissue type plasminogen activator (tPA) is a trypsine like serine protease important in clot lysis. In the presence of a fibrin clot, tPA converts plasminogen to plasmin, which degrades fibrin. TPA exhibits enhanced activity in the presence of fibrin and as a result, causes fibrin-specific plasminogen activation (M. W. Spellman, L. J. Basa, C. K. Leonard, J. A. Chakel, J. V. O'Connor, *J. Biol. Chem.* 264 (1989) p. 14100). Plasmin solubilizes fibrin, yielding fibrin degradation products. Through a positive feedback mechanism, fibrin enhances its own degradation by stimulating tPA mediated plasminogen activation (R. J. Stewart et. al. *J. Biol. Chem.* 275 (2000) pp. 10112-10120). htPA is a physiological activator of fibrinolysis, which is present in different types of tissues. It is a glycoprotein with a molecular weight of approx. 68 kD. In native form tPA exists in a one-chain-form (single-chain tissue-type plasminogen activator, sctPA), which can be converted by cleavage of plasmin at the peptide bond Arg 275-Ile 276 to a two chain structure (two-chain tissue-type plasminogen activator, tctPA). For therapy of fibrinolysis it is produced recombinant as rtPA (recombinant tissue-type plasminogen activator). Different types of tPA exist showing structural differences in the carbohydrate structure. Type I tPA has N-linked oligosaccharides at amino acids Asn117, Asn184 and Asn448. Type II tPA is glycosylated at Asn117 and Asn448. Both types contain an O-linked fucose residue at Thr61 (K. Mori et. al. *J. Biol. Chem.* 270 (1995) pp. 3261-3267). The carbohydrate structure of tPA expressed in CHO-cells was investigated, showing a large variety of di-, tri- and tetraantennary structures of the sugar chains (M. W. Spellman, L. J. Basa, C. K. Leonard, J. A. Chakel, J. V. O'Connor, *J. Biol. Chem.* 264 (1989) p. 14100). The primary structure of tPA contains several cysteines, that are believed to be cross-linked plus a free cysteine residue at site 83, which may interact with another tPA, forming a dimer. Several results indicate that the in-vivo clearance of tPA is influenced by the carbohydrate structure, particularly by the high mannose oligosaccharide attached at site Asn117. Another proposed clearance mechanism involves the recognition of the O-linked fucose residue at Thr61 by a high affinity receptor on hepatocytes. This residue is close to Cys83. A bioengineered tPA (TNK-tPA) was developed to prolong the half-life. The glycosylation site at position 117 was shifted to position 103 by substituting Asparagine at site 117 with Glutamine and Threonine at site 103 substituted with Asparagine. TNK-tPA is resistant to inactivation by plasminogen activator inhibitor 1 because of a tetra-alanine substitution in the protease domain (R. J. Stewart et. al. *J. Biol. Chem.* 275 (2000) pp. 10112-10120). TNK-tpA is on the market as Tenecteplase® (Boehringer Ingelheim) and can be administered as a single intravenous bolus, while tPA has to be administered as a bolus followed by an infusion.

Activated Protein C (APC) is a modulator of the coagulation and inflammation associated with severe sepsis. Activated Protein C is converted from its inactive precursor (protein C) by thrombin coupled to thrombomodulin. This complex cleaves off a short N-terminal activation peptide form the heavy chain of protein C, resulting in the activated protein C. Drotrecogin alpha (activated) is a recombinant human activated protein C (rhAPC) with an amino acid sequence identical to plasma derived activated protein C and with similar properties. Activated protein C is marketed by Eli Lilly as Xigris®. It is produced in a human cell line (HEK293), into which the protein C expression vectors were introduced. This particular cell line was used due to its ability to perform the correct series of complex post-translational modifications that are required for functional activity. Recombinant human activated protein C is a 2-chain glycoprotein containing 4 N-glycosylation sites and 12 disulfide bonds. The heavy chain contains 250 amino acids, of which seven residues are cysteines and it has three N-linked glycosylation sites (Asn-248, Asn-313 and Asn-329). The seven cysteine residues form three disulfide bonds within the heavy chain and one disulfide bond between the chains. The light chain contains one N-linked glycosylation site (Asn-97) and 17 cysteine residues, which form eight disulfide bonds within the light chain and one disulfide bond to the heavy chain. The first nine glutamic acids on the light chain are gamma carboxylated (Gla) and aspartic acid 71 is beta hydroxylated. rhAPC has an identical amino acid sequence to the human plasma-derived activated protein C, but differs from the latter in its glycosylation pattern. Activated protein C is a protease belonging to the serine protease family and plays a major role in the regulation of coagulation. Basis for the antithrombotic function of activated protein C is its ability to inhibit thrombin function. In addition, activated protein C is an important modulator of inflammation associated with severe sepsis. Endogenous serine protease inhibitors are natural inhibitors for activated protein C, causing activated protein C to have a very short circulatory activity half-life (less than 30 min) in vivo. Clearance of activated protein C from the circulation is mediated by a combination of at least three processes including the inhibition of the enzymatic activity of activated protein C by endogenous protease inhibitors, the clearance of activated protein C and/or activated protein C-serine protease inhibitor complexes by organs such as liver and kidney, and the degradation of activated protein C and/or activated protein C-serine protease inhibitor complexes by circulating or tissue proteases. Phase I clinical studies with 24 h-infusion at 24 µg/kg/h resulted in a steady state plasma concentration of 70 ng/ml. The half-life of rhAPC measured at the end of an infusion was 0.5-1.9 h. Plasma rhAPC concentrations fell below the detection limit of 10 ng/ml within 2 h after termination of the infusion. Due to its short physiological and pharmacokinetic half-life, activated protein C is continuously infused at a certain rate to maintain the desired plasma concentration in clinical use in sepsis therapy. Some effort is made to improve the pharmacokinetic profile of activated protein C. For example D. T. Berg et. al. Proc. Natl. Acad. Sci. USA 100 (2003) pp. 4423-4428, describe an engineered variant of activated protein C with a prolonged plasma half-life.

In the context of the present invention, the term "hydroxyalkyl starch" (HAS) refers to a starch derivative which has been substituted by at least one hydroxyalkyl group. A preferred hydroxyalkyl starch of the present invention has a constitution according to formula (I)

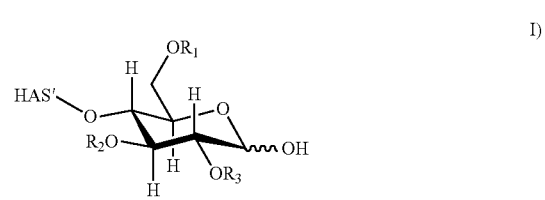

wherein the reducing end of the starch molecule is shown in the non-oxidized form and the terminal saccharide unit is shown in the acetal form which, depending on e.g. the solvent, may be in equilibrium with the aldehyde form.

The term hydroxyalkyl starch as used in the present invention is not limited to compounds where the terminal carbohydrate moiety comprises hydroxyalkyl groups $R_1$, $R_2$, and/or $R_3$ as depicted, for the sake of brevity, in formula (I), but also refers to compounds in which at least one hydroxy group present anywhere, either in the terminal carbohydrate moiety and/or in the remaining part of the starch molecule, HAS', is substituted by a hydroxyalkyl group $R_1$, $R_2$, or $R_3$.

Hydroxyalkyl starch comprising two or more different hydroxyalkyl groups are also possible.

The at least one hydroxyalkyl group comprised in HAS may contain two or more hydroxy groups. According to a preferred embodiment, the at least one hydroxyalkyl group comprised in HAS contains one hydroxy group.

The expression "hydroxyalkyl starch" also includes derivatives wherein the alkyl group is mono- or polysubstituted. In this context, it is preferred that the alkyl group is substituted with a halogen, especially fluorine, or with an aryl group. Furthermore, the terminal hydroxy group of a hydroxyalkyl group may be esterified or etherified.

Furthermore, instead of alkyl, also linear or branched substituted or unsubstituted alkene groups may be used.

Hydroxyalkyl starch is an ether derivative of starch. Besides of said ether derivatives, also other starch derivatives can be used in the context of the present invention. For example, derivatives are useful which comprise esterified hydroxy groups. These derivatives may be e.g. derivatives of unsubstituted mono- or dicarboxylic acids with 2-12 carbon atoms or of substituted derivatives thereof. Especially useful are derivatives of unsubstituted monocarboxylic acids with 2-6 carbon atoms, especially derivatives of acetic acid. In this context, acetyl starch, butyryl starch and propinoyl starch are preferred.

Furthermore, derivatives of unsubstituted dicarboxylic acids with 2-6 carbon atoms are preferred.

In the case of derivatives of dicarboxylic acids, it is useful that the second carboxy group of the dicarboxylic acid is also esterified. Furthermore, derivatives of monoalkyl esters of dicarboxylic acids are also suitable in the context of the present invention.

For the substituted mono- or dicarboxylic acids, the substitute groups may be preferably the same as mentioned above for substituted alkyl residues.

Techniques for the esterification of starch are known in the art (see e.g. Klemm D. et al, Comprehensive Cellulose Chemistry Vol. 2, 1998, Whiley-VCH, Weinheim, N.Y., especially chapter 4.4, Esterification of Cellulose (ISBN 3-527-29489-9).

According to a preferred embodiment of the present invention, hydroxyalkyl starch according to formula (I) is employed.

In formula (I), the saccharide ring described explicitly and the residue denoted as HAS' together represent the preferred hydroxyalkyl starch molecule. The other saccharide ring structures comprised in HAS' may be the same as or different from the explicitly described saccharide ring.

As far as the residues $R_1$, $R_2$ and $R_3$ according to formula (I) are concerned there are no specific limitations. According to a preferred embodiment, $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms in the respective alkyl residue or a group $(CH_2CH_2O)_n$—H, wherein n is an integer, preferably 1, 2, 3, 4, 5 or 6. Hydrogen and hydroxyalkyl groups having of from 2 to 10 are preferred. More preferably, the hydroxyalkyl group has from 2 to 6 carbon atoms, more preferably from 2 to 4 carbon atoms, and even more preferably from 2 to 4 carbon atoms. "Hydroxyalkyl starch" therefore preferably comprises hydroxyethyl starch, hydroxypropyl starch and hydroxybutyl starch, wherein hydroxyethyl starch and hydroxypropyl starch are particularly preferred and hydroxyethyl starch is most preferred.

The alkyl, aryl, aralkyl and/or alkaryl group may be linear or branched and optionally suitably substituted.

Therefore, the present invention also relates to a method as described above wherein $R_1$, $R_2$ and $R_3$ are independently hydrogen or a linear or branched hydroxyalkyl group with from 1 to 6 carbon atoms.

Thus, $R_1$, $R_2$ and $R_3$ preferably may be hydroxyhexyl, hydroxypentyl, hydroxybutyl, hydroxypropyl such as 2-hydroxypropyl, 3-hydroxypropyl, 2-hydroxyisopropyl, hydroxyethyl such as 2-hydroxyethyl, hydrogen and the 2-hydroxyethyl group being especially preferred.

Therefore, the present invention also relates to a method and a conjugate as described above wherein $R_1$, $R_2$ and $R_3$ are independently hydrogen or a 2-hydroxyethyl group, an embodiment wherein at least one residue $R_1$, $R_2$ and $R_3$ being 2-hydroxyethyl being especially preferred.

Hydroxyethyl starch (HES) is most preferred for all embodiments of the present invention.

Therefore, the present invention relates to the method and the conjugate as described above, wherein the polymer is hydroxyethyl starch and the polymer derivative is a hydroxyethyl starch derivative.

Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., 1987, Krankenhauspharmazie, 8(8), 271-278; and Weidler et al., 1991, Arzneim.-Forschung/Drug Res., 41, 494-498).

Amylopectin consists of glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. There are two possibilities of describing the substitution degree:

1. The degree of substitution can be described relatively to the portion of substituted glucose monomers with respect to all glucose moieties.
2. The degree of substitution can be described as the molar substitution, wherein the number of hydroxyethyl groups per glucose moiety are described.

In the context of the present invention, the degree of substitution, denoted as DS, relates to the molar substitution, as described above (see also Sommermeyer et al., 1987, Krankenhauspharmazie, 8(8), 271-278, as cited above, in particular p. 273).

HES solutions are present as polydisperse compositions, wherein each molecule differs from the other with respect to the polymerisation degree, the number and pattern of branching sites, and the substitution pattern. HES is therefore a mixture of compounds with different molecular weight. Consequently, a particular HES solution is determined by average molecular weight with the help of statistical means. In this context, $M_n$ is calculated as the arithmetic mean depending on the number of molecules. Alternatively, $M_w$ (or MW), the weight mean, represents a unit which depends on the mass of the HES.

In the context of the present invention, hydroxyethyl starch may preferably have a mean molecular weight (weight mean) of from 1 to 300 kD. Hydroxyethyl starch can further exhibit a preferred molar degree of substitution of from 0.1 to 3, preferably 0.1 to 2, more preferred, 0.1 to 0.9, preferably 0.1 to 0.8, and a preferred ratio between $C_2$:$C_6$ substitution in the range of from 2 to 20 with respect to the hydroxyethyl groups.

The term "mean molecular weight" as used in the context of the present invention relates to the weight as determined according to the LALLS-(low angle laser light scattering)-GPC method as described in Sommermeyer et al., 1987, Krankenhauspharmazie, 8(8), 271-278; and Weidler et al., 1991, Arzneim.-Forschung/Drug Res., 41, 494-498. For mean molecular weights of 10 kD and smaller, additionally, the calibration was carried out with a standard which had previously been qualified by LALLS-GPC.

According to a preferred embodiment of the present invention, the mean molecular weight of hydroxyethyl starch employed is from 1 to 300 kD, preferably from 2 to 200 kD, more preferably of from 3 to 100 kD, more preferably of from 4 to 70 kD.

An example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7.

An example for HES with a mean molecular weight of about 130 kD is Voluven® from Fresenius. Voluven® is an artifical colloid, employed, e.g., for volume replacement used in the therapeutic indication for therapy and prophylaxis of hypovolaemia. The characteristics of Voluven® are a mean molecular weight of 130,000+/−20,000 D, a molar substitution of 0.4 and a C2:C6 ratio of about 9:1.

Therefore, the present invention also relates to a method and to conjugates as described above wherein the hydroxyalkyl starch is hydroxyethyl starch having a mean molecular weight of from 4 to 100 kD, preferably 4 to 70 kD.

Preferred ranges of the mean molecular weight are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD.

According to particularly preferred embodiments of the present invention, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

As to the upper limit of the molar degree of substitution (DS), values of up to 3.0 such as 0.9, 1.0, 1.1, 1.2, 1.3, 1.4, 1.5, 1.6, 1.7, 1.8, 1.9 or 2.0 are also possible, values of below 2.0 being preferred, values of below 1.5 being more preferred, values of below 1.0 such as 0.7, 0.8 or 0.9 being still more preferred.

Therefore, preferred ranges of the molar degree of substitution are from 0.1 to 2 or from 0.1 to 1.5 or from 0.1 to 1.0 or from 0.1 to 0.9 or from 0.1 to 0.8. More preferred ranges of the molar degree of substitution are from 0.2 to 2 or from 0.2 to 1.5 or from 0.2 to 1.0 or from 0.2 to 0.9 or from 0.2 to 0.8. Still more preferred ranges of the molar degree of substitution are from 0.3 to 2 or from 0.3 to 1.5 or from 0.3 to 1.0 or from 0.3 to 0.9 or from 0.3 to 0.8. Even more preferred ranges of the molar degree of substitution are from 0.4 to 2 or from 0.4 to 1.5 or from 0.4 to 1.0 or from 0.4 to 0.9 or from 0.4 to 0.8.

As far as the degree of substitution (DS) is concerned, DS is preferably at least 0.1, more preferably at least 0.2, and more preferably at least 0.4. Preferred ranges of DS are from 0.1 to 0.8, more preferably from 0.2 to 0.8, more preferably from 0.3 to 0.8 and even more preferably from 0.4 to 0.8, still more preferably from 0.1 to 0.7, more preferably from 0.2 to 0.7, more preferably from 0.3 to 0.7 and more preferably from 0.4 to 0.7. Particularly preferred values of DS are, e.g., 0.1, 0.2, 0.3, 0.4, 0.5, 0.6, 0.7 or 0.8, with 0.2, 0.3, 0.4, 0.5, 0.6, 0.7 or 0.8 being more preferred, 0.3, 0.4, 0.5, 0.6, 0.7 or 0.8 being even more preferred, 0.4, 0.5, 0.6, 0.7 or 0.8 being still more preferred and, e.g. 0.4 and 0.7 being particularly preferred.

In the context of the present invention, a given value of the molar degree of substitution such as 0.8 may be the exact value or may be understood as being in a range of from 0.75 to 0.84. Therefore, for example, a given value of 0.1 may be the exact value of 0.1 or be in the range of from 0.05 to 0.14, a given value of 0.4 may be the exact value of 0.4 or in the range of from 0.35 to 0.44, or a given value of 0.7 may be the exact value of 0.7 or be in the range of from 0.65 to 0.74.

Particularly preferred combinations of molecular weight of the hydroxyalkyl starch, preferably hydroxyethyl starch, and its degree of substitution DS are, e.g., 10 kD and 0.4 or 10 kD and 0.7 or 12 kD and 0.4 or 12 kD and 0.7 or 18 kD and 0.4 or 18 kD and 0.7 or 30 kD and 0.4 or 30 kD and 0.7, or 50 kD and 0.4 or 50 kD and 0.7 or 100 kD and 0.7.

As far as the ratio of $C_2$:$C_6$ substitution is concerned, said substitution is preferably in the range of from 2 to 20, more preferably in the range of from 2 to 15 and even more preferably in the range of from 3 to 12.

According to a further embodiment of the present invention, also mixtures of hydroxyethyl starches may be employed having different mean molecular weights and/or different degrees of substitution and/or different ratios of $C_2$:$C_6$ substitution. Therefore, mixtures of hydroxyethyl starches may be employed having different mean molecular weights and different degrees of substitution and different ratios of $C_2$:$C_6$ substitution, or having different mean molecular weights and different degrees of substitution and the same or about the same ratio of $C_2$:$C_6$ substitution, or having different mean molecular weights and the same or about the same degree of substitution and different ratios of $C_2$:$C_6$ substitution, or having the same or about the same mean molecular weight and different degrees of substitution and different ratios of $C_2$:$C_6$ substitution, or having different mean molecular weights and the same or about the same degree of substitution and the same or about the same ratio of $C_2$:$C_6$ substitution, or having the same or about the same mean molecular weights and different degrees of substitution and the same or about the same ratio of $C_2$:$C_6$ substitution, or having the same or about the same mean molecular weight and the same or about the same degree of substitution and different ratios of $C_2$:$C_6$ substitution, or having about the same mean molecular weight and about the same degree of substitution and about the same ratio of $C_2$:$C_6$ substitution.

In different conjugates and/or different methods according to the present invention, different hydroxyalkyl starches, preferably different hydroxyethyl starches and/or different hydroxyalkyl starch mixtures, preferably different hydroxyethyl starch mixtures, may be employed.

According to one embodiment of the present invention, the functional group Z of the protein is an aldehyde group or a keto group. Therefore, the present invention relates to a method and conjugates as described above, wherein the functional group Z of the protein is an aldehyde group or a keto group.

While there are no general restrictions as to the location of the aldehyde or keto group within the protein, the aldehyde or keto group is, according to a preferred embodiment of the present invention, located in a carbohydrate side chain of the protein. Therefore, in the context of this embodiment, a glycosylated protein is employed.

As glycosylated protein, glycosylated forms of IFN beta such as natural human IFN beta or IFN beta 1a, natural or eucaryotic cell derived hGM-CSF containing both N- and O-glycans, recombinant human activated protein C (rhAPC) being a 2-chain glycoprotein containing 4 N-glycosylation sites, human tPA (htPA) or recombinant human tPA (rhtPA) such as type I tPA having N-linked oligosaccharides at amino acids Asn117, Asn184 and Asn448 or type II tPA being glycosylated at Asn117 and Asn448, plasma derived A1AT or recombinant human A1AT (pdA1AT or rhA1AT), recombinant human AT III (rhAT III), factor VII, factor VIII and factor IX are preferred.

Glycosylated forms of IFN beta, AT III and GM-CSF are especially preferred.

In the context of the present invention, the term "glycosylated protein", i.e. a protein having a "carbohydrate side chain" refers to proteins comprising carbohydrate moieties such as hydroxyaldehydes or hydroxyketones as well as to chemical modifications thereof (see Rompp Chemielexikon, Thieme Verlag Stuttgart, Germany, $9^{th}$ edition 1990, Volume 9, pages 2281-2285 and the literature cited therein). Furthermore, it also refers to derivatives of naturally occurring carbohydrate moieties like, galactose, N-acetylneuramic acid, and N-acetylgalactosamine) and the like.

In an even more preferred embodiment, the aldehyde group or the keto group is part of a galactose residue of the carbohydrate side chain. This galactose residue can be made available for reaction with the functional group A comprised in the polymer or polymer derivative by removal of terminal sialic acids, followed by oxidation, as described hereinunder.

In a still further preferred embodiment, the polymer or polymer derivative comprising functional group A is linked to a sialic acid residue of the carbohydrate side chains, preferably the terminal sialic acid residue of the carbohydrate side chain.

Oxidation of terminal carbohydrate moieties can be performed either chemically or enzymatically.

Methods for the chemical oxidation of carbohydrate moieties of polypeptides are known in the art and include the treatment with periodate (Chamow et al., 1992, J. Biol. Chem., 267, 15916-15922).

By chemically oxidizing, it is in principle possible to oxidize any carbohydrate moiety, being terminally positioned or not. However, by choosing mild reaction conditions it is possible to preferably oxidize the terminal sialic acid of a carbohydrate side chain to give the aldehyde group or the keto group.

According to one embodiment of the present invention, said mild reaction conditions relate to reacting the protein with a suitable aqueous periodate solution, having a preferred periodate concentration in the range of from 1 to 50 mM, more preferably of from 1 to 25 mM and especially preferably of from 1 to 10 mM such as about 1 mM, and at a preferred reaction temperature of from 0 to 40° C. and especially preferably of from 0 to 21° C. such as about 0° C., and for a preferred reaction time of from 5 min to 5 h, more preferably from 10 min to 2 h and especially preferably from 10 min. to 1 h such as about 1 h. The preferred molar ratio of periodate:protein is from 1:200 to 1:1 and more preferably from 1:50 to 1:5. such as about 15:1.

Therefore, the present invention also relates to a method and a conjugate as described above, wherein, prior to the reaction of the protein and the polymer or polymer derivative, a glycosylated protein is reacted with a periodate solution to give a protein having an aldehyde group or a keto group located in the oxidized carbohydrate side chain, said reaction preferably being carried out at mild oxidation reactions. The term "mild reaction conditions" as used in this context refers to, e.g., to a 1 mM periodate solution and a reaction temperature of 0° C. in contrast to harsh conditions such as a 10 mM periodate solution and a reaction temperature of 20 to 25° C.

Alternatively, the carbohydrate side chain may be oxidized enzymatically. Enzymes for the oxidation of the individual carbohydrate side chain are known in the art, e.g. in the case of galactose the enzyme is galactose oxidase. If it is intended to oxidize terminal galactose moieties, it will be eventually necessary to remove terminal sialic acids (partially or completely) if the polypeptide has been produced in cells capable of attaching sialic acids to carbohydrate chains, e.g. in mammalian cells or in cells which have been genetically modified to be capable of attaching sialic acids to carbohydrate chains. Chemical or enzymatic methods for the removal of sialic acids are known in the art (Chaplin and Kennedy (eds.), 1996, Carbohydrate Analysis: a practical approach, especially Chapter 5 Montreuill, Glycoproteins, pages 175-177; IRL Press Practical approach series (ISBN 0-947946-44-3)).

According to another preferred embodiment of the present invention, the aldehyde group or keto group may be located at the N terminus of the protein and is accessible by suitable oxidation. Especially in the case that a hydroxy group-containing amino acid is located at the N terminus of the protein at position -1, such as threonine or serine, oxidation of said N-terminal amino acid can be carried out leading to said keto group or an aldehyde group, preferably an aldehyde group. As method for the chemical oxidation of the suitable N-terminal amino acid, any conceivable method may be applied, with the oxidation with periodate being preferred, with mild oxidation conditions being especially preferred.

According to a further preferred embodiment of the present invention, said mild reaction conditions relate to reacting the protein with a suitable aqueous periodate solution, having a preferred periodate concentration in the range of from 1 to 50 mM, more preferably of from 1 to 25 mM and especially preferably of from 1 to 10 mM such as about 1 mM, and at a preferred reaction temperature of from 0 to 40° C. and especially preferably of from 0 to 21° C. such as about 0° C., and for a preferred reaction time of from 5 min to 5 h, more preferably from 10 min to 2 h and especially preferably from 10 min. to 1 h such as about 1 h. The preferred molar ratio of periodate:protein is from 1:200 to 1:1 and more preferably from 1:50 to 1:5, such as about 15:1.

Therefore, the present invention also relates to a method and a conjugate as described above, wherein the aldehyde group or the keto group is located in a carbohydrate side chain of the protein and/or at the N-terminal group of the protein.

The oligosaccharide pattern of proteins produced in eukaryotic cells thus having been posttranslationally glycosylated, are not identical to the human derived proteins. Moreover, many glycosylated proteins do not have the desired number of terminal sialic acid residues masking a further carbohydrate moiety such as a galactose residue. Those further carbohydrate moieties such as a galactose residue, however, if not masked, are possibly responsible for disadvantages such as a shorter plasma half-life of the protein in possible uses of the protein as a medicament It was surprisingly found that by providing a protein conjugate formed by a hydroxyalkyl starch polymer, preferably a hydroxyethyl starch polymer, which is covalently linked, e.g. via an oxime linkage as disclosed hereinunder, to a carbohydrate moiety of a carbohydrate side chain of the protein, either directly or via at least one linker compounds such as one or two linker compounds, it is possible to overcome at least the above mentioned disadvantage. Hence it is believed that by coupling a hydroxyalkyl starch polymer or derivative thereof, preferably a hydroxyethyl starch polymer or a derivative thereof, to at least one carbohydrate side chain of a glycosylated protein, the lack of suitable terminal carbohydrate residues located at a carbohydrate side chain is compensated. According to another aspect of the invention, providing the respective conjugate with a hydroxyalkyl starch polymer or derivative thereof, preferably a hydroxyethyl starch polymer or a derivative thereof, coupled to the oxidized carbohydrate moiety as described above, does not only compensate the disadvantage but provides a protein conjugate having better characteristics in the desired field of use than the respective naturally occurring protein. Therefore, the respective conjugates according to the invention have a compensational and even a synergistic effect on the protein. It also possible that even proteins which are identical to human proteins or which are human proteins do not have the desired number of suitable masking terminal carbohydrate residues such as silaic acid residues at naturally occurring carbohydrate moieties. In such cases, providing the respective conjugate with a hydroxyalkyl starch polymer or derivative thereof, preferably a hydroxyethyl starch polymer or a derivative thereof, coupled to the oxidized carbohydrate moiety as described above, does not only overcome and compensate a disadvantage of an artificially produced protein, but improves the characteristics of the a natural naturally occurring protein. As to the functional group of the hydroxyalkyl starch, preferably hydroxyethyl starch, or a derivative thereof, which is coupled to the aldehyde group or keto group of the oxidized carbohydrate moiety of the protein, reference is made to the functional groups A as disclosed hereinunder. This general concept is not only applicable to glycosylated G-CSF, but principally to all glycosylated proteins having said lack of terminal carbohydrate residues. Among others, erythropoietin (EPO), interferone beta 1a (IFN beta 1a), ATIII, factor VIII, alphal-antitrypsin (A1AT), htPA, or GM-CSF may be mentioned.

Therefore, the present invention also relates to the use of hydroxyalkyl starch, preferably hydroxyethyl starch, or a derivative thereof, for compensating the lack of terminal carbohydrate residues, preferably sialic acid residues, in naturally occurring or posttranslationally attached carbohydrate moieties of a protein, by covalently coupling the starch or derivative thereof to at least one oxidized carbohydrate moiety of a protein having at least one keto or aldehyde group.

Accordingly, the present invention also relates to a method for compensating the lack of terminal carbohydrate residues, preferably sialic acid residues, in naturally occurring or posttranslationally attached carbohydrate moieties of a protein, by covalently coupling hydroxyalkyl starch, preferably hydroxyethyl starch, or a derivative thereof to at least one oxidized carbohydrate moiety of a protein having at least one keto or aldehyde group, preferably via an oxime linkage.

Moreover, the present invention also relates to a conjugate formed by covalent linkage of a hydroxyalkyl starch, preferably hydroxyethyl starch, or a derivative thereof, to at least one oxidized carbohydrate moiety of a protein, said protein being either isolated from natural sources or produced by expression in eukaryotic cells, such as mammalian, insect or yeast cells, said carbohydrate moiety having at least one keto or aldehyde group, wherein the conjugate has in the desired field of use, preferably the use as medicament, the same or better characteristics than the respective unmodified protein.

In case functional group Z of the protein is an aldehyde group or a keto group, functional group A of the polymer or the derivative thereof comprises an amino group according to the structure —NH—.

Therefore, the present invention also relates to a method and a conjugate as described above wherein the functional group A capable of being reacted with the optionally oxidized reducing end of the polymer, comprises an amino group according to structure —NH—.

According to one preferred embodiment of the present invention, this functional group A is a group having the structure R'—NH— where R' is hydrogen or a alkyl, cycloalkyl, aryl, aralkyl, arylcycloalkyl, alkaryl or cycloalkylaryl residue where the cycloalkyl, aryl, aralkyl, arylcycloalkyl, alkaryl or cycloalkylaryl residue may be linked directly to the NH group or, according to another embodiment, may be linked by an oxygen bridge to the NH group. The alkyl, cycloalkyl, aryl, aralkyl, arylcycloalkyl, alkaryl, or cycloalkylaryl residues may be suitably substituted. As preferred substituents, halogenes such as F, Cl or Br may be mentioned. Especially preferred residues R' are hydrogen, alkyl and alkoxy groups, and even more preferred are hydrogen and unsubstituted alkyl and alkoxy groups.

Among the alkyl and alkoxy groups, groups with 1, 2, 3, 4, 5, or 6 C atoms are preferred. More preferred are methyl, ethyl, propyl, isopropyl, methoxy, ethoxy, propoxy, and isopropoxy groups. Especially preferred are methyl, ethyl, methoxy, ethoxy, and particular preference is given to methyl or methoxy.

Therefore, the present invention also relates to a method and a conjugate as described above wherein R' is hydrogen or a methyl or a methoxy group.

According to another preferred embodiment of the present invention, the functional group A has the structure R'—NH—R"— where R" preferably comprises the structure unit —NH— and/or the structure unit —(C=G)- where G is O or S, and/or the structure unit —SO$_2$—. According to more preferred embodiments, the functional group R" is selected from the group consisting of where, if G is present twice, it is independently O or S.

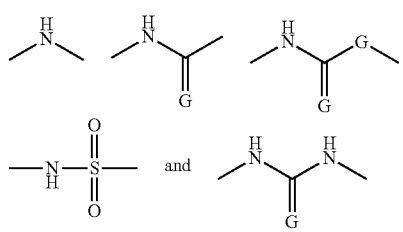

Therefore, preferred functional groups A comprising an amino group —NH$_2$, are, e.g.,

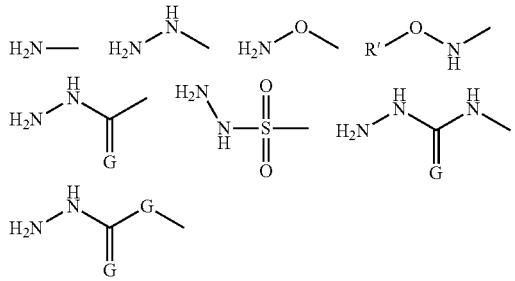

wherein G is O or S and, if present twice, independently O or S, and R' is methyl.

Especially preferred functional groups A comprising an amino group are aminooxy groups

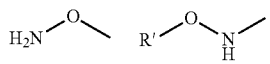

H$_2$N—O— being particularly preferred, and the hydrazido group

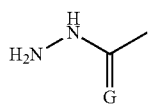

where G is preferably O.

Therefore, the present invention also relates to a method as described above, wherein the functional group Z of the protein is an aldehyde group or a keto group, and the functional group A is an aminooxy group or a hydrazido group. According to an especially preferred embodiment of the present invention, A is an aminooxy group.

Thus, the present invention also relates to a conjugate, as described above, wherein the functional group Z of the protein is an aldehyde group or a keto group, and the functional group A is an aminooxy group or a hydrazido group. According to an especially preferred embodiment of the present invention, A is an aminooxy group.

When reacting the aminooxy group of the polymer or polymer derivative with the aldehyde group or keto group of the protein, an oxime linkage is formed.

Therefore, the present invention also relates to a conjugate as described above, wherein the covalent linkage between the protein and the polymer or polymer derivative is an oxime linkage formed by the reaction of functional group Z of the protein, said functional group Z being an aldehyde group or a keto group, and functional group A of the polymer or polymer derivative, said functional group A being an aminooxy group.

When reacting the hydrazido group of the polymer or polymer derivative with the aldehyde group or keto group of the protein, a hydrazone linkage is formed.

Therefore, the present invention also relates to a conjugate as described above, wherein the covalent linkage between the protein and the polymer or polymer derivative is a hydrazone linkage formed by the reaction of functional group Z of the protein, said functional group Z being an aldehyde group or a keto group, and functional group A of the polymer or polymer derivative, said functional group A being a hydrazido group.

In order to introduce functional group A into the polymer, no specific restrictions exist given that a polymer derivative results comprising functional group A.

According to a preferred embodiment of the present invention, the functional group A is introduced into the polymer by reacting the polymer with an at least bifunctional compound, one functional group of which is capable of being reacted with at least one functional group of the polymer, and at least one other functional group of the at least bifunctional compound being functional group A or being capable of being chemically modified to give functional group A.

According to a still further preferred embodiment, the polymer is reacted with the at least bifunctional compound at its optionally oxidized reducing end.

In case the polymer is reacted with its non-oxidized reducing end, the polymer preferably has the constitution

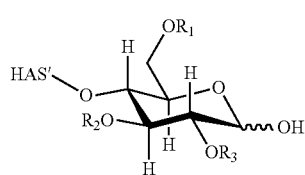

(I)

wherein in formula (I), the aldehyde form of the non-oxidized reducing end is included.

In case the polymer is reacted with its oxidized reducing end, the polymer preferably has the constitution according to formula (IIa)

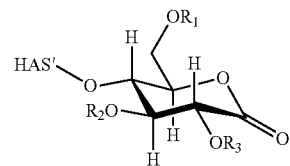

(IIa)

and/or according to formula (IIb)

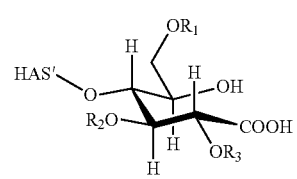

(IIb)

The oxidation of the reducing end of the polymer, preferably hydroxyethyl starch, may be carried out according to each method or combination of methods which result in compounds having the above-mentioned structures (IIa) and/or (IIb).

Although the oxidation may be carried out according to all suitable method or methods resulting in the oxidized reducing end of hydroxyalkyl starch, it is preferably carried out using an alkaline iodine solution as described, e.g., in DE 196 28 705 A1 the respective contents of which (example A, column 9, lines 6 to 24) is incorporated herein by reference.

As functional group of the at least bifunctional compound which is capable of being reacted with the optionally oxidized reducing end of the polymer, each functional group may be used which is capable of forming a chemical linkage with the optionally oxidized reducing end of the hydroxyalkyl starch.

According to a preferred embodiment of the present invention, this functional group comprises the chemical structure —NH—.

Therefore, the present invention also relates to a method and a conjugate as described above wherein the functional group of the at least bifunctional compound, said functional group being capable of being reacted with the optionally oxidized reducing end of the polymer, comprises the structure —NH—.

According to one preferred embodiment of the present invention, this functional group of the at least bifunctional compound is a group having the structure R'—NH— where R' is hydrogen or a alkyl, cycloalkyl, aryl, aralkyl, arylcycloalkyl, alkaryl or cycloalkylaryl residue where the cycloalkyl, aryl, aralkyl, arylcycloalkyl, alkaryl or cycloalkylaryl residue may be linked directly to the NH group or, according to another embodiment, may be linked by an oxygen bridge to the NH group. The alkyl, cycloalkyl, aryl, aralkyl, arylcycloalkyl, alkaryl, or cycloalkylaryl residues may be suitably substituted. As preferred substituents, halogenes such as F, Cl or Br may be mentioned. Especially preferred residues R' are hydrogen, alkyl and alkoxy groups, and even more preferred are hydrogen and unsubstituted alkyl and alkoxy groups.

Among the alkyl and alkoxy groups, groups with 1, 2, 3, 4, 5, or 6 C atoms are preferred. More preferred are methyl, ethyl, propyl, isopropyl, methoxy, ethoxy, propoxy, and isopropoxy groups. Especially preferred are methyl, ethyl, methoxy, ethoxy, and particular preference is given to methyl or methoxy.

Therefore, the present invention also relates to a method and a conjugate as described above wherein R' is hydrogen or a methyl or a methoxy group.

According to another preferred embodiment of the present invention, the functional group of the at least bifunctional compound has the structure R'—NH—R"— where R" preferably comprises the structure unit —NH— and/or the structure unit —(C=G)- where G is O or S, and/or the structure unit —SO$_2$—. According to more preferred embodiments, the functional group R" is selected from the group consisting of

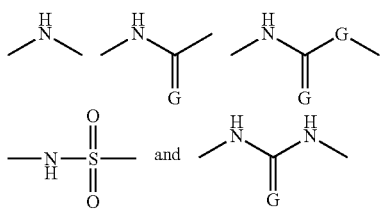

where, if G is present twice, it is independently O or S.

Therefore, the present invention also relates to a method and a conjugate as described above, wherein the functional group of the at least bifunctional compound, said functional group being capable of being reacted with the optionally oxidized reducing end of the polymer, is selected from the group consisting of

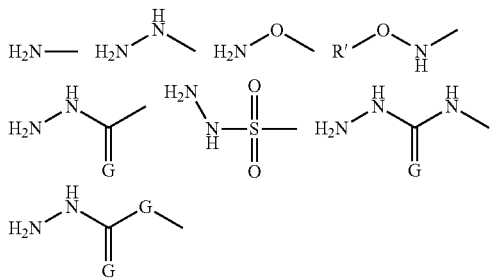

wherein G is O or S and, if present twice, independently O or S, and R' is methyl.

According to an even more preferred embodiment of the present invention, the functional group of the at least bifunctional compound, said functional group being capable of being reacted with the optionally oxidized reducing end of the polymer and comprising an amino group, is an aminooxy groups

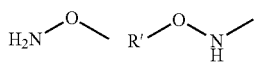

H$_2$N—O— being particularly preferred, or the hydrazido group

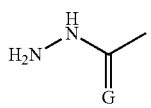

wherein G is preferably O.

Therefore, the present invention also relates to a method and a conjugate as described above, wherein the functional group Z of the protein is an aldehyde group or a keto group, and the functional group of the at least bifunctional compound, said functional group being capable of being reacted with the optionally oxidized reducing end of the polymer, is an aminooxy group or a hydrazido group, preferably an aminooxy group.

Thus, the present invention also relates to a conjugate, as described above, wherein the functional group Z of the protein is an aldehyde group or a keto group, and the functional group of the at least bifunctional compound, said functional group being capable of being reacted with the optionally oxidized reducing end of the polymer, is an aminooxy group or a hydrazido group, preferably an aminooxy group.

According to a still further preferred embodiment of the present invention, the at least bifunctional compound is reacted with the polymer at its non-oxidized reducing end.

According to yet another preferred embodiment of the present invention, the at least bifunctional compound which is reacted with the optionally oxidized reducing end of the polymer, comprises functional group A.

The at least bifunctional compound may be reacted with the polymer first to give a polymer derivative which is subsequently reacted with the protein via functional group A. It is also possible to react the at least bifunctional compound via functional group A with the protein first to give a protein derivative which is subsequently reacted with the polymer via at least one functional group of the at least bifunctional compound residue comprised in the protein derivative.

According to a preferred embodiment of the present invention, the at least bifunctional compound is reacted with the polymer first.

Therefore, the present invention relates to a method and a conjugate as described above, said method further comprising reacting the polymer at its non-oxidized reducing end with an at least bifunctional linking compound comprising a functional group capable of reacting with the non-oxidized reducing end of the polymer and a group A, prior to the reaction of the polymer derivative comprising A and the protein comprising Z.

The term "the polymer (or HAS) is reacted via the reducing end" or "the polymer (or HAS) is reacted via the selectively oxidized reducing end" as used in the context of the present invention relates to a process according to which the polymer (or HAS) is reacted predominantly via its (selectively oxidized) reducing end.

This term "predominantly via its (selectively oxidized) reducing end" relates to processes according to which statistically more than 50%, preferably at least 55%, more preferably at least 60%, more preferably at least 65%, more preferably at least 70%, more preferably at least 75%, more preferably at least 80%, more preferably at least 85%, more preferably at least 90%, and still more preferably at least 95% such as 95%, 96%, 97%, 98%, or 99% of the hydroxyalkyl starch molecules employed for a given reaction are reacted via at least one (selectively oxidized) reducing end per polymer (or HAS) molecule, wherein a given polymer (or HAS) molecule which is reacted via at least one reducing end can be reacted in the same given reaction via at least one further suitable functional group which is comprised in said polymer (or HAS) molecule and which is not a reducing end. If one or more polymer (or HAS) molecule(s) is (are) reacted via at least one reducing end simultaneously via at least one further suitable functional group which is comprised in this (these) polymer (or HAS) molecule(s) and which is not a reducing end, statistically preferably more than 50%, preferably at least 55%, more preferably at least 60%, more preferably at least 65%, more preferably at least 70%, more preferably at least 75%, more preferably at least 80%, more preferably at least 85%, more preferably at least 90%, and still more preferably at least 95% such as 95%, 96%, 97%, 98%, or 99% of all reacted functional groups of these polymer (or HAS) molecules, said functional groups including the reducing ends, are reducing ends.

The term "reducing end" as used in the context of the present invention relates to the terminal aldehyde group of a polymer (or HAS) molecule which may be present as aldehyde group and/or as corresponding acetal from. In case the reducing end is oxidized, the aldehyde or acetal group is in the form of a carboxy group and/or of the corresponding lactone.

The functional group of the at least bifunctional linking compound which is reacted with the polymer and the functional group A of the at least bifunctional linking compound which is reacted with functional group Z of the protein may be separated by any suitable spacer. Among others, the spacer may be an optionally substituted, linear, branched and/or cyclic hydrocarbon residue. Generally, the hydrocarbon residue has up to 60, preferably up to 40, more preferably up to 20, more preferably up to 10, more preferably up to 6 and especially preferably up to 4 carbon atoms. If heteroatoms are present, the separating group comprises generally from 1 to 20, preferably from 1 to 8, more preferably 1 to 6, more preferably 1 to 4 and especially preferably from 1 to 2 heteroatoms. As heteroatom, O is preferred. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group. According to an even more preferred embodiment of the present invention, the functional groups are separated by a linear hydrocarbon chain having 4 carbon atoms. According to another preferred embodiment of the present invention, the functional groups are separated by a linear hydrocarbon chain having 4 carbon atoms and at least one, preferably one heteroatom, particularly preferably an oxygen atom.

According to a further preferred embodiment, the at least bifunctional linking compound is a homobifunctional linking compound. Therefore, the present invention also relates to a method of producing a conjugate as described above, wherein the at least bifunctional linking compound is a homobifunctional compound.

Thus, with regard to the above mentioned preferred functional groups of the linking compound, said homobifunctional linking compound preferably comprises either two aminooxy groups H$_2$N—O— or two aminooxy groups R'—O—NH— or two hydrazido groups H$_2$N—NH—(C=G)-, the aminooxy groups H$_2$N—O— and the hydrazido groups H$_2$N—NH—(C=O)— being preferred, and the aminooxy groups H$_2$N—O— being especially preferred.

Among all conceivable homobifunctional compounds comprising two hydrazido groups H$_2$N—NH—(C=O)—, hydrazides are preferred where the two hydazido groups are separated by a hydrocarbon residue having up to 60, preferably up to 40, more preferably up to 20, more preferably up to 10, more preferably up to 6 and especially preferably up to 4 carbon atoms. More preferably, the hydrocarbon residue has 1 to 4 carbon atoms such as 1, 2, 3, or 4 carbon atoms. Most preferably, the hydrocarbon residue has 4 carbon atoms. Therefore, a homobifunctional compound according to formula

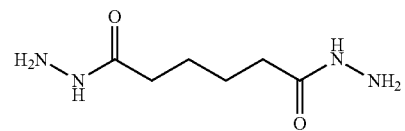 [SMILES: NNC(=O)CCCCC(=O)NN]

is preferred.

In the above decribed embodiment where an aldehyde group or a keto group of the protein is reacted with a compound comprising two hydrazido groups H$_2$N—NH—(C=O)—, particularly preferred hydroxyethyl starches are, e.g., hydroxyethyl starches having a mean molecular weight of about 10 kD and a DS of about 0.4. Also possible are, e.g., hydroxyethyl starch having a mean molecular weight of about 10 kD and a DS of about 0.7 or hydroxyethyl starch having a mean molecular weight of about 18 kD and a DS of about 0.4 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

According to an even more preferred embodiment of the present invention, the bifunctional linking compound is carbohydrazide

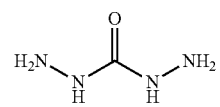

In the above described embodiment where an aldehyde group or a keto group of the protein is reacted with carbohydrazide, particularly preferred hydroxyethyl starches are, e.g., hydroxyethyl starches having a mean molecular weight of about 10 kD and a DS of about 0.4. Also possible are, e.g., hydroxyethyl starch having a mean molecular weight of about 10 kD and a DS of about 0.7 or hydroxyethyl starch having a mean molecular weight of about 18 kD and a DS of about 0.4 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

As described above, the present invention also relates to a method and a conjugate as described above, wherein the at least bifunctional linking compound is a homobifunctional compound and comprises two aminooxy groups. Hence, the present invention also relates to a method and a conjugate as described above, wherein the at least bifunctional linking compound is a homobifunctional compound and comprises two aminooxy groups $H_2N-O-$.

As described above, the polymer is preferably reacted at its reducing end which is not oxidized prior to the reaction with the bifunctional linking compound. Therefore, reacting the preferred homobifunctional compound comprising two aminooxy groups $H_2N-O-$ with the polymer results in a polymer derivative comprising an oxime linkage.

Therefore, since functional group Z of the protein is an aldehyde or a keto group which is preferably reacted with an aminooxy group of the polymer derivative, the present invention also relates to a conjugate as described above, said conjugate comprising the polymer and the protein, each being covalently linked to a linking compound by an oxime or a cyclic aminal linkage.

Among all conceivable homobifunctional compounds comprising two aminooxy groups $H_2N-O-$, bifunctional compounds are preferred where the two aminooxy groups are separated by a hydrocarbon residue having from 1 to 60, preferably from 1 to 40, more preferably from 1 to 20, more preferably from 1 to 10, more preferably from 1 to 6 and especially preferably 1 to 4 carbon atoms. More preferably, the hydrocarbon residue has 1 to 4 carbon atoms such as 1, 2, 3, or 4 carbon atoms. Most preferably, the hydrocarbon residue has 4 carbon atoms. Even more preferably, the hydrocarbon residue has at least one heteroatom, more preferably one heteroatom, and most preferably one oxygen atom. The compound O-[2-(2-aminooxy-ethoxy)-ethyl]hydroxyl amine according to formula

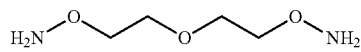

is especially preferred.

Therefore, the present invention relates to a conjugate as described above, said conjugate having a constitution according to formula

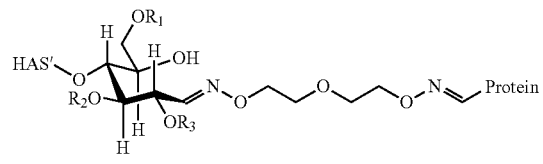

and/or

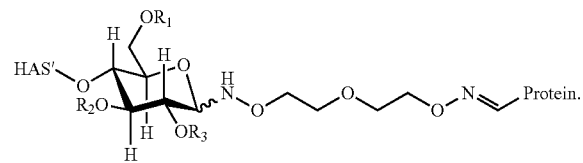

HAS' preferably being HES'. Particularly preferred hydroxyethyl starches are, e.g., hydroxyethyl starches having a mean molecular weight of about 10 kD and a DS of about 0.4 or hydroxyethyl starch having a mean molecular weight of about 10 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.4 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

In the above described embodiment where an aldehyde group or a keto group of the protein is reacted with a hydroxyamino group of the polymer or polymer derivative, particularly preferred hydroxyethyl starches are, e.g., hydroxyethyl starches having a mean molecular weight of about 10 kD and a DS of about 0.4 and hydroxyethyl starch having a mean molecular weight of about 10 kD and a DS of about 0.7 and hydroxyethyl starch having a mean molecular weight of about 18 kD and a DS of about 0.4 and hydroxyethyl starch having a mean molecular weight of about 50 kD and a DS of about 0.4 or hydroxyethyl starch having a mean molecular weight of about 50 kD and a DS of about 0.7. Also possible are, e.g., hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As proteins, glycosylated IFN beta, glycosylated AT III and glycosylated GM-CSF are especially preferred. Therefore, in case the hydroxyalkyl starch is preferably hydroxyethyl starch, the present invention also relates to a conjugate

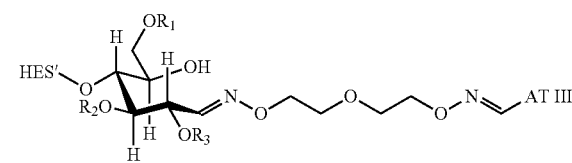

and/or a conjugate

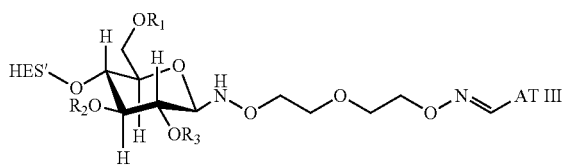

and/or a conjugate

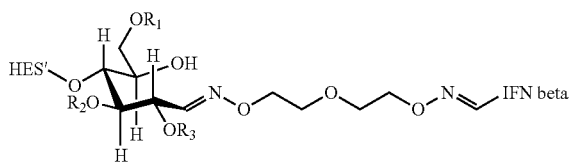

and/or a conjugate

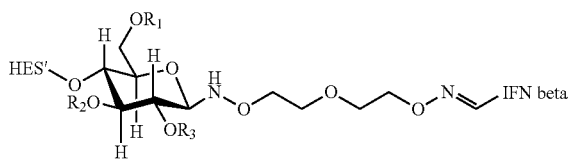

and/or a conjugate

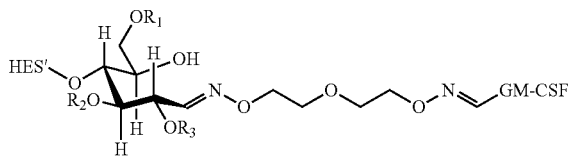

and/or a conjugate

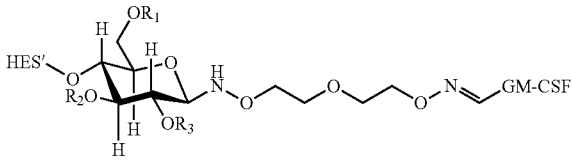

HES' especially preferably being derived independently for each protein from hydroxyethyl starch having a mean molecular weight of about 10 kD and a DS of about 0.4 and/or hydroxyethyl starch having a mean molecular weight of about 10 kD and/or a DS of about 0.7 and/or hydroxyethyl starch having a mean molecular weight of about 18 kD and a DS of about 0.4 and/or hydroxyethyl starch having a mean molecular weight of about 50 kD and a DS of about 0.4 and/or hydroxyethyl starch having a mean molecular weight of about 50 kD and a DS of about 0.7 and/or hydroxyethyl starch having a mean molecular weight of about 100 kD and a DS of about 0.7.

The reaction of the polymer at its non-oxidized reducing end with the linking compound, especially in the case said linking compound is a homobifunctional linking compound comprising two aminooxy groups $H_2N-O-$, is preferably carried out in an aqueous system.

The term "aqueous system" as used in the context of the present invention refers to a solvent or a mixture of solvents comprising water in the range of from at least 10% per weight, preferably at least 50% per weight, more preferably at least 80% per weight, even more preferably at least 90% per weight or up to 100% per weight, based on the weight of the solvents involved. The preferred reaction medium is water.

According to another embodiment, at least one other solvent may be used in which HAS, preferably HES is soluble. Examples of these solvents are, e.g., DMF, dimethylacetamide or DMSO.

As far as the temperatures which are applied during the reaction are concerned, no specific limitations exist given that the reaction results in the desired polymer derivative.

In case the polymer is reacted with the homobifunctional linking compound comprising two aminooxy groups $H_2N-O-$, preferably O-[2-(2-aminooxy-ethoxy)-ethyl]hydroxyl amine, the temperature is preferably in the range of from 5 to 45° C., more preferably in the range of from 10 to 30° C. and especially preferably in the range of from 15 to 25° C.

The reaction time for the reaction of the polymer with the homobifunctional linking compound comprising two aminooxy groups $H_2N-O-$, preferably O-[2-(2-aminooxy-ethoxy)-ethyl]hydroxyl amine, may be adapted to the specific needs and is generally in the range of from 1 h to 7 d, preferably in the range of from 1 h to 3 d and more preferably of from 2 h to 48 h.

The pH value for the reaction of the polymer with the homobifunctional linking compound comprising two aminooxy groups $H_2N-O-$, preferably O-[2-(2-aminooxy-ethoxy)-ethyl]hydroxyl amine, may be adapted to the specific needs such as the chemical nature of the reactants. The pH value is preferably in the range of from 4.5 to 6.5.

Specific examples of above mentioned reaction conditions are, e.g., a reaction temperature of about 25° C. and a pH of about 5.5.

The suitable pH value of the reaction mixture may be adjusted by adding at least one suitable buffer. Among the preferred buffers, sodium acetate buffer, phosphate or borate buffers may be mentioned.

Once the polymer derivative comprising the polymer and the bifunctional linking compound linked thereto is formed, it may be isolated from the reaction mixture by at least one suitable method. If necessary, the polymer derivative may be precipitated prior to the isolation by at least one suitable method.

If the polymer derivative is precipitated first, it is possible, e.g., to contact the reaction mixture with at least one solvent or solvent mixture other than the solvent or solvent mixture present in the reaction mixture at suitable temperatures, such as, for example acetone/ethanol mixtures in suitable volume/volume ratios, such as 1/1 v/v or isopropanol at suitable temperatures such as from −20° C. to 50° C. or from 0° C. to 25° C. According to a particularly preferred embodiment of the present invention where an aqueous medium, preferably water is used as solvent, the reaction mixture is contacted with a mixture of 2-propanol at a temperature, preferably in the range of from −20 to +50° C. and especially preferably in the range of from 0 to 25° C.

Isolation of the polymer derivative may be carried out by a suitable process which may comprise one or more steps. According to a preferred embodiment of the present invention, the polymer derivative is first separated off the reaction mixture or the mixture of the reaction mixture with, e.g., aqueous 2-propanol mixture, by a suitable method such as centrifugation or filtration. In a second step, the separated polymer derivative may be subjected to a further treatment such as an after-treatment like dialysis, centrifugal filtration or pressure filtration, ion exchange chromatography, reversed phase chromatography, HPLC, MPLC, gel filtration and/or lyophilisation. According to an even more preferred embodiment, the separated polymer derivative is first dialysed, preferably against water, and then lyophilized until the solvent content of the reaction product is sufficiently low according to the desired specifications of the product. Lyophilisation may be carried out at temperature of from 20 to 35° C., preferably of from 20 to 30° C.

The thus isolated polymer derivative is then further reacted, via functional group A, with the functional group Z of the protein, Z being an aldehyde group or a keto group. In the especially preferred case that A is an aminooxy group $H_2N-O-$ to give an oxime linkage between polymer derivative and protein, the reaction is preferably carried out in an aqueous medium, preferably water, at a preferred temperature in the range of from 0 to 40° C., more preferably from 4 to 25° C. and especially preferably from 15 to 25° C. The pH value of the reaction medium is preferably in the range of from 4 to 10, more preferably in the range of from 5 to 9 and especially preferably in the range of from 5 to 7. The reaction time is preferably in the range of from 1 to 72 h, more preferably in the range of from 1 to 48 h and especially preferably in the range of from 4 to 24 h.

The conjugate may be subjected to a further treatment such as an after-treatment like dialysis, centrifugal filtration or pressure filtration, ion exchange chromatography, reversed phase chromatography, HPLC, MPLC, gel filtration and/or lyophilisation.

According to another embodiment of the present invention, the functional group Z of the protein is an amino group and the protein is selected from the group consisting of IFN alpha, IFN beta, GM-CSF, APC, tPA, A1AT, AT III, factor VII, factor VIII and factor IX. Therefore, the present invention relates to a method and a conjugate as described above, wherein the functional group Z of the protein is an amino group and the protein is selected from the group consisting of IFN alpha, IFN beta, GM-CSF, APC, tPA, A1AT, AT III, factor VII, factor VIII and factor IX.

According to an especially preferred embodiment of the present invention, the functional group A to be reacted with the functional group Z being an amino group is a reactive carboxy group. Therefore, the present invention also relates to a method and a conjugate as described above, wherein the functional group Z is an amino group and the functional group A of the polymer or the polymer derivative is a reactive carboxy group.

According to a first preferred embodiment of the present invention, the reactive carboxy group is introduced into the polymer by selectively oxidizing the polymer at its reducing end.

Therefore, the polymer into which the reactive carboxy group is introduced preferably has the constitution according to formula (IIa)

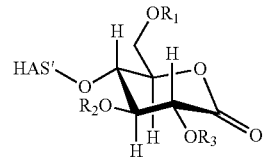

(IIa)

and/or according to formula (IIb)

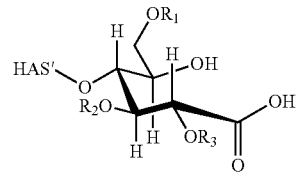

(IIb)

The oxidation of the reducing end of the polymer according to formula (I)

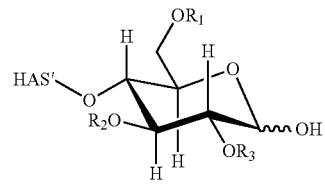

I)

preferably hydroxyethyl starch, may be carried out according to each method or combination of methods which result in compounds having the above-mentioned structures (IIa) and/or (IIb).

Although the oxidation may be carried out according to all suitable method or methods resulting in the oxidized reducing end of hydroxyalkyl starch, it is preferably carried out using an alkaline iodine solution as described, e.g., in DE 196 28 705 A1 the respective contents of which (example A, column 9, lines 6 to 24) is incorporated herein by reference.

Introducing the reactive carboxy group into the polymer which is selectively oxidized at its reducing end may be carried out by all conceivable methods.

The oxidized polymer may be employed as such or as a salt, such as an alkali metal salt, preferably as a sodium and/or a potassium salt.

According to a preferred method of the present invention, the polymer which is selectively oxidized at its reducing end is reacted at the oxidized reducing end with at least one alcohol, preferably with at least one acidic alcohol. Still further preferred are acidic alcohols having a $pK_A$ value in the range of from 6 to 12, more preferably of from 7 to 11 at 25° C. The molecular weight of the acidic alcohol is preferably in the range of from 80 to 500 g/mole, more preferably of from 90 to 300 g/mole and especially preferably of from 100 to 200 g/mole.

Suitable acidic alcohols are all alcohols $H-O-R_A$ having an acidic proton and are capable of being reacted with the oxidized polymer to give the respective reactive polymer ester, preferably according to the formula

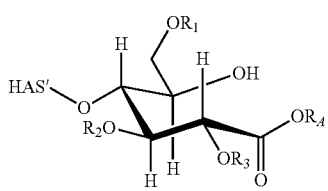

still more preferably according to formula

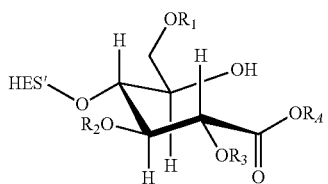

Preferred alcohols are N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N-hydroxy succinimides, with N-hydroxy succinimide and Sulfo-N-hydroxy succinimide being especially preferred. All alcohols may be employed alone or as suitable combination of two or more thereof. In the context of the present invention, it is also possible to employ a compound which releases the respective alcohol, e.g. by adding diesters of carbonic acids.

Therefore, the present invention also relates to a method and a conjugate as described above, wherein the polymer which is selectively oxidised at its reducing end is activated by reacting the oxidised polymer with an acidic alcohol, preferably with N-hydroxy succinimide and/or Sulfo-N-hydroxy succinimide.

According to an even more preferred embodiment of the present invention, the polymer which is selectively oxidized at its reducing end is reacted at the oxidized reducing end with at least one carbonic diester $R_B$—O—(C=O)—O—$R_C$, wherein $R_B$ and $R_C$ may be the same or different. Preferably, this method gives reactive polymers according to the formula

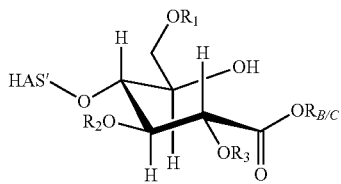

wherein HAS' is preferably HES'.

As suitable carbonic diester compounds, compounds may be employed whose alcohol components are independently N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole.

Especially preferred are N,N'-disuccinimidyl carbonate and Sulfo-N,N'-disuccinimidyl carbonate, with N,N'-disuccinimidyl carbonate being especially preferred.

Therefore, the present invention also relates to a method and a conjugate as described above, wherein the polymer which is selectively oxidised at its reducing end is activated by reacting the oxidised polymer with N,N'-disuccinimidyl carbonate.

The acidic alcohol is reacted with the oxidized polymer or the salt of the oxidized polymer at a molar ratio of acidic alcohol:polymer preferably of from 5:1 to 50:1, more preferably of from 8:1 to 20:1, at a preferred reaction temperature of from 2 to 40° C., more preferably of from 10 to 30° C. and especially preferably of from 15 to 25° C. The reaction time is preferably in the range of from 1 to 10 h, more preferably of from 2 to 5 h, more preferably of from 2 to 4 h and particularly of from 2 to 3 h.

The carbonic diester compound is reacted with the oxidized polymer or the salt of the oxidized polymer at a molar ratio of diester compound:polymer preferably of from 1:1 to 3:1, more preferably of from 1:1 to 1.5:1. The reaction time is preferably in the range of from 0.1 to 12 h, more preferably of from 0.2 to 6 h, more preferably of from 0.5 to 2 h and particularly of from 0.75 to 1.25 h.

According to a preferred embodiment of the present invention, reacting the oxidized polymer with acidic alcohol and/or carbonic diester is carried out in at least one aprotic solvent, particularly preferably in an anhydrous aprotic solvent having a water content of not more than 0.5 percent by weight, preferably of not more than 0.1 percent by weight. Suitable solvents are, among others, dimethyl sulfoxide (DMSO), N-methyl pyrrolidone, dimethyl acetamide (DMA), dimethyl formamide (DMF) and mixtures of two or more thereof. The reaction temperatures are preferably in the range of from 2 to 40° C., more preferably of from 10 to 30° C.

For reacting the oxidized polymer with the at least one acidic alcohol, at least one additional activating agent is employed.

Suitable activating agents are, among others, carbonyldiimidazole, carbodiimides such as diisopropyl carbodiimide (DIC), dicyclohexyl carbodiimides (DCC), 1-ethyl-3-(3-dimethylaminopropyl)carbodiimide (EDC), with dicyclohexyl carbodiimides (DCC) and 1-ethyl-3-(3-dimethylaminopropyl)carbodiimide (EDC) being especially preferred.

Therefore, the present invention also relates to a method and a conjugate as described above, where the polymer which is oxidized at its reducing end, is reacted with an acidic alcohol in the presence of an additional activating agent to give the reactive polymer ester.

According to an especially preferred embodiment of the present invention, the reaction of the oxidized polymer with carbonic diester and/or acidic alcohol is carried out at a low base activity which may be determined by adding the reaction mixture to water with a volume ratio of water to reaction mixture of 10:1. Prior to the addition, the water which comprises essentially no buffer, has a pH value of 7 at 25° C. After the addition of the reaction mixture and by measuring the pH value, the base activity of the reaction mixture is obtained, having a value of preferably not more than 9.0, more preferably of not more than 8.0 and especially preferably of not more than 7.5.

According to a preferred embodiment of the present invention, the oxidized polymer is reacted with N-hydroxy succinimide in dry DMA in the absence of water with EDC to selectively give the polymer N-hydroxy succinimide ester according to the formula

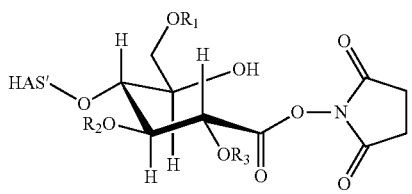

more preferably with HAS' being HES'.

Surprisingly, this reaction does not give by-products resulting from reactions of EDC with OH groups of HES, and the rearrangement reaction of the O-acyl isourea formed by EDC and the oxidized polymer to the respective N-acyl urea is surprisingly suppressed.

According to another preferred embodiment of the present invention, the oxidized polymer is reacted with N,N'-disuccinimidyl carbonate in anhydrous DMF and in the absence of an activating agent to selectively give the polymer N-hydroxy succinimide ester according to the formula

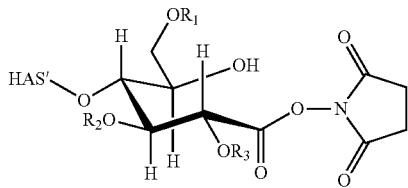

more preferably with HAS' being HES'.

The reactive polymer as described above is preferentially further reacted with at least one amino group of the protein to give an amide linkage. According to a preferred embodiment of the present invention, the reactive polymer is reacted with one amino group of the protein.

The amino group of the protein can be an amino group of a suitable amino acid residue of the protein such as a lysin residue or a histidine residue or the amino group located at the N terminus of the protein.

Therefore, the present relates to a conjugate preferably having a constitution according to the formula

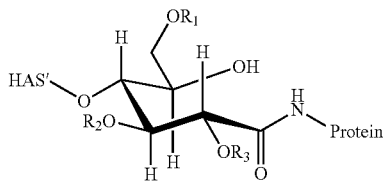

wherein the N atom of the amide linkage is derived from an amino group of the protein, with HAS' preferably being HES', the hydroxyethyl starch preferably being hydroxyethyl starch having a mean molecular weight if about 10 kD and a DS of about 0.4 or hydroxyethyl starch having a mean molecular weight if about 10 kD and a DS of about 0.7 or hydroxyethyl starch having a mean molecular weight if about 12 kD and a DS of about 0.4 or hydroxyethyl starch having a mean molecular weight if about 12 kD and a DS of about 0.7 or hydroxyethyl starch having a mean molecular weight if about 18 kD and a DS of about 0.4 or hydroxyethyl starch having a mean molecular weight if about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight if about 50 kD and a DS of about 0.4 or hydroxyethyl starch having a mean molecular weight if about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

An especially preferred protein coupled via above-mentioned amide linkage to hydroxyalkyl starch, preferably hydroxyethyl starch, is AT III. Therefore, the present invention also relates to a conjugate

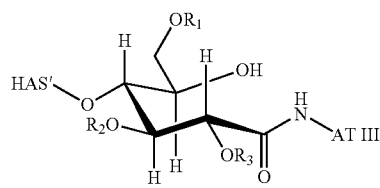

wherein the N atom of the amide linkage is derived from an amino group of AT III and where HAS' is preferably HES' and even more preferably hydroxyethyl starch having a molecular weight of about 10 kD and a DS value of about 0.4.

Another especially preferred protein coupled via above-mentioned amide linkage to hydroxyalkyl starch, preferably hydroxyethyl starch, is IFN alpha. Therefore, the present invention also relates to a conjugate

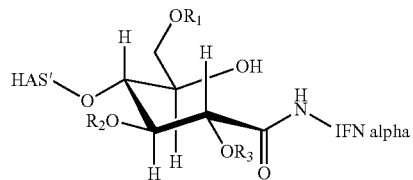

wherein the N atom of the amide linkage is derived from an amino group of IFN alpha and where HAS' is preferably HES' and even more preferably hydroxyethyl starch having a molecular weight of about 18 kD and a DS value of about 0.8.

In the above described embodiment where an amino group of the protein is reacted with a reactive carboxy group of the polymer or polymer derivative, particularly preferred hydroxyethyl starches are, e.g., hydroxyethyl starches having a mean molecular weight of about 10 kD and a DS of about 0.4 or hydroxyethyl starches having a mean molecular weight of about 18 kD and a DS of about 0.8. Also possible are hydroxyethyl starch having a mean molecular weight of about 10 kD and a DS of about 0.7 and hydroxyethyl starch having a mean molecular weight of about 18 kD and a DS of about 0.4 and hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

The reaction of the reactive polymer with the protein may be carried out by combining the reaction mixture of the preparation of the reactive polymer, i.e. without isolation of the reactive polymer, comprising at least 10, more preferably at least 30 and still more preferably at least 50 percent by weight reactive polymer, with an aqueous solution of the protein. Preferred aqueous solutions of the protein comprises of from 0.05 to 10, more preferably of from 0.5 to 5 and especially preferably of from 0.5 to 2 percent by weight protein at a preferred pH of from 5.0 to 9.0, more preferably of from 6.0 to 9.0 and especially preferably of from 7.5 to 8.5.

According to the present invention, it is also possible to purify the reactive polymer by at least one, preferably multiple precipitation with at least one suitable precipitation agent such as anhydrous ethanol, isopropanol and/or acetone to give a solid comprising at least 10, more preferably at least 30 and still more preferably at least 50 percent by weight reactive polymer.

The purified reactive polymer may be added to the aqueous solution of the protein. It is also possible to add a solution of the purified reactive polymer to the aqueous solution of the protein.

According to a preferred embodiment of the present invention, the reaction of the reactive polymer with the protein to give an amide linkage is carried out at a temperature of from 2 to 40° C., more preferably of from 5 to 35° C. and especially of from 10 to 30° C. and a preferred pH of from 7.0 to 9.0, preferably of from 7.5 to 9.0 and especially preferably of from 7.5 to 8.5, at a preferred reaction time of from 0.1 to 12 h, more preferably of from 0.5 to 5 h, more preferably of from 0.5 to 3 h, still more preferably of from 0.5 to 2 h and especially preferably of from 0.5 to 1 h, the molar ratio of reactive polymer ester:protein being preferably of from 1:1 to 70:1, more preferably of from 5:1 to 50:1 and especially preferably of from 10:1 to 50:1.

According to another embodiment of the present invention, the polymer which is selectively oxidized at its reducing end is reacted at the oxidized reducing end with an azolide such as carbonyldiimidazole or carbonyl dibenzimidazole to give a polymer having a reactive carboxy group. In the case of carbonyldiimidazole, a reactive polymer derivative according to formula

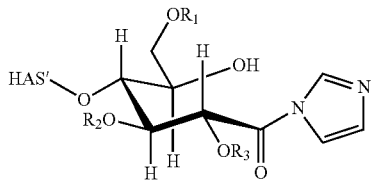

results, wherein HAS' is preferably HES'. The imidazolide resulting from the reaction of the polymer with the azolide may be preferentially reacted with an amino group of the protein to give an amide linkage. Also possible is a reaction, if present, with a hydroxy group of the protein to give an ester linkage, or with a thio group of the protein to give a thioester linkage, or, if present, with a carboxy group of the protein to give a —(C=O)—O—(C=O)— linkage.

In the above described embodiment where an azolide is used for introducing the reactive carboxy group in the polymer or polymer derivative, particularly preferred hydroxyethyl starches are, e.g., hydroxyethyl starches having a mean molecular weight of about 10 kD and a DS of about 0.4 or hydroxyethyl starch having a mean molecular weight of about 10 kD and a DS of about 0.7 or hydroxyethyl starch having a mean molecular weight of about 18 kD and a DS of about 0.4 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

According to another embodiment of the present invention, the polymer having a reactive carboxy group A resulting from the reaction of the selectively oxidized reducing end of the polymer with one of the above-mentioned compounds, preferably with at least one of the acidic alcohols and/or at least one of the carbonic diester compounds, may be linked to the functional group Z of the protein via at least one linker compound. In case a linker compound is used, said compound is an at least bifunctional compound having at least one functional group $F_1$ capable of being reacted with the functional group A of the polymer derivative, and at least one functional group $F_2$ being capable of being reacted with the functional group Z of the protein or a functional group $F_2$ being capable of being chemically modified to be reacted with the functional group Z of the protein. The chemical modification may be, e.g., a reaction of the functional group $F_2$ with a functional group $F_3$ of a further linker compound or an oxidation or a reduction of a suitable functional group $F_2$. In case at least one linker compound is used, the reaction is not restricted to the amino group of the protein but, depending on the chemical nature of the functional groups of the linker compound or linker compounds, may be used to form a linkage with each suitable functional group of the protein, such as a carboxy group, a reactive carboxy group, an aldehyde group, a keto group, a thio group, an amino group or a hydroxy group. In case two linker compounds are used, a first linker compound is employed having at least one functional group $F_1$ being capable of being reacted with the reactive carboxy group A of the polymer, such as an amino group, a thio group, a hydroxy group, or a carboxy group. Moreover, the first linker compound has at least one other functional group $F_2$ which is capable of being reacted with at least one functional group $F_3$ of the second linker compound. As to functional group $F_2$, the following functional groups are to be mentioned, among others:

C—C-double bonds or C—C-triple bonds or aromatic C—C-bonds;
the thio group or the hydroxy groups;
alkyl sulfonic acid hydrazide, aryl sulfonic acid hydrazide;
1,2-diols;
1,2-aminoalcohols;

1,2-amino-thioalcohols;
azides;
the amino group —NH$_2$ or derivatives of the amino groups comprising the structure unit —NH— such as aminoalkyl groups, aminoaryl group, aminoaralkyl groups, or alkarylaminogroups;
the hydroxylamino group —O—NH$_2$, or derivatives of the hydroxylamino group comprising the structure unit —O—NH—, such as hydroxylalkylamino groups, hydroxylarylamino groups, hydroxylaralkylamino groups, or hydroxyalkarylamino groups;
alkoxyamino groups, aryloxyamino groups, aralkyloxyamino groups, or alkaryloxyamino groups, each comprising the structure unit —NH—O—;
residues having a carbonyl group, -Q-C(=G)-M, wherein G is O or S, and M is, for example,
—OH or —SH;
an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trichlorophenyl;
wherein Q is absent or NH or a heteroatom such as S or O;
—NH—NH$_2$, or —NH—NH—;
—NO$_2$;
the nitril group;
carbonyl groups such as the aldehyde group or the keto group;
the carboxy group;
the —N=C=O group or the —N=C=S group;
vinyl halide groups such as the vinyl iodide or the vinyl bromide group or triflate;
—C≡C—H;
—(C=NH$_2$Cl)—OAlkyl
groups —(C=O)—CH$_2$-Hal wherein Hal is Cl, Br, or I;
—CH=CH—SO$_2$—;
a disulfide group comprising the structure —S—S—;

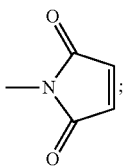

the group

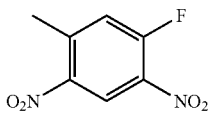

wherein F$_3$ is a group capable of forming a chemical linkage with one of the above-mentioned groups and is preferably selected from the above-mentioned groups. Moreover, the second linker compound has at least one functional group which is capable of being reacted with the functional group Z of the protein, which is, e.g., an amino group, a thio group, a carboxy group, a reactive carboxy group, an aldehyde group, a keto group, or a hydroxy group. In case one linking compound is used to covalently link the polymer and the protein, the polymer can be reacted with the linking compound and the resulting polymer derivative is reacted with the protein, or the protein can be reacted with the linking compound and the resulting protein derivative is reacted with the polymer. In case two linking compounds L1 and L2 are used, it is possible to react the polymer with L1, react the resulting polymer derivative with L2 and react the resulting polymer derivative with the protein, or to react the protein with L2, react the resulting protein derivative with L1 and react the resulting protein derivative with the polymer. It is also possible to react the polymer with L1 and react the protein with L2 and react the polymer derivative with the protein derivative. Furthermore, it is possible to react L1 with L2, react the resulting compound with the polymer and the resulting polymer derivative with the protein. Furthermore, it is possible to react L1 with L2, react the resulting compound with the protein and the resulting protein derivative with the polymer.

wherein F$_3$ is a group capable of forming a chemical linkage with one of the above-mentioned groups and is preferably selected from the above-mentioned groups. Moreover, the second linker compound has at least one functional group which is capable of being reacted with the functional group Z of the protein, which is, e.g., an amino group, a thio group, a carboxy group, a reactive carboxy group, an aldehyde group, a keto group, or a hydroxy group. In case one linking compound is used to covalently link the polymer and the protein, the polymer can be reacted with the linking compound and the resulting polymer derivative is reacted with the protein, or the protein can be reacted with the linking compound and the resulting protein derivative is reacted with the polymer. In case two linking compounds L1 and L2 are used, it is possible to react the polymer with L1, react the resulting polymer derivative with L2 and react the resulting polymer derivative with the protein, or to react the protein with L2, react the resulting protein derivative with L1 and react the resulting protein derivative with the polymer. It is also possible to react the polymer with L1 and react the protein with L2 and react the polymer derivative with the protein derivative. Furthermore, it is possible to react L1 with L2, react the resulting compound with the polymer and the resulting polymer derivative with the protein. Furthermore, it is possible to react L1 with L2, react the resulting compound with the protein and the resulting protein derivative with the polymer.

In the above described embodiment where linker compound is used in combination with an acidic alcohol and/or an diester carbonate and/or an azolide, particularly preferred hydroxyethyl starches are, e.g., hydroxyethyl starches having a mean molecular weight of about 10 kD and a DS of about 0.4 or hydroxyethyl starch having a mean molecular weight of about 10 kD and a DS of about 0.7 or hydroxyethyl starch having a mean molecular weight of about 18 kD and a DS of about 0.4 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

According to a second preferred embodiment of the present invention regarding the introduction of a reactive carboxy group into the polymer, the reactive carboxy group is introduced into the polymer whose reducing end is not oxidized, by reacting at least one hydroxy group of the polymer with a carbonic diester.

Therefore, the present invention also relates to a method and a conjugate as described above, wherein A is a reactive carboxy group, and wherein A is introduced in the polymer whose reducing end is not oxidized, by reacting at least one hydroxy group of the polymer with at least one carbonic diester carbonic diester $R_B$—O—(C=O)—O—$R_C$, wherein $R_B$ and $R_C$ may be the same or different.

According to another embodiment of the present invention, the polymer whose reducing end is not oxidized, is reacted at at least one hydroxy group with an azolide such as carbonyldiimidazole, carbonyl-di-(1,2,4-triazole) or carbonyl dibenzimidazol to give a polymer having a reactive carboxy group.

As suitable carbonic diester compounds, compounds may be employed whose alcohol components are independently N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole.

Especially preferred are symmetrical carbonic diester compounds, $R_B$ and $R_C$ thus being the same. The alcohol component of the carbonic diester is preferably selected from the group consisting of N-hydroxy succinimide, sulfonated N-hydroxy succinimide, N-hydroxy benzotriazole, and nitro- and halogen-substituted phenols. Among others, nitrophenol, dinitrophenol, trichlorophenol, trifluorophenol, pentachlorophenol, and pentafluorophenol are preferred. Especially preferred are N,N'-disuccinimidyl carbonate and Sulfo-N,N'-disuccinimidyl carbonate, with N,N'-disuccinimidyl carbonate being especially preferred.

Therefore, the present invention also relates to a hydroxyalkyl starch derivative and a method of producing same, preferably a hydroxyethyl starch derivative, wherein at least one hydroxy group, preferably at least two hydroxy groups of said starch have been reacted with a carbonic diester compound to give the respective reactive ester.

According to a preferred embodiment of the present invention, the reaction of the polymer whose reducing end is not oxidized, with the at least one carbonic diester compound is carried out at a temperature of from 2 to 40° C., more preferably of from 10 to 30° C. and especially of from 15 to 25° C. and at a preferred reaction time of from 0.5 to 5 h, more preferably of from 1 to 3 h, and especially preferably of from 2 to 3 h.

According to another embodiment of the present invention, the polymer whose reducing end is not oxidized, is reacted at at least one hydroxy group with an azolide such as carbonyldiimidazole, carbonyl-di-(1,2,4-triazole) or carbonyl dibenzimidazol to give a polymer having a reactive carboxy group.

The molar ratio of carbonic diester and/or azolide, preferably carbonic diester compound:polymer depends on the degree of substitution of the polymer regarding the number of hydroxy groups reacted with carbonic diester compound relative to the number of hydroxy groups present in the non-reacted polymer.

According to one preferred embodiment of the present invention, the molar ratio of carbonic diester compound:polymer is in the range of from 1:2 to 1:1000, more preferably of from 1:3 to 1:100 and especially preferably of from 1:10 to 1:50, to give a degree of substitution in the range of from 0.5 to 0.001, preferably of from 0.33 to 0.01 and especially preferably of from 0.1 to 0.02. The degree of substitution is determined by UV-spectroscopy.

According to a preferred embodiment of the present invention, reacting the polymer whose reducing end is not oxidized, with carbonic diester is carried out in at least one aprotic solvent, particularly preferably in an anhydrous aprotic solvent having a water content of not more than 0.5 percent by weight, preferably of not more than 0.1 percent by weight. Suitable solvents are, among others, dimethyl sulfoxide (DMSO), N-methyl pyrrolidone, dimethyl acetamide (DMA), dimethyl formamide (DMF) and mixtures of two or more thereof.

Therefore, the present invention also relates to a method and a conjugate as described above, wherein the reaction of the at least one hydroxy group of the polymer whose reducing end is not oxidised, with the carbonic diester to give a reactive ester group A is carried out in an anhydrous aprotic polar solvent, the solvent preferably being dimethyl acetamide, dimethyl formamide or a mixture thereof.

The reaction of the reactive polymer comprising at least one reactive ester group, preferably at least two reactive ester groups, with the protein to give at least one amide linkage, preferably at least two amide linkages, may be carried out by combining the reaction mixture of the preparation of the reactive polymer, i.e. without isolation of the reactive polymer, comprising at least 5, more preferably at least 10 and still more preferably at least 15 percent by weight reactive polymer, with an aqueous solution of the protein. Preferred aqueous solutions of the protein comprises of from 0.05 to 10, more preferably of from 0.5 to 5 and especially preferably of from 0.5 to 2 percent by weight protein at a preferred pH of from 7.0 to 9, more preferably of from 7.5 to 9 and especially preferably of from 7.5 to 8.5.

According to the present invention, it is also possible to purify the reactive polymer by at least one, preferably by multiple precipitation with at least one suitable precipitation agent such as anhydrous ethanol, isopropanol and/or acetone to give a solid comprising at least 20, more preferably at least 50 and still more preferably at least 80 percent by weight reactive polymer.

The purified reactive polymer may be added to the aqueous solution of the protein. It is also possible to add a solution of the purified reactive polymer to the aqueous solution of the protein.

According to a preferred embodiment of the present invention, the reaction of the reactive polymer with the protein to give at least one, preferably at least two amide linkages is carried out at a temperature of from 2 to 40° C., more preferably of from 5 to 35° C. and especially of from 10 to 30° C. and a preferred pH of from 7.0 to 9.5, preferably of from 7.5 to 9 and especially preferably of from 7.5 to 8.5, at a preferred reaction time of from 0.5 to 5 h, more preferably of from 0.5 to 3 h and especially preferably of from 0.5 to 1 h, the molar ratio of reactive polymer ester:protein being preferably of from 1:1 to 70:1, more preferably of from 5:1 to 50:1 and especially preferably of from 10:1 to 50:1.

According to a preferred embodiment of the present invention, oligo- or multiprotein-substituted polymers are obtained wherein the protein molecules are linked to the polymer via an amide linkage.

PDS is in the range of from 0.001 to 1, preferably from 0.005 to 0.5, more preferably from 0.005 to 0.2.

In the above described embodiment where at least one reactive carboxy group is introduced in the polymer or polymer derivative by reaction with at least one hydroxy group of the polymer or polymer derivative, particularly preferred hydroxyethyl starches are, e.g., hydroxyethyl starches having a mean molecular weight of about 10 kD and a DS of about 0.4 or hydroxyethyl starch having a mean molecular weight of about 10 kD and a DS of about 0.7 or hydroxyethyl starch having a mean molecular weight of about 18 kD and a DS of about 0.4 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

According to another embodiment of the present invention, the polymer having a reactive carboxy group A resulting from the reaction of at least one hydroxy group of the polymer with one of the above-mentioned compounds, preferably with at least one of the carbonic diester compounds, may be linked to the functional group Z of the protein via at least one linker compound. In case a linker compound is used, said compound is an at least bifunctional compound having at least one functional group $F_1$ capable of being reacted with the functional group A of the polymer derivative, and at least one functional group $F_2$ being capable of being reacted with the functional group Z of the protein or a functional group $F_2$ being capable of being chemically modified to be reacted with the functional group Z of the protein. The chemical modification may be, e.g., a reaction of the functional group $F_2$ with a functional group $F_3$ of a further linker compound or an oxidation or a reduction of a suitable functional group $F_2$. In case at least one linker compound is used, the reaction is not restricted to the amino group of the protein but, depending on the chemical nature of the functional groups of the linker compound or linker compounds, may be used to form a linkage with each suitable functional group of the protein, such as a carboxy group, a reactive carboxy group, an aldehyde group, a keto group, a thio group, an amino group or a hydroxy group. In case two linker compounds are used, a first linker compound is employed having at least one functional group $F_1$ being capable of being reacted with the reactive carboxy group A of the polymer, such as an amino group, a thio group, a hydroxy group, or a carboxy group. Moreover, the first linker compound has at least one other functional group $F_2$ which is capable of being reacted with at least one functional group $F_3$ of the second linker compound. As to functional group $F_2$, the following functional groups are to be mentioned, among others:

C—C-double bonds or C—C-triple bonds or aromatic C—C-bonds;
the thio group or the hydroxy groups;
alkyl sulfonic acid hydrazide, aryl sulfonic acid hydrazide;
1,2-dioles;
1,2-aminoalcohols;
azides;
1,2-amino-thioalcohols;
the amino group —$NH_2$ or derivatives of the amino groups comprising the structure unit —NH— such as aminoalkyl groups, aminoaryl group, aminoaralkyl groups, or alkarylaminogroups;
the hydroxylamino group —O—$NH_2$, or derivatives of the hydroxylamino group comprising the structure unit —O—NH—, such as hydroxylalkylamino groups, hydroxylarylamino groups, hydroxylaralkylamino groups, or hydroxyalkarylamino groups;
alkoxyamino groups, aryloxyamino groups, aralkyloxyamino groups, or alkaryloxyamino groups, each comprising the structure unit —NH—O—;
residues having a carbonyl group, -Q-C(=G)-M, wherein G is O or S, and M is, for example,
—OH or —SH;
an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trichlorophenyl;
wherein Q is absent or NH or a heteroatom such as S or O;
—NH—$NH_2$, or —NH—NH—;
—$NO_2$;
the nitril group;
carbonyl groups such as the aldehyde group or the keto group;
the carboxy group;
the —N=C=O group or the —N=C=S group;
vinyl halide groups such as the vinyl iodide or the vinyl bromide group or triflate;
—C≡C—H;
—(C=$NH_2$Cl)—OAlkyl
groups —(C=O)—$CH_2$-Hal wherein Hal is Cl, Br, or I;
—CH=CH—$SO_2$—;
a disulfide group comprising the structure —S—S—;

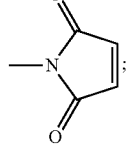

the group

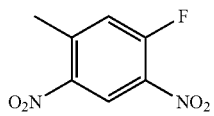

wherein $F_3$ is a group capable of forming a chemical linkage with one of the above-mentioned groups and is preferably selected from the above-mentioned groups. Moreover, the second linker compound has at least one functional group which is capable of being reacted with the functional group Z of the protein, which is, e.g., an amino group, a thio group, a carboxy group, a reactive carboxy group, an aldehyde group, a keto group, or a hydroxy group. In case one linking compound is used to covalently link the polymer and the protein, the polymer can be reacted with the linking compound and the resulting polymer derivative is reacted with the protein, or the protein can be reacted with the linking compound and the resulting protein derivative is reacted with the polymer. In case two linking compounds L1 and L2 are used, it is possible to react the polymer with L1, react the resulting polymer derivative with L2 and react the resulting polymer derivative with the protein, or to react the protein with L2, react the resulting protein derivative with L1 and react the resulting protein derivative with the polymer. It is also possible to react the polymer with L1 and react the protein with L2 and react the polymer derivative with the protein derivative. Furthermore, it is possible to react L1 with L2, react the resulting compound with the polymer and the resulting polymer derivative with the protein. Furthermore, it is possible to react L1 with L2, react the resulting compound with the protein and the resulting protein derivative with the polymer.

In the above described embodiment where a linker compound is used, particularly preferred hydroxyethyl starches are, e.g., hydroxyethyl starches having a mean molecular weight of about 10 kD and a DS of about 0.4 or hydroxyethyl starch having a mean molecular weight of about 10 kD and a DS of about 0.7 or hydroxyethyl starch having a mean molecular weight of about 18 kD and a DS of about 0.4 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

According to a further especially preferred embodiment of the present invention, the functional group A to be reacted with the functional group Z being an amino group is an aldehyde group, a keto group or a hemiacetal group. Therefore, the present invention also relates to a method and a conjugate as described above, wherein the functional group Z is an amino group and the functional group A of the polymer or the derivative thereof is an aldehyde group, a keto group or a hemiacetal group, wherein the protein is selected from the group consisting of IFN alpha, IFN beta, GM-CSF, APC, tPA, A1AT, AT III, factor VII, factor VIII, and factor IX.

According to a particularly preferred embodiment, functional group Z and functional group A are reacted via a reductive amination reaction.

The reductive amination reaction according to the invention, wherein the polymer or polymer derivative is covalently linked via at least one aldehyde group to at least one amino group of the protein by reductive amination, is preferably carried out at a temperature of from 0 to 40° C., more preferably 0 to 37° C., more preferably of from 0 to 25° C., in particular from 4 to 21° C., but especially preferably of from 0 to 21° C. The reaction time preferably ranges of from 0.5 to 72 h, more preferably of from 2 to 48 h and especially preferably of from 4 to 7 h. As solvent for the reaction, an aqueous medium is preferred.

Thus, the present invention also relates to a method and a conjugate as described above, wherein the reductive amination is carried out at a temperature of from 4 to 21° C., but especially preferably 0 to 21° C.

Therefore, the present invention also relates to a method and a conjugate as described above, wherein reductive amination is carried out in an aqueous medium.

Thus, the present invention also relates to a method and conjugate as described above, wherein the reductive amination is carried out at a temperature of from 4 to 21° C., but especially preferably 0 to 21° C., in an aqueous medium.

The term "aqueous medium" as used in the context of the present invention relates to a solvent or a mixture of solvents comprising water in the range of from at least 10% per weight, more preferably at least 20% per weight, more preferably at least 30% per weight, more preferably at least 40% per weight, more preferably at least 50% per weight, more preferably at least 60% per weight, more preferably at least 70% per weight, more preferably at least 80% per weight, even more preferably at least 90% per weight or up to 100% per weight, based on the weight of the solvents involved. The preferred reaction medium is water.

The pH value of the reaction medium is generally in the range of from 4 to 9 or from 4 to 8 or from 4 to 7.3.

According to a preferred embodiment of the present invention, the pH at which the reductive amination reaction is carried out, is below 10, preferably below 7.5, preferably below 7.3, more preferably smaller or equal 7 and most preferably below 7, i.e. in the acidic range. Preferred ranges are therefore of from 3 to below 7, more preferably of from 3.5 to 6.5, still more preferably of from 4 to 6, still more preferably of from 4.5 to 5.5 and especially preferably about 5.0, i.e. 4.6 or 4.7 or 4.8 or 4.9 or 5.0. or 5.1 or 5.2 or 5.3 or 5.4. Preferred ranges, are among others, 3 to 6.9 or 3 to 6.5 or 3 to 6 or 3 to 5.5 or 3 to 5 or 3 to 4.5 or 3 to 4 or 3 to 3.5 or 3.5 to 6.9 or 3.5 to 6.5 or 3.5 to 6 or 3.5 to 5.5 or 3.5 to 5 or 3.5 to 4.5 or 3.5 to 4 or 4 to 6.9 or 4 to 6.5 or 4 to 6.0 or 4 to 5.5 or 4 to 5 or 4 to 4.5 or 4.5 to 6.9 or 4.5 to 6.5 or 4.5 to 6 or 4.5 to 5.5 or 4.5 to 5 or 5 to 6.9 or 5 to 6.5 or 5 to 6 or 5 to 5.5 or 5.5 to 6.9 or 5.5 to 6.5 or 5.5 to 6 or 6 to 6.9 or 6 to 6.5 or 6.5 to 6.9.

Therefore, the present invention also relates to a method and a conjugate as described above, wherein the reductive amination is carried out at a pH of 7 or less, more preferably at a pH of 6 or less.

Thus, the present invention also relates to a method and conjugate as described above, wherein the reductive amination is carried out at a temperature of from 0 to 21° C., preferably 4 to 21° C. at a pH of 7.5 or less, preferably 7 or less, preferably of 6 or less.

Hence, the present invention also relates to a method and conjugate as described above, wherein the reductive amination is carried out in an aqueous medium at a pH of 7 or less, preferably of 6 or less.

Accordingly, the present invention also relates to a method and conjugate as described above, wherein the reductive amination is carried out at a temperature of from 4 to 21° C. in an aqueous medium at a pH of 7 or less, preferably of 6 or less.

The molar ratio of polymer derivative:protein used for the reaction is preferably in the range of from 200:1 to 5:1, more preferably of from 100:1 to 10:1 and especially preferably of from 75:1 to 20:1.

It was surprisingly found that it was possible, especially at the preferred pH ranges given above, particularly at a pH below 7 and greater or equal 4, to react the polymer derivative predominantly with the amino group located at the N terminus of the protein. The term "predominantly" as used in the context of the present invention relates to an embodiment where at least 80%, preferably at least 85% of the N-terminal amino groups available are reacted via reductive amination. It is also possible to react at least 90% or at least 95% or at least 96% or at least 97% or at least 98% or at least 99% of the N-terminal amino groups available. Although coupling to amino groups other than the N-terminal amino group could not be ruled out completely, it is believed that coupling via reductive amination according to the present invention at a pH of below 7, preferably below 6, took place essentially selectively at the N-terminal amino group. In particular, these reaction conditions are preferred for proteins which are stable at these conditions. Should a protein e.g. be acid labile, such as alpha1-antitrypsin, then it is preferred to chose appropriate reaction conditions, in particular a pH from lower than 7.5 to greater than 5.

Therefore, the present invention also relates to a method and a conjugate as described above, wherein the protein comprises the N-terminal amino group and at least one further amino group, said conjugate comprises the polymer being predominantly coupled to the N-terminal amino group.

According to an especially preferred embodiment, the present invention relates to a method of linking aldehyde or keto or hemiacetal functionalized hydroxyalkyl starch or an aldehyde or keto or hemiacetal functionalized hydroxyalkyl starch derivative predominantly to the N-terminal amino group of a protein, said method comprising subjecting said hydroxyalkyl starch or derivative thereof to a reductive amination reaction, at a pH of 7 or less, preferably at a pH of 6 or less, said reductive amination reaction being carried out preferably in an aqueous medium.

According to the present invention, aldehyde functionalized hydroxyalkyl starch or an aldehyde functionalized hydroxyalkyl starch derivative is preferred.

According to a still further preferred embodiment, the present invention relates to a method of linking aldehyde or keto or hemiacetal functionalized hydroxyethyl starch or an aldehyde or keto or hemiacetal functionalized hydroxyethyl starch derivative selectively to the N-terminal amino group of a protein, said method comprising subjecting said hydroxyalkyl starch or derivative thereof to a reductive amination reaction, at a pH of 7 or less, preferably at a pH of 6 or less, said reductive amination reaction being carried out preferably in an aqueous medium, the hydroxyethyl starch employed preferably being hydroxyethyl starch having a mean molecular weight of about 10 kD and a DS of about 0.4 or hydroxyethyl starch having a mean molecular weight of about 10 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.4 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

The reaction of the polymer derivative and the protein between the aldehyde group or keto group or hemiacetal group and the amino group is a reductive amination wherein a Schiff's base is produced. Subsequently after the reaction, this base may be reduced by at least one reductive agent to give a stable linkage between the polymer derivative and the protein. It is also possible to carry out the reaction in the presence of at least one reductive agent. According to a preferred embodiment, the reductive amination reaction is carried out in the presence of at least one reductive agent.

Preferred reductive agents are sodium borohydride, sodium cyanoborohydride, organic borane complex compounds such as a 4-(dimethylamin)pyridine borane complex, N-ethyldiisopropylamine borane complex, N-ethylmorpholine borane complex, N-methylmorpholine borane complex, N-phenylmorpholine borane complex, lutidine borane complex, triethylamine borane complex, or trimethylamine borane complex. Particularly preferred is sodium cyanoborohydride.

Therefore, the present invention also relates to a method and a conjugate as described above, wherein the reductive amination is carried out in the presence of $NaCNBH_3$.

Hence, the present invention also relates to a method and conjugate as described above, wherein the reductive amination is carried out in an aqueous medium at a pH of 7 or less, preferably of 6 or less in the presence of reductive agent, preferably $NaCNBH_3$.

Accordingly, the present invention also relates to a method and conjugate as described above, wherein the reductive amination is carried out at a temperature of from 4 to 21° C. in an aqueous medium at a pH of 7 or less, preferably of 6 or less in the presence of reductive agent, preferably $NaCNBH_3$.

The molar ratio of polymer derivative:protein used for the reaction is preferably in the range of from 200:1 to 10:1 more preferably of from 100:1 to 10:1 and especially preferably of from 75:1 to 20:1.

Therefore, the present invention also relates to a method of producing a conjugate, said method comprising reacting a polymer or a polymer derivative comprising an aldehyde group in an aqueous medium with an amino group of the protein in the presence of a reductive agent, said reductive agent preferably being $NaCNBH_3$.

According to the first preferred embodiment of the present invention, according to which the polymer comprises at least two aldehyde groups which are introducing in the polymer by a ring-opening oxidation reaction, the polymer preferably comprises at least one structure according to formula

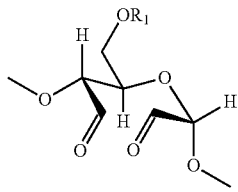

According to this embodiment of the present invention, each oxidation agent or combination of oxidation agents may be employed which is capable of oxidizing at least one saccharide ring of the polymer to give an opened saccharide ring having at least one, preferably at least two aldehyde groups. This reaction is illustrated by the following reaction scheme which shows a saccharide ring of the polymer which is oxidized to give an opened ring having two aldehyde groups:

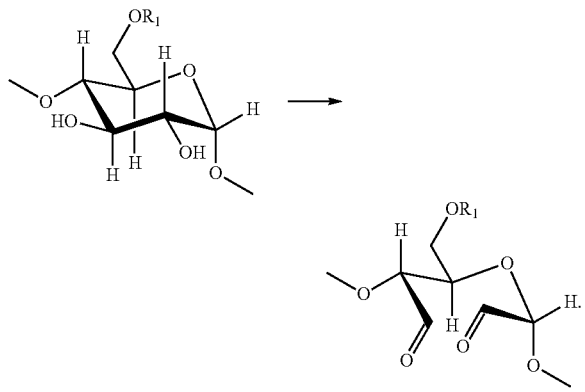

Suitable oxidating agents are, among others, periodates such as alkaline metal periodates or mixtures of two or more thereof, with sodium periodate and potassium periodate being preferred.

Therefore, the present invention also relates to a method and a conjugate as described above, wherein the polymer is subjected to a ring-opening oxidation reaction using a periodate to give a polymer derivative having at least one, preferably at least two aldehyde groups.

For this oxidation reaction, the polymer may be employed with its reducing end either in the oxidized or in the non-oxidized form, the non-oxidized form being preferred.

Therefore, the present invention also relates to a method and a conjugate as described above, wherein the polymer is employed with its reducing end in the non-oxidized form.

The reaction temperature is in a preferred range of from 0 to 40° C., more preferably of from 0 to 25° C. and especially preferably of from 0 to 5° C. The reaction time is in a preferred range of from 1 min to 5 h and especially preferably of from 10 min to 4 h. Depending on the desired degree of oxidation, i.e. the number of aldehyde groups resulting from the oxidation reaction, the molar ratio of periodate:polymer may be appropriately chosen.

Therefore, the present invention also relates to a method and a conjugate as described above, wherein the ring-opening oxidation reaction is carried out at a temperature of from 0 to 5° C.

The oxidation reaction of the polymer with periodate is preferably carried out in an aqueous medium, most preferably in water.

Therefore, the present invention also relates to a method and a conjugate as described above, wherein the ring-opening oxidation reaction is carried out in an aqueous medium. The suitable pH value of the reaction mixture may be adjusted by adding at least one suitable buffer. Among the preferred buffers, sodium acetate buffer, phosphate or borate buffers may be mentioned.

The hydroxyethyl starch subjected to said ring-opening oxidation reaction is preferably hydroxyethyl starch having a mean molecular weight of about 10 kD and a DS of about 0.4 or hydroxyethyl starch having a mean molecular weight of about 10 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.4 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

The resulting polymer derivative may be purified from the reaction mixture by at least one suitable method. If necessary, the polymer derivative may be precipitated prior to the isolation by at least one suitable method.

If the polymer derivative is precipitated first, it is possible, e.g., to contact the reaction mixture with at least one solvent or solvent mixture other than the solvent or solvent mixture present in the reaction mixture at suitable temperatures. According to a particularly preferred embodiment of the present invention where an aqueous medium, preferably water is used as solvent, the reaction mixture is contacted with 2-propanol or with am mixture of acetone and ethanol, preferably a 1:1 mixture (v/v), indicating equal volumes of said compounds, at a temperature, preferably in the range of from −20 to +50° C. and especially preferably in the range of from −20 to 25° C.

Isolation of the polymer derivative may be carried out by a suitable process which may comprise one or more steps. According to a preferred embodiment of the present invention, the polymer derivative is first separated off the reaction mixture or the mixture of the reaction mixture with, e.g., aqueous 2-propanol mixture, by a suitable method such as centrifugation or filtration. In a second step, the separated polymer derivative may be subjected to a further treatment such as an after-treatment like dialysis, centrifugal filtration or pressure filtration, ion exchange chromatography, reversed phase chromatography, HPLC, MPLC, gel filtration and/or lyophilisation. According to an even more preferred embodiment, the separated polymer derivative is first dialysed, preferably against water, and then lyophilized until the solvent content of the reaction product is sufficiently low according to the desired specifications of the product. Lyophilisation may be carried out at temperature of from 20 to 35° C., preferably of from 20 to 30° C.

According to a preferred embodiment, the oxidized polymer resulting from the oxidation reaction is purified using at least one suitable method such as ultrafiltration and/or dialysis in order to, e.g., remove undesirable low molecular weight salts and polymer components, thereby also offering a means of controlling the molecular weight range of oxidized polymer.

The oxidized polymer can be used directly for the reaction with the protein or is suitably recovered in a first step, e.g. by lyophilization, and redissolved in water for conjugation to the protein in a second step. As to the coupling of at least one amino group of the protein with at least one aldehyde group of the polymer by reductive amination, reference is made to the detailed disclosure above concerning the specific reaction parameters of the reductive amination reaction such as pH or temperature. According to especially preferred embodiments of the present invention, the reductive amination is preferably carried out at a temperature of from 0 to 5° C. such as about 4° C. at a pH of about 4.5 to 5.5 such as about 5.0 and for a reaction time of about 20 to 30 h such as about 24 h.

According to the second preferred embodiment, the polymer is reacted with an at least bifunctional compound comprising at least one functional group M capable of being reacted with the polymer and at least one functional group Q which is an aldehyde group, a keto group or a hemiacetal group and which is reacted with an amino group of the protein by reductive amination.

It is preferred to employ a compound having, apart from the aldehyde group or keto group or hemiacetal group, at least one carboxy group or at least one reactive carboxy group, preferably one carboxy group or one reactive carboxy group. The aldehyde group or keto group or hemiacetal group and the carboxy group or the reactive carboxy group may be separated by any suitable spacer. Among others, the spacer may be an optionally substituted, linear, branched and/or cyclic hydrocarbon residue. Generally, the hydrocarbon residue has from 1 to 60, preferably from 1 to 40, more preferably from 1 to 20, more preferably from 2 to 10, more preferably from 2 to 6 and especially preferably from 2 to 4 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group.

According to a preferred embodiment, the hydrocarbon residue is an alkyl group having 2 to 6 and preferably 2 to 4 carbon atoms. It is also possible that no carbon atom is present between the aldehyd or keto group and the carboxy group. Alternatively, the hydrocarbon residue can be a substituted or unsubstituted cyclic hydrocarbon group having 3 to 11 carbon atoms, preferably, 3 to 6 or 3 to 5 carbon atoms. When the cyclic hydrocarbon group is substituted, the substituent can be selected from the group consisting of substituted or unsubstituted amino or alkoxy groups. If present, the number of substituents is preferably 1 to 3. Further, the alkyl and/or cyclic hydrocarbon group can contain one or more heteroatoms, such as O or S, in particular O. In this case, preferably 1 to 3, in particular 1 or 2 heteroatoms are present. Preferred compounds in this context are selected from the following group of compounds.

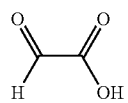

1

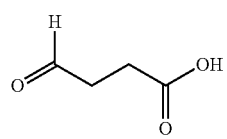

2

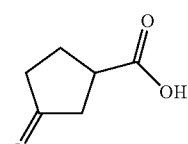

3

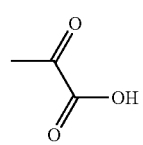

4

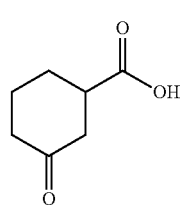

5

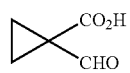

6

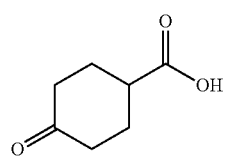

7

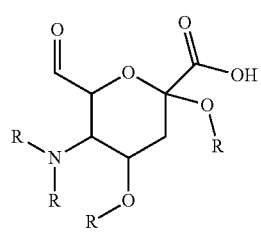

8

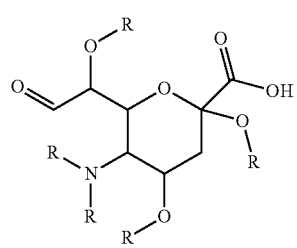

9

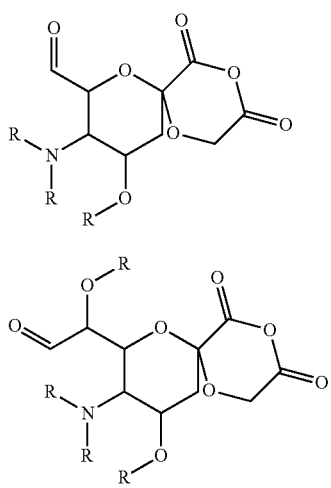

R = H, Alkyl, Aryl, Acyl, SiR'₃
R' = Alkyl, Aryl

According to an even more preferred embodiment, the hydrocarbon residue is an aryl residue having 5 to 7 and preferably 6 carbon atoms. Most preferably, the hydrocarbon residue is the benzene residue. According to this preferred embodiment, the carboxy group and the aldehyde group may be located at the benzene ring in 1,4-position, 1,3-position or 1,2-position, the 1,4-position being preferred.

As reactive carboxy group, a reactive ester, isothiocyanates or isocyanate may be mentioned. Preferred reactive esters are derived from N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N-hydroxy succinimides, with N-hydroxy succinimide and Sulfo-N-hydroxy succinimide being especially preferred. All alcohols may be employed alone or as suitable combination of two or more thereof. As reactive esters, pentafluorophenyl ester and N-hydroxy succinimide ester are especially preferred.

Specific examples of the at least bifunctional compound comprising a carboxy group which may be reacted to obtain a reactive carboxy group are the compounds 1 to 11 of the list hereinabove. In this context, the term "carboxy group" also relates to a lacton and an internal anhydride of a dicarboxylic acid compound.

Thus, according to a preferred embodiment, the present invention relates to a method and a conjugate as described above, wherein the polymer is reacted with formylbenzoic acid.

According to another preferred embodiment, the present invention relates to a method and a conjugate as described above, wherein the polymer is reacted with formylbenzoic acid pentafluorophenyl ester.

According to yet another preferred embodiment, the present invention relates to a method and a conjugate as described above, wherein the polymer is reacted with formylbenzoic acid N-hydroxysuccinimide ester.

According to yet another embodiment, the present invention relates to a method and a conjugate as described above, wherein the polymer is reacted with 4-(4-formyl-3,5-dimethoxyphenoxy)butyric acid.

The hydroxyethyl starch subjected to the reaction with the compound comprising M, M preferably being a carboxy group or a reactive carboxy group and Q being an aldehyde group or a keto group or a hemiacetal group, is most preferably hydroxyethyl starch having a mean molecular weight of about 10 kD and a DS of about 0.7. Also possible are hydroxyethyl starches having a mean molecular weight of about 10 kD and a DS of about 0.4 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.4 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

Particularly preferably, the hydroxyalkyl starch and even more preferably the hydroxyethyl starch is employed with its reducing end in the oxidized form.

The resulting polymer derivative with the aldehyde group or the keto group or the hemiacetal group is subsequently reacted with an amino group of the protein via reductive amination. As to the coupling of at least one amino group of the protein with at least one aldehyde group or keto group or hemiacetal group of the polymer by reductive amination, reference is made to the detailed disclosure above concerning the specific reaction parameters of the reductive amination reaction such as pH or temperature. According to an especially preferred embodiment of the present invention, the reaction with the amino group of the protein is preferably carried out at a temperature of from 0 to 40° C., more preferably of from 0 to 25° C. and especially preferably of from 4 to 21° C. The reaction time preferably ranges of from 30 min to 72 h, more preferably of from 2 to 48 h and especially preferably of from 4 h to 17 h. As solvent for the reaction, an aqueous medium is preferred. The pH value of the reaction medium is preferably in the range of from 4 to 9, more preferably of from 4 to 8 and especially preferably of from 4.5 to 5.5.

According to the third preferred embodiment, the polymer is reacted at its optionally oxidized reducing end with an at least bifunctional compound comprising an amino group M and a functional group Q, wherein said amino group M is reacted with the optionally oxidized reducing end of the polymer and wherein the functional group Q is chemically modified to give an aldehyde functionalized polymer derivative which is reacted with an amino group of the protein by reductive amination.

As to functional group Q, the following functional groups are to be mentioned, among others:
  C—C-double bonds or C—C-triple bonds or aromatic C—C-bonds;
  the thio group or the hydroxy groups;
  alkyl sulfonic acid hydrazide, aryl sulfonic acid hydrazide;
  1,2-dioles;
    1,2 amino-thioalcohols;
    azides;

1,2-aminoalcohols;
the amino group —NH$_2$ or derivatives of the amino groups comprising the structure unit —NH— such as aminoalkyl groups, aminoaryl group, aminoaralkyl groups, or alkarylaminogroups;
the hydroxylamino group —O—NH$_2$, or derivatives of the hydroxylamino group comprising the structure unit —O—NH—, such as hydroxylalkylamino groups, hydroxylarylamino groups, hydroxylaralkylamino groups, or hydroxalalkarylamino groups;
alkoxyamino groups, aryloxyamino groups, aralkyloxyamino groups, or alkaryloxyamino groups, each comprising the structure unit —NH—O—;
residues having a carbonyl group, -Q-C(=G)-M, wherein G is O or S, and M is, for example,
—OH or —SH;
an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trichlorophenyl;
wherein Q is absent or NH or a heteroatom such as S or O;
—NH—NH$_2$, or —NH—NH—;
—NO$_2$;
the nitril group;
carbonyl groups such as the aldehyde group or the keto group;
the carboxy group;
the —N=C=O group or the —N=C=S group;
vinyl halide groups such as the vinyl iodide or the vinyl bromide group or triflate;
—C≡C—H;
—(C=NH$_2$Cl)—OAlkyl
groups —(C=O)—CH$_2$-Hal wherein Hal is Cl, Br, or I;
—CH=CH—SO$_2$—;
a disulfide group comprising the structure —S—S—;

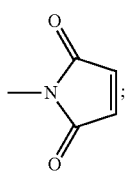

the group

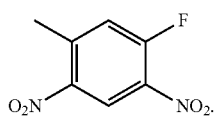

According to a preferred embodiment of the present invention, the term "functional group Q" relates to a functional group Q which comprises the chemical structure —NH—.

According to one preferred embodiment of the present invention, the functional group M is a group having the structure R'—NH— where R' is hydrogen or a alkyl, cycloalkyl, aryl, aralkyl, arylcycloalkyl, alkaryl or cycloalkylaryl residue where the cycloalkyl, aryl, aralkyl, arylcycloalkyl, alkaryl or cycloalkylaryl residue may be linked directly to the NH group or, according to another embodiment, may be linked by an oxygen bridge to the NH group. The alkyl, cycloalkyl, aryl, aralkyl, arylcycloalkyl, alkaryl, or cycloalkylaryl residues may be suitably substituted. As preferred substituents, halogenes such as F, Cl or Br may be mentioned. Especially preferred residues R' are hydrogen, alkyl and alkoxy groups, and even more preferred are hydrogen and unsubstituted alkyl and alkoxy groups.

Among the alkyl and alkoxy groups, groups with 1, 2, 3, 4, 5, or 6 C atoms are preferred. More preferred are methyl, ethyl, propyl, isopropyl, methoxy, ethoxy, propoxy, and isopropoxy groups. Especially preferred are methyl, ethyl, methoxy, ethoxy, and particular preference is given to methyl or methoxy.

According to another embodiment of the present invention, the functional group M has the structure R'—NH—R"— where R" preferably comprises the structure unit —NH— and/or the structure unit —(C=G)- where G is O or S, and/or the structure unit —SO$_2$—. Specific examples for the functional group R" are

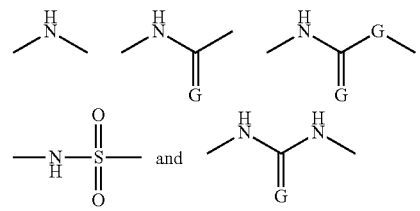

where, if G is present twice, it is independently O or S.

Therefore, the present invention also relates to a method and a conjugate as mentioned above wherein the functional group M is selected from the group consisting of

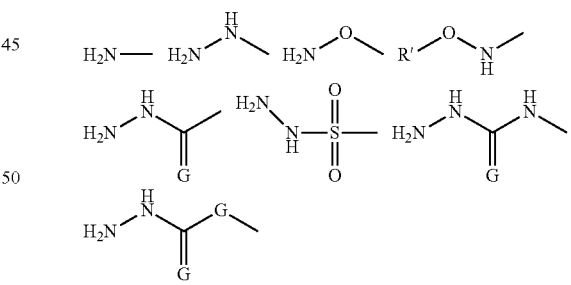

wherein G is O or S and, if present twice, independently O or S, and R' is methyl.

According to a particularly preferred embodiment of the present invention, the functional group M is an amino group —NH$_2$.

The term "amino group Q" relates to a functional group Q which comprises the chemical structure —NH—.

According to a preferred embodiment of the present invention, the functional group Q is a group having the structure R'—NH— where R' is hydrogen or a alkyl, cycloalkyl, aryl, aralkyl, arylcycloalkyl, alkaryl or cycloalkylaryl residue where the cycloalkyl, aryl, aralkyl, arylcycloalkyl, alkaryl or cycloalkylaryl residue may be linked directly to the NH group or, according to another embodiment, may be linked by an oxygen bridge to the NH group. The alkyl, cycloalkyl, aryl, aralkyl, arylcycloalkyl, alkaryl, or cycloalkylaryl residues may be suitably substituted. As preferred substituents, halogenes such as F, Cl or Br may be mentioned. Especially preferred residues R' are hydrogen, alkyl and alkoxy groups, and even more preferred are hydrogen and unsubstituted alkyl and alkoxy groups.

Among the alkyl and alkoxy groups, groups with 1, 2, 3, 4, 5, or 6 C atoms are preferred. More preferred are methyl, ethyl, propyl, isopropyl, methoxy, ethoxy, propoxy, and isopropoxy groups. Especially preferred are methyl, ethyl, methoxy, ethoxy, and particular preference is given to methyl or methoxy.

According to another embodiment of the present invention, the functional group Q has the structure R'—NH—R"— where R" preferably comprises the structure unit —NH— and/or the structure unit —(C=G)- where G is O or S, and/or the structure unit —SO$_2$—. According to more preferred embodiments, the functional group R" is selected from the group consisting of

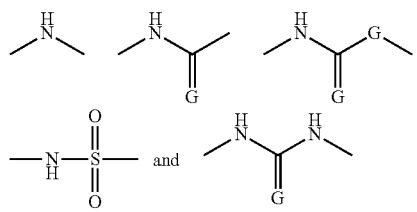

where, if G is present twice, it is independently O or S.

Therefore, the present invention also relates to a method and a conjugate as mentioned above wherein the functional group Q is selected from the group consisting of

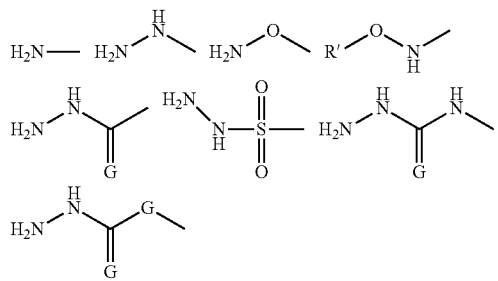

wherein G is O or S and, if present twice, independently O or S, and R' is methyl.

According to a particularly preferred embodiment of the present invention, the functional group Q is an amino group —NH$_2$.

According to a still further preferred embodiment of the present invention, both M and Q comprise an amino group —NH—. According to a particularly preferred embodiment, both M and Q are an amino group —NH$_2$.

According to a preferred embodiment of the present invention, the compound comprising M and Q is a homobifunctional compound, more preferably a homobifunctional compound comprising, as functional groups M and Q, most preferably the amino group —NH$_2$, or according to other embodiments, the hydroxylamino group —O—NH$_2$ or the group

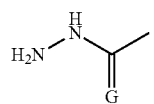

with G preferably being O. Specific examples for these compounds comprising M and Q are

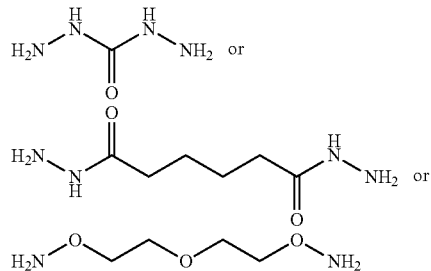

The hydroxyethyl starch subjected to the reaction with the compound comprising M, M preferably being an amino group —NH— and more preferably being an amino group —NH$_2$, still more preferably both M and Q comprising an amino group —NH— and particularly preferably both M and Q comprising an amino group —NH$_2$, is preferably hydroxyethyl starch having a mean molecular weight of about 10 kD and a DS of about 0.4 or hydroxyethyl starch having a mean molecular weight of about 10 kD and a DS of about 0.7. Also possible are or hydroxyethyl starches having mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.4 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

In case both M and Q are an amino group —NH$_2$, M and Q may be separated by any suitable spacer. Among others, the spacer may be an optionally substituted, linear, branched and/or cyclic hydrocarbon residue. Generally, the hydrocarbon residue has from 1 to 60, preferably from 1 to 40, more preferably from 1 to 20, more preferably from 2 to 10, more preferably from 2 to 6 and especially preferably from 2 to 4 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group. According to an even more preferred embodiment, the hydrocarbon residue is an alkyl chain of from 1 to 20, preferably from 2 to 10, more preferably from 2 to 6, and especially preferably from 2 to 4 carbon atoms.

Therefore, the present invention also relates to a method and a conjugate as described above, wherein the polymer is reacted with 1,4-diaminobutane, 1,3-diaminopropane or 1,2-diaminoethane to give a polymer derivative.

According to a first alternative, the functional group M being an amino group $NH_2$ is reacted with the oxidized reducing end of the polymer resulting in an amido group linking the polymer and the compound comprising M and Q.

According to a second alternative, the functional group M being an amino group $NH_2$ is reacted with the non-oxidized reducing end of the polymer via reductive amination resulting in an imino group which is subsequently preferably hydrogenated to give a amino group, the imino group and the amino group, respectively, linking the polymer and the compound comprising M and Q. In this case, it is possible that the functional group Q is an amino group. In case that the resulting polymer derivative shall be subjected to a subsequent reaction with an at least bifunctional compound via a carboxy group or a reactive carboxy group, as described hereinunder, or another group of an at least bifunctional compound which is to be reacted with an amino group, it is preferred that the compound comprising M and Q is a primary amine which contains—as functional group—only one amino group. In this specific case, although the compound contains only one functional group, it is regarded as bifunctional compound comprising M and Q wherein M is the amino group contained in the compound subjected to the reductive amination with the reducing end of the polymer, and wherein Q is the secondary amino group resulting from the reductive amination and subsequent hydrogenation.

According to a third alternative, the non-oxidized reducing end of the polymer is reacted with ammonia via reductive amination resulting in a terminal imino group of the polymer which is subsequently preferably hydrogenated to give a terminal amino group of the polymer and thus a terminal primary amino group. In this specific case, ammonia is regarded as bifunctional compound comprising M and Q wherein M is $NH_2$ comprised in the ammonia employed, and wherein Q is the primary amino group resulting from reductive amination and subsequent hydrogenation.

The reaction of the at least bifunctional compound comprising M and Q with the polymer is preferably carried out at a temperature of from 0 to 100° C., more preferably of from 4 to 80° C. and especially preferably of from 20 to 80° C.; the reaction time preferably ranges of from 4 h to 7 d, more preferably of from 10 h to 5 d and especially preferably of from 17 to 4 h. The molar ratio of at least bifunctional compound:polymer is preferably in the range of from 10 to 200, specially from 50 to 100.

As solvent for the reaction of the at least bifunctional compound with the polymer, at least one aprotic solvent, particularly preferably an anhydrous aprotic solvent having a water content of not more than 0.5 percent by weight, preferably of not more than 0.1 percent by weight is preferred. Suitable solvents are, among others, dimethyl sulfoxide (DMSO), N-methyl pyrrolidone, dimethyl acetamide (DMA), dimethyl formamide (DMF) and mixtures of two or more thereof.

As solvent for the reaction of the at least bifunctional compound with the polymer, also an aqueous medium may be used.

According to a preferred embodiment, the polymer derivative comprising the polymer and the at least bifunctional compound is chemically modified at the free functional group Q to give a polymer derivative comprising an aldehyde group or keto group or hemiacetal group. According to this embodiment, it is preferred to react the polymer derivative with at least one at least bifunctional compound which comprises a functional group capable of being reacted with the functional group Q and an aldehyde group or keto group or hemiacetal group.

As at least bifunctional compound, each compound is suitable which has an aldehyde group or keto group or hemiacetal group and at least one functional group which is capable of forming a linkage with the functional group Q of the polymer derivative. The at least one functional group is selected from the same pool of functional groups as Q and is chosen to be able to be reacted with Q. In the preferred case that Q is an amino group —$NH_2$, it is preferred to employ a compound having, apart from the aldehyde group or keto group or hemiacetal group, at least one carboxy group or at least one reactive carboxy group, preferably one carboxy group or one reactive carboxy group. The aldehyde group group or keto group or hemiacetal group and the carboxy group or the reactive carboxy group may be separated by any suitable spacer. Among others, the spacer may be an optionally substituted, linear, branched and/or cyclic hydrocarbon residue. Generally, the hydrocarbon residue has from 1 to 60, preferably from 1 to 40, more preferably from 1 to 20, more preferably from 2 to 10, more preferably from 2 to 6 and especially preferably from 2 to 4 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group.

According to a preferred embodiment, the hydrocarbon residue is an alkyl group having 2 to 6 and preferably 2 to 4 carbon atoms. It is also possible that no carbon atom is present between the aldehyd or keto group and the carboxy group. Alternatively, the hydrocarbon residue can be a substituted or unsubstituted cyclic hydrocarbon group having 3 to 11 carbon atoms, preferably, 3 to 6 or 3 to 5 carbon atoms. When the cyclic hydrocarbon group is substituted, the substituent can be selected from the group consisting of substituted or unsubstituted amino or alkoxy groups. If present, the number of substituents is preferably 1 to 3. Further, the alkyl and/or cyclic hydrocarbon group can contain one or more heteroatoms, such as O or S, in particular O. In this case, preferably 1 to 3, in particular 1 or 2 heteroatoms are present. Preferred compounds in this context are selected from the following group of compounds.

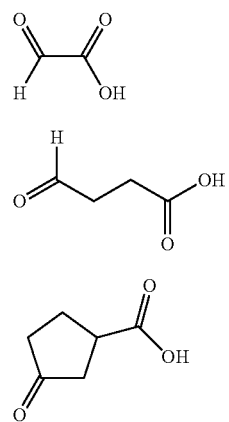

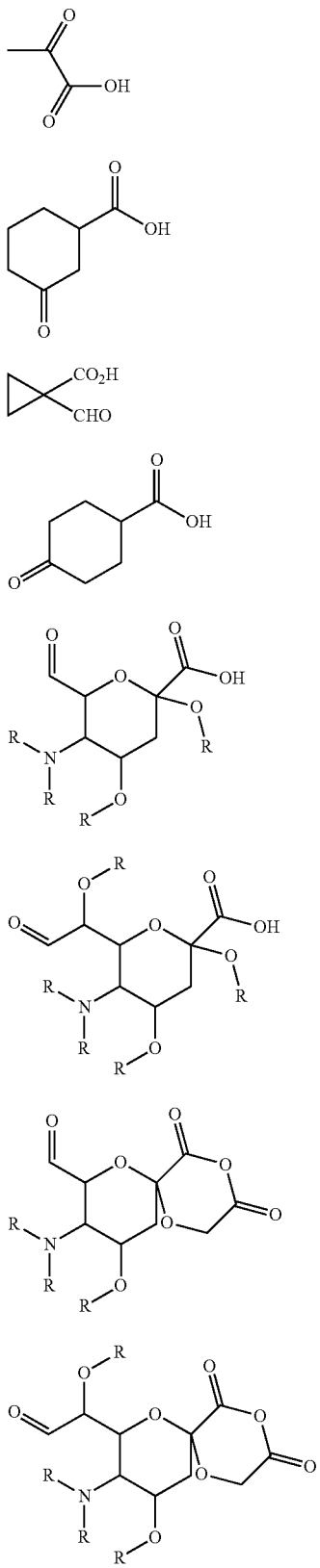

According to an even more preferred embodiment, the hydrocarbon residue is an aryl residue having 5 to 7 and preferably 6 carbon atoms. Most preferably, the hydrocarbon residue is the benzene residue. According to this preferred embodiment, the carboxy group and the aldehyde group may be located at the benzene ring in 1,4-position, 1,3-position or 1,2-position, the 1,4-position being preferred.

As reactive carboxy group, a reactive ester, isothiocyanates or isocyanate may be mentioned. Preferred reactive esters are derived from N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N-hydroxy succinimides, with N-hydroxy succinimide and Sulfo-N-hydroxy succinimide being especially preferred. All alcohols may be employed alone or as suitable combination of two or more thereof. As reactive esters, pentafluorophenyl ester and N-hydroxy succinimide ester are especially preferred.

According to a specific embodiment, the functional group which is capable of forming a chemical linkage with the functional group Q, Q preferably being $NH_2$ or a derivative of the amino group comprising the structure unit —NH— such as aminoalkyl groups, aminoaryl group, aminoaralkyl groups, or alkarylamino groups, in particular being $NH_2$, is a reactive carboxy group.

In this case, the functional group which is capable of forming a chemical linkage with the functional group Q and which is a carboxy group, is suitably reacted to obtain a reactive carboxy group as described hereinabove. Therefore, it is preferred to subject the at least one at least bifunctional compound which comprises a carboxy group and an aldehyde group or keto group or hemiacetal group, to a reaction wherein the carboxy group is transformed into a reactive carboxy group, and the resulting at least bifunctional compound is purified and reacted with functional group Q of the polymer derivative.

Specific examples of the at least bifunctional compound comprising a carboxy group which may be reacted to obtain a reactive carboxy group are the compounds 1 to 11 of the list hereinabove. In this context, the term "carboxy group" also relates to a lacton and an internal anhydride of a dicarboxylic acid compound.

Thus, according to a preferred embodiment, the present invention relates to a method and a conjugate as described above, wherein the polymer derivative comprising Q, Q being an amino group —$NH_2$, is further reacted with formylbenzoic acid.

According to another embodiment, the present invention relates to a method and a conjugate as described above, wherein the polymer derivative comprising Q, Q being an amino group, is further reacted with formylbenzoic acid pentafluorophenyl ester.

According to yet another embodiment, the present invention relates to a method and a conjugate as described above, wherein the polymer derivative comprising Q, Q being an amino group, is further reacted with formylbenzoic acid N-hydroxysuccinimide ester.

According to yet another embodiment, the present invention relates to a method and a conjugate as described above, wherein the polymer derivative comprising Q, Q being an amino group, is further reacted with 4-(4-formyl-3,5-dimethoxyphenoxy)butyric acid.

According to another preferred embodiment, the present invention relates to a method and a conjugate as described above, wherein the polymer derivative comprising Q, Q being an amino group —$NH_2$, is further reacted with a bifunctional compound which is a biocompatible compound selected from the group consisting of alpha-keto carboxylic acids, sialic acids or derivatives thereof and pyridoxal phosphate.

As regards alpha-keto carboxylic acids, those are preferably alpha-keto carboxylic acids derived from amino acids and can in most instances also be found in the human body. Preferred alpha-keto carboxylic acids derived from amino acids are selected from the group consisting of keto-valine, keto-leucine, keto-isoleucine and keto-alanine. The carboxy group of the alpha-keto carboxylic acids is reacted with group Q of the polymer being an amino group. Therewith an amido group is formed. The remaining free keto group of the alpha-keto carboxylic acid may then be reacted with a functional group of the protein, in particular an amino group. Therewith an imino group is formed which may be hydrogenated.

Accordingly, the present invention relates to a method and a conjugate as described above, wherein the polymer derivative comprising Q, Q being an amino group, is further reacted with an alpha-keto carboxylic acid.

As regards sialic acids or derivatives thereof those are preferably biocompatible, in particular they are sugars found in the human body, which are N- and/or O-acetylated. In a preferred embodiment, the neuramic acids or sialic acids are N-acetyl neuramic acids. These compounds show a desired rigidity because of the pyranose structure in order to fulfill the function as a spacer. On the other hand, it may be possible to introduce an aldehyde group into these compounds through selective oxidation. Sialic acids are found in the human body e.g. as terminal monosaccharides in glycan chains of glycosylated proteins.

In a preferred embodiment, the sialic acid may be selectively oxidized to an aldehyde group.

Methods to electively oxidize sialic acids or neuramic acids are known in the art, e.g. from L. W. Jaques, B. F. Riesco, W. Weltner, Carbohydrate Research, 83 (1980), 21-32 and T. Masuda, S. Shibuya, M. Arai, S. Yoshida, T. Tomozawa, A. Ohno, M. Yamashita, T. Honda, Bioorganic & Medicinal Chemistry Letters, 13 (2003), 669-673. Preferably the oxidation of the sialic acid may be conducted prior to the reaction with the polymer containing Q, Q being an amino group.

The optionally oxidized sialic acid, may then be reacted via its carboxylic acid group with the amino group of the polymer.

The resulting compounds contain an aldehyde group which can then further be reacted by reductive amination with an amino group of a protein.

Accordingly, the present invention relates to a method and a conjugate as described above, wherein the polymer derivative comprising Q, Q being an amino group, is further reacted with an optionally oxidized sialic acid.

As regards pyridoxal phosphate (PyP), this is a highly biocompatible bifunctional compound and is also called vitamin B6. PyP is a co-enzyme which participates in transaminations, decarboxylations, racemizations, and numerous modifications of amino acid side chains. All PyP requiring enzymes act via the formation of a Schiff's base between the amino acid and the co-enzyme.

The phosphate group of the PyP may be reacted with the amino group of the polymer, preferably hydroxyalkyl starch, in particular hydroxyethyl starch, forming a phosphoramide. The aldehyde group of PyP may then be reacted with the amino group of a protein, forming a Schiff's base, which may then be reduced. In a preferred embodiment, the structure of the conjugate is HES-NH—P(O)2-O-(pyridoxal)-CH—NH-protein.

In case of PyP, the functional group Q of the polymer is preferably introduced into the polymer by use of a di-amino compound as described above.

Accordingly, the present invention relates to a method and a conjugate as described above, wherein the polymer derivative comprising Q, Q being an amino group, is further reacted with pyridoxal phosphate.

As solvent for the reaction of the polymer derivative comprising an amino group and, e.g., formylbenzoic acid, at least one aprotic solvent or at least one polar solvent is preferred. Suitable solvents are, among others, water, dimethyl sulfoxide (DMSO), N-methyl pyrrolidone, dimethyl acetamide (DMA), dimethyl formamide (DMF) and mixtures of two or more thereof.

As solvent for the reaction of the polymer derivative comprising an amino group and the at least bifunctional compound comprising a carboxy group, it is also possible to use an aqueous medium. The term "aqueous medium" as used in this context of the present invention relates to a solvent or a mixture of solvents comprising water in the range of from at least 10% per weight or at least 20% per weight or at least 30% per weight or at least 40% per weight or at least 50% per weight or at least 60% per weight or at least 70% per weight or at least 80% per weight or at least 90% per weight or up to 100% per weight, based on the weight of the solvents involved.

The reaction is preferably carried out at a temperature of from 0 to 40° C., more preferably of from 0 to 25° C. and especially preferably of from 15 to 25° C. for a reaction time preferably of from 0.5 to 24 h and especially preferably of from 1 to 17 h.

According to a preferred embodiment, the reaction is carried out in the presence of an activating agent. Suitable activating agents are, among others, carbodiimides such as diisopropyl carbodiimde (DIC), dicyclohexyl carbodiimides (DCC), 1-ethyl-3-(3-dimethylaminopropyl)carbodiimide (EDC), with diisopropyl carbodiimide (DIC) being especially preferred.

The resulting polymer derivative may be purified from the reaction mixture by at least one suitable method. If necessary, the polymer derivative may be precipitated prior to the isolation by at least one suitable method.

If the polymer derivative is precipitated first, it is possible, e.g., to contact the reaction mixture with at least one solvent or solvent mixture other than the solvent or solvent mixture present in the reaction mixture at suitable temperatures. According to a particularly preferred embodiment of the present invention where an aqueous medium, preferably water is used as solvent, the reaction mixture is contacted with 2-propanol or with am mixture of acetone and ethanol, preferably a 1:1 mixture (v/v), indicating equal volumes of said compounds, at a temperature, preferably in the range of from −20 to +50° C. and especially preferably in the range of from −20 to 25° C.

Isolation of the polymer derivative may be carried out by a suitable process which may comprise one or more steps. According to a preferred embodiment of the present invention, the polymer derivative is first separated off the reaction mixture or the mixture of the reaction mixture with, e.g., aqueous 2-propanol mixture, by a suitable method such as centrifugation or filtration. In a second step, the separated polymer derivative may be subjected to a further treatment such as an after-treatment like dialysis, centrifugal filtration or pressure filtration, ion exchange chromatography, reversed phase chromatography, HPLC, MPLC, gel filtration and/or lyophilisation. According to an even more preferred embodiment, the separated polymer derivative is first dialysed, preferably against water, and then lyophilized until the solvent content of the reaction product is sufficiently low according to the desired specifications of the product. Lyophilisation may be carried out at temperature of from 20 to 35° C., preferably of from 20 to 30° C.

The resulting polymer derivative with the aldehyde group or keto group or hemiacetal group is subsequently reacted with an amino group of the protein via reductive amination. As to the coupling of at least one amino group of the protein with at least one aldehyde group or keto group or hemiacetal group of the polymer by reductive amination, reference is made to the detailed disclosure above concerning the specific reaction parameters of the reductive amination reaction such as pH or temperature. According to an especially preferred embodiment of the present invention, the reductive amination is carried out at a temperature of from 0 to 10° C. such as from 1 to 8° C. or from 2 to 6° C. such as about 4° C. at a pH of about 4.5 to 5.5 such as about 5.0. The reaction time is about 10 to 20 h such as from 12 to 19 h or from 14 to 18 h such as about 17 h or about 20 to 30 h such as about 24 h.

Thus, according to the above-mentioned preferred embodiments, the present invention also relates, in case the polymer was reacted via its oxidized reducing end, to a conjugate according to the formula

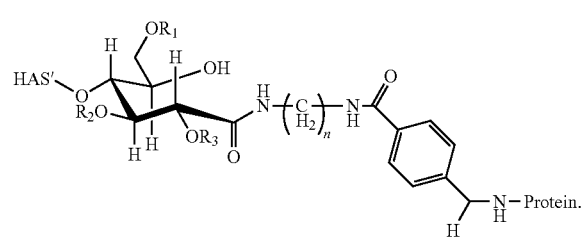

According to an especially preferred embodiment, the polymer is hydroxyethyl starch, i.e. HAS' is HES', and n=2, 3, or 4, most preferably 4, as described above. Therefore, in case the polymer was reacted via its oxidized reducing end, the present invention also relates to a conjugate according to the formula

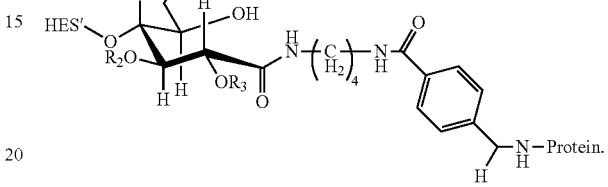

According to another preferred embodiment, the present invention also relates, in case the polymer was reacted via its oxidized reducing end, to a conjugate according to the formula

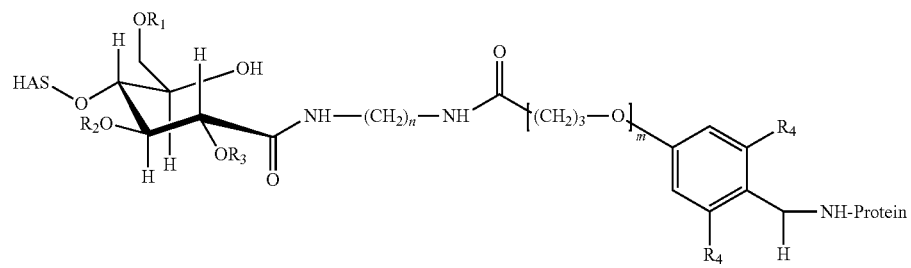

wherein n=2, 3, or 4, $R_4$ being independently hydrogen or a methoxy group, and m=0 in case $R_4$ is hydrogen and m=1 in case $R_4$ is methoxy, HAS preferably being HES'.

In each of the formulae above, the nitrogen attached to the protein derives from the amino group of the protein the polymer derivative is linked to via the aldehyde group.

With respect to the above-mentioned embodiments according to which the functional groups M and Q comprise an amino group —$NH_2$, it is also possible that M is an amino group —$NH_2$ and Q comprises a beta hydroxy amino group —CH(OH)—$CH_2$—$NH_2$ and preferably is a beta hydroxy amino group.

Therefore, the present invention also relates to a method and a conjugate as described above, wherein the amino group Q of the compound comprising two amino groups M and Q, is a beta hydroxy amino group —CH(OH)—$CH_2$—$NH_2$.

In this case, M and Q may be separated by any suitable spacer. Among others, the spacer may be an optionally substituted, linear, branched and/or cyclic hydrocarbon residue. Generally, the hydrocarbon residue has from 1 to 60, preferably from 1 to 40, more preferably from 1 to 20, more preferably from 2 to 10, more preferably from 1 to 6 and especially preferably from 1 to 2 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group. According to an even more preferred embodiment, the hydrocarbon residue is an alkyl chain of from 1 to 20, preferably from 1 to 10, more preferably from 1 to 6, more preferably from 1 to 4 carbon atoms and especially preferably from 1 to 2 carbon atoms. Still more preferably, M and Q are separated by a methylene group.

Therefore, the present invention also relates to a method and a conjugate as described above, wherein the polymer is reacted with 1,3-diamino-2-hydroxypropane.

In case the polymer is reacted via its oxidized reducing end, a polymer derivative according to the formula results

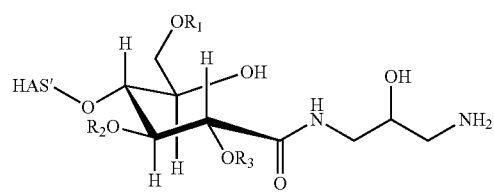

especially preferably with HAS'=HES'

The reaction of the at least bifunctional compound comprising M and Q, particularly preferably 1,3-diamino-2-hydroxypropane, with the polymer is preferably carried out at a temperature of from 40 to 120° C., more preferably of from 40 to 90° C. and especially preferably of from 60 to 80° C. The reaction time preferably ranges from 17 to 168 h, more preferably from 17 to 96 h and especially preferably from 48 to 96 h. The molar ratio of at least bifunctional compound:polymer is preferably in the range of from 200:1 to 10:1, specially from 50:1 to 100:1.

As solvent for the reaction of the at least bifunctional compound with the polymer, at least one aprotic solvent, preferably an anhydrous aprotic solvent having a water content of not more than 0.5 percent by weight, preferably of not more than 0.1 percent by weight is preferred. Suitable solvents are, among others, dimethyl sulfoxide (DMSO), N-methyl pyrrolidone, dimethyl acetamide (DMA), dimethyl formamide (DMF) and mixtures of two or more thereof.

The beta hydroxy amino group Q of the polymer derivative generally may be reacted with an at least bifunctional compound comprising at least one functional group capable of being reacted with Q and further comprising at least one functional group being an aldehyde group or keto group or hemiacetal group or a functional group capable of being modified to give an aldehyde group or keto group or hemiacetal group. According to another embodiment of the present invention, the beta hydroxy amino group is directly chemically modified to give an aldehyde group by chemical oxidation.

This oxidation may be carried with all suitable oxidation agents, which are capable of converting the beta hydroxy amino group to an aldehyde group. Preferred oxidation reagents are periodates such as alkaline metal periodates. Especially preferred is sodium periodate which is preferably employed as aqueous solution. This solution has a preferred iodate concentration of from 1 to 50 mM, more preferably from 1 to 25 mM and especially preferably of from 1 to 10 mM. Oxidation is carried out at a temperature of from 0 to 40° C., preferably from 0 to 25° C. and especially preferably from 4 to 20° C.

The resulting polymer derivative may be purified from the reaction mixture by at least one suitable method. If necessary, the polymer derivative may be precipitated prior to the isolation by at least one suitable method.

If the polymer derivative is precipitated first, it is possible, e.g., to contact the reaction mixture with at least one solvent or solvent mixture other than the solvent or solvent mixture present in the reaction mixture at suitable temperatures. According to a particularly preferred embodiment of the present invention where an aqueous medium, preferably water is used as solvent, the reaction mixture is contacted with 2-propanol or with am mixture of acetone and ethanol, preferably a 1:1 mixture (v/v), indicating equal volumes of said compounds, at a temperature, preferably in the range of from −20 to +50° C. and especially preferably in the range of from −20 to 25° C.

Isolation of the polymer derivative may be carried out by a suitable process which may comprise one or more steps. According to a preferred embodiment of the present invention, the polymer derivative is first separated off the reaction mixture or the mixture of the reaction mixture with, e.g., aqueous 2-propanol mixture, by a suitable method such as centrifugation or filtration. In a second step, the separated polymer derivative may be subjected to a further treatment such as an after-treatment like dialysis, centrifugal filtration or pressure filtration, ion exchange chromatography, reversed phase chromatography, HPLC, MPLC, gel filtration and/or lyophilisation. According to an even more preferred embodiment, the separated polymer derivative is first dialysed, preferably against water, and then lyophilized until the solvent content of the reaction product is sufficiently low according to the desired specifications of the product. Lyophilisation may be carried out at temperature of from 20 to 35° C., preferably of from 20 to 30° C.

Therefore, the present invention also relates to a method and a conjugate as described above, wherein the oxidation of the beta hydroxy amino group Q is carried out using a periodate.

Therefore, the present invention also relates to a method of producing a conjugate, wherein, in case the polymer was employed with oxidized reducing end, a polymer derivative having a beta hydroxy amino group, especially preferably

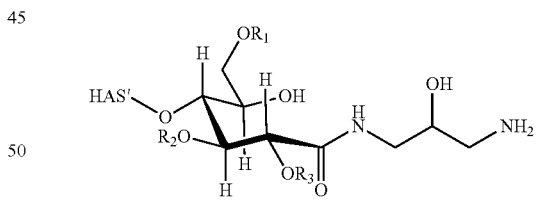

and particularly with HAS'=HES', is oxidized, preferably with a periodate, to a polymer derivative having an aldehyde group, especially preferably

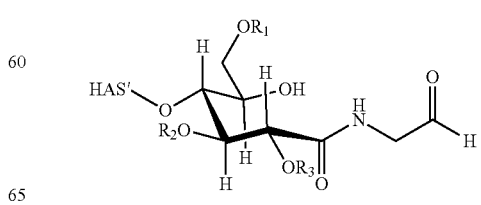

and particularly with HAS'=HES'.

According to the present invention, it is also possible to react the compound comprising an 1-amino 2-hydroxy structure depicted above with an at least bifunctional compound comprising a carboxy group or a reactive carboxy group and an aldehyde, keto or acetal group described hereinabove to obtain a polymer derivative which can be subjected to reductive amination with an amino group of the protein.

The resulting polymer derivative with the aldehyde group A is subsequently reacted with the protein. Therefore, the present invention also relates to a method of producing a conjugate, said method comprising reacting a polymer derivative having a beta hydroxy amino group, in case the polymer was employed with oxidized reducing end especially preferably according to the formula

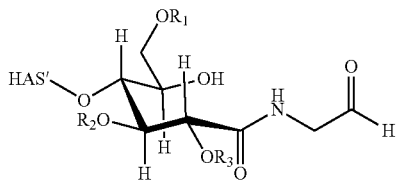

and particularly with HAS'=HES', with an amino group of the protein.

The resulting polymer derivative with the aldehyde group is subsequently reacted with an amino group of the protein via reductive amination. As to the coupling of at least one amino group of the protein with at least one aldehyde group of the polymer by reductive amination, reference is made to the detailed disclosure above.

Thus, according to the above-mentioned preferred embodiment, the present invention also relates to a conjugate according to the formula

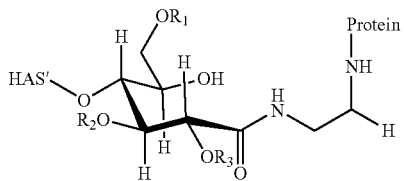

particularly with HAS'=HES', in case the polymer was employed with oxidized reducing end. In the formula above, the nitrogen attached to the protein derives from the amino group of the protein the polymer derivative is linked to via the aldehyde group.

According to a further embodiment of the present invention, the polymer is first reacted with a suitable compound to give a first polymer derivative comprising at least one reactive carboxy group. This first polymer derivative is then reacted with a further, at least bifunctional compound wherein at least one functional group of this further compound is reacted with at least one reactive carboxy group of the polymer derivative and at least one other functional group of the further compound is an aldehyde group or keto group or hemiacetal group or is a functional group which is chemically modified to give an aldehyde group or keto group or hemiacetal group, and wherein the resulting polymer derivative comprising said aldehyde group or keto group or hemiacetal group is reacted via reductive amination, as described above, with at least one amino group of the protein. It is also possible to alter the sequence of reacting the respective compounds with each other.

According to a first alternative of said further embodiment, the polymer comprising at least one reactive carboxy group is prepared by selectively oxidizing the polymer at its reducing end and subsequently reacting the oxidized polymer being a lactone

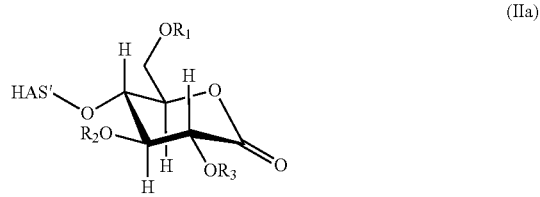

and/or a carboxylic acid

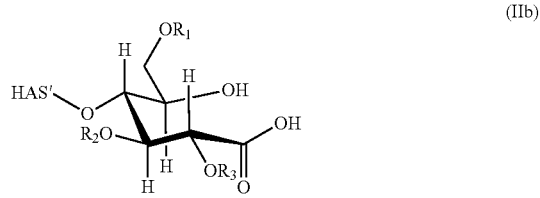

or a suitable salt of the carboxylic acid such as alkali metal salt, preferably as sodium and/or potassium salt, and HAS' preferably being HES', with a suitable compound to give the polymer comprising at least one reactive carboxy group.

Oxidation of the polymer, preferably hydroxyethyl starch, may be carried out according to each method or combination of methods which result in compounds having the above-mentioned structures (IIa) and/or (IIb).

Although the oxidation may be carried out according to all suitable method or methods resulting in the oxidized reducing end of hydroxyalkyl starch, it is preferably carried out using an alkaline iodine solution as described, e.g., in DE 196 28 705 A1 the respective contents of which (example A, column 9, lines 6 to 24) is incorporated herein by reference.

Introducing the reactive carboxy group into the polymer which is selectively oxidized at its reducing end may be carried out by all conceivable methods and all suitable compounds.

According to a specific method of the present invention, the polymer which is selectively oxidized at its reducing end is reacted at the oxidized reducing end with at least one alcohol, preferably with at least one acidic alcohol such as acidic alcohols having a $pK_A$ value in the range of from 6 to 12 or of from 7 to 11 at 25° C. The molecular weight of the acidic alcohol may be in the range of from 80 to 500 g/mole, such as of from 90 to 300 g/mole or of from 100 to 200 g/mole.

Suitable acidic alcohols are all alcohols H—O—$R_A$ having an acidic proton and are capable of being with reacted with the oxidized polymer to give the respective reactive polymer ester, preferably according to the formula

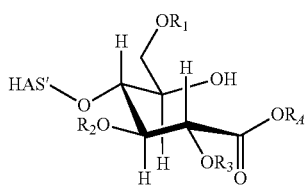

still more preferably according to formula

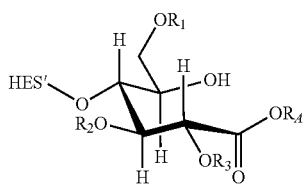

Preferred alcohols are N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N-hydroxy succinimides, with N-hydroxysuccinimide and Sulfo-N-hydroxysuccinimide being especially preferred. All alcohols may be employed alone or as suitable combination of two or more thereof. In the context of the present invention, it is also possible to employ a compound which releases the respective alcohol, e.g. by adding diesters of carbonic acid.

Therefore, the present invention also relates to a method as described above, wherein the polymer which is selectively oxidised at its reducing end is activated by reacting the oxidised polymer with an acidic alcohol, preferably with N-hydroxy succinimide and/or Sulfo-N-hydroxy succinimide.

According to a preferred embodiment of the present invention, the polymer which is selectively oxidized at its reducing end is reacted at the oxidized reducing end with at least one carbonic diester $R_B$—O—(C=O)—O—$R_C$, wherein $R_B$ and $R_C$ may be the same or different. Preferably, this method gives reactive polymers according to the formula

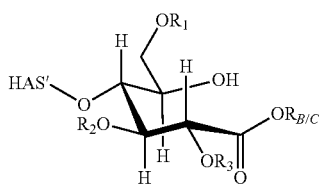

wherein HAS' is preferably HES'.

As suitable carbonic diester compounds, compounds may be employed whose alcohol components are independently N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N,N'-disuccinimidyl carbonate and Sulfo-N,N'-disuccinimidyl carbonate, with N,N'-disuccinimidyl carbonate being especially preferred.

Therefore, the present invention also relates a method as described above, wherein the polymer which is selectively oxidised at its reducing end is activated by reacting the oxidised polymer with N,N'-disuccinimidyl carbonate.

The acidic alcohol is reacted with the oxidized polymer or the salt of the oxidized polymer at a molar ratio of acidic alcohol:polymer preferably of from 5:1 to 50:1, more preferably of from 8:1 to 20:1, at a preferred reaction temperature of from 2 to 40° C., more preferably of from 10 to 30° C. and especially preferably of from 15 to 25° C. The reaction time is preferably in the range of from 1 to 10 h, more preferably of from 2 to 5 h, more preferably of from 2 to 4 h and particularly of from 2 to 3 h.

The carbonic diester compound is reacted with the oxidized polymer or the salt of the oxidized polymer at a molar ratio of diester compound:polymer generally of from 1:1 to 3:1, such as of from 1:1 to 1.5:1. The reaction time is generally in the range of from 0.1 to 12 h, like of from 0.2 to 6 h, or of from 0.5 to 2 h or of from 0.75 to 1.25 h.

According to a preferred embodiment of the present invention, reacting the oxidized polymer with acidic alcohol and/or carbonic diester is carried out in at least one aprotic solvent, such as in an anhydrous aprotic solvent having a water content of not more than 0.5 percent by weight, preferably of not more than 0.1 percent by weight. Suitable solvents are, among others, dimethyl sulfoxide (DMSO), N-methyl pyrrolidone, dimethyl acetamide (DMA), dimethyl formamide (DMF) and mixtures of two or more thereof. The reaction temperatures are preferably in the range of from 2 to 40° C., more preferably of from 10 to 30° C.

For reacting the oxidized polymer with the at least one acidic alcohol, at least one additional activating agent is employed.

Suitable activating agents are, among others, carbonyldiimidazole, carbodiimides such as diisopropyl carbodiimide (DIC), dicyclohexyl carbodiimides (DCC), 1-ethyl-3-(3-dimethylaminopropyl)carbodiimide (EDC), with dicyclohexyl carbodiimides (DCC) and 1-ethyl-3-(3-dimethylaminopropyl)carbodiimide (EDC) being especially preferred.

Therefore, the present invention also relates to the method as described above, where the polymer which is oxidized at its reducing end and is reacted with an acidic alcohol in the presence of an additional activating agent to give the reactive polymer ester.

According to one embodiment of the present invention, the reaction of the oxidized polymer with carbonic diester and/or acidic alcohol is carried out at a low base activity which may be determined by adding the reaction mixture to water with a volume ratio of water to reaction mixture of 10:1. Prior to the addition, the water which comprises essentially no buffer, has a pH value of 7 at 25° C. After the addition of the reaction mixture and by measuring the pH value, the base activity of the reaction mixture is obtained, having a value of preferably not more than 9.0, more preferably of nor more than 8.0 and especially preferably of not more than 7.5.

According to another embodiment of the present invention, the oxidized polymer is reacted with N-hydroxy succinimide in dry DMA in the absence of water with EDC to selectively give the polymer N-hydroxy succinimide ester according to the formula

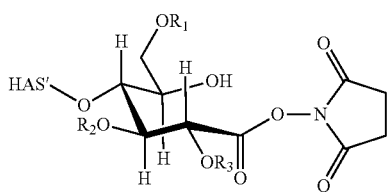

more preferably with HAS' being HES'.

Surprisingly, this reaction does not give by-products resulting from reactions of EDC with OH groups of HES, and the rearrangement reaction of the O-acyl isourea formed by EDC and the oxidized polymer to the respective N-acyl urea is surprisingly suppressed.

According to another preferred embodiment of the present invention, the oxidized polymer is reacted with N,N'-disuccinimidyl carbonate in dry DMF in the absence of water and in the absence of an activating agent to selectively give the polymer N-hydroxy succinimide ester according to the formula

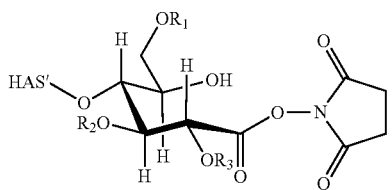

more preferably with HAS' being HES'.

According to another embodiment of the present invention, the polymer which is selectively oxidized at its reducing end is reacted at the oxidized reducing end with an azolide such as carbonyldiimidazole or carbonyl dibenzimidazole to give a polymer having a reactive carboxy group. In the case of carbonyldiimidazole, a reactive imidazolide polymer derivative according to formula

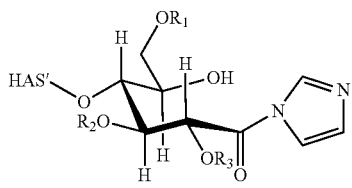

results, wherein HAS' is preferably HES'.

According to a second alternative of said further embodiment of the present invention regarding the introduction of at least one reactive carboxy group into the polymer, the reactive carboxy group is introduced into the polymer whose reducing end is not oxidized, by reacting at least one hydroxy group of the polymer with a carbonic diester.

Therefore, the present invention also relates to a method and conjugates wherein the reactive carboxy group is introduced in the polymer whose reducing end is not oxidized, by reacting at least one hydroxy group of the polymer with at least one carbonic diester carbonic diester $R_B$—O—(C=O)—O—$R_C$, wherein $R_B$ and $R_C$ may be the same or different.

According to another embodiment of the present invention, the polymer whose reducing end is not oxidized, is reacted at at least one hydroxy group with an azolide such as carbonyl-diimidazole, carbonyl-di-(1,2,4-triazole) or carbonyl dibenzimidazol to give a polymer having a reactive carboxy group.

As suitable carbonic diester compounds, compounds may be employed whose alcohol components are independently N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole.

Especially preferred are symmetrical carbonic diester compounds, $R_B$ and $R_C$ thus being the same. The alcohol component of the carbonic diester is preferably selected from the group consisting of N-hydroxy succinimide, sulfonated N-hydroxy succinimide, N-hydroxy benzotriazole, and nitro- and halogen-substituted phenols. Among others, nitrophenol, dinitrophenol, trichlorophenol, trifluorophenol, pentachlorophenol, and pentafluorophenol are preferred. Especially preferred are N,N'-disuccinimidyl carbonate and Sulfo-N,N'-disuccinimidyl carbonate, with N,N'-disuccinimidyl carbonate being especially preferred.

Therefore, the present invention also relates to a hydroxyalkyl starch derivative, preferably a hydroxyethyl starch derivative, wherein at least one hydroxy group, preferably at least two hydroxy groups of said starch have been reacted with a carbonic diester compound to give the respective reactive ester.

According to one embodiment of the present invention, the reaction of the polymer whose reducing end is not oxidized, with the at least one carbonic diester compound is carried out at a temperature of from 2 to 40° C., more preferably of from 10 to 30° C. and especially of from 15 to 25° C. A preferred reaction time ranges from 0.5 to 5 h, more preferably from 1 to 3 h, and especially preferably from 2 to 3 h.

The molar ratio of carbonic diester compound:polymer depends on the degree of substitution of the polymer regarding the number of hydroxy groups reacted with carbonic diester compound relative to the number of hydroxy groups present in the non-reacted polymer.

According to one embodiment of the present invention, the molar ratio of carbonic diester compound:anhydroglucose units of the polymer is in the range of from 1:2 to 1:1000, more preferably of from 1:3 to 1:100 and especially preferably of from 1:10 to 1:50, to give a degree of substitution in the range of from 0.5 to 0.001, preferably of from 0.33 to 0.01 and especially preferably of from 0.1 to 0.02

According to one embodiment of the present invention, reacting the polymer whose reducing end is not oxidized, with carbonic diester is carried out in at least one aprotic solvent, particularly preferably in an anhydrous aprotic solvent having a water content of not more than 0.5 percent by weight, preferably of not more than 0.1 percent by weight. Suitable solvents are, among others, dimethyl sulfoxide (DMSO), N-methyl pyrrolidone, dimethyl acetamide (DMA), dimethyl formamide (DMF) and mixtures of two or more thereof.

Therefore, the present invention also relates to a method as described above wherein the reaction of the at least one hydroxy group of the polymer whose reducing end is not oxidised, with the carbonic diester to give a reactive carboxy group is carried out in an anhydrous aprotic polar solvent, the solvent preferably being dimethyl acetamide, dimethyl formamide or a mixture thereof.

The reactive polymer derivative comprising at least one reactive carboxy group, preferably resulting from the reaction of the polymer with the acidic alcohol, the carbonate and/or the azolide, as described above, is further reacted with a further, at least bifunctional compound wherein at least one functional group $F_1$ of this further compound is reacted with at least one reactive carboxy group of the polymer derivative. As at least one functional group $F_1$ of the further compound no specific limitations exist given that a reaction with the at least one reactive carboxy group of the polymer is possible. Preferred functional groups $F_1$ are, e.g. an amino group or a hydroxy group or a thio group or a carboxy group.

The further, at least bifunctional compound comprises at least one other functional group $F_2$ being an aldehyde group or a functional group $F_2$ being capable of being chemically modified to give an aldehyde group. The chemical modification may be, e.g., a reaction of the functional group $F_2$ with a functional group $F_3$ a further linker compound or an oxidation or a reduction of a suitable functional group $F_2$.

In case $F_2$ is reacted with a functional group $F_3$ of a further compound, the functional group $F_2$ may be selected from, among others, C—C-double bonds or C—C-triple bonds or aromatic C—C-bonds;
the thio group or the hydroxy group;
alkyl sulfonic acid hydrazide, aryl sulfonic acid hydrazide;
1,2-dioles;
1,2-aminoalcohols;
1,2 amino-thioalcohols;
azides;
the amino group —NH$_2$ or derivatives of the amino groups comprising the structure unit —NH— such as aminoalkyl groups, aminoaryl group, aminoaralkyl groups, or alkarlyamino groups;
the hydroxylamino group —O—NH$_2$, or derivatives of the hydroxylamino group comprising the structure unit —O—NH—, such as hydroxylalkylamino groups, hydroxylarylamino groups, hydroxylaralkylamino groups, or hydroxalalkarylamino groups;
alkoxyamino groups, aryloxyamino groups, aralkyloxyamino groups, or alkaryloxyamino groups, each comprising the structure unit —NH—O—;
residues having a carbonyl group, -Q-C(=G)-M, wherein G is O or S, and M is, for example,
—OH or —SH;
an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trichlorophenyl;
wherein Q is absent or NH or a heteroatom such as S or O;
—NH—NH$_2$, or —NH—NH—;
—NO$_2$;
the nitril group;
carbonyl groups such as the aldehyde group or the keto group;
the carboxy group;
the —N=C=O group or the —N=C=S group;
vinyl halide groups such as the vinyl iodide or the vinyl bromide group or triflate;
—C≡C—H;
—(C=NH$_2$Cl)—OAlkyl
groups —(C=O)—CH$_2$-Hal wherein Hal is Cl, Br, or I;
—CH=CH—SO$_2$—;
a disulfide group comprising the structure —S—S—;
the group

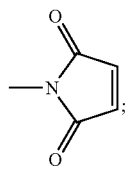

the group

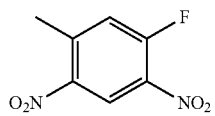

wherein $F_3$ is a group capable of forming a chemical linkage with one of the above-mentioned groups and is preferably selected from the above-mentioned groups. Moreover, the second linker compound preferably has at least one aldehyde group or keto group or hemiacetal group which is capable of being reacted with an amino group of the protein via reductive amination.

The functional group $F_1$ and the aldehyde group or keto group or hemiacetal group of the at least bifunctional linking compound which is reacted with the polymer, and/or the functional groups $F_1$ and $F_2$ of the at least bifunctional linking compound which is reacted with the polymer, and/or the functional group $F_3$ and the aldehyde group or keto group or hemiacetal group of the further, at least bifunctional linking compound, may be independently separated by any suitable spacer. Among others, the spacer may be an optionally substituted, linear, branched and/or cyclic, aliphatic and/or aromatic hydrocarbon residue. Generally, the hydrocarbon residue has up to 60, preferably up to 40, more preferably up to 20, more preferably up to 10 carbon atoms. If heteroatoms are present, the separating group comprises generally from 1 to 20, preferably from 1 to 8, more preferably 1 to 6, more preferably 1 to 4 and especially preferably from 1 to 2 heteroatoms. As heteroatom, O is preferred. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group.

Examples of a compound with functional groups $F_1$ and $F_2$ are, e.g., optionally substituted diaminoalkane having from 2 to 20 carbon atoms, especially preferably 1,2-diaminoethane, 1,3-diaminopropane, and 1,4-diaminobutane. Preferred examples of a compound with functional groups $F_3$ and an aldehyde group or a keto group or a hemiacetal group are, e.g., formylbenzoic acid, 4-formylbenzoic acid pentafluorophenyl ester, 4-formylbenzoic acid-N-hydroxysuccinimide ester and 4-(4-formyl-3,5-dimethoxyphenoxy)butyric acid.

Therefore, the present invention also relates to a method of producing a conjugate, said method comprising reacting the polymer, preferably hydroxyethyl starch, at its optionally oxidized reducing end with a compound, selected from the group consisting of acidic alcohols, carbonic diesters and azolides, to give a polymer derivative comprising at least one reactive carboxy group, reacting said polymer derivative with at least one at least bifunctional compound to give a polymer derivative comprising an aldehyde group or a keto group or a hemiacetal group or a functional group capable of being chemically modified to give an aldehyde group or a keto group or a hemiacetal group, optionally chemically modifying said functional group to give a polymer derivative comprising an aldehyde group or a keto group or a hemiacetal group, and reacting the polymer derivative comprising an aldehyde group or a keto group or a hemiacetal group with an amino group of a protein via reductive amination.

Accordingly, the present invention also relates to a conjugate comprising a polymer, preferably hydroxyethyl starch, and a protein covalently linked to each other, obtainable by a method of producing a conjugate, said method comprising reacting the polymer, at its optionally oxidized reducing end with a compound, selected from the group consisting of acidic alcohols, carbonic diesters and azolides, to give a polymer derivative comprising at least one reactive carboxy group, reacting said polymer derivative with at least one at least bifunctional compound to give a polymer derivative comprising an aldehyde group or a keto group or a hemiacetal group or a functional group capable of being chemically modified to give an aldehyde group or a keto group or a hemiacetal group, optionally chemically modifying said functional group to give a polymer derivative comprising an aldehyde group or a keto group or a hemiacetal group, and reacting the polymer derivative comprising an aldehyde group or a keto group or a hemiacetal group with an amino group of a protein via reductive amination.

A specific example of a compound having a functional group $F_1$ and a functional group $F_2$ which is oxidized to give an aldehyde group is, e.g., a compound having an amino group as $F_1$ and a beta hydroxy amino group as $F_2$. An especially preferred example is 1,3-diamino-2-hydroxypropane. This oxidation may be carried with all suitable oxidation agents, which are capable of converting the beta hydroxy amino group to an aldehyde group. Preferred oxidation reagents are periodates such as alkaline metal periodates. Especially preferred is sodium periodate which is preferably employed as aqueous solution. This solution has a preferred iodate concentration of from 1 to 50 mM, more preferably from 1 to 25 mM and especially preferably of from 1 to 10 mM. Oxidation is carried out at a temperature of from 0 to 40° C., preferably from 0 to 25° C. and especially preferably from 4 to 20° C.

The resulting polymer derivative may be purified from the reaction mixture by at least one suitable method. If necessary, the polymer derivative may be precipitated prior to the isolation by at least one suitable method.

If the polymer derivative is precipitated first, it is possible, e.g. to contact the reaction mixture with at least one solvent or solvent mixture other than the solvent or solvent mixture present in the reaction mixture at suitable temperatures. According to a particularly preferred embodiment of the present invention where an aqueous medium, preferably water is used as solvent, the reaction mixture is contacted with 2-propanol or with a mixture of acetone and ethanol, preferably a 1:1 mixture (v/v), indicating equal volumes of said compounds, at a temperature, preferably in the range of from −20 to +50° C. and especially preferably in the range of from −20 to 25° C.

Isolation of the polymer derivative may be carried out by a suitable process which may comprise one or more steps. According to a preferred embodiment of the present invention, the polymer derivative is first separated off the reaction mixture or the mixture of the reaction mixture with, e.g., aqueous 2-propanol mixture, by a suitable method such as centrifugation or filtration. In a second step, the separated polymer derivative may be subjected to a further treatment such as an after-treatment like dialysis, centrifugal filtration or pressure filtration, ion exchange chromatography, reversed phase chromatography, HPLC, MPLC, gel filtration and/or lyophilisation. According to an even more preferred embodiment, the separated polymer derivative is first dialysed, preferably against water, and then lyophilized until the solvent content of the reaction product is sufficiently low according to the desired specifications of the product. Lyophilisation may be carried out at temperature of from 20 to 35° C., preferably of from 20 to 30° C.

According to another preferred embodiment of the present invention, the functional group Z of the protein to be reacted with functional group A of the polymer or polymer derivative is a thiol group, wherein the protein is selected from the group consisting of IFN alpha, IFN beta, tPA, and A1AT. Most preferred are IFN alpha and IFN beta.

The thiol group may be present in the protein as such. Moreover, it is possible to introduce a thiol group into the protein according to a suitable method. Among others, chemical methods may be mentioned. If a disulfide bridge is present in the protein, it is possible to reduce the —S—S— structure to get a thiol group. It is also possible to transform an amino group present in the polypeptide into a SH group by reaction the polypeptide via the amino group with a compound which has at least two different functional groups, one of which is capable of being reacted with the amino group and the other is an SH group or a precursor of an SH group. It is also possible to introduce an SH group by mutation of the protein such as by introducing a cystein or a suitable SH functional amino acid into the protein or such as removing a cystein from the protein so as to disable another cystein in the protein to form a disulfide bridge.

Most preferably, the polymer is linked to a free cystein of the protein, especially preferably to the free cystein at position 17 of IFN beta (in case of variants with a cysteine at position 17), to a cystein at position 1 and/or 98 of IFN alpha.

According to a first embodiment, the functional group Z of the protein is a thiol group and functional group A of the polymer is a halogenacetyl group and wherein A is introduced by reacting the polymer at its optionally oxidized reducing end with an at least bifunctional compound having at least two functional groups each comprising an amino group to give a polymer derivative having at least one functional group comprising an amino group and reacting the polymer derivative with a monohalogen-substituted acetic acid and/or a reactive monohalogen-substituted acetic acid derivative.

As to the at least bifunctional compound having at least two functional groups each comprising an amino group, all compounds are conceivable which are capable of being reacted with the polymer at its optionally reducing end to give a polymer derivative comprising an amino group which can be reacted with a monohalogen-substituted acetic acid and/or a reactive monohalogen-substituted acetic acid derivative.

According to a preferred embodiment, one functional group of the at least bifunctional compound, said functional group being reacted with the optionally oxidized reducing end of the polymer, is selected from the group consisting of

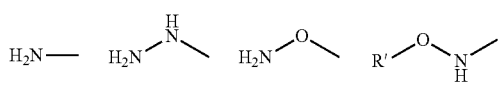

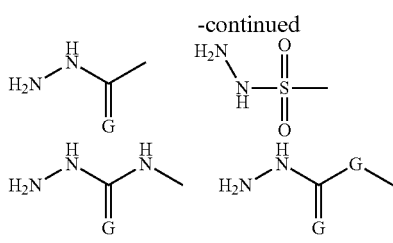

wherein G is O or S and, if present twice, independently O or S, and R' is methyl.

According to an especially preferred embodiment of the present invention, the functional group of the at least bifunctional compound, said functional group being reacted with the optionally oxidized reducing end, is the amino group —$NH_2$. According to a still further preferred embodiment, this functional group, most preferably the amino group, is reacted with the oxidized reducing end of the polymer.

According to a preferred embodiment of the present invention, the functional group of the at least bifunctional compound, said functional group being reacted with the monohalogen-substituted acetic acid and/or a reactive monohalogen-substituted acetic acid derivative, is an amino group —$NH_2$.

The functional groups, preferably both being an amino group —$NH_2$, of the at least bifunctional compound, said functional groups being reacted with the polymer at its optionally oxidized reducing end, preferably the oxidized reducing end, and the monohalogen-substituted acetic acid and/or a reactive monohalogen-substituted acetic acid derivative, may be separated by any suitable spacer. Among others, the spacer may be an optionally substituted, linear, branched and/or cyclic hydrocarbon residue. Suitable substituents are, among others, alkyl, aryl, aralkyl, alkaryl, halogen, carbonyl, acyl, carboxy, carboxyester, hydroxy, thio, alkoxy and/or alkylthio groups. Generally, the hydrocarbon residue has from 1 to 60, preferably from 1 to 40, more preferably from 1 to 20, more preferably from 2 to 10, more preferably from 2 to 6 and especially preferably from 2 to 4 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group. According to an even more preferred embodiment, the hydrocarbon residue is an alkyl chain of from 1 to 20, preferably from 2 to 10, and especially preferably from 2 to 8 carbon atoms. Thus, preferred at least bifunctional compounds are bifunctional amino compounds, especially preferably 1,8-diamino octane, 1,7-diamino heptane, 1,6-diamino hexane, 1,5-diamino pentane, 1,4-diamino butane, 1,3-diamino propane, and 1,2-diamino ethane. According to a further preferred embodiment, the at least bifunctional compound is a diaminopolyethylenglycol, preferably a diaminopolyethylenglycol according to formula

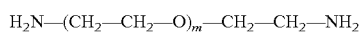

wherein m is an integer, m preferably being 1, 2, 3, or 4.

Therefore, the present invention also relates to a method and a conjugate as described above, wherein the polymer is reacted with 1,8-diaminooctane, 1,7-diaminoheptane, 1,6-diaminohexane, 1,5-diaminopentane, 1,4-diaminobutane, 1,3-diaminopropane, and 1,2-diaminoethane at its oxidized reducing end with to give a polymer derivative according to the formula

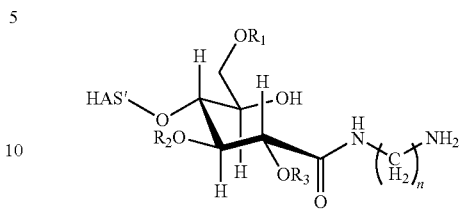

with n=2, 3, 4, 5, 6, 7, or 8, and the polymer especially preferably being HES.

Therefore, the present invention also relates to a method and a conjugate as described above, wherein the polymer is reacted with $H_2N$—$(CH_2$—$CH_2$—$O)_m$—$CH_2$—$CH_2$—$NH_2$ at its oxidized reducing end, wherein m is 1, 2, 3, or 4, to give a polymer derivative according to the formula

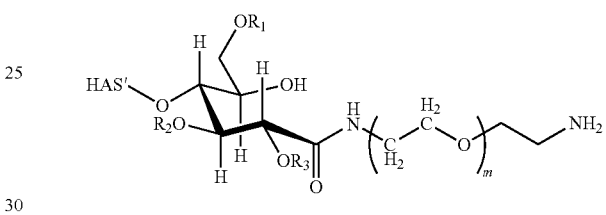

with m=1, 2, 3, or 4, and the polymer especially preferably being HES.

The oxidation of the reducing end of the polymer, preferably hydroxyethyl starch, may be carried out according to each method or combination of methods which result in compounds having the structures (IIa) and/or (IIb):

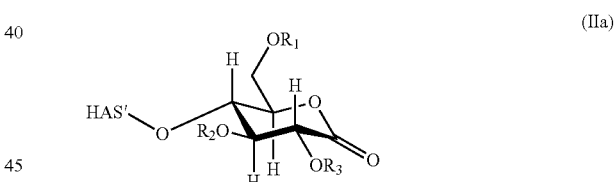

(IIa)

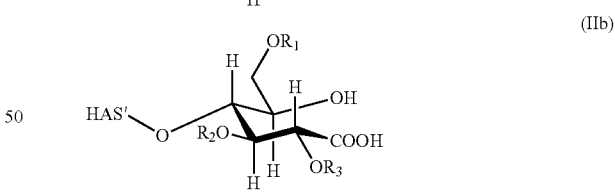

(IIb)

Although the oxidation may be carried out according to all suitable method or methods resulting in the oxidized reducing end of hydroxyalkyl starch, it is preferably carried out using an alkaline iodine solution as described, e.g., in DE 196 28 705 A1 the respective contents of which (example A, column 9, lines 6 to 24) is incorporated herein by reference.

The polymer derivative resulting from the reaction of the polymer with the at least bifunctional compound is further reacted with the monohalogen-substituted acetic acid and/or a reactive monohalogen-substituted acetic acid derivative.

As monohalogen-substituted acetic acid or reactive acid, Cl-substituted, Br-substituted and I-substituted acetic acid are preferred.

If the halogen-substituted acid is employed as such, it is preferred to react the acid with the polymer derivative in the presence of an activating agent. Suitable activating agents are, among others, Suitable activating agents are, among others, carbodiimides such as diisopropyl carbodiimide (DIC), dicyclohexyl carbodiimides (DCC), 1-ethyl-3-(3-dimethylaminopropyl)carbodiimide (EDC), with dicyclohexyl carbodiimides (DCC) and 1-ethyl-3-(3-dimethylaminopropyl) carbodiimide (EDC) being especially preferred.

Therefore, the present invention also relates to a method and a conjugate as described above, wherein the polymer, preferably HES, is reacted with a diamino compound, preferably a diaminoalkane with 2 to 8 carbon atoms or $H_2N-(CH_2-CH_2-O)_m-CH_2-CH_2-NH_2$ with m=1, 2, 3, or 4, and reacting the resulting polymer derivative with Br-substituted and I-substituted acetic acid in the presence of an activating agent, preferably EDC.

Therefore, the present invention also relates to a polymer derivative according to the formula

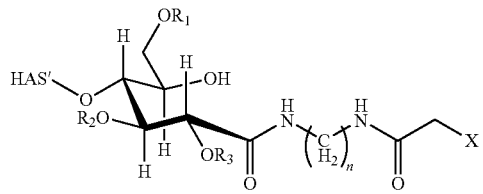

with X=Cl, Br or I, n=2, 3, 4, 5, 6, 7, or 8, and the polymer especially preferably being HES, or a polymer derivative according to the formula

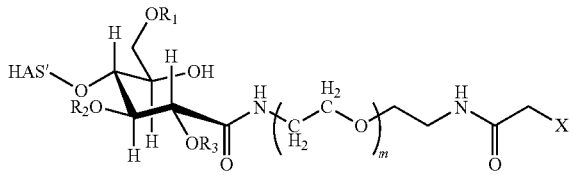

with X=Cl, Br or I, m=1, 2, 3, or 4, and the polymer especially preferably being HES.

The reaction of the polymer derivative with the halogen-substituted acetic acid is preferably carried out it in an aqueous system, preferably water, at a preferred pH of from 3.5 to 5.5, more preferably of 4.0 to 5.0 and especially preferably from 4.5 to 5.0; and a preferred reaction temperature of from 4 to 30° C., more preferably from 15 to 25° C. and especially preferably from 20 to 25° C.; and for a preferred reaction time of from 1 to 8 h, more preferably from 2 to 6 h and especially preferably from 3 to 5 h.

The reaction mixture comprising the polymer derivative which comprises the polymer, the at least bifunctional compound and the halogen-substituted acetic acid, can be used for the reaction with the protein as such. According to a preferred embodiment of the present invention, the polymer derivative is separated from the reaction mixture, preferably by ultrafiltration, subsequent precipitation, optional washing and drying in vacuo.

The reaction of the polymer derivative with the protein is carried out at a preferred pH of from 6.5 to 8.5, more preferably from 7.0 to 8.5 and especially preferably from 7.5 to 8.5; and a preferred reaction temperature of from 4 to 30° C., more preferably from 15 to 25° C. and especially preferably from 20 to 25° C.; and for a preferred reaction time of from 0.5 to 8 h, more preferably from 1 to 6 h and especially preferably from 2 to 5 h.

The reaction of the polymer derivative with the thiol group of the protein results in a thioether linkage between the polymer derivative and the protein.

Therefore, the present invention also relates to a method and a conjugate as described above, wherein the polymer, preferably HES, is reacted with a diamino compound, preferably a diaminoalkane with 2 to 8 carbon atoms or $H_2N-(CH_2-CH_2-O)_m-CH_2-CH_2-NH_2$ with m=1, 2, 3, or 4, the resulting polymer derivative is reacted with Br-substituted and I-substituted acetic acid in the presence of an activating agent, preferably EDC, and the resulting polymer derivative is reacted with a thiol group of the protein to give a conjugate comprising a thioether linkage between the protein and the polymer derivative.

Therefore, the present invention also relates to a conjugate according to the formula

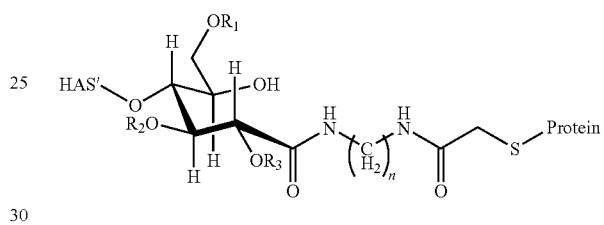

with n=2, 3, 4, 5, 6, 7, or 8, and the polymer especially preferably being HES and the protein being IFN alpha, IFN beta, tPA, or A1AT, preferably IFN alpha or IFN beta, the S atom being derived from the free cystein at position 17 of IFN beta 1a or a available free cystein, or a conjugate according to the formula

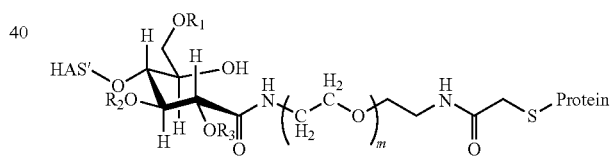

with m=1, 2, 3, or 4, and the polymer especially preferably being HES and the protein being IFN alpha, IFN beta, tPA, or A1AT or APC, preferably IFN alpha or IFN beta, the S atom being derived, e.g., from the free cystein at position 17 of IFN beta 1a.

The hydroxyethyl starch is preferably hydroxyethyl starch having a mean molecular weight of about 10 kD and a DS of about 0.4 or hydroxyethyl starch having a mean molecular weight of about 10 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.4 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7, or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

According to a second embodiment, functional group Z of the protein is a thiol group and functional group A of the polymer comprises a maleimido group.

According to this embodiment, several possibilities exist to produce the conjugate. In general, the polymer is reacted at its optionally oxidized reducing end with at least one at least bifunctional compound, wherein this at least bifunctional compound comprises one functional group which is capable of being reacted with the optionally oxidized reducing end of the polymer, and at least one functional group which either comprises the maleimido group or is chemically modified to give a polymer derivative which comprises the maleimido group. According to a preferred embodiment, said functional group is chemically modified to give a polymer derivative which comprises the maleimido group.

Therefore, the present invention relates to a method and a conjugate as described above, by reacting a polymer derivative comprising a maleimido group with a thiol group of the protein, said method comprising reacting the polymer at its optionally oxidized reducing end with an at least bifunctional compound comprising a functional group U capable of reacting with the optionally oxidised reducing end, the at least bifunctional compound further comprising a functional group W capable of being chemically modified to give a maleimido group, the method further comprising chemically modifying the functional group W to give a maleimido group.

As to functional group U, each functional group is conceivable which is capable of being reacted with optionally oxidised reducing end of the polymer.

According to a preferred embodiment of the present invention, the functional group U comprises the chemical structure —NH—.

Therefore, the present invention also relates to a method and a conjugate as described above, wherein the functional group U comprises the structure —NH—.

According to one preferred embodiment of the present invention, the functional group U is a group having the structure R'—NH— where R' is hydrogen or a alkyl, cycloalkyl, aryl, aralkyl, arylcycloalkyl, alkaryl or cycloalkylaryl residue where the cycloalkyl, aryl, aralkyl, arylcycloalkyl, alkaryl or cycloalkylaryl residue may be linked directly to the NH group or, according to another embodiment, may be linked by an oxygen bridge to the NH group. The alkyl, cycloalkyl, aryl, aralkyl, arylcycloalkyl, alkaryl, or cycloalkylaryl residues may be suitably substituted. As preferred substituents, halogenes such as F, Cl or Br may be mentioned. Especially preferred residues R' are hydrogen, alkyl and alkoxy groups, and even more preferred are hydrogen and unsubstituted alkyl and alkoxy groups.

Among the alkyl and alkoxy groups, groups with 1, 2, 3, 4, 5, or 6 C atoms are preferred. More preferred are methyl, ethyl, propyl, isopropyl, methoxy, ethoxy, propoxy, and isopropoxy groups. Especially preferred are methyl, ethyl, methoxy, ethoxy, and particular preference is given to methyl or methoxy.

Therefore, the present invention also relates to a method and a conjugate as described above, wherein R' is hydrogen or a methyl or a methoxy group.

According to another preferred embodiment of the present invention, the functional group U has the structure R'—NH—R"— where R" preferably comprises the structure unit —NH— and/or the structure unit —(C=G)- where G is O or S, and/or the structure unit —$SO_2$—. According to more preferred embodiments, the functional group R" is selected from the group consisting of

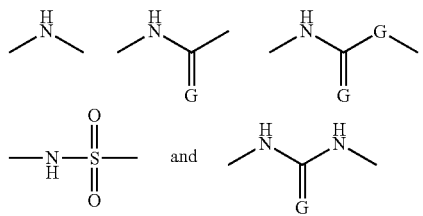

where, if G is present twice, it is independently O or S.

Therefore, the present invention also relates to a method and a conjugate as described above, wherein the functional group U is selected from the group consisting of

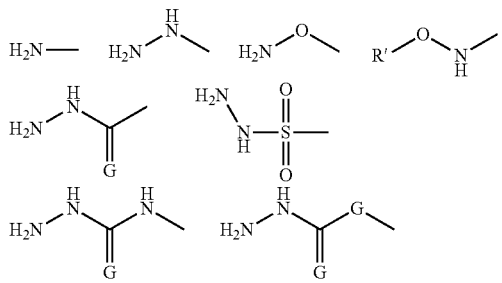

wherein G is O or S and, if present twice, independently O or S, and R' is methyl.

According to a still more preferred embodiment of the present invention, U comprises an amino group —$NH_2$.

According to an embodiment of the present invention, the functional group W of the at least bifunctional compound is chemically modified by reacting the polymer derivative comprising W with a further at least bifunctional compound comprising a functional group capable of being reacted with W and further comprising a maleimido group.

As to functional group W and the functional group of said further at least bifunctional compound which is capable of being reacted with W, the following functional groups are to be mentioned, among others:

C—C-double bonds or C—C-triple bonds or aromatic C—C-bonds;
the thio group or the hydroxy groups;
alkyl sulfonic acid hydrazide, aryl sulfonic acid hydrazide;
1,2-dioles;
1,2-aminoalcohols;
  1,2 amino-thioalcohols;
  azides;
the amino group —$NH_2$ or derivatives of the amino groups comprising the structure unit —NH— such as aminoalkyl groups, aminoaryl group, aminoaralkyl groups, or alkarylamino groups;
the hydroxylamino group —O—$NH_2$, or derivatives of the hydroxylamino group comprising the structure unit —O—NH—, such as hydroxylalkylamino groups, hydroxylarylamino groups, hydroxylaralkylamino groups, or hydroxylalkarylamino groups;
alkoxyamino groups, aryloxyamino groups, aralkyloxyamino groups, or alkaryloxyamino groups, each comprising the structure unit —NH—O—;

residues having a carbonyl group, -Q-C(=G)-M, wherein G is O or S, and M is, for example,
—OH or —SH;
an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trichlorophenyl;
wherein Q is absent or NH or a heteroatom such as S or O;
—NH—NH$_2$, or —NH—NH—;
—NO$_2$;
the nitril group;
carbonyl groups such as the aldehyde group or the keto group;
the carboxy group;
the —N=C=O group or the —N=C=S group;
vinyl halide groups such as the vinyl iodide or the vinyl bromide group or triflate;
—C≡C—H;
—(C=NH$_2$Cl)—OAlkyl
groups —(C=O)—CH$_2$-Hal wherein Hal is Cl, Br, or I;
—CH=CH—SO$_2$—;
a disulfide group comprising the structure —S—S—;
the group

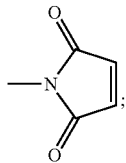

the group

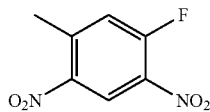

where W and the functional group of the further at least bifunctional compound, respectively, is a group capable of forming a chemical linkage with one of the above-mentioned groups.

According to a still more preferred embodiment of the present invention, W comprises an amino group —NH$_2$.

According to preferred embodiments of the present invention, both W and the other functional group are groups from the list of groups given above.

According to one embodiment of the present invention, one of these functional groups is a thio group. In this particular case, the other functional group is preferably selected from the group consisting of

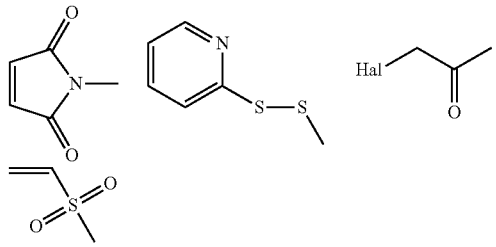

wherein Hal is Cl, Br, or I, preferably Br or I.

According to an especially preferred embodiment of the present invention, one of these functional groups is selected from the group consisting of a reactive ester such as an ester of hydroxylamines having imide structure such as N-hydroxysuccinimide or having a structure unit O—N where N is part of a heteroaryl compound or such as an aryloxy compound with a substituted aryl residue such as pentafluorophenyl, paranitrophenyl or trichlorophenyl, or a carboxy group which is optionally transformed into a reactive ester. In this particular case, the other functional group comprises the chemical structure —NH—.

According to an especially preferred embodiment of the present invention, W comprises the structure —NH— and the further at least bifunctional compound comprises a reactive ester and the maleimido group.

As to the functional group W comprising the structure —NH—, reference can be made to the functional group as described above, wherein W may be the same or different from U. According to a preferred embodiment of the present invention, U and W are the same. More preferably, both U and W comprise an amino group. Particularly preferred, both U and W are an amino group —NH$_2$.

According to one embodiment of the present invention, the polymer may be reacted with the at least bifunctional compound comprising U and W at its non-oxidized reducing end in an aqueous medium. According to a preferred embodiment where U and W both are an amino group, the reaction is carried out using the polymer with the reducing end in the oxidized form, in at least one aprotic solvent, particularly preferably in an anhydrous aprotic solvent having a water content of not more than 0.5 percent by weight, preferably of not more than 0.1 percent by weight. Suitable solvents are, among others, dimethyl sulfoxide (DMSO), N-methyl pyrrolidone, dimethyl acetamide (DMA), dimethyl formamide (DMF) and mixtures of two or more thereof.

Especially in case both U and W are an amino group —NH$_2$, U and W may be separated by any suitable spacer. Among others, the spacer may be an optionally substituted, linear, branched and/or cyclic hydrocarbon residue. Suitable substituents are, among others, alkyl, aryl, aralkyl, alkaryl, halogen, carbonyl, acyl, carboxy, carboxyester, hydroxy, thio, alkoxy and/or alkylthio groups. Generally, the hydrocarbon residue has from 1 to 60, preferably from 1 to 40, more preferably from 1 to 20, more preferably from 2 to 10, more preferably from 2 to 6 and especially preferably from 2 to 4 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group. According to an even more preferred embodiment, the hydrocarbon residue is an alkyl chain of from 1 to 20, preferably from 2 to 10, more preferably from 2 to 6, and especially preferably from 2 to 4 carbon atoms.

Therefore, the present invention also relates to a method and a conjugate as described above, wherein the polymer is reacted with its oxidized reducing end with 1,4-diaminobutane, 1,3-diaminopropane or 1,2-diaminoethane to give a polymer derivative according to the formula

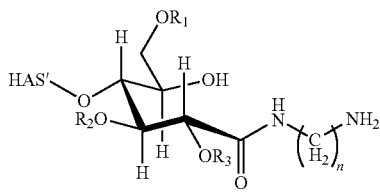

with n=2, 3, or 4, the polymer preferably being HES.

According to the above-mentioned preferred embodiment, the polymer derivative comprising an amino group is further reacted with an at least bifunctional compound comprising a reactive ester group and the maleimido group. The reactive ester group and the maleimido group may be separated by a suitable spacer. As to this spacer, reference can be made to the spacer between the functional groups U and W. According to a preferred embodiment of the present invention, the reactive ester group and the maleimido group are separated by a hydrocarbon chain having from 1 to 10, preferably from 1 to 8, more preferably from 1 to 6, more preferably from 1 to 4, more preferably from 1 to 2 and particularly preferably 1 carbon atom. According to a still further preferred embodiment, the reactive ester is a succinimide ester, and according to a particularly preferred embodiment, the at least bifunctional compound comprising the maleimido group and the reactive ester group is N-(alpha-maleimidoacetoxy)succinimide ester.

Therefore, the present invent also relates to a polymer derivative according to the formula

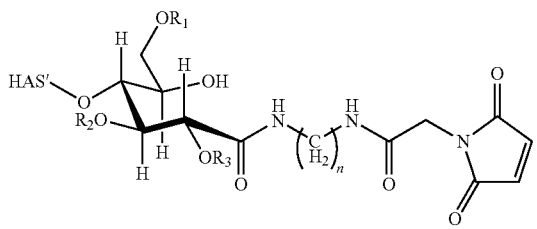

with n=2, 3, or 4, the polymer preferably being HES.

The polymer derivative comprising the maleimido group is further reacted with the thiol group of the protein to give a conjugate comprising the polymer derivative linked to the protein via a thioether group.

Therefore, the present invention also relates to a conjugate, comprising the protein and the polymer, according to the formula

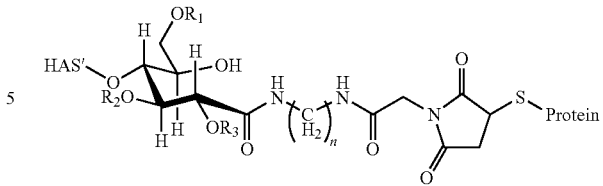

with n=2, 3, or 4, preferably 4, the polymer preferably being HES, the protein being IFN alpha, IFN beta, tPA, or A1AT, preferably IFN alpha or IFN beta, and wherein the S atom in the formula above derives, e.g., from Cys17 of IFN beta 1a.

The hydroxyethyl starch is preferably hydroxyethyl starch having a mean molecular weight of about 10 kD and a DS of about 0.4 or hydroxyethyl starch having a mean molecular weight of about 10 kD and a DS of about 0.7 or hydroxyethyl starch having a mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.4 or hydroxyethyl starch having a mean molecular weight of about 18 kD and a DS of about 0.7 or hydroxyethyl starch having a mean molecular weight of about 30 kD and a DS of about 0.4 or hydroxyethyl starch having a mean molecular weight of about 30 kD and a DS of about 0.7 or hydroxyethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

As to each of these combinations of mean molecular weight and DS, also a DS value of about 0.8 is preferred.

The reaction of the polymer derivative comprising the maleimido group with the thiol group of the protein is preferably carried in a buffered aqueous system, at a preferred pH of from 5.5 to 8.5, more preferably from 6 to 8 and especially preferably from 6.5 to 7.5, and a preferred reaction temperature of from 0 to 40° C., more preferably from 0 to 25 and especially preferably from 4 to 21° C., and for a preferred reaction time of from 0.5 to 24 h, more preferably from 1 to 20 h and especially from 2 to 17 h. The suitable pH value of the reaction mixture may be adjusted by adding at least one suitable buffer. Among the preferred buffers, sodium acetate buffer, phosphate or borate buffers may be mentioned, containing either urea at a preferred concentration of from 0 to 8 M, more preferred from 2 to 8 M and especially preferred from 4 to 8 M, and/or containing SDS at a preferred concentration of from 0 to 1% (w/v), more preferred from 0.4 to 1% (w/v) and especially prefferd from 0.8 to 1% (w/v).

The conjugate may be subjected to a further treatment such as an after-treatment like dialysis, centrifugal filtration or pressure filtration, ion exchange chromatography, reversed phase chromatography, HPLC, MPLC, gel filtration and/or lyophilisation.

In the methods for preparing a conjugate of the invention the conversion rate in the above described methods may be at least 50%, more preferred at least 70%, even more preferred at least 80% and in particular 95% or even more, such as at least 98% or 99%.

The present invention also relates to a conjugate comprising a protein and a polymer or a derivative thereof, wherein the polymer is a hydroxyalkyl starch (HAS) and the protein is selected from the group consisting of IFN beta, GM-CSF, APC, tPA, A1AT, AT III, factor VII, factor VIII, and factor IX, said conjugate having a structure according to the formula

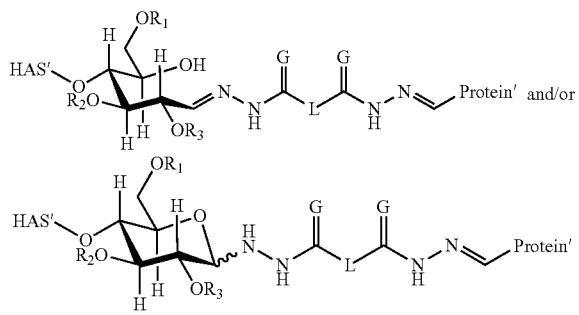

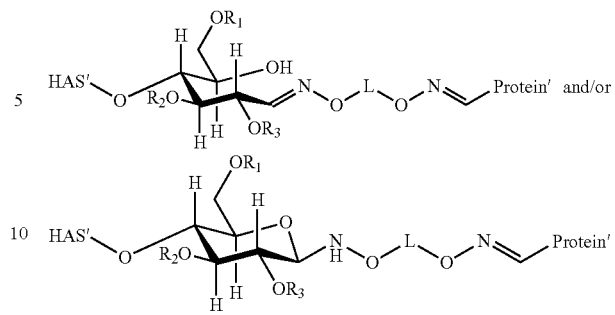

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, wherein G is selected from the group consisting of O and S, preferably O, and wherein L is an optionally suitably substituted, linear, branched and/or cyclic hydrocarbon residue, optionally comprising at least one heteroatom, preferably an alkyl, aryl, aralkyl, heteroaryl, heteroaralkyl residue having from 2 to 60 carbon atoms.

The present invention also relates to a conjugate as described above, wherein -L- is —(CH$_2$)n- with n=2, 3, 4, 5, 6, 7, 8, 9, 10, preferably 2, 3, 4, 5, 6, more preferably 2, 3, 4, and especially preferably 4.

The present invention also relates to a conjugate comprising a protein and a polymer or a derivative thereof, wherein the polymer is a hydroxyalkyl starch (HAS) and the protein is selected from the group consisting of IFN beta, GM-CSF, APC, tPA, A1AT, AT III, factor VII, factor VIII, and factor IX, said conjugate having a structure according to the formula

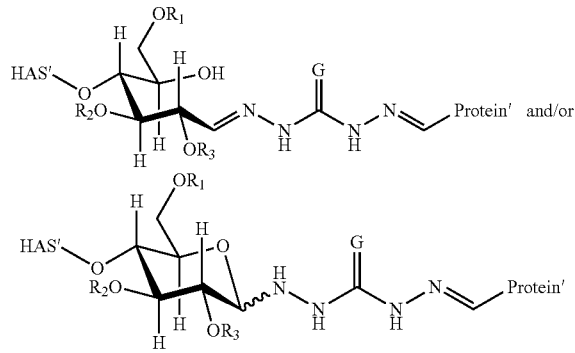

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein G is selected from the group consisting of O and S, preferably O.

The present invention also relates to a conjugate comprising a protein and a polymer or a derivative thereof, wherein the polymer is a hydroxyalkyl starch (HAS) and the protein is selected from the group consisting of IFN beta, GM-CSF, APC, tPA, A1AT, AT III, factor VII, factor VIII, and factor IX, said conjugate having a structure according to the formula wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein L is an optionally suitably substituted, linear, branched and/or cyclic hydrocarbon residue, optionally comprising at least one heteroatom, preferably an alkyl, aryl, aralkyl, heteroaryl, heteroaralkyl residue having from 2 to 60 carbon atoms.

The present invention also relates to a conjugate as described above, wherein -L- is

wherein $R_a$; $R_b$, $R_c$, $R_d$ are independently hydrogen, alkyl, aryl, preferably hydrogen,
wherein G is selected from the group consisting of O and S, preferably O, and wherein
m 1, 2, 3 or 4, wherein the residues $R_a$ and $R_b$ may be the same or different in the m groups C $R_aR_b$;
n 0 to 20, preferably 0 to 10, more preferably 1, 2, 3, 4, 5, most preferably 1 or 2;
o 0 to 20, preferably 0 to 10, more preferably 1, 2, 3, 4, 5, most preferably 1 or 2, wherein the residues $R_c$ and $R_d$ may be the same or different in the o groups C $R_cR_d$;
wherein the integers for n and o are selected in a way that in the formula above no peroxy moiety results, e.g. n and o are not 0 at the same time.

The present invention also relates to a conjugate as described above, wherein $R_a$; $R_b$, $R_c$, $R_d$ are hydrogen, m=2, n=1, and o=2.

The present invention also relates to a conjugate comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, said conjugate having a structure according to the formula

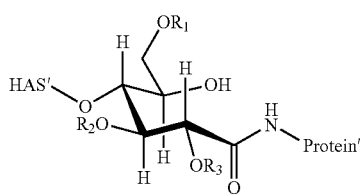

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group.

The present invention also relates to a conjugate comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, having a structure according to the formula

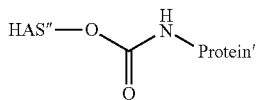

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein the linkage —O—(C=O)— was formed by a reaction of a carboxy group or a reactive carboxy group with a hydroxy group of the HAS molecule.

The present invention also relates to a conjugate, comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, said conjugate having a structure according to the formula

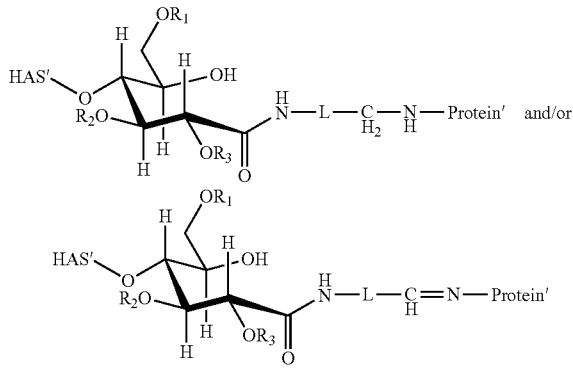

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein L is an optionally substituted, linear, branched and/or cyclic hydrocarbon residue, optionally comprising at least one heteroatom, having from 1 to 60 preferably from 1 to 40, more preferably from 1 to 20, more preferably from 1 to 10, more preferably from 1 to 6 more preferably from 1 to 2 carbon atoms and especially preferably 1 carbon atom, L being in particular $CH_2$.

The present invention also relates to a conjugate, comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, said conjugate having a structure according to the formula

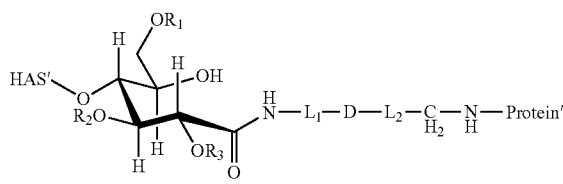

wherein $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein $L_1$ and $L_2$ are independently an optionally substituted, linear, branched and/or cyclic hydrocarbon residue, optionally comprising at least one heteroatom, comprising an alkyl, aryl, aralkyl heteroalkyl, and/or heteroaralkyl moiety, said residue having from 1 to 60 preferably from 1 to 40, more preferably from 1 to 20, more preferably from 1 to 10 carbon atoms, and wherein D is a linkage, preferably a covalent linkage which was formed by a suitable functional group $F^2$ linked to $L_1$ and a suitable functional group $F_3$ linked to $L_2$.

The present invention also relates to a conjugate as described above, wherein $L_1$ is —$(CH_2)n$- with n=2, 3, 4, 5, 6, 7, 8, 9, 10, preferably 2, 3, 4, 5, 6, more preferably 2, 3, 4, and especially preferably 4.

The present invention also relates to a conjugate as described above, wherein $L_2$ comprises an optionally suitably substituted aryl moiety, preferably an aryl moiety containing 6 carbon atoms, $L_2$ being especially preferably $C_6H_4$.

The present invention also relates to a conjugate as described above, wherein is selected from the group consisting of C—C-double bonds or C—C-triple bonds or aromatic C—C-bonds;

the thio group or the hydroxy groups;

alkyl sulfonic acid hydrazide, aryl sulfonic acid hydrazide;

1,2-dioles;

1,2 amino-thioalcohols;

azides;

1,2-aminoalcohols;

the amino group —$NH_2$ or derivatives of the amino groups comprising the structure unit —NH— such as aminoalkyl groups, aminoaryl group, aminoaralkyl groups, or alkarlyamino groups;

the hydroxylamino group —O—$NH_2$, or derivatives of the hydroxylamino group comprising the structure unit —O—NH—, such as hydroxylalkylamino groups, hydroxylarylamino groups, hydroxylaralkylamino groups, or hydroxalalkarylamino groups;

alkoxyamino groups, aryloxyamino groups, aralkyloxyamino groups, or alkaryloxyamino groups, each comprising the structure unit —NH—O—;

residues having a carbonyl group, -Q-C(=G)-M, wherein G is O or S, and M is, for example, —OH or —SH;

an alkoxy group, an aryloxy group, an aralkyloxy group, or an alkaryloxy group;

an alkylthio group, an arylthio group, an aralkylthio group, or an alkarylthio group;

an alkylcarbonyloxy group, an arylcarbonyloxy group, an aralkylcarbonyloxy group, an alkarylcarbonyloxy group;

activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trichlorophenyl;

wherein Q is absent or NH or a heteroatom such as S or O;

—NH—NH$_2$, or —NH—NH—;

—NO$_2$;

the nitril group;

carbonyl groups such as the aldehyde group or the keto group;

the carboxy group;

the —N=C=O group or the —N=C=S group;

vinyl halide groups such as the vinyl iodide or the vinyl bromide group or triflate;

—C≡C—H;

—(C=NH$_2$Cl)-OAlkyl groups —(C=O)—CH$_2$-Hal wherein Hal is Cl, Br, or I;

—CH=CH—SO$_2$—;

a disulfide group comprising the structure —S—S—;

the group

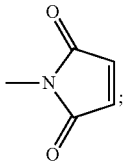

the group

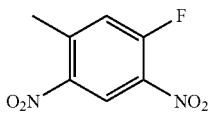

and wherein F$_3$ is a functional group capable of forming a chemical linkage with F$_2$ and is preferably selected from the above-mentioned group, F$_2$ preferably comprising the moiety —NH—, more preferably comprising an amino group, F$_3$ preferably comprising the moiety —(C=G)-, more preferably —(C=O)—, more preferably the moiety —(C=G)-G-, still more preferably —(C=O)-G-, and especially preferably —(C=O)—O, D being particularly preferably an amide linkage.

The present invention also relates to a conjugate, comprising a protein and a polymer or a derivative thereof, wherein the polymer is a hydroxyalkyl starch (HAS) and the protein is selected from the group consisting of IFN alpha, IFN beta, GM-CSF, APC, tPA, A1AT, AT III, factor VII, factor VIII, and factor IX, said conjugate having a structure according to the formula

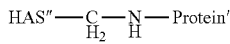

wherein the carbon atom of the moiety —CH$_2$—NH— is derived from an aldehyde group which was introduced in the polymer by a ring-opening oxidation reaction, and wherein the nitrogen atom is derived from an amino group of the protein, wherein HAS" refers to the HAS molecule without the carbon atom of said aldehyde involved in the reaction.

The present invention also relates to a conjugate, comprising a protein and a polymer or a derivative thereof, wherein the polymer is a hydroxyalkyl starch (HAS) and the protein is selected from the group consisting of IFN alpha, IFN beta, tPA, A1AT, factor VII and factor IX, said conjugate having a structure according to the formula

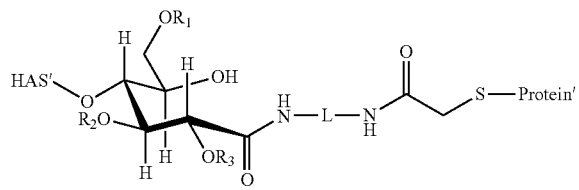

wherein R$_1$, R$_2$ and R$_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein L is an optionally substituted, linear, branched and/or cyclic hydrocarbon residue, optionally comprising at least one heteroatom, comprising an alkyl, aryl, aralkyl heteroalkyl, and/or heteroaralkyl moiety, said residue having from 2 to 60 preferably from 2 to 40, more preferably from 2 to 20, more preferably from 2 to 10 carbon atoms, and wherein the sulfur atom is derived from a cysteine residue or a disulfide group of the protein.

The present invention also relates to a conjugate as described above, wherein -L- is

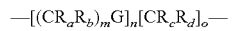

wherein R$_a$; R$_b$, R$_c$, R$_d$ are independently hydrogen, alkyl, aryl, preferably hydrogen, wherein G is selected from the group consisting of O and S, preferably O, and wherein m 1, 2, 3 or 4, most preferably 2, wherein the residues R$_a$ and R$_b$ may be the same or different in the m groups (CR$_a$R$_b$);

n 1 to 20, preferably 1 to 10, most preferably 1, 2, 3, or 4;

o 1 to 20, preferably 1 to 10, more preferably 1, 2, 3, 4, 5, more preferably 1 or 2, most preferably 1, wherein the residues R$_C$ and R$_d$ may be the same or different in the o groups CR$_c$R$_d$;

or wherein n 0, and o 2 to 20, preferably 2 to 10, more preferably 2, 3, 4, 5, 6, 7, or 8, wherein the residues R$_c$ and R$_d$ may be the same or different in the o groups CR$_c$R$_d$.

The present invention also relates to a conjugate, comprising a protein and a polymer or a derivative thereof, wherein the polymer is a hydroxyalkyl starch (HAS) and the protein is selected from the group consisting of IFN alpha, IFN beta, tPA, A1AT, factor VII and factor IX, said conjugate having a structure according to the formula

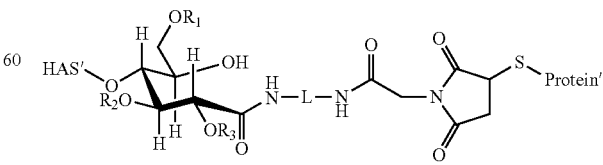

wherein R$_1$, R$_2$ and R$_3$ are independently hydrogen or a hydroxyalkyl group, a hydroxyaryl group, a hydroxyaralkyl group or a hydroxyalkaryl group having of from 2 to 10 carbon atoms, preferably hydrogen or a hydroxyalkyl group, more preferably hydrogen or a hydroxyethyl group, and wherein L is an optionally substituted, linear, branched and/or cyclic hydrocarbon residue, optionally comprising at least one heteroatom, comprising an alkyl, aryl, aralkyl heteroalkyl, and/or heteroaralkyl moiety, said residue having from 2 to 60 preferably from 2 to 40, more preferably from 2 to 20, more preferably from 2 to 10 carbon atoms, and wherein the sulfur atom is derived from a cysteine residue or a disulfide group of the protein.

The present invention also relates to a conjugate as described above, wherein -L- is $$-[(CR_aR_b)_mG]_n[CR_cR_d]_o-$$

wherein $R_a$; $R_b$, $R_c$, $R_d$ are independently hydrogen, alkyl, aryl, preferably hydrogen, wherein G is selected from the group consisting of O and S, preferably O, and wherein m 1, 2, 3 or 4, most preferably 2, wherein the residues $R_a$ and $R_b$ may be the same or different in the m groups $(CR_aR_b)$;

n 1 to 20, preferably 1 to 10, most preferably 1, 2, 3, or 4;

o 1 to 20, preferably 1 to 10, more preferably 1, 2, 3, 4, 5, more preferably 1 or 2, most preferably 1, wherein the residues $R_C$ and $R_d$ may be the same or different in the o groups $CR_cR_d$;

or wherein n 0, and o 2 to 20, preferably 2 to 10, more preferably 2, 3, 4, 5, 6, 7, or 8, wherein the residues $R_C$ and $R_d$ may be the same or different in the o groups $CR_cR_d$.

The present invention also relates to a conjugate as described above, wherein the hydroxyalkyl starch is hydroxyethyl starch.

The present invention also relates to a conjugate as described above, wherein the hydroxyethyl starch has a molecular weight of from 2 to 200 kD, preferably of from 4 to 130 kD, more preferably of from 4 to 70 kD.

According to a further aspect, the present invention relates to a conjugate as described above, or a conjugate, obtainable by a method as described above, for use in a method for the treatment of the human or animal body.

The conjugates according to the invention may be at least 50% pure, even more preferred at least 70% pure, even more preferred at least 90%, in particular at least 95% or at least 99% pure. In a most preferred embodiment, the conjugates may be 100% pure, i.e. there are no other by-products present.

Therefore, according to another aspect, the present invention also relates to a composition which may comprise the conjugate(s) of the invention, wherein the amount of the conjugate(s) may be at least 50 wt-%, even more preferred at least 70 wt-%, even more preferred at least 90 wt-%, in particular at least 95 wt.-% or at least 99 wt.-%. In a most preferred embodiment, the composition may consist of the conjugate(s), i.e. the amount of the conjugate(s) is 100 wt.-%.

Furthermore, the present invention relates to a pharmaceutical composition comprising in a therapeutically effective amount a conjugate as described above or a conjugate, obtainable by a method as described above.

All protein-HAS conjugates of the present invention are administered by suitable methods such as e.g. entheral, parentheral or pulmonary methods preferably administered by i.v., s.c. or i.m. routes. The specific route chosen will depend upon the condition being treated. Preferably, the conjugates are administered together with a suitable carrier, such as known in the art (e.g. as used in the first generation/unmodified biopharmaceutical, albumin-free or with albumin as an excipient), a suitable diluent, such as sterile solutions for i.v., i.m., or s.c. application. The required dosage will depend on the severity of the condition being treated, the patients individual response, the method of administration used, and the like. The skilled person is able to establish a correct dosage based on his general knowledge.

According to another aspect, the present invention also relates to the use a HAS-, preferably a HES-protein conjugate as described above or a HAS-, preferably a HES-protein conjugate, obtainable by a method as described above, wherein the protein is Factor VIII, for the preparation of a medicament for the treatment of haemophilia A.

According to another aspect, the present invention also relates to the use of a HAS-AT III conjugate as described above or a HAS-protein conjugate, obtainable by a method as described, for the preparation of a medicament for the treatment of AT III hereditary deficiency, veno-Occlusive disease, burns and heparin resistance in coronary arterial bypass Graft (CABG) surgery, bowel perforation resulting from trauma or gastrointestinal surgery; disseminated intravascular coagulation (DIC) and/or sepsis as well as for the prevention of micro-clot formation associated with ventilation therapy. The pharmaceutical composition comprising the HAS-AT III conjugate of the invention may therefore be used for these purposes.

According to another aspect, the present invention also relates to the use a HAS-, preferably a HES-protein conjugate as described above or a HAS-, preferably a HES-protein conjugate, obtainable by a method as described above, wherein the protein is A1AT, for the preparation of a medicament for the treatment of emphysema, cystic fibrosis, atopic dermatitis, and/or bronchitis. The pharmaceutical composition of the invention comprising the HAS-A1AT-conjugate of the invention may also be used for these purposes.

According to another aspect, the present invention also relates to the use a HAS-, preferably a HES-protein conjugate as described above or a HAS-, preferably a HES-protein conjugate, obtainable by a method as described above, wherein the protein is tPA, for the preparation of a medicament for the treatment of myocardial infarctions (heart attacks), thrombosis, thromboembolim or occlusive diseases, especially occlusive arterial diseases.

According to another aspect, the present invention also relates to the use a HAS-, preferably a HES-protein conjugate as described above or a HAS-, preferably a HES-protein conjugate, obtainable by a method as described above, wherein the protein is APC, for the preparation of a medicament for the treatment of severe sepsis, thrombosis, thromboembolim or occlusive diseases, especially occlusive arterial diseases.

According to another aspect, the present invention also relates to the use a HAS-, preferably a HES-protein conjugate as described above or a HAS-, preferably a HES-protein conjugate, obtainable by a method as described above, wherein the protein is IFN alpha, for the preparation of a medicament for the treatment of leukemia e.g. hairy cell leukemia, chronic myelogeneous leukemia, multiple myeloma, follicular lymphoma, cancer, e.g. carcinoid tumour, malignant melanoma and hepatitis, eg. chronic hepatitis B and chronic hepatitis C.

According to another aspect, the present invention also relates to the use a HAS-, preferably a HES-protein conjugate as described above or a HAS-, preferably a HES-protein conjugate, obtainable by a method as described above, wherein the protein is IFN beta, for the preparation of a medicament for the treatment of multiple sclerosis, preferably relapsing forms of multiple sclerosis.

The invention further relates to the use of a GM-CSF-HAS conjugate as described above, for the preparation of a medicament for myeloid reconstitution following bone marrow transplant or induction chemotherapy in older adults with acute myelogenous leukemia, bone marrow transplant engraftment failure or delay, mobilization and following transplantation of autologous peripheral blood progenitor cells.

The present invention also relates to the use of a HAS-Factor VII conjugate for the preparation of a medicament for the treatment of episodes in hemophilia A or B patients with inhibitors to Factor VIII or Factor IX.

The present invention also relates to the use of a HAS-Factor IX conjugate for the preparation of a medicament for the control and prevention of hemorrhagic episodes in patients with hemophillia B (e.g. congenital factor IX deficiency or Christmas disease), including control and prevention of bleeding in surgical settings.

The invention will be further described in the following examples, which do not limit the scope of the invention described in the claims.

EXAMPLES

Example 1

Synthesis of IFN Beta Conjugates

Example 1.1

Synthesis of Hydroxyamino Functionalized Hydroxyethyl Starch Derivatives

Example 1.1(a)

Synthesis of HydroxylaminoHES10/0.4

2 g of HES10/0.4 (MW=10000 D, DS=0.4, Supramol Parenteral Colloids GmbH, Rosbach-Rodheim, D) were dissolved in 17 mL 0.1M sodium acetate buffer, pH 5.2 and 20 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8500 D and the DS was 0.41.

Example 1.1(b)

Synthesis of HydroxylaminoHES10/0.7

2 g of HES10/0.7 (MW=10000 D, DS=0.7, Supramol Parenteral Colloids GmbH, Rosbach-Rodheim, D) were dissolved in 18 mL 0.1M sodium acetate buffer, pH 5.2 and 20 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized.

The molecular weight of the HES10/0.7 when measured with LALLS-GPC was 10500 D and the DS was 0.76.

Example 1.1(c)

Synthesis of HydroxylaminoHES50/0.7

2 g of HES50/0.7 (MW=50000 D, DS=0.7, Supramol Parenteral Colloids GmbH, Rosbach-Rodheim, D) were dissolved in 20 mL 0.1M sodium acetate buffer, pH 5.2 and 4 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized.

The molecular weight of the HES50/0.7 when measured with LALLS-GPC was 47000 D and the DS was 0.76.

Example 1.1(d)

Synthesis of HydroxylaminoHES50/0.4

2 g of HES50/0.4 (MW=50000 D, DS=0.4, Supramol Parenteral Colloids GmbH, Rosbach-Rodheim, D) were dissolved in 20 mL 0.1M sodium acetate buffer, pH 5.2 and 4 mmol O-[2-(2-aminooxy-ethoxy)-ethyl]-hydroxyl amine were added. After shaking for 17.5 h at 22° C., the reaction mixture was added to 70 mL of an ice-cold 1:1 mixture of acetone and ethanol (v/v). The precipitated product was collected by centrifugation at 0° C., washed with 30 mL of an ice-cold 1:1 mixture of acetone and ethanol (v/v), re-dissolved in 50 mL water, dialysed for 19.5 h against water (SnakeSkin dialysis tubing, 3.5 kD cut off, Perbio Sciences Deutschland GmbH, Bonn, D) and lyophilized.

The molecular weight of the HES50/0.4 when measured with LALLS-GPC was 56000 D and the DS was 0.41.

Example 1.1(e)

Synthesis of HydroxylaminoHES18/0.4

Oxidized HES was prepared as described in DE 196 28 705 A1. 200 mg of oxidized HES18/0.4 (MW=18000 D, DS=0.4) were heated at 80° C. in vacuo for 17 h and dissolved in 2 mL dry DMSO (Fluka, Sigma-Aldrich Chemie GmbH, Taufkirchen, D). To the solution 2 mmol O-[2-(2-aminooxy-ethoxy)-ethyl]-hydroxyl amine were added. After incubation for 5 d at 65° C., the reaction mixture was added to 20 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES18/0.4 when measured with LALLS-GPC was 18000 D and the DS was 0.41.

Example 1.1(f)

Synthesis of HydrazidoHES10/0.4

Oxidized HES was prepared as described in DE 196 28 705 A1. 200 mg of oxidized HES10/0.4 (MW=10000 D, DS=0.4, Supramol Parenteral Colloids GmbH, Rosbach-Rodheim, D) were heated at 80° C. in vacuo for 17 h and dissolved in 2 mL dry DMSO (Fluka, Sigma-Aldrich Chemie GmbH, Taufkirchen, D). To the solution 2 mmol adipic dihydrazide (Lancaster Synthesis GmbH, Frankfurt/Main D) were added. After incubation for 5 d at 65° C., the reaction mixture was added to 20 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 11000 D and the DS was 0.41.

Example 1.1(g)

Synthesis of CarbohydrazidoHES10/0.4

Oxidized HES was prepared as described in DE 196 28 705 A1. 200 mg of oxidized HES10/0.4 (MW=10000 D, DS=0.4, Supramol Parenteral Colloids GmbH, Rosbach-Rodheim, D) were heated at 80° C. in vacuo for 17 h and dissolved in 2 mL dry DMSO (Fluka, Sigma-Aldrich Chemie GmbH, Taufkirchen, D). To the solution 2 mmol carbohydrazide (Fluka, Sigma-Aldrich Chemie GmbH, Taufkirchen, D) were added. After incubation for 5 d at 65° C., the reaction mixture was added to 20 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 11000 D and the DS was 0.41.

Example 1.1(h)

Synthesis of HydrazidoHES10/0.4

200 mg of HES10/0.4 (MW=10000 D, DS=0.4, Supramol Parenteral Colloids GmbH, Rosbach-Rodheim, D) were dissolved in 2 mL 0.1M sodium acetate buffer, pH 5.2. To the solution 2 mmol adipic dihydrazide (Lancaster Synthesis GmbH, Frankfurt/Main D) were added. After stirring for 19 h at 22° C., the reaction mixture was added to 21 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8500 D and the DS was 0.41.

Example 1.1(i)

Synthesis of CarboydrazidoHES10/0.4

200 mg of HES10/0.4 (MW=10000 D, DS=0.4, Supramol Parenteral Colloids GmbH, Rosbach-Rodheim, D) were dissolved in 2 mL 0.1M sodium acetate buffer, pH 5.2. To the solution 2 mmol carbohydrazide (Fluka, Sigma-Aldrich Chemie GmbH, Taufkirchen, D) were added. After stirring for 19 h at 22° C., the reaction mixture was added to 21 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8500 D and the DS was 0.41.

Example 1.2

Synthesis of the IFN Beta Conjugates

Example 1.2(a)

Oxidation of IFN Beta

Recombinant human interferon beta-1a comprising identical amino acid sequence as the market products AVONEX™ (BIOGEN) and Rebif (Serono) and was expressed from a CHO cell line transfected as described (Dittmar et al., 1989) and purified as described in Example 6.1. Oxidation was essentially as described in Example 6.2, followed by buffer exchange as described in Example 6.3.

Example 1.2(b)

Reaction of Oxidized IFN-Beta of Example 1.2(a) with HES Derivatives of Examples 1.1(a)-1.1(i)

To 25.9 μL of a solution of oxidized IFN-beta in 0.1 M sodium acetate buffer, pH 5.5, 5.27 μL of a solution of the HES-derivative in 0.1 M sodium acetate buffer, pH 5.5 were added and the solution was incubated for 16.5 h at 22° C. The following concentrations were employed:
(i) 78.9 mg/mL for HES derivatives prepared according to example 1.1(a), 1.1(b), 1.1(f), 1.1(g), 1.1(h) and 1.1(j)
(ii) 395 mg/mL for HES derivatives prepared according to example 1.1(c) and 1.1(d)
(iii) 142 mg/mL for HES derivative prepared according to example 1.1(e)

Figure 1:
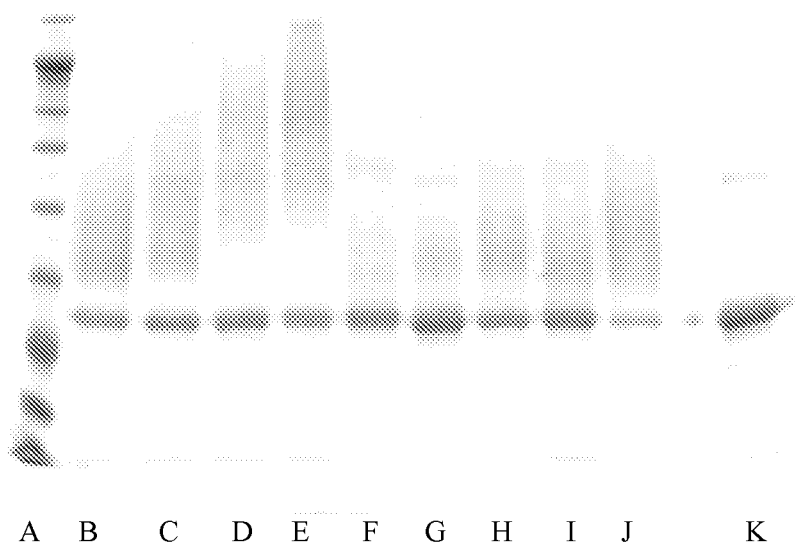
FIG. 1 shows an SDS page analysis of HES-IFN beta conjugates, produced according to Example 1.2. A 12% Bis-Tris gel together with a MOPS SDS running buffer at reducing conditions (both Invitrogen GmbH, Karlsruhe, D) were used according to the manufacturer's instruction.

The respective reaction mixture was analysed by gel electrophoresis (see FIG. 1).

Example 1.3

Synthesis of Aldehyde Functionalized Hydroxyethyl Starch Derivatives

Example 1.3(a)

Synthesis of Aldehydo-HES10/0.4 from Amino-HES10/0.4 and 4-formylbenzoic Acid

Oxo-HES10/0.4 (MW=10 kD, DS=0.4) was prepared by Supramol Parenteral Colloids GmbH, Rosbach-Rodheim, D; according to DE 196 28 705 A1. The molecular weight of the HES10/0.4 when measured with LALLS-GPC was 14500 D and the DS was 0.41.

5.1 g (0.51 mmol) of oxo-HES10/0.4 were dissolved in 15 ml anhydrous dimethyl sulfoxide (DMSO, Fluka, Sigma-Aldrich Chemie GmbH, Taufkirchen, D)) and added dropwise under nitrogen to a solution of 5.1 ml (51 mmol) 1,4-diaminobutane in 10 ml anhydrous dimethyl sulfoxide and stirred at 40° C. for 19 h. The reaction mixture was added to a mixture of 80 ml ethanol and 80 ml acetone. The resulting precipitate was separated by centrifugation, washed with a mixture of 20 ml ethanol and 20 ml acetone and re-dissolved in 80 ml water. The solution was dialyzed for 4 days against water (SnakeSkin dialysis tubing, 3.5 kD cut off, Perbio Science Deutschland GmbH, Bonn, D) and subsequently lyophilized. The yield was 67% (3.4 g) amino-HES10/0.4.

150 mg 4-formylbenzoic acid and 230 mg 1-hydroxy-1H-benzotriazole (both Aldrich, Sigma-Aldrich Chemie GmbH, Taufkirchen, D) were dissolved in 10 ml N,N-dimethylformamide (peptide synthesis grade, Biosolve, Valkenswaard, NL) and 204 µl N,N'-diisopropylcarbodiimide were added. After incubation at 21° C. for 30 min, 1 g of the amino-HES10/0.4 were added. After shaking for 19 h at 22° C., the reaction mixture was added to 84 ml of an ice-cold 1:1 mixture of acetone and ethanol (v/v). The precipitated product was collected by centrifugation at 4° C., re-dissolved in 50 ml water, dialysed for 2 d against water (SnakeSkin dialysis tubing, 3.5 kD cut off, Perbio Sciences Deutschland GmbH, Bonn, D) and lyophilized.

Example 1.3(b)

Synthesis of Aldehydo-HES10/0.4 by Periodate Oxidation of HES10/0.4 Oxidized at its Reducing End Oxo-HES10/0.4 (MW=10 kD, DS=0.4) was prepared by Supramol Parenteral Colloids GmbH, Rosbach-Rodheim, D; according to DE 196 28 705 A1. The molecular weight of the HES10/0.4 when measured with LALLS-GPC was 8500 D and the DS was 0.41.

300 mg of oxo-HES10/0.4 were dissolved in 15 ml 20 mM sodium phosphate buffer, pH 7.2. 64.2 mg sodium periodate (Fluka, Sigma-Aldrich Chemie GmbH, Taufkirchen, D) were dissolved in 15 ml of the same buffer. Both solutions were mixed and after incubation for 30 min at 21° C., 2 ml glycerol were added and the reaction mixture was incubated at 21° C. for 10 min. The reaction mixture was dialysed for 24 h against water (SnakeSkin dialysis tubing, 3.5 kD cut off, Perbio Sciences Deutschland GmbH, Bonn, D) and lyophilized.

Example 1.4

Synthesis of IFN Beta Conjugates by Reductive Amination with Aldehyde Functionalized Hydroxyethyl Starch Synthesized According to Examples 1.3(a) and 1.3(b)

Recombinant human interferon beta-1a comprising identical amino acid sequence as the market products AVONEX™ (BIOGEN) and Rebif (Serono) and was expressed from a CHO cell line transfected as described (Dittmar et al., 1989) and purified as described in Example 6.1.

To 40 µl of a solution of IFN beta in 0.1 M sodium acetate buffer pH 5.0 (0.5 mg/ml 5 µl of a solution of the HES-derivative (synthesized as described in Examples 1.3(a) or 1.3(b)) in the same buffer (200 mg/mL) were added. The mixture was cooled to 4° C. and 9 µl of a 120 mM solution of sodium cyanoborohydride in the same buffer at 4° C. were added and the mixture was incubated for 24 h at 4° C. The crude reaction mixture was analysed by gel electrophoresis. A successful conjugation was observed, as indicated by the migration of the protein band to higher molecular weight (see FIG. 2). The increased band-width is due to the molecular weight distribution of the HES derivative used and the number of HES derivatives linked to the protein.

Example 1.5

Description of IFN Beta Antiviral Activity Bioassay

General Remarks

In the European Pharmacopeia, currently only assays are given for the determination of the activity of Interferon-α and Interferon-γ. However, because the antiviral potency of Interferon-α is measured in these tests using an in vitro cytopathic effect (CPE) bioassay as described in Supplement 2001 (chapter 5.6) and as it is applied for the IFN-β drug products approved to date, antiviral activity can be tested in analogy to Interferon-α.

The antiviral activity of IFN-β can be tested utilizing a specific in vitro cytopathic effect bioassay e.g. with lung carcinoma cells (A549) and encephalomyo-carditis virus (EMCV). Other possible combinations, which can be used for the determination of the antiviral activity of interferons are WISH cell lines or Madin-Darby bovine kidney (MDBK) cell lines and VSV (vesicular stomatis virus).

Interferon Antiviral Assay—Outline

In a first step the in vitro antiviral activity of HES-IFN-beta-conjugates was compared to unmodified IFN-beta.

In the CPE assay (MDBK/VSV), dilutions of standard interferon and HES-IFN-beta-conjugate were compared. The cells were pretreated with the test samples for about 48 h before they were brought into contact with the virus.

After an incubation period (ca. 22 h), the protective effect of the interferon against the viral cytopathic effect was estimated.

Interferon Antiviral Assay—Experimental Details

The following steps were performed:
- Interferon solutions were pre-diluted in cell culture medium for MDBK cells (1:10)
- These solutions were sequentially diluted to 1:2-1:2,097, 152 (=1:$2^{21}$)
- 4 replicates (100 µl each well)
- fresh trypsinated MDBK cells were added (5,000 cells/well in 50 µl)
- Incubation: 48 hours at 37° C.
- 50 µl prediluted VSV solution was added (250 viruses/well)
- Incubation: 22 hours at 37° C.
- Determination of the protective effect of the Interferon against viral cytopathic effect
- Calculation of Interferon titer using the Spearman-Kärber's method Controls:
- MDBK-cells with Interferon-solutions, no virus (negative control)
- MDBK-cells without Interferon with virus (positive control)

Results:

Two Interferon beta samples and the respective HES-conjugates were tested in the CPE assay using two different dilutions (estimated 1,000,000 IU/ml and 200,000 IU/ml).

The interferon titer was calculated according to the formula of Spearman and Kärber. The ratio of the activities of the different samples was calculated. Taking into account the estimated specific activity of the samples, the EC50 concentrations, at which 50% of the cells are protected against the virus incubation, were calculated and compared (data not shown).

The modified IFN-beta retained bioactivity.

Example 2

Synthesis of IFN Alpha Conjugates

Example 2.1(a)

Synthesis of Aldehydo-HES10/0.4 from Amino-HES10/0.4 and 4-formylbenzoic Acid

Aldehydo-HES10/0.4 was prepared according to Example 1.3(a).

Example 2.1(b)

Synthesis of Aldehydo-HES10/0.4 from Amino-HES10/0.4 and 4-formylbenzoic Acid

Aldehydo-HES10/0.4 was prepared according to Example 1.3(b).

Example 2.2

Synthesis of IFN Alpha Conjugates by Reductive Amination with Aldehyde Functionalized Hydroxyethyl Starch Synthesized According to Examples 2.1(a) and 2.1(b)

Commercially available rhIFN alpha was used (Strathmann Biotec, Hamburg, D, product code hIFNa) was used.

To 15 µl of a solution of IFN beta in 0.1 M sodium acetate buffer pH 5.0 (1 mg/ml) 3.91 µl of a solution of the HES-derivative (synthesized as described in Examples 2.1(a) or 0.21(b)) in the same buffer (200 mg/mL) were added. The mixture was cooled to 4° C. and 3.78 µl of a 120 mM solution of sodium cyanoborohydride in the same buffer at 4° C. were added and the mixture was incubated for 24 h at 4° C. The crude reaction mixture was analysed by gel electrophoresis. A successful conjugation was observed, as indicated by the migration of the protein band to higher molecular weight (see FIG. 3). The increased band-width is due to the molecular weight distribution of the HES derivatives used and the number of HES derivatives linked to the protein.

Example 3

Synthesis of AT III conjugates

Example 3.1

Synthesis of Hydroxyamino Functionalized Hydroxyethyl Starch Derivatives

Example 3.1(a)

Synthesis of HydroxylaminoHES10/0.4

2 g of HES10/0.4 (MW=10000 D, DS=0.4, Supramol Parenteral Colloids GmbH, Rosbach-Rodheim, D) were dissolved in 17 mL 0.1M sodium acetate buffer, pH 5.2 and 20 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8500 D and the DS was 0.41.

Example 3.1(b)

Synthesis of HydroxylaminoHES10/0.7

2 g of HES10/0.7 (MW=10000 D, DS=0.7, Supramol Parenteral Colloids GmbH, Rosbach-Rodheim, D) were dissolved in 18 mL 0.1M sodium acetate buffer, pH 5.2 and 20 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized.

The molecular weight of the HES10/0.7 when measured with LALLS-GPC was 10500 D and the DS was 0.76.

Example 3.1(c)

Synthesis of HydroxylaminoHES50/0.7

2 g of HES50/0.7 (MW=50000 D, DS=0.7, Supramol Parenteral Colloids GmbH, Rosbach-Rodheim, D) were dissolved in 20 mL 0.1M sodium acetate buffer, pH 5.2 and 4 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized.

The molecular weight of the HES50/0.7 when measured with LALLS-GPC was 47000 D and the DS was 0.76.

Example 3.1(d)

Synthesis of HydroxylaminoHES18/0.4

Oxidized HES was prepared essentially as described in DE 19628705A1. 200 mg of oxidized HES18/0.4 (MW=18000 D, DS=0.4) were heated at 80° C. in vaccuo for 17 h and dissolved in 2 mL dry DMSO (Fluka, Sigma-Aldrich Chemie GmbH, Taufkirchen, D). To the solution 2 mmol O-[2-(2-aminooxy-ethoxy)-ethyl]-hydroxyl amine were added. After incubation for 5 d at 65° C., the reaction mixture was added to 20 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES18/0.4 when measured with LALLS-GPC was 18000 D and the DS was 0.41.

Example 3.1(e)

Synthesis of HydrazidoHES10/0.4

Oxidized HES was prepared essentially as described in DE 19628705A1. 200 mg of oxidized HES10/0.4 (MW=10000 D, DS=0.4, Supramol Parenteral Colloids GmbH, Rosbach-Rodheim, D) were heated at 80° C. in vaccuo for 17 h and dissolved in 2 mL dry DMSO (Fluka, Sigma-Aldrich Chemie GmbH, Taufkirchen, D). To the solution 2 mmol adipic dihydrazide (Lancaster Synthesis GmbH, Frankfurt/Main D) were added. After incubation for 5 d at 65° C., the reaction mixture was added to 20 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 11000 D and the DS was 0.41.

Example 3.1(f)

Synthesis of CarbohydrazidoHES10/0.4

Oxidized HES was prepared essentially as described in DE 19628705A1. 200 mg of oxidized HES10/0.4 (MW=10000 D, DS=0.4, Supramol Parenteral Colloids GmbH, Rosbach-Rodheim, D) were heated at 80° C. in vaccuo for 17 h and dissolved in 2 mL dry DMSO (Fluka, Sigma-Aldrich Chemie GmbH, Taufkirchen, D). To the solution 2 mmol carbohydrazide (Fluka, Sigma-Aldrich Chemie GmbH, Taufkirchen, D) were added. After incubation for 5 d at 65° C., the reaction mixture was added to 20 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 11000 D and the DS was 0.41.

Example 3.1(g)

Synthesis of HydrazidoHES10/0.4

200 mg of HES10/0.4 (MW=10000 D, DS=0.4, Supramol Parenteral Colloids GmbH, Rosbach-Rodheim, D) were dissolved in 2 mL 0.1M sodium acetate buffer, pH 5.2. To the solution 2 mmol adipic dihydrazide (Lancaster Synthesis GmbH, Frankfurt/Main D) were added. After stirring for 19 h at 22° C., the reaction mixture was added to 21 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8500 D and the DS was 0.41.

Example 3.1(h)

Synthesis of CarboydrazidoHES10/0.4

200 mg of HES10/0.4 (MW=10000 D, DS=0.4, Supramol Parenteral Colloids GmbH, Rosbach-Rodheim, D) were dissolved in 2 mL 0.1M sodium acetate buffer, pH 5.2. To the solution 2 mmol carbohydrazide (Fluka, Sigma-Aldrich Chemie GmbH, Taufkirchen, D) were added. After stirring for 19 h at 22° C., the reaction mixture was added to 21 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8500 D and the DS was 0.41.

Example 3.2

Synthesis of AT III Conjugates

Example 3.2(a)

Oxidation of AT III

AT III used was recombinant human AT III (ATryn® from GTC Biotherapeutics).

Oxidation was essentially as described in Example 7.2, followed by buffer exchange as described in Example 7.3.

Example 3.2(b)

Reaction of Oxidized AT III of Example 3.2(a) with HES Derivatives of Examples 3.1(a)-3.1(h)

To 4 µL of a solution of oxidized ATIII in 0.1 M sodium acetate buffer, pH 5.5, 3 µL of a solution of the HES-derivative in 0.1 M sodium acetate buffer, pH 5.5 were added and the solution was incubated for 16.5 h at 22° C. The following concentrations were employed:
(i) 57 mg/mL for HES derivatives prepared according to example 3.1(a), 3.1(b), 3.1(e), 3.1(f), 3.1(g) and 3.1(h)
(ii) 287 mg/mL for HES derivatives prepared according to example 3.1(c)
(iii) 103 mg/mL for HES derivative prepared according to example 3.1(d)

The reaction mixture was analysed by gel electrophoresis (see FIG. 4).

Example 3.3

Synthesis of AT III Conjugates

Example 3.3(a)

Synthesis of Aldehydo-HES10/0.4 from Amino-HES10/0.4 and 4-formylbenzoic Acid

Aldehydo-HES10/0.4 was prepared according to Example 1.3(a).

Example 3.3(b)

Synthesis of aldehydo-HES10/0.4 from Amino-HES10/0.4 and 4-formylbenzoic Acid

Aldehydo-HES10/0.4 was prepared according to Example 1.3(b).

Example 3.4

Synthesis of AT III Conjugates by Reductive Amination with Aldehyde Functionalized Hydroxyethyl Starch Synthesized According to Examples 3.3(a) and 3.3(b)

AT III used was recombinant human AT III (ATryn® from GTC Biotherapeutics).

To 6.67 µl of a solution of AT III in 0.1 M sodium acetate buffer pH 5.0 (3 mg/ml) 1.73 µl of a solution of the HES-derivative (synthesized as described in Examples 3.3(a) or 3.3(b)) in the same buffer (200 mg/mL) were added. The mixture was cooled to 4° C. and 1.68 μl of a 120 mM solution of sodium cyanoborohydride in the same buffer at 4° C. were added and the mixture was incubated for 24 h at 4° C. The crude reaction mixture was analysed by gel electrophoresis. A successful conjugation was observed, as indicated by the migration of the protein band to higher molecular weight (see FIG. 5). The increased band-width is due to the molecular weight distribution of the HES derivative used and the number of HES derivatives linked to the protein.

Example 3.5

Synthesis of AT III Conjugates by Reaction of Hydroxyethyl Starch Having a Reactive Ester Group with AT III An AT III solution with a concentration of about 25 mg/ml in a 5 mM sodium citrate buffer, 66 mM glycerol, 67 mM NaCl, pH about 7 was used for this Example.

AT III used was recombinant human AT III (ATryn® from GTC Biotherapeutics).

AT III was liberated from unwanted glycerol by ultrafiltration with a phosphate buffer, pH 7.2, and a membrane with a cut-off of 10 kD. The final concentration of the resulting purified solution was about 25 mg/1.25 ml. The quality of the protein was controlled by HPGPC analysis (see FIG. 6).

The following parameters were used in the HPGPC analysis:

| | |
|---|---|
| Column: | Superose 12 HR 10/30 300 × 10 mm I.D. (Pharmacia) |
| Eluent: | 27.38 mM $Na_2HPO_4$; 12.62 mM $NaH_2PO_4$; 0.2M NaCl; 0.005% $NaN_3$ in 1 l of demineralized water |
| Flux: | 0.24 ml/h |
| Detector 1: | MALLS detector |
| Detector 2: | UV (280 nm) |
| Detector 3: | RI |

Oxo-HES10/0.4 (MW=10,559 D, DS=0.4) was prepared by Supramol Parenteral Colloids GmbH, Rosbach-Rodheim, D; according to DE 196 28 705 A1. The degree of oxidation of oxo-HES was 95%

52 mg of oxo-HES10/0.4 were dissolved in 0.2 ml anhydrous DMF. To this solution, 2.6 mg of N,N'-disuccinimidyl carbonate were added, and the mixture was stirred for 2 h at room temperature.

0.5 ml of 1 M sodium bicarbonate solution were added to 0.5 ml of the AT III solution resulting in a solution having a concentration of about 10 mg/ml AT III, pH 8.2. To this solution, the solution containing the reactive oxo-HES, as prepared above, was added in portions of 50 μl until, after about 30 min., the reaction had come to an end. Then, the pH of the mixture was adjusted to 7 using 0.1 N HCl and freezed at −18° C. until A HPGPC analysis (High-Performance Gel Permeation Chromatography) gave a yield of about 60% conjugate. This result is shown in FIG. 7.

The following parameters were used in the HPGPC analysis:

| | |
|---|---|
| Column: | Superose 12 HR 10/30 300 × 10 mm I.D. (Pharmacia) |
| Eluent: | 27.38 mM $Na_2HPO_4$; 12.62 mM $NaH_2PO_4$; 0.2M NaCl; 0.005% $NaN_3$ in 1 l of demineralized water |
| Flux: | 0.24 ml/h |
| Detector 1: | MALLS detector |
| Detector 2: | UV (280 nm) |
| Detector 3: | RI |

Example 4

Synthesis of GM-CSF Conjugates

Example 4.1

Synthesis of Hydroxyamino Functionalized Hydroxyethyl Starch Derivatives

Example 4.1(a)

Synthesis of HydroxylaminoHES10/0.4

2 g of HES10/0.4 (MW=10000 D, DS=0.4, Supramol Parenteral Colloids GmbH, Rosbach-Rodheim, D) were dissolved in 17 mL 0.1M sodium acetate buffer, pH 5.2 and 20 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8500 D and the DS was 0.41.

Example 4.1(b)

Synthesis of HydroxylaminoHES10/0.7

2 g of HES10/0.7 (MW=10000 D, DS=0.7, Supramol Parenteral Colloids GmbH, Rosbach-Rodheim, D) were dissolved in 18 mL 0.1M sodium acetate buffer, pH 5.2 and 20 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized.

The molecular weight of the HES10/0.7 when measured with LALLS-GPC was 10500 D and the DS was 0.76.

Example 4.1(c)

Synthesis of HydroxylaminoHES50/0.7

2 g of HES50/0.7 (MW=50000 D, DS=0.7, Supramol Parenteral Colloids GmbH, Rosbach-Rodheim, D) were dissolved in 20 mL 0.1M sodium acetate buffer, pH 5.2 and 4 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized.

The molecular weight of the HES50/0.7 when measured with LALLS-GPC was 47000 D and the DS was 0.76.

Example 4.1(d)

Synthesis of HydroxylaminoHES50/0.4

2 g of HES50/0.4 (MW=50000 D, DS=0.4, Supramol Parenteral Colloids GmbH, Rosbach-Rodheim, D) were dissolved in 20 mL 0.1M sodium acetate buffer, pH 5.2 and 4 mmol O-[2-(2-aminooxy-ethoxy)-ethyl]-hydroxyl amine were added. After shaking for 17.5 h at 22° C., the reaction mixture was added to 70 mL of an ice-cold 1:1 mixture of acetone and ethanol (v/v). The precipitated product was collected by centrifugation at 0° C., washed with 30 mL of an ice-cold 1:1 mixture of acetone and ethanol (v/v), re-dissolved in 50 mL water, dialysed for 19.5 h against water (SnakeSkin dialysis tubing, 3.5 kD cut off, Perbio Sciences Deutschland GmbH, Bonn, D) and lyophilized.

The molecular weight of the HES50/0.4 when measured with LALLS-GPC was 56000 D and the DS was 0.41.

Example 4.1(e)

Synthesis of HydroxylaminoHES18/0.4

Oxidized HES was prepared as described in DE 19628705A1. 200 mg of oxidized HES18/0.4 (MW=18000 D, DS=0.4) were heated at 80° C. in vaccuo for 17 h and dissolved in 2 mL dry DMSO (Fluka, Sigma-Aldrich Chemie GmbH, Taufkirchen, D). To the solution 2 mmol O-[2-(2-aminooxy-ethoxy)-ethyl]-hydroxyl amine were added. After incubation for 5 d at 65° C., the reaction mixture was added to 20 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES18/0.4 when measured with LALLS-GPC was 18000 D and the DS was 0.41.

Example 4.1(f)

Synthesis of HydrazidoHES10/0.4

Oxidized HES was prepared essentially as described in DE 19628705A1. 200 mg of oxidized HES10/0.4 (MW=10000 D, DS=0.4, Supramol Parenteral Colloids GmbH, Rosbach-Rodheim, D) were heated at 80° C. in vaccuo for 17 h and dissolved in 2 mL dry DMSO (Fluka, Sigma-Aldrich Chemie GmbH, Taufkirchen, D). To the solution 2 mmol adipic dihydrazide (Lancaster Synthesis GmbH, Frankfurt/Main D) were added. After incubation for 5 d at 65° C., the reaction mixture was added to 20 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 11000 D and the DS was 0.41.

Example 4.1(g)

Synthesis of CarbohydrazidoHES10/0.4

Oxidized HES was prepared as described in DE 19628705A1. 200 mg of oxidized HES10/0.4 (MW=10000 D, DS=0.4, Supramol Parenteral Colloids GmbH, Rosbach-Rodheim, D) were heated at 80° C. in vaccuo for 17 h and dissolved in 2 mL dry DMSO (Fluka, Sigma-Aldrich Chemie GmbH, Taufkirchen, D). To the solution 2 mmol carbohydrazide (Fluka, Sigma-Aldrich Chemie GmbH, Taufkirchen, D) were added. After incubation for 5 d at 65° C., the reaction mixture was added to 20 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 11000 D and the DS was 0.41.

Example 4.1(h)

Synthesis of HydrazidoHES10/0.4

200 mg of HES10/0.4 (MW=10000 D, DS=0.4, Supramol Parenteral Colloids GmbH, Rosbach-Rodheim, D) were dissolved in 2 mL 0.1M sodium acetate buffer, pH 5.2. To the solution 2 mmol adipic dihydrazide (Lancaster Synthesis GmbH, Frankfurt/Main D) were added. After stirring for 19 h at 22° C., the reaction mixture was added to 21 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8500 D and the DS was 0.41.

Example 4.1(i)

Synthesis of Carbohydrazido HES10/0.4

200 mg of HES10/0.4 (MW=10000 D, DS=0.4, Supramol Parenteral Colloids GmbH, Rosbach-Rodheim, D) were dissolved in 2 mL 0.1M sodium acetate buffer, pH 5.2. To the solution 2 mmol carbohydrazide (Fluka, Sigma-Aldrich Chemie GmbH, Taufkirchen, D) were added. After stirring for 19 h at 22° C., the reaction mixture was added to 21 mL of ice-cold 2-propanol and was incubated at −20° C. for 1 h. The precipitated product was collected by centrifugation at 4° C., washed with 42 ml ice-cold 2-propanol, re-dissolved in 10 mL water, dialysed for 27 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8500 D and the DS was 0.41.

Example 4.2

Synthesis of GM-CSF Conjugates

Example 4.2(a)

Oxidation of GM-CSF

GM-CSF was purified as described in Example 8.1. Oxidation was essentially as described in Example 8.2, followed by buffer exchange as described in Example 8.3.

Example 4.2(b)

Reaction of Oxidized GM-CSF of Example 4.2(a) with HES Derivatives of Examples 4.1(a)-4.1(i)

To 27 μL of a solution of oxidized GM-CSF in 0.1 M sodium acetate buffer, pH 5.5, 3.81 μL of a solution of the HES-derivative in 0.1 M sodium acetate buffer, pH 5.5 were added and the solution was incubated for 16.5 h at 22° C. The following concentrations were employed:

(i) 78.9 mg/mL for HES derivatives prepared according to example 4.1(a), 4.1(b), 4.1(f), 4.1(g), 4.1(h) and 4.1(i)
(ii) 395 mg/mL for HES derivatives prepared according to example 4.1(c) and 4.1(d)
(iii) 142 mg/mL for HES derivative prepared according to example 4.1(e)

The reaction mixture was analysed by gel electrophoresis (see FIG. 8).

Example 4.3

Synthesis of GM-CSF Conjugates

Example 4.3(a)

Synthesis of Aldehydo-HES10/0.4 from Amino-HES10/0.4 and 4-formylbenzoic Acid

Aldehydo-HES10/0.4 was prepared according to Example 1.3(a).

Example 4.3(b)

Synthesis of Aldehydo-HES10/0.4 from Amino-HES10/0.4 and 4-formylbenzoic Acid

Aldehydo-HES10/0.4 was prepared according to Example 1.3(b).

Example 4.4

Synthesis of GM-CSF Conjugates by Reductive Amination with Aldehyde Functionalized Hydroxyethyl Starch Synthesized According to Examples 4.3(a) and 4.3(b)

To 20 μl of a solution of GM-CSF in 0.1 M sodium acetate buffer pH 5.0 (1 mg/ml) 1.91 μl of a solution of the HES-derivative (synthesized as described in Examples 3.3(a) or 3.3(b)) in the same buffer (200 mg/mL) were added. The mixture was cooled to 4° C. and 4.38 μl of a 120 mM solution of sodium cyanoborohydride in the same buffer at 4° C. were added and the mixture was incubated for 24 h at 4° C. The crude reaction mixture was analysed by gel electrophoresis. A successful conjugation was observed, as indicated by the migration of the protein band to higher molecular weight (see FIG. 9). The increased band-width is due to the molecular weight distribution of the HES derivative used and the number of HES derivatives linked to the protein.

Example 5

Synthesis of AT III, IFN beta and GM-CSF Conjugates with Hydroxylamino Functionalized Hydroxyethyl Starch

Example 5.1

Synthesis of Hydroxylamino Functionalized Hydroxyethyl Starch (a) HydroxylaminoHES10/0.4 was synthesized as described in Example 1.1(a) hereinabove.
(b) HydroxylaminoHES50/0.7 was synthesized as described in Example 1.1(c) hereinabove.

Example 5.2

Synthesis of an IFN Beta Conjugate with HydroxylaminoHES 50/0.7 According to Example 5.1(b)

To 1190 μL of a solution of oxidized IFN beta in 0.1 M sodium acetate buffer, pH 5.5 (obtained after the step of Example 6.3), a solution of 81.4 mg of hydroxylamino-HES50/0.7 in 200 μL 0.1 M sodium acetate buffer, pH 5.5 were added and the solution was incubated for 19 h at 22° C.

The reaction mixture was analysed by gel electrophoresis (see FIG. 10).

Example 5.3

Synthesis of an AT III Conjugate with HydroxylaminoHES 10/0.4 According to Example 5.1(a)

To 500 μL of a solution of oxidized AT III in 0.1 M sodium acetate buffer, pH 5.5 (obtained after the step of Example 7.3) a solution of 21.6 mg of HydroxylaminoHES10/0.4 in 1500 μL 0.1 M sodium acetate buffer, pH 5.5 were added and the solution was incubated for 20.5 h at 22° C.

Example 5.4

Synthesis of a GM-CSF Conjugate with HydroxylaminoHES 10/0.4 According to Example 5.1(a)

To 720 μL of a solution of oxidized GM-CSF in 0.1 M sodium acetate buffer, pH 5.5 (obtained after the step of Example 8.3), a solution of 14.0 mg of Hydroxylamino-HES10/0.4 in 180 μL 0.1 M sodium acetate buffer, pH 5.5 were added and the solution was incubated for 18 h at 22° C.

Example 6

Further Characterization of Conjugates of IFN-Beta1a

Example 6.1(a)

Purification and Analysis of Human Recombinant Interferon Beta

Recombinant human interferon beta-1a comprising identical amino acid sequence as the market products AVONEX™ (BIOGEN) and Rebif (Serono) and was expressed from a CHO cell line transfected as described (Dittmar et al., 1989) IFN-β was purified by a three step procedure comprising adsorption of the culture supernatant onto Blue Sepharose, elution with 0.05 M Na-Phosphate buffer pH 7.0 containing 0.7 M NaCl+60% ethylene glycol and chromatography on a 10 ml FF Zn-chelate column at ambient temperature. The column was pre-equilibrated with 30 ml 20 mM Na-phosphate buffer, 0.3M NaCl, pH 7.4. Sample was applied after 1:2 dilution with 15 ml 20 mM Na-phosphate, pH 7.2-7.5. The column was then washed with 25 ml 20 mM Na-phosphate, 0.3M NaCl, pH 7.4, followed by elution I (20 ml 0.1 M Na-acetate, 0.5 M NaCl, pH 5.9) and elution II (15 ml 0.1 M Na-acetate, 0.5 M NaCl, pH 4.7). Final purification was performed by RP-HPLC on a Vydac C4 column equilibrated in 0.1% TFA (solvent A) using a gradient from 0-100% solvent B (80% acetonitrile in 0.1% TFA).

Example 6.1(b)

The IFN-beta 1a used was >95% pure (based on SDS-PAGE analysis and RP-HPLC and contained <5% of dimers (nonreducing conditions). The carbohydrate structures of the preparation was essentially the same as those in AVONEX™ and showed the presence of 42% of diantennary structures, 16% of diantennary minus proximal fucose, 12% triantennary, 7% tetraantennary and 9% triantennary with 1 N-acetyl-lactosamine repeat (the remaining 12% were agalacto structures and small amounts of chains with peripheral fucose). Based on HPAEC-PAD response about 14% of oligosaccharide chains were asialo, 21% were monosialo, 35% were disialo and 19% were trisialo. Small amounts of tetrasialo structures were present. The vast majority of sialic acids was found as N-acetylneuraminic acid and <5% of N-glycolylneuraminic acid was present in the preparation, therefore the preparation used resembles more the AVONEX™ market product since Rebif (Serono product) contains >15% of N-glycolylneuraminic acid (data not shown).

Example 6.2

Periodate Oxidation of N-Acetylneuraminic Acid Residues by Mild Perjodate Treatment of IFN-β1a from CHO Cells To a 500 µg/ml solution of IFN-β (in 0.1M Na-acetate buffer pH5.5 precooled and kept at 0° C.) was added an ice-cold solution of 10 mM Natrium-meta-periodate resulting in a final concentration of 1 mM Natrium-meta-periodate. The mixture was incubated at 0° C. for 1 hour in an ice-bath in the dark and the reaction was terminated by addition of 20 µl of glycerol and incubated for further 5 minutes. Subsequently IFN-β samples were concentrated using a Vivaspin concentrator unit as described below.

Example 6.3

Buffer Exchange of Perjodate Oxidised IFN-β1a for Subsequent Hesylation

Buffer exchange was performed using 0.5 ml Vivaspin 2 concentrator units (Vivaspin AG, Hannover, Germany) with a polyethersulfone (PES) membrane and a 10 Kda cut-off First, the concentrator unit was washed by addition of 0.5 ml of 0.1 M Na-acetate buffer pH 5.5 and centrifugation at 4000 rpm at 6° C. in a Megafuge 1.0R (Kendro Laboratory Equipment, Osterode, Germany). Subsequently, 0.5 ml of the periodate oxidised IFN-β solution was added to the concentrator unit and was centrifuged at 4000 rpm for 25 min until an at least 5-fold concentration was achieved. 0.1 M Na-acetate buffer pH 5.5 was added to the concentrate to a final volume of 0.5 ml which was centrifuged as described above. The centrifugation cycle was repeated 3 times, the final concentrate was removed and transferred into a 2 ml plastic vial (Eppendorff, Germany) and kept on ice until further use in the HAS-modification reaction.

Example 6.4

Synthesis of Conjugates of HAS and IFN-β

Synthesis was carried out as described in Example 5.2 above.

Example 6.5

Separation of HESylated IFN-β and Excess HAS Derivatives from Incubations of the Periodate-Oxidized Protein with Hydroxylamino-HES 50/0.7.

Summary: RP-HPLC Runs were performed at room temperature using an AKTA explorer 10 equipment and flow rate of 1.25 ml/min. Aliquots of the incubation mixtures containing 400 µg IFN-β were applied onto a 250 mm×10 mm $C_{18}$-phase column equilibrated with 1.25 CV of 11% Solvent B (0.1% TFA, 90% acetonitrile) and 89% Solvent A (0.1% TFA). The samples (ca. 1.25 ml) were then injected and the sample loop was washed with 11 ml of 11% solvent B. Following washing of the column with 0.2 CV of 11% solvent B, a linear gradient from 11% to 90% solvent B over 2 CV was applied. Elution of the column was continued by using 0.8 CV of 90% solvent B, and finally the column was re-equilibrated with 1.0 CV of 11% Solvent B.

The IFN-β proteins eluted in a volume of 7.5 ml at a concentration of 62% solvent B. The recovery of the protein was 60% (HES IFN-β CHO) based on the specific peak area of 790 mAU×ml×mg$^{-1}$ that was obtained with a standard IFN-β preparation on a $C_4$-phase column by using the same equipment.

Materials and Methods for Example 6.5

Equipment and Materials

| | |
|---|---|
| Equipment: | ÄKTA explorer 10 (Amersham Pharmacia Biotech), with: |
| | Pump P-903 |
| | Mixer M-925, with 0.6 ml chamber |
| | Monitor UV-900, with 10 mm flow cell |
| | Monitor pH/C-900 |
| | Fraction Collector Frac-900 |
| | Sample loop 2 ml |
| | Software Unicorn Version 3.21 |
| Column: | 250 mm × 10 mm, Macherey-Nagel 250-½"-10 Nucleosil 7 C18, |
| | Cat. No. 715002, Lot-No. 4020854 |
| Column volume: | 20 ml |
| Flow rate: | 1.25 ml/min |
| Solvent A: | 0.1% TFA in HPLC-water |
| Solvent B: | 90% acetonitrile, 0.1% TFA in HPLC-water |

Method for the RP-HPLC Run of Example 6.5

| Volume | Step | Solvent A | Solvent B |
|---|---|---|---|
| 0.25 CV | Equilibration | 89% | 11% |
| 11 ml | Sample injection | 89% | 11% |
| | Fractionation | 89% | 11% |
| 0.20 CV | Wash out unbound sample | 89% | 11% |
| 2.00 CV | Linear gradient | 89-10% | 11-90% |
| 0.80 CV | Isocratic | 10% | 90% |
| | End Fractionation | 10% | 90% |
| 1.00 CV | Re-equilibration | 89% | 11% |
| Detection: | A 280 nm | | |
| | A 221 nm | | |
| | A 206 nm | | |
| | Conductivity | | |
| Fractionation: | 1.25 ml/fraction | | |

Example 6.6

Analytical Experiments

Example 6.6(a)

Liberation of N-Linked Oligosaccharides with Recombinant Polypeptide N-Glycosidase (Roche, Penzberg, Germany)

To 100-120 μg of native, periodated oxidised or HAS-modified IFN-β1a in 50 mM Na-phosphate buffer pH 7.2 were added 25 μl of recombinant polypeptide N-glycosidase (Roche, Penzberg, Germany; 250 units/250 μl lot: 101610420). The reaction mixture was incubated at 37° C. for 12-18 hours and the release of N-glycosidically bound oligosaccharides was checked by SDS-PAGE analysis of 3-5 μg protein under reducing conditions and subsequent staining of protein bands with Coomassie Blue (Carl Roth GmbH Karlsruhe, Germany) and detection of the specific shift of the IFN-beta protein band to the migration position of the de-N-glycosylated form.

Example 6.6(b)

The released N-glycans were separated from the polypeptide by addition of 3 volumes of −20° C. 100% ethanol and incubation at −20° C. was performed for at least 2 hours. The precipitated protein was removed by centrifugation at 13,000 rpm for 10 minutes at 4° C. The pellet was then subjected to two additional washes with 500 μl ice-cold 70% ethanol. The oligosaccharides in the pooled supernatants were dried in a vacuum centrifuge (Speed Vac concentrator, Savant Instruments Inc., USA). The glycan samples were desalted using Hypercarb cartridges (100 or 200 mg) as follows: prior to use, the cartridges were washed three times with 500 μl 80% (v/v) acetonitrile in 0.1% (v/v) TFA followed by three washes with 500 μl water. The samples were diluted with water to a final volume of at least 300 μl before loading onto the cartridges. They were rigorously washed with water. Oligosaccharides were eluted with 1.2 ml 25% acetonitrile containing 0.1% (v/v) TFA. The eluted oligosaccharides were neutralised with 2 M $NH_4OH$ and were dried in a Speed Vac concentrator. They were stored at −20° C. in $H_2O$.

Example 6.6(c)

Mild Acid Hydrolysis

Mild acid hydrolysis of oligosaccharides (liberation of sialic acids and HAS-modified sialic acid derivatives from N-glycans) was performed as follows: aliquots of the desalted oligosaccharides or HAS-modified oligosaccharides were mixed with the same volume of 10 mM $H_2SO_4$ and were incubated for 90 minutes at 80° C. After neutralisation with 50 mM NaOH the desialylated glycan mixture was dried in a speed-vac concentrator and was adjusted to an appropriate concentration for analysis in HPAEC-PAD (high-pH-anion exchange chromatography with pulsed amperometric detection). For subsequent MALDI/TOF MS analysis of neutral oligosacharide samples (0.05-1 nmol) were desalted using small Hypercarb columns prepared by adding 25-40 μl of graphitisized carbon into 200 μl pipet tips.

Example 6.6(d)

Oligosaccharide Mapping by HPAEC-PAD (High-pH-Anion Exchange Chromatography with Pulsed Amperometric Detection)

BioLC System, (Dionex, Sunnyvale) consisting of a AS50 Autosampler, AS50 Thermal Compartment, ED50 Electrochemical Detector, GS50 Gradient Pump, Software Chromeleon Chromatography Management System, was used along with a CarboPac PA-100 separation column (4×250 mm) and a CarboPac PA-100 pre-column (4×50 mm). Two different modes were used for the mapping and for quantitation of oligosaccharides.

I) Asialo-Mode:

Neutral oligosaccharides were subjected to HPAEC-PAD mapping using a gradient of solvent A (200 mM NaOH) and solvent B (200 mM NaOH plus 600 mM Na-acetate) as depicted in the following table:

TABLE

| Gradient for mapping of neutral oligosacharides | | |
|---|---|---|
| Time [min] | solvent A [%] | solvent B [%] |
| 0 | 100 | 0 |
| 5 | 100 | 0 |
| 35 | 80 | 20 |
| 45 | 70 | 30 |
| 47 | 0 | 100 |
| 52 | 0 | 100 |
| 53 | 100 | 0 |
| 60 | 100 | 0 |

Flow rate: 1 ml/min

The detector potentials for the electrochemical detector were:

TABLE

| Detector-Potentials for oligosaccharides | |
|---|---|
| Time [ms] | potential [mV] |
| 0 | 50 |
| 200 | 50 |
| 400 | 50 |
| 410 | 750 |
| 600 | 750 |
| 610 | −150 |
| 1000 | −150 |

II) Oligos-Mode:

Native oligosaccharides were subjected to HPAEC-PAD mapping using a gradient of solvent C (100 mM NaOH) and solvent D (100 mM NaOH plus 600 mM Na-acetate) as depicted in the following table:

TABLE

| Gradient mapping of native (sialylated) oligosaccharides | | |
|---|---|---|
| Time [min] | solvent C [%] | solvent D [%] |
| 0 | 100 | 0 |
| 2 | 100 | 0 |
| 50 | 65 | 35 |
| 60 | 0 | 100 |
| 63 | 0 | 100 |
| 64 | 100 | 0 |
| 70 | 100 | 0 |

Flow rate: 1 ml/min

The detector potentials for the electrochemical detector were:

TABLE

Detector-Potentials for oligosaccharides

| Time [ms] | potential [mV] |
|---|---|
| 0 | 50 |
| 200 | 50 |
| 400 | 50 |
| 410 | 750 |
| 600 | 750 |
| 610 | −150 |
| 1000 | −150 |

The specific peak areas (nC×min×nmol$^{-1}$) were calculated using response factors obtained with defined oligosaccharide standards (disialylated diantennary, trisialylated triantennary, and tetrasialylated tetraantennary structures with and without N-acetyllactosamine repeats (Nimtz et al., 1993, Schroeter et al., 1999, Grabenhorst et al., 1999).

Results for HAS-Modified IFN-β

Upon RP-HPLC on C-18 phase HAS-modified IFN-β was detected in fractions 32-37. The recovery of HAS-IFN-β was calculated.

The arrow in FIG. 11 indicates the migration position of unmodified IFN-β presumably due to forms lacking terminal sialic acid derivatives whereas the HAS modified IFN-β was detected as a broad diffuse Coomassie stained area spanning molecular masses of 35 Kda-120 Kda.

Fractions 32-37 from the RP-HPLC eluate were pooled and concentrated in a speed Vac concentrator after neutralisation. Typically, 100-200 μg aliquots of the IFN-β sample were dried and dissolved in 50 mM Na-phosphate pH 7.2 plus 0.05% Tween-20 and was incubated with polypeptide N-glycosidase for 20-30 hours at 37° C. The resulting oligosaccharides were subjected to HPAEC-PAD analysis (Example 6.6d) before and after mild acid treatment.

As depicted in FIG. 12, the oligosaccharide material from HAS-modified IFN-β eluted after 52 minutes from the column under conditions where the asialo, mono-, di- and trisialylated were detected at 16-20 min, 21-26 min, 28-33 min and 34-38 min, respectively. After mild acid treatment of the oligosacharide sample under conditions where complete liberation of sialic acids is achieved, the expected neutral complex-type N-glycans of IFN-β were detected in the HPAEC-PAD profile and the released HAS-derivative was detected at a retention time of 46-49 min (using gradient Asialo-mode, see Example 6.6 dI) this indicates that HAS is attached to the N-linked oligosaccharides of IFN-β via a acid labile linkage as is expected (FIG. 13).

Example 7

Further Characterization of Conjugates of AT III

Example 7.1

Human AT III

AT III used was recombinant human AT III (ATryn® from GTC Biotherapeutics).

Example 7.2

Periodate Oxidation of N-acetylneuraminic Acid Residues by Mild Perjodate Treatment of AT III Periodate oxidation was carried out essentially as described for IFN-beta in Example 6.2.

Example 7.3

Buffer Exchange of Perjodate Oxidised AT III for Subsequent Hesylation

Buffer exchange was carried out essentially as described for IFN-beta in Example 6.3.

Example 7.4

Synthesis of Conjugates of HAS and AT III

Synthesis was as described in Example 5.3. above.

Example 7.5

AT III Ion Exchange Chromatography for Separation of HAS-Modified AT III from Excess HAS-Reagent 7.5.1. Buffer exchange of antithrombin III samples for subsequent purification by ion-exchange chromatography was performed using Vivaspin concentrators (10.000 MW CO PES, Vivascience Cat. No. VS0602, Lot-No. 03VS0633). Samples from HAS-modification reactions (2 mg AT III in 1.6 ml) were diluted to 5 ml with buffer A (20 mM N-morpholio-propane sulfonic acid adjusted to pH 8.0 with NaOH, MOPS). Samples were spun down according to manufacturer's recommendations to approximately 0.4-0.6 ml and the dilution/concentration step was repeated twice. Finally, protein samples were washed out of the concentrator unit.

7.5.2. The purification of the AT III sample was performed at ambient temperature using an AKTA explorer 10 system (Amersham Pharmacia Biotech) consisting of a Pump P-903, Mixer M-925, with a 0.6 ml chamber, a monitor UV-900 along with a 10 mm flow cell was used, a monitor pH/C-900, a sample pump P-950 and a 5 ml sample loop. The AKTA system was run under the Software Unicorn Version 3.21. The incubation mixture in buffer A (20 mM MOPS, pH 8.0) was applied at a flow rate of 0.6 ml/min to a column containing 2 ml Q-Sepharose Fast Flow (Amersham, code no. 17-0510-01, lot no. 254665) column (Amersham Biosciences C 10/10) equilibrated with 6 CV of buffer A at a flow rate of 1 ml/min. The column was washed with 6 CV of buffer A at a flow rate of 0.8 ml/min and elution was performed by using 4 CV of buffer B (0.5 M NaCl in 20 mM Na-phosphate, pH 6.5) at a flow rate of 0.6 ml/min. The column was regenerated by using 4 CV of buffer C (1.5 M NaCl in 20 mM Na-phosphate, pH 6.5) at a flow rate of 0.6 ml/min and re-equilibrated with buffer A. The AT III protein was eluted from the column in a volume of approximately 4 ml.

Method

| Volume | Step | Buffer | Flow rate |
|---|---|---|---|
| 1 CV | Equilibration | 100% buffer A | 1.0 ml/min |
| | Start Fractionation | 100% buffer A | 1.0 ml/min |
| 10 ml | Load sample | sample in buffer A | 0.6 ml/min |

-continued

| Volume | Step | Buffer | Flow rate |
|---|---|---|---|
| 6 CV | Wash out unbound sample | 100% buffer A | 0.8 ml/min |
| 4 CV | Elution | 100% buffer B | 0.6 ml/min |
| 4 CV | Regeneration (Elution 2) | 100% buffer C | 0.6 ml/min |
|  | Stop Fractionation | 100% buffer C | 0.6 ml/min |
| 5 CV | Reequilibration | 100% buffer A | 1.0 ml/min |

Buffer A: 20 mM MOPS/NaOH pH 8.0; Buffer B: 20 mM Na-phosphate, 0.5 M NaCl, pH 6.5; Buffer C: 20 mM Na-phosphate, 1.5 M NaCl, pH 6.5. Protein elution was detected at A280 nm and 1 ml fractions were collected.

Example 7.6

Analytical Experiments

Example 7.6(a)

Liberation of N-Glycans from Unmodified, Periodate Oxidised and HAS Modified AT III Samples was Performed with Recombinant 300-600 µg of AT III samples were reduced in the presence of 5 mM dithioerythreitol for 10 min at 90° C. at pH 8.1 in the presence of 0.6% SDS, thereafter NP 40 was added to a final concentration of 0.6%. To 0.3-0.6 mg of native, periodate oxidised or HAS-modified AT III in 50 mM Na-phosphate buffer pH 7.2 were added 40 µl of recombinant polypeptide N-glycosidase (Roche, Penzberg, Germany; 250 units/250 µl lot: 101610420). The reaction mixture was incubated at 37° C. for 12-18 hours and the release of N-glycosidically bound oligosaccharides was checked by SDS-PAGE analysis of 5-10 µg protein under reducing conditions and subsequent staining of protein bands with Coomassie Blue (Carl Roth GmbH Karlsruhe, Germany) and detection of the specific shift of the AT III protein band to the migration position of the de-N-glycosylated protein form.

Example 7.6(b)

The released N-glycans were separated from the polypeptide by addition of 3 volumes of −20° C. 100% ethanol and incubation at −20° C. was performed for at least 2 hours. The precipitated protein was removed by centrifugation at 13,000 rpm for 10 minutes at 4° C. The pellet was then subjected to two additional washes with 500 µl ice-cold 70% ethanol. The oligosaccharides in the pooled supernatants were dried in a vacuum centrifuge (Speed Vac concentrator, Savant Instruments Inc., USA). The glycan samples were desalted using Hypercarb cartridges (100 or 200 mg) as follows: prior to use, the cartridges were washed three times with 500 µl 80% (v/v) acetonitrile in 0.1% (v/v) TFA followed by three washes with 500 µl water. The samples were diluted with water to a final volume of at least 300 µl before loading onto the cartridges. They were rigorously washed with water. Oligosaccharides were eluted with 1.2 ml 25% acetonitrile containing 0.1% (v/v) TFA. The eluted oligosaccharides were neutralised with 2 M NH$_4$OH and were dried in a Speed Vac concentrator. They were stored at −20° C. in H$_2$O.

Example 7.6(c)

Mild Acid Hydrolysis

Mild acid hydrolysis of oligosaccharides (liberation of sialic acids and HAS-modified sialic acid derivatives from N-glycans) was performed as follows: aliquots of the desalted oligosaccharides or HAS-modified oligosaccharides were mixed with the same volume of 10 mM H$_2$SO$_4$ and were incubated for 90 minutes at 80° C. After neutralisation with 50 mM NaOH the desialylated glycan mixture was dried in a speed-vac concentrator and was adjusted to an appropriate concentration for analysis in HPAEC-PAD (high-pH-anion exchange chromatography with pulsed amperometric detection). For subsequent MALDI/TOF MS analysisi of neutral oligosacharide samples (0.05-1 nmol) were desalted using small Hypercarb columns prepared by adding 25-40 µl of graphitisized carbon into 200 µl pipet tips.

Example 7.6(d)

Oligosaccharide Mapping by HPAEC-PAD (High-pH-Anion Exchange Chromatography with Pulsed Amperometric Detection)

A BioLC System, (Dionex, Sunnyvale) consisting of a AS50 Autosampler, AS50 Thermal Compartment, ED50 Electrochemical Detector, GS50 Gradient Pump, Software Chromeleon Chromatography Management System, was used along with a CarboPac PA-100 separation column (4×250 mm) and a CarboPac PA-100 pre-column (4×50 mm). Two different modes were used for the mapping and for quantitation of oligosaccharides.

I) Asialo-Mode:

Neutral oligosaccharides were subjected to HPAEC-PAD mapping using a gradient of solvent A (200 mM NaOH) and solvent B (200 mM NaOH plus 600 mM Na-acetate) as depicted in the following table:

TABLE

Gradient for mapping of neutral oligosacharides

| Time [min] | solvent A [%] | solvent B [%] |
|---|---|---|
| 0 | 100 | 0 |
| 5 | 100 | 0 |
| 35 | 80 | 20 |
| 45 | 70 | 30 |
| 47 | 0 | 100 |
| 52 | 0 | 100 |
| 53 | 100 | 0 |
| 60 | 100 | 0 |

Flow rate: 1 ml/min

The detector potentials for the electrochemical detector were

TABLE

Detector-Potentials for oligosaccharides

| Time [ms] | potential [mV] |
|---|---|
| 0 | 50 |
| 200 | 50 |
| 400 | 50 |
| 410 | 750 |
| 600 | 750 |
| 610 | −150 |
| 1000 | −150 |

II) Oligos-Mode:

Native oligosaccharides were subjected to HPAEC-PAD mapping using a gradient of solvent C (100 mM NaOH) and solvent D (100 mM NaOH plus 600 mM Na-acetate) as depicted in the following table:

TABLE

Gradient mapping of native (sialylated) oligosaccharides

| Time [min] | solvent C [%] | solvent D [%] |
|---|---|---|
| 0 | 100 | 0 |
| 2 | 100 | 0 |
| 50 | 65 | 35 |
| 60 | 0 | 100 |
| 63 | 0 | 100 |
| 64 | 100 | 0 |
| 70 | 100 | 0 |

Flow rate: 1 ml/min

The detector potentials for the electrochemical detector were:

TABLE

Detector-Potentials for oligosaccharides

| Time [ms] | potential [mV] |
|---|---|
| 0 | 50 |
| 200 | 50 |
| 400 | 50 |
| 410 | 750 |
| 600 | 750 |
| 610 | −150 |
| 1000 | −150 |

The specific peak areas (nC×min×nmol$^{-1}$) were calculated using response factors obtained with defined oligosaccharide standards (disialylated diantennary, trisialylated triantennary, and tetrasialylated tetraantennary structures with and without N-acetyllactosamine repeats containing proximal fucose (Nimtz et al., 1993, Schroeter et al., 1999, Grabenhorst et al., 1999).

Results

HAS modification of AT III resulted in a significant molecular mass shift in SDS-PAGE indicating covalent attachment of HAS to the protein (see FIG. 14a.)

Ion exchange chromatography of the AT III subjected to HAS modification afforded an AT III fraction (>85% recovery based on comparison with untreated AT IIII).

De-N-glycosylation of the untreated AT III, the periodate treated AT IIII and the HAS-modified AT-III obtained after anion exchange on Q-Sepharose resulted in a comparable molecular weight shift in SDS-PAGE as depicted in FIG. 14B.

The liberated N-glycans of the AT III samples were isolated by adsobtion to and elution from Hypercarb cartridges and subjected to HPAEC-PAD analysis. The native N-glycans from HAS-modified AT III revealed the presence of all neutral oligosaccharide peaks detected in control samples (see trace 1 in FIG. 15). Upon mild acid treatment, all three N-glycan preparations showed a very similar pattern of the neutral oligosaccharides indicating the acid labile nature of the HAS-modification which is compatible with HAS-modification at the sialic acid derivatives of the oligosaccharides (cf. FIG. 16). The comparability of the desialylated structures was confirmed by MALDI/TOF analysis (data not shown).

Example 8

Further Characterization of Conjugates of GM-CSF

Example 8.1

Description of GM-CSF

Human recombinant GM-CSF was prepared after expression from CHO K1 cells essentially as described by Forno et al., 2004, (Guillermina Forno, Mariela Bollati Fogolin, Marcos Oggero, Ricardo Kratje, Marina Etcheverrigaray, Harald S. Conradt, Manfred Nimtz (2004) N- and O-linked carbohydrates and glycosylation site occupancy in recombinant human granulocyte-macrophage colony-stimulating factor secreted by a Chinese hamster ovary cell line; *Eur J Biochem*, 271 (5),907-919), and had the carbohydrate structures described therein.

The recombinant GM-CSF can also be purified by conventional chromatographic steps e.g. as described in: Okamoto, M., Nakai, M., Nakayama, C., Yanagi, H., Matsui, H., Noguchi, H., Namiki, M., Sakai, J., Kadota, K., Fukui, M. & Hara, H. (1991) Purification and characterization of three forms of differently glycosylated recombinant human Granulocyte-Macrophage Colony-Stimulating Factor. *Archives of Biochemistry and Biophysics* 286, 562-568.

Amino acid sequence of human GM-CSF used in this study:

```
                                      (SEQ ID NO: 1)
APA RSPSPSTQPW EHVNAIQEAR RLLNLSRDTA AEMNETVEVI

SEMFDLQEPT CLQTRLELYK QGLRGSLTKL KGPLTMMASH

YKQHCPPTPE TSCATQIITF ESFKENLKDF LLVIPFDCWE PVQE.
```

(according to reference Forno et al., supra)

Example 8.2

Periodate Oxidation of N-acetylaneuraminic Acid Residues by Mild Perjodate Treatment of Recombinant GM-CSF To a 0.80 mg/ml solution of GM-CSF in 0.1M Na-acetate pH 5.5 kept at 0° C. were added an ice-cold solution of 10 mM Natrium-meta-periodate resulting in a final concentration of 1 mM Natrium-meta-perjodate. The mixture was incubated at 0° C. for 1 hour in an ice-bath in the dark and the reaction was terminated by addition of 20 μl of glycerol and incubated for further 5 minutes.

Example 8.3

Buffer Exchange of Perjodate Oxidised GM-CSF for Subsequent HAS-Modification

Buffer exchange was performed using a 5 ml Vivaspin 6 concentrator (Vivaspin AG, Hannover, Germany) with a polyethersulfone (PES) membrane. The concentrator unit was washed by addition of 5 ml of 0.1 M Na-acetate buffer pH 5.5 and centrifugation of the concentrator unit at 4000 rpm at 6° C. in a Megafuge 1.0R (Kendro Laboratory Equipment, Osterode, Germany). Subsequently, 1-5 ml of the perjodate oxidised GM-CSF solution was added to the concentrator unit and was centrifuged at 4000 rpm for 25 min until a 5-fold concentration was achieved. 4 ml of 0.1 M Na-acetate buffer pH 5.5 was added to the concentrate which was centrifuged as described above. The centrifugation cycle was repeated 3 times, the final concentrate was removed and transferred into a 2.0 ml plastic vial, after washing of the concentrator unit 2 times with each 150 μl of Na-acetate buffer pH 5.5; the volume of the protein was adjusted with Na-acetate buffer pH 5.5 to

141

Example 8.4

Synthesis of Conjugates of HAS and GM-CSF

Synthesis was as described in Example 5.4. above.

Example 8.5

Purification of GM-CSF After HAS-Modification

Separation of HAS-modified GM-CSF from excess activated HES derivatives from incubations of the periodate-oxidized protein with Hydroxylamino-HES 10/0.7.

Summary: Runs were performed at room temperature using an ÄKTA explorer 10 equipment and flow rate of 1.25 ml/min. Aliquots of the incubation mixtures with 400 µg IFN-β were applied onto a 250 mm×10 mm $C_{18}$-phase column equilibrated with 1.25 CV of 11% Eluent B (0.1% TFA, 90% acetonitrile) and 89% Eluent A (0.1% TFA). The samples (ca. 1.25 ml) were then injected and the sample loop was washed with 11 ml of 11% Eluent B. Following washing of the column with 0.2 CV of 11% Eluent B, a linear gradient from 11% to 90% Eluent B over 2 CV was applied. Elution of the column was continued by using 0.8 CV of 90% Eluent B, and finally the column was re-equilibrated with 1.0 CV of 11% Eluent B.

The GM-CSF protein eluted in a volume of 7.5 ml at a concentration of % Eluent B. The recovery of the protein was 60% (HES GM-CSF) based on a standard GM-CSF preparation run on the column by using the same gradient.

Materials and Methods for Example 8.5

Equipment and Materials

| Equipment: | ÄKTA explorer 10 (Amersham Pharmacia Biotech), with:<br>Pump P-903<br>Mixer M-925, with 0.6 ml chamber<br>Monitor UV-900, with 10 mm flow cell<br>Monitor pH/C-900<br>Fraction Collector Frac-900<br>Sample loop 2 ml<br>Software Unicorn Version 3.21 |
|---|---|
| Column: | 250 mm × 10 mm, Macherey-Nagel 250-½"-10 Nucleosil 7 $C_{18}$, Cat. No. 715002, Lot-No. 4020854 |
| Column volume: | 20 ml |
| Flow rate: | 1.25 ml/min |
| Solvent A: | 0.1% TFA in HPLC-water |
| Solvent B: | 90% acetonitrile, 0.1% TFA in HPLC-grade water |

Method for the RP-HPLC run of Example 8.5

| Volume | Step | solvent A | solvent B |
|---|---|---|---|
| 0.25 CV | Equilibration | 89% | 11% |
| 11 ml | Sample injection | 89% | 11% |
|  | Fractionation | 89% | 11% |
| 0.20 CV | Wash out unbound sample | 89% | 11% |
| 2.00 CV | Linear gradient | 89-10% | 11-90% |
| 0.80 CV | Isocratic | 10% | 90% |
|  | End Fractionation | 10% | 90% |
| 1.00 CV | Re-equilibration | 89% | 11% |
| Detection: | 280 nm | | |
|  | 221 nm | | |
|  | 206 nm | | |
|  | Conductivity | | |
| Fraction volume: | 1.25 ml/fraction | | |

142

Results from Example 8.5

RP-HPLC separation of GM-CSF (Example 8.5) from excess HAS(10 Kda)-derivative afforded fractions 26-32 which contained all of the HAS-modified GM-CSF eluting from the column. The SDS-PAGE pattern of the protein after HAS modification showed a broad diffuse band in the molecular mass region between 35-90 Kda, whereas the unmodified GM-CSF showed the pattern of the nonglycosylated, mono-N-glycosylated and di-N-glycosylated forms (FIG. 17, cf. reference Forno et. al., 2004).

Example 8.6

Analytical Experiments a) Liberation of N-Linked Oligosaccharides with Recombinant Polypeptide N-Glycosidase To 200 µg-1 mg of native, periodated oxidised or HAS-modified GM-CSF in 50 mM Na-phosphate buffer pH 7.2 were added 25 µl of recombinant polypeptide N-glycosidase (Roche, Penzberg, Germany; 250 units/250 µl lot: 101610420). The reaction mixture was incubated at 37° C. for 12-18 hours and the release of N-glycosidically bound oligosaccharides was checked by SDS-PAGE analysis of 5-10 µg protein under reducing conditions and subsequent staining of protein bands with Coomassie Blue (Carl Roth GmbH Karlsruhe, Germany) and detetection of the shift of the GM-CSF protein band to the migration position of the de-N-glycosylated protein forms (cf. FIG. 18).

b) Isolation and Desalting of Enzymatically Released N-Glycans and HAS-Modified N-Glycans The released N-glycans were separated from the polypeptide by addition of 3 volumes of cold 100% ethanol and incubation at −20° C. for at least 2 hours. The precipitated protein was removed by centrifugation at 13,000 rpm for 10 minutes at 4° C. The pellet was then subjected to two additional washes with 500 µl ice-cold 70% ethanol. The oligosaccharides in the pooled supernatants were dried in a vacuum centrifuge (Speed Vac concentrator, Savant Instruments Inc., USA). The glycan samples were desalted using Hypercarb cartridges (100 or 200 mg) as follows: prior to use, the cartridges were washed three times with 500 µl 80% (v/v) acetonitrile in 0.1% (v/v) TFA followed by three washes with 500 µl water. The samples were diluted with water to a final volume of at least 300 µl before loading onto the cartridges. They were then rigorously washed with water 83 cartridge volumes). Oligosaccharides were eluted with 1.2 ml 25% acetonitrile containing 0.1% (v/v) TFA. The eluted oligosaccharides were neutralised with 2 M $NH_4OH$ and were dried in a Speed Vac concentrator. They were stored at −20° C. in $H_2O$ until further use.

c) Mild Acid Hydrolysis of Oligosaccharides (Removal of Sialic Acids and HAS-Modified Sialic Acid Deivatives from Oligosacharides)

Aliquots of the desalted oligosaccharides were mixed with the same volume of 10 mM $H_2SO_4$ and were incubated for 90 minutes at 80° C. After neutralisation with 50 mM NaOH the desialylated glycans were dried in a speed-vac and were adjusted to an appropriate concentration for analysis in HPAEC-PAD (high-pH-anion exchange chromatography with pulsed amperometric detection). For MALDI/TOF-MS analysis neutral N-glycans were desalted using pipette tips containing 20-30 µl of Hypercarb material for adsorption, washing and elution with 25% acetonitrile in 0.1% trifluoro acetic acid in $H_2O$.

d) Oligosaccharide Mapping by HPAEC-PAD (High-pH-Anion Exchange Chromatography with Pulsed Amperometric Detection)

Mapping and for quantitation of oligosaccharides was carried out essentially as described in Example 7.6.d).

Results

RP-HPLC purified material from Example 8.5 was used to demonstrate modification of the protein with HAS-derivatives at its carbohydrate chain via oxidised sialic acids. Monosaccharide compositional analysis by gas chromatographic analysis of their trimethylsialylated derivatives revealed the presence of glucose and the mono and di-hydroxyethylated glucose derivatives as well as mannose, galactose and N-acetylglucosamine and small amounts of N-acetylgalactosamine.

The HPAEC-PAD analysis of the native oligosaccharides liberated from the HAS-modified GM-CSF revealed a peak corresponding to HAS modification of the complex-type oligosaccharides (see FIG. 19).

Upon mild acid treatment the neutral N-glycans of GM-CSF were detected in the sample of the HAS-modified protein and also the modified HAS-derivative eluting at 47-49 minutes.

Example 9

Synthesis of ATIII-Conjugates

Example 9.1

Synthesis of Hydroxylamino-HES Derivatives

Example 9.1(a)

Synthesis of HydroxylaminoHES10/0.4

0.8 g of HES10/0.4 (MW=10000 D, DS=0.4, Supramol Parenteral Colloids GmbH, Rosbach-Rodheim, D) were dissolved in 8 mL 0.1M sodium acetate buffer, pH 5.5 and 8 mmol O-[2-(2-aminooxy-ethoxy)-ethyl]-hydroxyl amine were added. After shaking for 19 h at 22° C., the reaction mixture was added to 40 mL of 2-propanol at −20° C. The precipitated product was collected by centrifugation at 4° C., re-dissolved in 50 mL water, dialysed for 45 h against water (SnakeSkin dialysis tubing, 3.5 kD cut off, Perbio Sciences Deutschland GmbH, Bonn, D) and lyophilized. The isolated product yield was 73%.

The molecular weight of the HES10/0.4 when measured with LALLS-GPC was 8500 D and the DS was 0.41.

Example 9.1(b)

Synthesis of HydroxylaminoHES10/0.7

1.06 g of HES10/0.7 (MW=10000 D, DS=0.7, Supramol Parenteral Colloids GmbH, Rosbach-Rodheim, D) were dissolved in 10 mL 0.1M sodium acetate buffer, pH 5.5 and 10.9 mmol O-[2-(2-aminooxy-ethoxy)-ethyl]-hydroxyl amine were added. After shaking for 19 h at 22° C., the reaction mixture was added to 40 mL of 2-propanol at −20° C. The precipitated product was collected by centrifugation at 4° C., re-dissolved in 50 mL water, dialysed for 45 h against water (SnakeSkin dialysis tubing, 3.5 kD cut off, Perbio Sciences Deutschland GmbH, Bonn, D) and lyophilized. The isolated product yield was 60%.

The molecular weight of the HES10/0.7 when measured with LALLS-GPC was 10500 D and the DS was 0.76.

Example 9.1(c)

Synthesis of HydroxylaminoHES30/0.4

2 g of HES30/0.4 (MW=30000 D, DS=0.4, Supramol Parenteral Colloids GmbH, Rosbach-Rodheim, D) were dissolved in 18 mL 0.1M sodium acetate buffer, pH 5.5 and 6.67 mmol O-[2-(2-aminooxy-ethoxy)-ethyl]-hydroxyl amine were added. After shaking for 15.5 h at 22° C., the reaction mixture was added to 80 mL of 2-propanol at −20° C. The precipitated product was collected by centrifugation at 4° C., re-dissolved in 50 mL water, dialysed for 45 h against water (SnakeSkin dialysis tubing, 3.5 kD cut off, Perbio Sciences Deutschland GmbH, Bonn, D) and lyophilized. The isolated product yield was 83%.

The molecular weight of the HES30/0.4 when measured with LALLS-GPC was 33000 D and the DS was 0.41.

Example 9.1(d)

Synthesis of HydroxylaminoHES30/0.7

2 g of HES30/0.7 (MW=30000 D, DS=0.7, Supramol Parenteral Colloids GmbH, Rosbach-Rodheim, D) were dissolved in 18 mL 0.1M sodium acetate buffer, pH 5.5 and 6.67 mmol O-[2-(2-aminooxy-ethoxy)-ethyl]-hydroxyl amine were added. After shaking for 15 h at 22° C., the reaction mixture was added to 80 mL of 2-propanol at −20° C. The precipitated product was collected by centrifugation at 4° C., re-dissolved in 50 mL water, dialysed for 45 h against water (SnakeSkin dialysis tubing, 3.5 kD cut off, Perbio Sciences Deutschland GmbH, Bonn, D) and lyophilized. The isolated product yield was 86%.

The molecular weight of the HES30/0.7 when measured with LALLS-GPC was 31000 D and the DS was 0.76.

Example 9.1(e)

Synthesis of HydroxylaminoHES50/0.4

2 g of HES50/0.4 (MW=50000 D, DS=0.4, Supramol Parenteral Colloids GmbH, Rosbach-Rodheim, D) were dissolved in 20 mL 0.1M sodium acetate buffer, pH 5.5 and 4 mmol O-[2-(2-aminooxy-ethoxy)-ethyl]-hydroxyl amine were added. After shaking for 19.5 h at 22° C., the reaction mixture was added to 80 mL of 2-propanol at −20° C. The precipitated product was collected by centrifugation at 4° C., re-dissolved in 50 mL water, dialysed for 45 h against water (SnakeSkin dialysis tubing, 3.5 kD cut off, Perbio Sciences Deutschland GmbH, Bonn, D) and lyophilized. The isolated product yield was 94%.

The molecular weight of the HES50/0.4 when measured with LALLS-GPC was 56000 D and the DS was 0.41.

Example 9.1(f)

Synthesis of HydroxylaminoHES50/0.7

2.5 g of HES50/0.7 (MW=50000 D, DS=0.7, Supramol Parenteral Colloids GmbH, Rosbach-Rodheim, D) were dissolved in 25 mL 0.1M sodium acetate buffer, pH 5.5 and 5 mmol O-[2-(2-aminooxy-ethoxy)-ethyl]-hydroxyl amine were added. After shaking for 19.5 h at 22° C., the reaction mixture was added to 80 mL of 2-propanol at −20° C. The precipitated product was collected by centrifugation at 4° C., re-dissolved in 50 mL water, dialysed for 45 h against water (SnakeSkin dialysis tubing, 3.5 kD cut off, Perbio Sciences Deutschland GmbH, Bonn, D) and lyophilized. The isolated product yield was 85%.

The molecular weight of the HES50/0.7 when measured with LALLS-GPC was 47000 D and the DS was 0.76.

Example 9.1(g)

Synthesis of HydroxylaminoHES10/0.7

2 g of HES10/0.7 (MW=10000 D, DS=0.7, Supramol Parenteral Colloids GmbH, Rosbach-Rodheim, D) were dissolved in 18 mL 0.1M sodium acetate buffer, pH 5.2 and 20 mmol O-[2-(2-aminooxy-ethoxy)-ethyl]-hydroxyl amine were added. After shaking for 19 h at 22° C., the reaction mixture was added to 100 mL of an ice-cold 1:1 mixture of acetone and ethanol (v/v). The precipitated product was collected by centrifugation at 4° C., re-dissolved in 50 mL water, dialysed for 21 h against water (SnakeSkin dialysis tubing, 3.5 kD cut off, Perbio Sciences Deutschland GmbH, Bonn, D) and lyophilized. The isolated product yield was not determined.

The molecular weight of the HES10/0.7 when measured with LALLS-GPC was 10500 D and the DS was 0.76.

Example 9.2

Synthesis of Aldehydo-HES Derivatives

Example 9.2(a)

Synthesis of AminoHES10/0.7

6.02 g of oxo-HES10/0.7 (MW=10000 D, DS=0.7, Supramol Parenteral Colloids GmbH, Rosbach-Rodheim, D, prepared according to DE 196 28 705 A1) were dissolved under nitrogen in 32 mL dry dimethyl sulphoxide (Fluka, Sigma-Aldrich Chemie GmbH, Taufkirchen, D) and 6.03 ml of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 ml water, dialysed for 4 d against water (SnakeSkin dialysis tubing, 3.5 kD cut off, Perbio Sciences Deutschland GmbH, Bonn, D) and lyophilized. The isolated product yield was 52%.

The molecular weight of the HES10/0.7 when measured with LALLS-GPC was 15000 D and the DS was 0.76.

Example 9.2(b)

Synthesis of AldehydoHES10/0.7

150 mg 4-formylbenzoic acid and 230 mg 1-hydroxy-1H-benzotriazole (both Aldrich, Sigma-Aldrich Chemie GmbH, Taufkirchen, D) were dissolved in 10 mL N,N-dimethylformamide (Peptide synthesis grade, Biosolve, Valkenswaard, NL) and 204 µL N,N'-diisopropylcarbodiimide (Fluka, Sigma-Aldrich Chemie GmbH, Taufkirchen, D) were added. After incubation at 21° C. for 30 min, 1 g of aminoHES10/0.7 (synthesised as described in 9.2(a)) were added. After shaking for 19 h at 22° C., the reaction mixture was added to 84 mL of an ice-cold 1:1 mixture of acetone and ethanol (v/v). The precipitated product was collected by centrifugation at 4° C., re-dissolved in 50 mL water, dialysed for 2 d against water (SnakeSkin dialysis tubing, 3.5 kD cut off, Perbio Sciences Deutschland GmbH, Bonn, D) and lyophilized. The isolated product yield was 83%.

Example 9.2(c)

Synthesis of AminoHES50/0.7

6.09 g of oxo-HES 50/0.7 (MW=50000 D, DS=0.7, Supramol Parenteral Colloids GmbH, Rosbach-Rodheim, D prepared according to DE 198 26 705 A1 with adaptation of the molar ratios of the ingredients) were dissolved under nitrogen in 32 mL dry dimethyl sulphoxide (Fluka, Sigma-Aldrich Chemie GmbH, Taufkirchen, D) and 1.22 ml of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 ml water, dialysed for 4 d against water (SnakeSkin dialysis tubing, 3.5 kD cut off, Perbio Sciences Deutschland GmbH, Bonn, D) and lyophilized. The isolated product yield was 67%.

The molecular weight of the HES50/0.7 when measured with LALLS-GPC was 57000 D and the DS was 0.76.

Example 9.2(d)

Synthesis of AldehydoHES50/0.7

124 mg 4-formylbenzoic acid and 174 mg 1-hydroxy-1H-benzotriazole (both Aldrich, Sigma-Aldrich Chemie GmbH, Taufkirchen, D) were dissolved in 38 mL N,N-dimethylformamide (Peptide synthesis grade, Biosolve, Valkenswaard, NL) and 155 µL N,N'-diisopropylcarbodiimide (Fluka, Sigma-Aldrich Chemie GmbH, Taufkirchen, D) were added. After incubation at 21° C. for 30 min, 3.8 g of aminoHES50/0.7 (synthesised as described in 9.2(c)) were added. After shaking for 19 h at 22° C., the reaction mixture was added to 160 mL of an ice-cold 1:1 mixture of acetone and ethanol (v/v). The precipitated product was collected by centrifugation at 4° C., re-dissolved in 20 mL N,N-dimethylformamide and precipitated with 80 mL of an ice-cold 1:1 mixture of acetone and ethanol (v/v) as described above. After centrifugation, the precipitate was dissolved in 50 mL water, dialysed for 2 d against water (SnakeSkin dialysis tubing, 3.5 kD cut off, Perbio Sciences Deutschland GmbH, Bonn, D) and lyophilized. The isolated product yield was 77%.

Example 9.3

Synthesis of the ATIII-Conjugates by the Glycan Strategy

Example 9.3(a)

Reaction of Oxidized ATIII with Reaction Products of Examples 9.1(a)-9.1(g)

To 685 µL of a solution of oxidized ATIII in 0.1 M sodium acetate buffer, pH 5.5 (GlycoThera, B52 perj-ox STM 112-366, 4.375 mg/ml, see example 3.2.), 814 µL 0.1 M sodium acetate buffer, pH 5.5 and 1.5 mL of a solution of the HES-derivative in 0.1 M sodium acetate buffer, pH 5.5 were added and the solution was incubated for 26 h at 22° C.

The following final HES concentrations were employed:

0.46 mg/mL for HES derivatives prepared according to example 9.1(a) and 9.1(b).

1.38 mg/mL for HES derivatives prepared according to example 9.1(c) and 9.1(d).

9.1 mg/mL for the HES derivative prepared according to example 9.1(e).

10.5 mg/mL for the HES derivative prepared according to example 9.1(f).

17.25 mg/mL for the HES derivative prepared according to example 9.1(g).

9 mg/mL HES50/0.7 (Supramol Parenteral Colloids GmbH, Rosbach-Rodheim, D) as reaction control. The molecular weight of the HES50/0.7 when measured with LALLS-GPC was 47000 D and the DS was 0.76.

The respective reaction mixture was analysed by gel electrophoresis (see FIG. 20).

Example 9.4

Synthesis of the ATIII-Conjugates by Reductive Amination

Example 9.4(a)

Buffer Exchange

ATIII (Atryn, GTC Biotherapeutics, Framingham, Mass., USA) was dissolved with 10 ml water to yield a solution of 25 mg/ml ATIII in 5 mM sodium citrate, 67 mM glycine and 68 mM sodium chloride, pH7.0. 1 ml of this solution was diluted with cold 0.1 M sodium acetate buffer, pH 5.0, concentrated by diafiltration at 4° C. to 4 ml with a Vivaspin 20 mL concentrator (VS2001, 10 KD MWCO, PES membrane, Vivascience AG, Hannover, D) and re-diluted to 20 ml with buffer. This diafiltration was repeated twice. The final concentration in the last diafiltration step was 3 mg/ml.

Example 9.4(b)

Reaction of ATIII with Reaction Products of Example 9.2(b) and 9.2(d)

To 1 mL of a solution of ATIII after buffer exchange into 0.1 M sodium acetate buffer, pH 5.0 1 mL of a solution of the HES-derivative in 0.1 M sodium acetate buffer, pH 5.0 and 1 ml of a 60 mM solution of sodium cyanoborohydride in the same buffer were added and the solution was incubated for 15.5 h at 4° C. All the solutions were cooled to 0° C. before mixing.

The following final HES concentrations were employed:

13 mg/mL for the HES derivative prepared according to example 9.2(b).

64.7 mg/mL for the HES derivative prepared according to example 9.2(d).

64.7 mg/mL HES50/0.7 (Supramol Parenteral Colloids GmbH, Rosbach-Rodheim, D) as reaction control.

The respective reaction mixture was analysed by gel electrophoresis.

Example 10

Synthesis of IFN-Alpha Conjugates via Activated Aldonic Acids

The IFN-alpha used was a recombinant human Interferon alpha-2b manufactured by recombinant DNA technology using *Escherichia coli* (*E. coli*). It is composed of 165 amino acids and presents an amino acid sequence, which is identical to the natural human interferon alpha 2b (hIFN-alpha 2b).

Example 10.1

Synthesis of Oxidized HES (Oxo-HES)

Oxidized HES was prepared from HES (MW=57 kD, DS=0.76, Supramol Parenteral Colloids GmbH, Rosbach-Rodheim, D) according to DE 196 28 705 A1.

Example 10.2

Synthesis of NHS-Activated Oxo-HES 4.81 g ox-HES 50/0.7 as prepared in example 10.1 were dried in an oven at 80° C. over night. The ox-HES is dissolved at 80° C. in dry DMF and cooled to room temperature.

From a solution of 102.1 mg N,N'-Disuccinimidylcarbonate (Aldrich) in 1 ml dry DMF, 400 ml are dropped to the stirred reaction vessel and stirred for 2 hours at room temperature.

The reaction mixture is dropwise added to 50 ml dry acetone and the precipitated product collected by centrifugation and washed with 4×50 ml dry acetone, where the resuspended product is centrifuged. The residual solvent is removed at room temperature in vacuo.

Example 10.3

Synthesis of an IFN-Alpha Conjugate via Activated Aldonic Acid (AAA)

The protein was concentrated using Amicon Ultra filtration modules 4 (5 kDa molecular weight cut-off (MWCO)) in a cooled centrifuge (4° C.) to a final concentration of 10 mg/ml. The buffer was exchanged during this procedure to isotonic phosphate buffer, pH 8.

For coupling, 9 mg of the protein solution were incubated with the 20 fold molar amount of the NHS activated ox-HES of example 10.1 for two hours at room temperature. The reaction mixture was purified from NHS by ultrafiltration using Amicon Ultra filtration modules 4 (5 kDa MWCO) in a cooled centrifuge (4° C.). The buffer was exchanged during this procedure to 25 mM sodium phosphate, 30 mM sodium chloride, 0.3 mM EDTA, at pH 7.5.

The reaction yield of the experiment was >90% as determined by SEC (see FIG. 22).

Example 10.4

Purification of IFN-Alpha-HES

The purification of the sample was performed at room temperature using an ÄKTA explorer 10 equipment. The column containing 5 ml Q-Sepharose Fast Flow was equilibrated with 5 CV of buffer A1 (20 mM Tris/HCl, pH 8.0). The samples were diluted 1:16 with buffer A and were applied by using the sample pump at a flow rate of 6 ml/min. Following washing of the sample pump with 20 ml of buffer A1, the column was further washed with 15 ml of buffer A1 at a flow rate of 1.0 ml/min. Elution was performed by using a linear gradient from 0-100% of buffer B1 (0.3 M NaCl in 20 mM Tris/HCl, pH 8.0) over 37.5 min and an isocratic run with buffer B over 12.5 min at a flow rate of 0.8 ml/min. The column was regenerated by using 15 ml of buffer B2 (1.5 M NaCl in 20 mM Tris/HCl, pH 8.0) followed by 5 ml of buffer B at a flow rate of 0.8 ml/min. Reequilibration for the next run was performed by using 25 ml of buffer A1 and a flow rate of 1.0 ml/min.

| Equipment: | Äkta explorer 10 (Amersham Bioscience) with: |
| --- | --- |
| | Pump P-903 |
| | Mixer M-925 with 0.6 ml chamber |
| | Monitor UV-900 with 10 mm flow cell |
| | Monitor pH/C-900 |
| | Pump P-950 (sample pump) |
| | Software Unicorn Version 3.21 |
| Column: | Amersham Bioscience C 10/10 |
| Column material: | Q-Sepharose Fast Flow, Lot No. OD 06453 |
| Column volume: | 5 ml |
| Program: | Q Seph 5 ml without Inject for IFN-α |
| Eluent A1: | 20 mM Tris/HCl, pH 8.0 (PL0935) |
| Eluent B1: | 0.3M NaCl in 20 mM Tris/HCl, pH 8.0 (PL0938) |
| Eluent B2: | 1.5M NaCl in 20 mM Tris/HCl, pH 8.0 (PL0937) |

Method

| Volume | Step | Eluent | Flow rate |
| --- | --- | --- | --- |
| 25 ml | Equilibration | 100% Eluent A1 | 1 ml/min |
| 40 ml | Load sample | Probe in Eluent A1 | 6 ml/min |
| 20 ml | Wash sample pump | 100% Eluent A1 | 6 ml/min |
| 15 ml | Wash column | 100% Eluent A1 | 1 ml/min |
| 30 ml | Elution (Gradient) | 0 to 100% Eluent B1 | 0.8 ml/min |
| 10 ml | Elution (Isokratic) | 100% Eluent B1 | 0.8 ml/min |
| 15 ml | Regeneration | 100% Eluent B2 | 0.8 ml/min |
| 5 ml | Regeneration | 100% Eluent B1 | 0.8 ml/min |
| 25 ml | Reequilibration | 100% Eluent A1 | 1.0 ml/min |
| Detection | 280 nm, 260 nm, 220 nm | | |
| | pH | | |
| | Conductivity | | |
| Fractionation | 1 ml fractions | | |

Example 11

Description of IFN Alpha Antiviral Activity Bioassay

After pre-diluting the Test Items in cell culture medium, serial two-fold dilutions were prepared. In 96 well microtiter plates, diluted Interferon was added—in four-fold replicate per dilution—to freshly trypsinized MDBK cells (40.000 cells per well). The assays were incubated for 24 hours at 37° C. (total volume per well: 150 µL (example 11.1) or 175 µl (example 11.2)).

Subsequently, 50 µL diluted VSV stock solution were added to each well (except for the positive control wells) resulting in a multiplicity of infection of 0.1.

The following controls were included in each assay: 12 wells that received virus plus cell culture medium instead of Interferon (negative control) and 12 wells that received cell culture medium instead of Interferon and virus (positive control). The assays were incubated for 42 hours at 37° C.

At the end of the incubation period, the cell culture supernatant of each well was replaced with 50 µL of a solution of MTT (at least 2 mg/mL in cell culture medium). The cells were incubated for three hours. The purple formazan dye formed by the proliferating cells was solubilized by adding 100 µL solution of isopropanol/HCl (isopropanol with 40 mM HCl) to each well. Subsequently, the absorbance values of the solutions were measured at 570/630 nm in a microtiter plate reader.

The proliferative activity of MDBK cells grown in the presence of Interferon and VSV was calculated for each dilution of Interferon as follows:

$$\frac{\left(\text{Mean absorbance of four Interferon treated wells} - \text{Mean absorbance of negative control}\right)}{(\text{Mean absorbance of positive control}) - (\text{Mean absorbance of negative control})} * 100$$

The antiviral activity of Interferon-alpha was determined in four separate assays for each of the Test Items.

Example 11.1

Antiviral Activity of Intron® A Relative to NIH Standard

In all experiments, Intron® A (IFN-alpha 2b, Schering-Plough), calibrated against NIH-standard rhIFN-alpha 2a (NIAID, NIH, Bethesda, USA, Gxa01-901-535) was used as an internal lab reference. The NIH-standard had a specific activity of 9,000 IU/ml. The internal lab reference Intron® A had a specific activity of 8,487,000 IU/ml in the test as described in example 11 (see FIG. 23).

Example 11.2

Antiviral Activity of IFN-Alpha-HES Relative to Intron® A

In the assay system described in example 11, the conjugate from example 10.4 was tested compared to Intron® A. The CPE50 concentration of both materials was calculated. IFN-alpha-HES had more than 25% of the activity of Intron® A (see FIG. 24).

Example 12

In vivo Bioactivity of IFN-Alpha-HES (PK Study in Mice)

Example 12.1

Influence of Mouse Serum on Assay System as Described in Example 11

Dilutions of Interferon-alpha were prepared in cell culture medium (control) and in mouse serum (1:40 dilution and 1:80 dilution). The assay was performed as described in example 11.

The antiviral activity of Interferon-alpha was determined in two separate assays for the control, for mouse serum 1:40 diluted as well as for mouse serum 1:80 diluted. The results indicated that mouse serum at 1:40 dilution and 1:80 does not affect the bioassay for antiviral activity of Interferon-alpha.

Example 12.2

In vivo Study in Mice

Antiviral activity of pooled serum was tested in the antiviral assay. Serum was collected from two mice (female BALB/c mice, aged 8 weeks) at each time, which were sacrificed 2 h, 4 h, 12 h, and 24 h post i.v.-injection of 30 µg/kg (based on the protein content) of IFN-alpha or the conjugate.

The serum samples were thawed and thoroughly homogenised by vortexing. Serial two-fold dilutions were prepared in cell culture medium. A vial of Intron® A was thawed and thoroughly homogenised by vortexing. Serial two-fold dilutions were prepared in cell culture medium.

The EC50-dilutions in the CPE-assay were determined from dose response curves of a 1:2 dilution series as described in example 11.

The half life of the materials was determined compared to unmodified starting material and Pegasys. The half life was calculated from a semi-logarithmic plot of the EC50-dilution vs. time post injection (see FIG. 25).

Antiviral activity was detected for IFN-alpha-HES up to 24 h. A half-life increase by derivatisation of IFN-alpha with HES was observed (half life approx. 5 h). For unmodified IFN-alpha, the antiviral activity of serum was too low to calculate a serum half-life.

Example 13

A1AT (α1AT, Alpha1aT) Conjugates Synthesized via Reductive Amination

Example 13.1

Synthesis of Amino-HES (A) from Oxidized HES 6.09 g of oxo-HES (MW=57,000 D, DS=0.76, Supramol Parenteral Colloids GmbH, Rosbach-Rodheim, D, prepared according to DE 196 28 705 A1) were heated over night at 80° C. in vacuo, dissolved under nitrogen in 32 ml dry dimethyl sulphoxide (Fluka, Sigma-Aldrich Chemie GmbH, Taufkirchen, D,) and 1.22 ml of 1,4-diaminobutane (Fluka, Sigma-Aldrich Chemie GmbH, Taufkirchen, D) were added. After stirring at 40° C. for 17 h the reaction mixture was added to 150 ml of an ice-cold 1:1 mixture of acetone and ethanol (v/v). The precipitated product was collected by centrifugation at 4° C., washed with 40 ml of an ice-cold 1:1 mixture of acetone and ethanol (v/v) and collected by centrifugation. The crude product was dissolved in 80 ml water, dialysed for 4 d against water (SnakeSkin dialysis tubing, 3.5 kD cut off, Perbio Sciences Deutschland GmbH, Bonn, D) and lyophilized. The yield of isolated product was 82%.

Example 13.2

Synthesis of Aldehydo-HES (A) from Amino-HES (A) of Example 13.1

125 mg 4-formylbenzoic acid and 174 mg 1-hydroxy-1H-benzotriazole (both Aldrich, Sigma-Aldrich Chemie GmbH, Taufkirchen, D) were dissolved in 38 ml N,N-dimethylformamide (Peptide synthesis grade, Biosolve, Valkenswaard, NL), and 155 μL N,N'-diisopropylcarbodiimide (Fluka, Sigma-Aldrich Chemie GmbH, Taufkirchen, D) were added. After incubation at 21° C. for 30 min, 3.8 g of amino-HES (A) (prepared as described in example 13.1) were added. After shaking for 19 h at 22° C., the reaction mixture was added to 160 ml of an ice-cold 1:1 mixture of acetone and ethanol (v/v). The precipitated product was collected by centrifugation at 4° C., re-dissolved in 20 ml N,N-dimethylformamide and precipitated with 80 ml of an ice-cold 1:1 mixture of acetone and ethanol (v/v) as described in example 13.1. After centrifugation, the precipitate was dissolved in 50 ml water, dialysed for 2 d against water (SnakeSkin dialysis tubing, 3.5 kD cut off, Perbio Sciences Deutschland GmbH, Bonn, D) and lyophilized. The yield of isolated product was 77%.

Example 13.3

Synthesis of Amino-HES (B) from Oxidized HES 10 g of oxo-HES (MW=57 kD, DS=0.76, Supramol Parenteral Colloids GmbH, Rosbach-Rodheim, D, prepared according to DE 196 28 705 A1) were heated over night at 80° C. in vacuo, dissolved under nitrogen in 52 ml dry dimethyl sulphoxide (Fluka, Sigma-Aldrich Chemie GmbH, Taufkirchen, D) and 2 ml of 1,4-diaminobutane (Fluka, Sigma-Aldrich Chemie GmbH, Taufkirchen, D) were added. After stirring at 40° C. for 17 h the reaction mixture was added to 350 ml of ice-cold 2-propanol (Carl Roth GmbH+Co. KG, Karlsruhe, D). The precipitated product was collected by centrifugation at 4° C., washed with 80 ml of ice-cold 2-propanol and collected by centrifugation. The crude product was dissolved in 80 ml water, dialysed for 2 d against water (SnakeSkin dialysis tubing, 3.5 kD cut off, Perbio Sciences Deutschland GmbH, Bonn, D) and lyophilized. The yield of isolated product was 85%.

Example 13.4

Synthesis of Aldehydo-HES (B) from Amino-HES (B) of Example 13.3

153 mg 4-formylbenzoic acid and 241 mg 1-hydroxy-1H-benzotriazole (both Aldrich, Sigma-Aldrich Chemie GmbH, Taufkirchen, D) were dissolved in 51 ml N,N-dimethylformamide (Peptide synthesis grade, Biosolve, Valkenswaard, NL) and 170 μL N,N'-diisopropylcarbodiimide (Fluka, Sigma-Aldrich Chemie GmbH, Taufkirchen, D) were added. After incubation at 21° C. for 30 min, 5.1 g of amino-HES (B) (prepared as described in example 13.3) were added. After shaking for 16 h at 22° C., the reaction mixture was added to 360 ml of an ice-cold 1:1 mixture of acetone and ethanol (v/v). The precipitated product was collected by centrifugation at 4° C., re-dissolved in 50 ml water and precipitated with 360 ml of an ice-cold 1:1 mixture of acetone and ethanol (v/v) as described in example 13.1. After centrifugation, the precipitate was dissolved in 50 ml water, dialysed for 2 d against water (SnakeSkin dialysis tubing, 3.5 kD cut off, Perbio Sciences Deutschland GmbH, Bonn, D) and lyophilized. The yield of isolated product was 87%.

Example 13.5

Conjugation of Aldehydo-HES (A) and (B) to A1AT by Reductive Amination

A mixture of 189 mg aldehydo-HES (B) (prepared as described in example 13.4) and 172 mg aldehydo-HES (A) (prepared as described in example 13.2) were dissolved in 2.88 ml reaction buffer (0.1 M sodium phosphate buffer, 150 mM sodium chloride, pH 7.2). At 20° C., 1.67 ml of a 60 mM sodium cyanoborohydride solution in the same buffer were added followed by 0.455 ml of an A1AT solution (c (A1AT) =11.0 mg/ml in 0.1 M sodium phosphate buffer, 150 mM sodium chloride, pH 7.2, A1AT=rh A1AT provided by GTC Biotherapeutics Inc., Framingham, Mass., lot No. 080604A). The mixture was incubated at 20° C. After 17 h, additional 6.7 mg sodium cyanoborohydride dissolved in 200 μl of the reaction buffer were added and the mixture was incubated for additional 24 h at the same temperature. 10 μL of this solution were analysed after a total incubation time of 25 h by gel electrophoresis (see FIG. 26)

Example 13.6

Conjugation of HES to A1AT by Reductive Amination (Reaction Control)

362 mg HES (MW=42 kD, DS=0.41, Supramol Parenteral Colloids GmbH, Rosbach-Rodheim, D) were dissolved in 2.88 ml reaction buffer (0.1 M sodium phosphate buffer, 150 mM sodium chloride, pH 7.2). At 20° C., 1.67 ml of a 60 mM sodium cyanoborohydride solution in the same buffer were added followed by 0.455 ml of a A1AT solution (c (A1AT) =11.0 mg/ml in 0.1 M sodium phosphate buffer, 150 mM sodium chloride, pH 7.2, α1AT=rh α1AT provided by GTC Biotherapeutics Inc., Framingham, Mass., lot No. 080604A). The mixture was incubated at 20° C. After 17 h, additional 6.7 mg sodium cyanoborohydride dissolved in 200 μl of the reaction buffer were added and the mixture was incubated for additional 24 h at the same temperature. 10 μL of this solution were analysed after a total incubation time of 25 h by gel electrophoresis (see FIG. 27).

Example 13.7

Purification of HES-A1AT Conjugate by Ion Exchange Chromatography (IEC)

Conjugates of A1AT were purified by Ion Exchange Chromatography on a HiTrap Q HP column using an ÄKTA-Explorer chromatography system (both from Amersham Biosciences). The purification was performed in accordance with the isolation of A1AT from human plasma as described in "Chen, Hammond, Lang and Lebing, Purification of $α_1$ Proteinase Inhibitor from Human Plasma Fraction IV-1 by Ion Exchange Chromatography, VoxSanguinis 1998, 74, 232-241".

Sample preparation: buffer exchange on a HiPrep 26/10 Desalting column (Amersham Biosciences) in combination with the ÄKTA-Explorer chromatography system using 20 mM sodium phosphate, 20 mM sodium chloride, pH 8 as eluent.

Buffer exchange was performed after dilution of the crude reaction mixture (preparation as described in example 13.5, approximately 5 ml) with desalted water to a final volume of 10 ml using the following parameters:

| | |
|---|---|
| Column: | HiPrep 26/10 Desalting |
| Flow rate: | 10 ml/min |
| Eluent: | 20 mM sodium phosphate, 20 mM sodium chloride, pH 8 |
| Sample volume: | 10 ml |
| Eluate fractionation: | 2.5 ml |
| Equilibration: | 5 column volumes |
| Length of elution: | 2 column volumes |

The first 14 ml of eluent were pooled, and binding buffer was added to yield a final volume of 20 ml. This solution, containing approximately 5 mg protein, was purified by IEC using the following parameters:

| | |
|---|---|
| Column: | HiTrap Q HP 1 ml |
| Flow rate: | 1 ml/min |
| Binding Buffer (BB): | 20 mM sodium phosphate, 20 mM sodium chloride, pH 8 |
| Elution Buffer (EB): | 20 mM sodium phosphate, 1 M sodium chloride, pH 8 |
| Sample volume: | 20 ml |
| Flow trough fractionation: | 2 ml |
| Eluate fractionation: | 1 ml |
| Start concentration EB: | 0% |
| Equilibration: | 5 column volumes |
| Wash out unbound sample: | 15 ml |
| Target concentration EB: | 15% |
| Length of gradient: | 20 ml |

The fractions collected after chromatography were analysed by SDS-Page. Fractions containing HES-A1AT conjugate were pooled (elution volume from 40 to 47 ml corresponding to fractions B1-C6, see FIG. 27). In some of the pooled fractions a small amount of unreacted A1AT was detectable. The initial concentration of the pooled fraction after chromatography determined by BCA (Pierce Cat. No. 23225), using A1AT (provided by GTC Biotherapeutics Inc., Framingham, Mass., lot No. 080604A) as reference standard) was 170 μg/ml. After dilution and buffer exchange into 20 mM sodium phosphate, 150 mM sodium chloride, pH 7.2 the resulting protein concentration was 54.5 μg/ml (BCA (pierce with A1AT from GTC as reference standard)). This final solution was used to determinate the inhibitory efficiency of the conjugate.

Example 13.8

Determination of the in vitro Inhibition Capacity of HES-A1AT Conjugate for Human Granulocyte Elastase Elastase Inhibitory activity tests of the conjugates were performed according to *Castillo* et al., *Anal. Biochem.* 1979, 99, 53-64 using a Tecan UV-VIS-Platereader Model Sunrise.

This assay is based on the release of p-nitroaniline from N-Met-O-succinyl-Ala-Ala-Pro-Val-p-$NO_2$-anilin catalyzed by elastase. This hydrolysis can be followed by the increase of absorbance at 405 nm. The initial hydrolysis rate is in close correlation to the activity of the enzyme. The assay was carried out in absence and in the presence of different concentrations of the inhibitor to be tested. The decrease of enzyme activity according to the inhibitory activity of the substances tested is represented in a decrease of the slope in the $A_{405}$ versus time plot. The residual elastase activity in presence of a certain inhibitor concentration is given by the slope of the inhibited curve divided by the slope of the uninhibited curve. There is a linear correlation between the residual enzyme activity and the inhibitor concentration. By using linear regression, a linear smooth line can be achieved and the residual enzyme activity for a given inhibitor concentration can be calculated. By this way the inhibitory activity (=1-residual enzyme activitiy) of the same concentration of different inhibitors can be compared. (see FIG. 28)

The following parameters were used:

| | |
|---|---|
| Substrate concentration: | 1.5 mM |
| Elastase activity: | 7.5 mU |
| Wavelength: | 405 nm |
| Temperature: | 20° C. |
| Time interval: | 15 s |
| Kinetic cycles: | 25 |
| Measure Mode: | Center |

The assay solution consisted of 300 μl buffer (0.1 M Hepes, 0.5 M NaCl, 0.05% (m/v) Triton X-100, pH 7.5) containing 10% DMSO, 1.5 mM N-Met-O-succinyl-Ala-Ala-Pro-Val-p-NO$_2$-anilin, 7.5 mU Elastase and varying amounts of inhibitors.

Elastase was purchased from Serva Electrophoresis GmbH, Heidelberg. All other substances were purchased from Sigma Aldrich, Taufkirchen.

The inhibitory activity of the conjugate synthesized as described in example 13.5 was tested in comparison with Prolastin® HS (Bayer Vital GmbH, Leverkusen, Germany Lot No. PR4HA43) as reference and with A1AT (GTC Biotherapeutics Inc., Framingham, Mass., lot No. 080604A) as starting material for the conjugation. The residual enzyme activity vs. concentration plot is given in FIG. 28. Linearity for all curves was $R^2 > 0.98$. In the below, $IC_{50}$-values and elastase inhibition for c (inhibitor)=1 μg/ml are given, as well as the inhibitory activity of starting material and conjugate in relation to the reference. Data outlined in the table below clearly demonstrate that the major part of the A1AT activity remained after conjugation with HES.

Table of Example 13.8

| inhibitor | linear smooth line equitation | $IC_{50}$ [μg/ml] | elastase inhibition c (inhibitor) = 1 μg/ml [%] | inhibition activity in relation to Prolastin [%] |
|---|---|---|---|---|
| Prolastin | Y = −0.6754x + 0.9627 | 0.685 | 71.3 | |
| α1AT | Y = −0.5046x + 0.9558 | 0.903 | 54.9 | 77.0 |
| HES-A1AT-conjugate | Y = −0.3757x + 0.9627 | 1.232 | 41.3 | 57.9 |

Example 13.9

Determination of the in-vivo Half-Live of HES-rh alpha1AT Conjugate in Comparison to rh alpha1AT and Plasma Derived h alpha1AT Female mice aged 8-10 weeks (BALB/cOlaHsd, Harlan GmbH, Borchen, Germany) were utilized as test organism (42 mice, 14 per sample). The "is bodyweight" of each animal was detected right before administration of the different sample solutions. 100 μl of a 50 μg/ml solution of the samples outlined below in a puffer pH=7.2 (20 mmol sodium phosphate, 150 mmol sodium chloride) were injected intravenously in the tail vein of the mice.

Sample 1: rh alpha1AT (GTC Biotherapeutics Inc., Framingham, MA, lot No. 080604A)
Sample 2: rh alpha1AT-HES conjugate as prepared in example 13.5
Sample 3: plasma derived h alpha1AT (SERVA Electrophoresis GmbH, Heidelberg, Germany)

At 1, 2, 4, 10, 24, 31.5 and 48, hours after injection, two mice of each group were killed and whole blood samples (~500 μl) were withdrawn from the heart of the animals. Serum was prepared using Microvette® 500 Z-Gel (Sarstedt, Nümbrecht, Germany). The serum samples were stored at −80° C. until the beginning of the alpha1AT concentration measurements.

alpha1AT concentrations were detected using a commercially available alpha1AT-ELISA (Immundiagnostik, Bensheim, Germany) following the manufacturers instructions.

The results obtained demonstrate a significant plasma half-life increase for the rh alpha1AT-HES conjugate in comparison to the not modified rh alpha1AT starting material. The measured half-life of the conjugate is in the same range than the one of the plasma derived h alpha1AT according to the following table.

Table of Example 13.9

Plasma Half-Life of Samples 1-3

| Sample No | Plasma half-life in mice [h] |
|---|---|
| 1 | 1.2 |
| 2 | 3.6 |
| 3 | 3.2 |

Example 14

Synthesis of HES-IFN-Alpha Conjugates via Reducitve Amination

The IFN-α used was a recombinant human Interferon alpha-2b manufactured by recombinant DNA technology using *Escherichia coli* (*E. coli*). It is composed of 165 amino acids and presents an amino acid sequence which is identical to the natural human interferon alpha 2b (hIFN-alpha 2b).

Example 14.1

Synthesis of Oxo-HES

HES oxidised at its reducing end as described hereinunder (oxo-HES) was prepared from HES using an alkaline iodine solution as described in DE 196 28 705 A1 the respective contents of which (example A, column 9, lines 6 to 24) is incorporated herein by reference.

Example 14.2

Synthesis of HES Derivatives

In a two step procedure, oxo-HES of example 14.1 was modified at its reducing end with an amine, and an aldehydo group was introduced in a second reaction. The resulting aldhydo-HES was used to produce the IFN-alpha-HES conjugates via reductive amination as described in example 14.3.

Example 14.2.1

Synthesis of Amino-HES from Oxo-HES of Example 14.1

5.12 g of oxo-HES of example 14.1 (MW=14.5 kD, DS=0.41, Supramol Parenteral Colloids GmbH, Rosbach-Rodheim, D) were heated over night at 80° C. in vacuo and dissolved under nitrogen in 25 mL dry dimethyl sulphoxide (Fluka, Sigma-Aldrich Chemie GmbH, Taufkirchen, D) and 5.13 mL of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 mL water, dialysed for 4 d against water (SnakeSkin dialysis tubing, 3.5 kD cut off, Perbio Sciences Deutschland GmbH, Bonn, D) and lyophilized. The yield of isolated product was 67%.

Example 14.2.2

Synthesis of Aldehydo-HES from Amino-HES of Example 14.2.1

105 mg 4-formylbenzoic acid and 135 mg 1-hydroxy-1H-benzotriazole (both Aldrich, Sigma-Aldrich Chemie GmbH, Taufkirchen, D) were dissolved in 7 mL N,N-dimethylformamide (Peptide synthesis grade, Biosolve, Valkenswaard, NL) and 135 µL N,N'-diisopropylcarbodiimide (Fluka, Sigma-Aldrich Chemie GmbH, Taufkirchen, D) were added. After incubation at 21° C. for 30 min, 0.7 g of amino-HES (synthesised as described in example 14.2.1) were added. After shaking for 18 h at 22° C., the reaction mixture was added to 42 mL of an ice-cold 1:1 mixture of acetone and ethanol (v/v). The precipitated product was collected by centrifugation at 4° C., re-dissolved in 5 mL DMF and precipitated with 42 mL ethanol/acetone as described above. After centrifugation, the collected precipitate was dissolved with water, dialysed for 4 d against water (SnakeSkin dialysis tubing, 3.5 kD cut off, Perbio Sciences Deutschland GmbH, Bonn, D) and lyophilized. The yield of isolated product was 95%.

Example 14.2.3

Synthesis of Amino-HES from Oxo-HES of Example 14.1

6.02 g of oxo-HES of example 14.1 (MW=14.7 kD, DS=0.76, Supramol Parenteral Colloids GmbH, Rosbach-Rodheim, D) were heated over night at 80° C. in vacuo and dissolved under nitrogen in 32 mL dry dimethyl sulphoxide (Fluka, Sigma-Aldrich Chemie GmbH, Taufkirchen, D) and 6.03 mL of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 mL water, dialysed for 4 d against water (SnakeSkin dialysis tubing, 3.5 kD cut off, Perbio Sciences Deutschland GmbH, Bonn, D) and lyophilized. The yield of isolated product was 52%.

Example 14.2.4

Synthesis of Aldehydo-HES from Amino-HES of Example 14.2.3

150 mg 4-formylbenzoic acid and 230 mg 1-hydroxy-1H-benzotriazole (both
Aldrich, Sigma-Aldrich Chemie GmbH, Taufkirchen, D) were dissolved in 10 mL N,N-dimethylformamide (Peptide synthesis grade, Biosolve, Valkenswaard, NL) and 204 µL N,N'-diisopropylcarbodiimide (Fluka, Sigma-Aldrich Chemie GmbH, Taufkirchen, D) were added. After incubation at 21° C. for 30 min, 1 g of amino-HES (synthesised as described in example 14.2.3) were added. After shaking for 19 h at 22° C., the reaction mixture was added to 84 mL of ice-cold 2-propanol. The precipitated product was collected by centrifugation at 4° C., re-dissolved in 50 mL water, dialysed for 2 d against water (SnakeSkin dialysis tubing, 3.5 kD cut off, Perbio Sciences Deutschland GmbH, Bonn, D) and lyophilized. The yield of isolated product was 83%.

Example 14.2.5

Synthesis of Amino-HES from oxo-HES of Example 14.1

5 g of oxo-HES of example 14.1 (MW=28 kD, DS=0.41, Supramol Parenteral Colloids GmbH, Rosbach-Rodheim, D) were heated over night at 80° C. in vacuo and were then dissolved under nitrogen in 28 mL dry dimethyl sulphoxide (Fluka, Sigma-Aldrich Chemie GmbH, Taufkirchen, D) and 1.67 mL of 1,4-diaminobutane were added. After stirring at 40° C. for 17 h the reaction mixture was added to 175 mL of an ice-cold 1:1 mixture of acetone and ethanol (v/v). The precipitated product was collected by centrifugation at 4° C. The crude product was dissolved in 40 mL water, dialysed for 2 d against water (SnakeSkin dialysis tubing, 3.5 kD cut off, Perbio Sciences Deutschland GmbH, Bonn, D) and lyophilized. The yield of isolated product was not determined.

Example 14.2.6

Synthesis of Aldehydo-HES from Amino-HES of Example 14.2.5

130 mg 4-formylbenzoic acid and 153 mg 1-hydroxy-1H-benzotriazole (both Aldrich, Sigma-Aldrich Chemie GmbH, Taufkirchen, D) were dissolved in 36 mL N,N-dimethylformamide (Peptide synthesis grade, Biosolve, Valkenswaard, NL) and 110 µL N,N'-diisopropylcarbodiimide (Fluka, Sigma-Aldrich Chemie GmbH, Taufkirchen, D) were added. After incubation at 21° C. for 30 min, 2.61 g of amino-HES (synthesised as described in example 14.2.5) were added. After shaking for 22.5 h at 22° C., the reaction mixture was added to 160 mL of an ice-cold 1:1 mixture of acetone and ethanol (v/v). The precipitated product was collected by centrifugation at 4° C. and washed with an ice-cold 1:1 mixture of acetone and ethanol (v/v). After centrifugation, the precipitate was dissolved in 30 mL water, dialysed for 1 d against water (SnakeSkin dialysis tubing, 3.5 kD cut off, Perbio Sciences Deutschland GmbH, Bonn, D) and lyophilized. The yield of isolated product was 81%.

Example 14.2.7

Synthesis of Amino-HES from Oxo-HES of Example 14.1

5 g of oxo-HES of example 14.1 (MW=30.8 kD, DS=0.76, Supramol Parenteral Colloids GmbH, Rosbach-Rodheim, D) were heated over night at 80° C. in vacuo and were then dissolved under nitrogen in 28 mL dry dimethyl sulphoxide (Fluka, Sigma-Aldrich Chemie GmbH, Taufkirchen, D) and 1.67 mL of 1,4-diaminobutane were added. After stirring at 40° C. for 17 h the reaction mixture was added to 175 mL of an ice-cold 1:1 mixture of acetone and ethanol (v/v). The precipitated product was collected by centrifugation at 4° C. The crude product was dissolved in 40 mL water, dialysed for 2 d against water (SnakeSkin dialysis tubing, 3.5 kD cut off, Perbio Sciences Deutschland GmbH, Bonn, D) and lyophilized. The yield of isolated product was not determined.

Example 14.2.8

Synthesis of Aldehydo-HES from Amino-HES of Example 14.2.7

122 mg 4-formylbenzoic acid and 144 mg 1-hydroxy-1H-benzotriazole (both Aldrich, Sigma-Aldrich Chemie GmbH, Taufkirchen, D) were dissolved in 34 mL N,N-dimethylformamide (Peptide synthesis grade, Biosolve, Valkenswaard, NL) and 103 μL N,N'-diisopropylcarbodiimide (Fluka, Sigma-Aldrich Chemie GmbH, Taufkirchen, D) were added. After incubation at 21° C. for 30 min, 2.46 g of amino-HES (synthesised as described in example 14.2.7) were added. After shaking for 22.5 h at 22° C., the reaction mixture was added to 160 mL of an ice-cold 1:1 mixture of acetone and ethanol (v/v). The precipitated product was collected by centrifugation at 4° C. and washed with an ice-cold 1:1 mixture of acetone and ethanol (v/v). After centrifugation, the precipitate was dissolved in 30 mL water, dialysed for 4 d against water (SnakeSkin dialysis tubing, 3.5 kD cut off, Perbio Sciences Deutschland GmbH, Bonn, D) and lyophilized. The yield of isolated product was 87%.

Example 14.2.9

Synthesis of Amino-HES from Oxo-HES of Example 14.1

10 g of oxo-HES (MW=42.1 kD, DS=0.41, Supramol Parenteral Colloids GmbH, Rosbach-Rodheim, D) were heated for two days at 80° C. in vacuo and were then dissolved under nitrogen in 53 mL dry dimethyl sulphoxide (Fluka, Sigma-Aldrich Chemie GmbH, Taufkirchen, D) and 2.01 mL of 1,4-diaminobutane were added. After stirring at 40° C. for 17 h the reaction mixture was added to 350 mL of ice-cold 2-propanol (Carl Roth GmbH+Co. KG, Karlsruhe, D). The precipitated product was collected by centrifugation at 4° C., washed with 80 mL of ice-cold 2-propanol and collected by centrifugation. The crude product was dissolved in 80 mL water, dialysed for 2 d against water (SnakeSkin dialysis tubing, 3.5 kD cut off, Perbio Sciences Deutschland GmbH, Bonn, D) and lyophilized. The yield of isolated product was 76%.

Example 14.2.10

Synthesis of Aldehydo-HES from Amino-HES of Example 14.2.9

900 mg 4-formylbenzoic acid and 1053 mg 1-hydroxy-1H-benzotriazole (both Aldrich, Sigma-Aldrich Chemie GmbH, Taufkirchen, D) were dissolved in 30 mL N,N-dimethylformamide (Peptide synthesis grade, Biosolve, Valkenswaard, NL) and 930 μL N,N'-diisopropylcarbodiimide (Fluka, Sigma-Aldrich Chemie GmbH, Taufkirchen, D) were added. After incubation at 21° C. for 30 min, 3 g of amino-HES (synthesised as described in example 14.2.9 and dissolved in 20 mL N,N-dimethylformamide) were added. After shaking for 22.5 h at 22° C., the reaction mixture was added to 210 mL of an ice-cold 1:1 mixture of acetone and ethanol (v/v). The precipitated product was collected by centrifugation at 4° C. and washed with an ice-cold 1:1 mixture of acetone and ethanol (v/v). After centrifugation, the precipitate was dissolved in 30 mL water, dialysed for 2 d against water (SnakeSkin dialysis tubing, 3.5 kD cut off, Perbio Sciences Deutschland GmbH, Bonn, D) and lyophilized. The yield of isolated product was 97%.

Example 14.2.11

Synthesis of Amino-HES from Oxo-HES of Example 14.1 (A)

6.09 g of oxo-HES (MW=56.8 kD, DS=0.76, Supramol Parenteral Colloids GmbH, Rosbach-Rodheim, D) were heated over night at 80° C. in vacuo and were then dissolved under nitrogen in 32 mL dry dimethyl sulphoxide (Fluka, Sigma-Aldrich Chemie GmbH, Taufkirchen, D) and 1.22 mL of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 mL water, dialysed for 4 d against water (SnakeSkin dialysis tubing, 3.5 kD cut off, Perbio Sciences Deutschland GmbH, Bonn, D) and lyophilized. The yield of isolated product was 82%.

Example 14.2.12

Synthesis of Aldehydo-HES from Amino-HES of Example 14.2.11

125 mg 4-formylbenzoic acid and 174 mg 1-hydroxy-1H-benzotriazole (both Aldrich, Sigma-Aldrich Chemie GmbH, Taufkirchen, D) were dissolved in 38 mL N,N-dimethylformamide (Peptide synthesis grade, Biosolve, Valkenswaard, NL) and 155 μL N,N'-diisopropylcarbodiimide (Fluka, Sigma-Aldrich Chemie GmbH, Taufkirchen, D) were added. After incubation at 21° C. for 30 min, 3.8 g of amino-HES (synthesised as described in example 14.2.11) were added. After shaking for 19 h at 22° C., the reaction mixture was added to 160 mL of an ice-cold 1:1 mixture of acetone and ethanol (v/v). The precipitated product was collected by centrifugation at 4° C., re-dissolved in 20 mL N,N-dimethylformamide and precipitated with 80 mL of an ice-cold 1:1 mixture of acetone and ethanol (v/v) as described above. After centrifugation, the precipitate was dissolved in 50 mL water, dialysed for 2 d against water (SnakeSkin dialysis tubing, 3.5 kD cut off, Perbio Sciences Deutschland GmbH, Bonn, D) and lyophilized. The yield of isolated product was 77%.

Example 14.2.13

Synthesis of Amino-HES from Oxo-HES of Example 14.1 (B)

10 g of oxo-HES (MW=56.8 kD, DS=0.76, Supramol Parenteral Colloids GmbH, Rosbach-Rodheim, D) were heated over night at 80° C. in vacuo and were then dissolved under nitrogen in 53 mL dry dimethyl sulphoxide (Fluka, Sigma-Aldrich Chemie GmbH, Taufkirchen, D) and 2 mL of 1,4-diaminobutane were added. After stirring at 40° C. for 17 h the reaction mixture was added to 350 mL of ice-cold 2-propanol (Carl Roth GmbH+Co. KG, Karlsruhe, D). The precipitated product was collected by centrifugation at 4° C., washed with 80 mL of ice-cold 2-propanol and collected by centrifugation. The crude product was dissolved in 80 mL water, dialysed for 2 d against water (SnakeSkin dialysis tubing, 3.5 kD cut off, Perbio Sciences Deutschland GmbH, Bonn, D) and lyophilized. The yield of isolated product was 85%.

Example 14.2.14

Synthesis of Aldehydo-HES from Amino-HES of Example 14.2.13

153 mg 4-formylbenzoic acid and 241 mg 1-hydroxy-1H-benzotriazole (both Aldrich, Sigma-Aldrich Chemie GmbH, Taufkirchen, D) were dissolved in 51 mL N,N-dimethylformamide (Peptide synthesis grade, Biosolve, Valkenswaard, NL) and 170 µL N,N'-diisopropylcarbodiimide (Fluka, Sigma-Aldrich Chemie GmbH, Taufkirchen, D) were added. After incubation at 21° C. for 30 min, 5.1 g of amino-HES (synthesised as described in example 14.2.13) were added. After shaking for 16 h at 22° C., the reaction mixture was added to 360 mL of an ice-cold 1:1 mixture of acetone and ethanol (v/v). The precipitated product was collected by centrifugation at 4° C., re-dissolved in 50 mL water and precipitated with 360 mL of an ice-cold 1:1 mixture of acetone and ethanol (v/v) as described above. After centrifugation, the precipitate was dissolved in 50 mL water, dialysed for 2 d against water (SnakeSkin dialysis tubing, 3.5 kD cut off, Perbio Sciences Deutschland GmbH, Bonn, D) and lyophilized. The yield of isolated product was 87%.

Example 14.2.15

Synthesis of Amino-HES from Oxo-HES of Example 14.1

5.0 g of oxo-HES (MW=29.3 kD, DS=0.86, Supramol Parenteral Colloids GmbH, Rosbach-Rodheim, D) were heated over night at 80° C. in vacuo, dissolved under nitrogen in 20 ml dry dimethyl sulphoxide (Fluka, Sigma-Aldrich Chemie GmbH, Taufkirchen, D) and 1.67 ml of 1,4-diaminobutane (Fluka, Sigma-Aldrich Chemie GmbH, Taufkirchen, D) were added. After stirring at 40° C. for 30.5 h the reaction mixture was added to 175 ml of ice-cold 1:1 (v/v) mixture of acetone (Carl Roth GmbH+Co. KG, Karlsruhe, D) and ethanol (Sonnenberg, DAB, Braunschweig, D). The precipitated product was collected by centrifugation for 120 min at 4° C., dissolved in 40 ml water, dialysed for 2 d against water (SnakeSkin dialysis tubing, 10 kD cut off, Perbio Sciences Deutschland GmbH, Bonn, D) and lyophilized. The yield of isolated product was 87%.

Example 14.2.16

Synthesis of Aldehydo-HES from Amino-HES of Example 14.2.15

150 mg 4-formylbenzoic acid and 230 mg 1-hydroxy-1H-benzotriazole (both Aldrich, Sigma-Aldrich Chemie GmbH, Taufkirchen, D) were dissolved in 10 ml N,N-dimethylformamide (Peptide synthesis grade, Biosolve, Valkenswaard, NL) and 166 µL N,N'-diisopropylcarbodiimide (Fluka, Sigma-Aldrich Chemie GmbH, Taufkirchen, D) were added. After incubation at 21° C. for 30 min, a solution of 3.02 g AminoHES (synthesized as described in example 14.2.15) in 20 ml DMF were added. After shaking for 16 h at 22° C., the reaction mixture was added to 215 ml of an ice-cold 1:1 mixture (v/v) of acetone (Carl Roth GmbH+Co. KG, Karlsruhe, D) and ethanol (Sonnenberg, DAB, Braunschweig, D). The precipitated product was collected by centrifugation at 4° C., re-dissolved in 20 ml water and precipitated with acetone/ethanol as described above. After centrifugation, the precipitate was dissolved in 30 ml water, dialysed for 2.5 d against water (SnakeSkin dialysis tubing, 10 kD cut off, Perbio Sciences Deutschland GmbH, Bonn, D) and lyophilized. The yield of isolated product was 87%.

Example 14.2.17

Synthesis of Amino-HES from Oxo-HES of Example 14.1

5.0 g of oxo-HES (MW=97.9 kD, DS=0.76, Supramol Parenteral Colloids GmbH, Rosbach-Rodheim, D) were heated over night at 80° C. in vacuo, dissolved under nitrogen in 20 ml dry dimethyl sulphoxide (Fluka, Sigma-Aldrich Chemie GmbH, Taufkirchen, D) and 0.50 ml of 1,4-diaminobutane (Fluka, Sigma-Aldrich Chemie GmbH, Taufkirchen, D) were added. After stirring at 40° C. for 30.5 h the reaction mixture was added to 175 ml of ice-cold 1:1 (v/v) mixture of acetone (Carl Roth GmbH+Co. KG, Karlsruhe, D) and ethanol (Sonnenberg, DAB, Braunschweig, D). The precipitated product was collected by centrifugation for 120 min at 4° C., dissolved in 40 ml water, dialysed for 2 d against water (SnakeSkin dialysis tubing, 10 kD cut off, Perbio Sciences Deutschland GmbH, Bonn, D) and lyophilized. The yield of isolated product was 90%.

Example 14.2.18

Synthesis of Aldehydo-HES from Amino-HES of Example 14.2.17

73 mg 4-formylbenzoic acid and 112 mg 1-hydroxy-1H-benzotriazole (both Aldrich, Sigma-Aldrich Chemie GmbH, Taufkirchen, D) were dissolved in 10 ml N,N-dimethylformamide (Peptide synthesis grade, Biosolve, Valkenswaard, NL) and 81.3 µL N,N'-diisopropylcarbodiimide (Fluka, Sigma-Aldrich Chemie GmbH, Taufkirchen, D) were added. After incubation at 21° C. for 30 min, a solution of 3.09 g AminoHES (prepared as decribed in example 14.2.17) in 20 ml DMF were added. After shaking for 16 h at 22° C., the reaction mixture was added to 215 ml of an ice-cold 1:1 mixture (v/v) of acetone (Carl Roth GmbH+Co. KG, Karlsruhe, D) and ethanol (Sonnenberg, DAB, Braunschweig, D). The precipitated product was collected by centrifugation at 4° C., re-dissolved in 20 ml water and precipitated with acetone/ethanol as described above. After centrifugation, the precipitate was dissolved in 30 ml water, dialysed for 2.5 d against water (SnakeSkin dialysis tubing, 10 kD cut off, Perbio Sciences Deutschland GmbH, Bonn, D) and lyophilized. The yield of isolated product was 96%.

Example 14.3

Synthesis IFN-Alpha Conjugates via Reductive Amination

Example 14.3.1

Conjugation to IFN-Alpha at a 20 µg Scale

To 0.675 mg IFN-alpha, dissolved in 0.375 ml of 25 mM sodium phosphate buffer pH 7.5, containing 150 mM NaCl and 0.3 mM EDTA, were added 4 ml of the reaction buffer (0.1 M sodium acetate buffer pH 5.0) and the solution was centrifuged for 30 min at 3939×g in a Vivaspin 6 concentrator (Viva Science, 5 kD MWCO, Hannover, Germany). The washing procedure was repeated twice by dilution of the residual solution with the reaction buffer to 6 ml and centrifugation as described. The volume of the final IFN-alpha solution was 0.236 ml, corresponding to a calculated final concentration of 2.86 mg/ml IFN-alpha. The protein concentration was not checked experimentally.

To 7 µl of the IFN-alpha solution prepared as described above and cooled to 0° C., 10 µl (50 equiv.) of the respective aldehydo-HES (see table below) solution and 11.3 µL of a 60 mM sodium cyanoborohydride solution, both in the same buffer (sodium acetate, pH 5.0) and cooled to 0° C., were added and the mixture was incubated for 17 h at 0° C. The reaction mixture was analysed by gel electrophoresis. The following concentrations of the aldehydo-HES solutions were employed:

Table of example 14.3.1

| Entry | HES-Derivative | Concentration [mg/ml] |
|---|---|---|
| A | aldehydo-HES (example 14.2.2) | 52 |
| B | aldehydo-HES (example 14.2.4) | 52 |
| C | aldehydo-HES (example 14.2.6) | 156 |
| D | aldehydo-HES (example 14.2.8) | 156 |
| E | aldehydo-HES (example 14.2.10) | 260 |
| F | aldehydo-HES (A) (example 14.2.12) | 260 |
| G | Without HES derivative but with NaCNBH$_3$ | — |
| I | Without HES derivative and without NaCNBH$_3$ | — |
| J | non-oxidized HES (Mw 7.6 kD, DS = 0.41) with NaCNBH$_3$ | 52 |
| K | non-oxidized HES (Mw 7.6 kD, DS = 0.41), without NaCNBH$_3$ | 52 |

SDS-Page analysis of the conjugates is shown in FIG. 29.

Example 14.3.2

Conjugation to IFN-Alpha at a 3 mg Scale

To 20 mg IFN-alpha, dissolved in 25 mM sodium phosphate buffer pH 7.5, containing 150 mM NaCl and 0.3 mM EDTA, were added 8 ml of the reaction buffer (0.1 M sodium acetate buffer pH 5.0) and the solution was centrifuged for 99 min at 3939×g in a Vivaspin 15R concentrator (Viva Science, 5 kD MWCO, Hannover, Germany). The washing procedure was repeated twice by dilution of the residual solution with the reaction buffer to 18 ml and centrifugation as described. The final IFN-alpha solution was diluted with reaction buffer to 6.66 ml giving a final calculated concentration of 3 mg/ml IFN-alpha. The protein concentration was not checked experimentally.

To 1 ml of the IFN-alpha solution prepared as described above and cooled to 0° C., 1 ml of the aldehydoHES solution (75 equiv.) and 1 ml of a 60 mM sodium cyanoborohydride solution, both in the same buffer (sodium acetate, pH 5.0) and cooled to 0° C., were added and the mixture was incubated for 22 h at 0° C. The reaction mixture was purified after analysis by gel electrophoresis. For the reaction described in entry G, only 0.666 µl of the corresponding solutions were used. The following concentrations of the aldehydoHES solutions were employed:

Table of example 14.3.2

| Entry | HES-Derivative | Concentration [mg/ml] |
|---|---|---|
| A | aldehydo-HES (example 14.2.2) | 117 |
| B | aldehydo-HES (example 14.2.4) | 117 |
| C | aldehydo-HES (example 14.2.6) | 350 |
| D | aldehydo-HES (example 14.2.8) | 350 |
| E | aldehydo-HES (example 14.2.10) | 584 |
| F | aldehydo-HES (A) (example 14.2.12) | 584 |
| G | non-oxidized HES (Mw 7.6 kD, DS = 0.41) | 117 |

SDS-Page analysis of the conjugates is shown in FIG. 30.

Example 14.3.3

Conjugation to IFN-Alpha at a 3 mg Scale 14.3.3.1 Conjugation of AldehydoHES as Prepared in Example 14.2.16 to IFNα by Reductive Amination To 10 mg IFNα, dissolved in 25 mM sodium phosphate buffer pH 7.5, containing 150 mM NaCl and 0.3 mM EDTA, were added 8 ml of the reaction buffer (0.1 M sodium acetate buffer pH 5.0) and the solution was centrifuged for 30 min at 3939×g in a Vivaspin 15R concentrator (Viva Science, 5 kD MWCO, Hannover, Germany). The washing procedure was repeated twice by dilution of the residual solution with the reaction buffer to 18 ml and centrifugation as described. The final IFNα solution was diluted with reaction buffer to 3.33 ml giving a final calculated concentration of 3 mg/ml IFNα. The protein concentration was not checked experimentally.

To 1 ml of the IFNα solution prepared as described above and cooled to 0° C., 1 ml of the aldehydoHES solution as prepared in example 14.2.16 (75 equiv., 352 mg/ml) and 1 ml of a 60 mM sodium cyanoborohydride solution, both in the same buffer and cooled to 0° C., were added and the mixture was incubated for 22 h at 0° C. The reaction mixture was purified after analysis by gel electrophoresis. For gel electrophoresis an XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.

14.3.3.2 Conjugation of AldehydoHES as Prepared in Example 14.3.18 to IFNα by Reductive Amination To 1 ml of the IFNα solution prepared as described in 14.3.3.1 and cooled to 0° C., 2 ml of the aldehydoHES solution as prepared in example 14.3.18 (75 equiv., 369 mg/ml) and 1.5 ml of a 60 mM sodium cyanoborohydride solution, both in the same buffer and cooled to 0° C., were added and the mixture was incubated for 22 h at 0° C. The reaction mixture was purified after analysis by gel electrophoresis. For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.

14.3.3.3 Reaction Control: Conjugation of HES10/0.4 (Mw 7.6 kD DS=0.41) to IFNα by Reductive Amination To 1 ml of the IFNα solution prepared as described in 14.3.3.1 and cooled to 0° C., 1 ml of the HES10/0.4 solution (75 equiv., 117 mg/ml) and 1 ml of a 60 mM sodium cyanoborohydride solution, both in the same buffer and cooled to 0° C., were added and the mixture was incubated for 22 h at 0° C. The reaction mixture was purified after analysis by gel electrophoresis. For gel electrophoresis an XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.

SDS-Page analysis of the conjugates is shown in FIG. 31.

Example 14.3.4

Conjugation to IFN-Alpha at a 16 mg Scale

The buffer of 20 mg IFN-alpha solution was exchanged as described in example 14.3.2. The final IFN-alpha solution was diluted with reaction buffer to 6.37 ml giving a final calculated concentration of 3.14 mg/ml IFN-alpha. 100 µl of this solution were diluted with 900 µl reaction buffer and the protein concentration was determined spectrophotometrically at 279 nm to 3.01 mg/ml, based on the molar extinction coefficient of 18000. After combination with the material used for protein concentration determination the final volume was 7.0 ml with a protein concentration of 2.74 mg/ml.

To 5.91 ml of this IFN-alpha solution (16.2 mg) prepared as described above and cooled to 0° C., a solution of 3.152 g of aldehydo-HES of example 14.2.14 (75 equiv.) in 5 ml reaction buffer and 6 ml of a 60 mM sodium cyanoborohydride solution, both in the same buffer (sodium acetate, pH 5.0) and cooled to 0° C., were added and the mixture was incubated for 22 h at 0° C. (see FIG. 32, Line A).

As a reaction control, 1.09 ml of the pre-cooled IFN-alpha solution (3 mg) were mixed with 1 ml of a solution of 122 mg non-oxidzed HES (Mw 7.6 kD, DS=0.41) in the reaction buffer and 1 ml of a 60 mM sodium cyanoborohydride solution, both in the same buffer and cooled to 0° C. (see FIG. 32, line B).

SDS-Page analysis of the conjugate is shown in FIG. 32.

Example 14.4

Purification of the IFN-Alpha-HES Conjugates

14.4.1 Purification of HES-IFN-α from Incubations of the Reductively Aminated Protein with Activated HES Derivatives (Separation of the Modified and Unmodified Protein from HES-Derivatives)

The purification of all samples was performed at room temperature using an ÄKTA explorer 10 equipment. The column containing 3 ml Q-Sepharose Fast Flow was equilibrated with 10 CV of buffer A (20 mM Tris/HCl, pH 8.0). The samples were diluted 1:10 with buffer A and were applied by using the sample pump at a flow rate of 1 ml/min. Following washing of the sample pump with 10 ml of buffer A, the column was further washed with 6 CV of buffer A at a flow rate of 1.0 ml/min. Elution was performed by using a linear gradient from 0-100% of buffer B (0.3 M NaCl in 20 mM Tris/HCl, pH 8.0) over 2 CV and an isocratic run with 0.5 CV of buffer B at a flow rate of 0.8 ml/min. The column was regenerated by using 2 CV of buffer C (1.5 M NaCl in 20 mM Tris/HCl, pH 8.0) followed by 0.5 CV of buffer B at a flow rate of 0.8 ml/min. Reequilibration for the next run was performed by using 6 CV of buffer A and a flow rate of 1.0 ml/min.

14.4.2 Materials and Methods

| | |
|---|---|
| Equipment: | ÄKTA explorer 10 (Amersham Pharmacia Biotech), with: |
| | Pump P-903 |
| | Mixer M-925, with 0.6 ml chamber |
| | Monitor UV-900, with 10 mm flow cell |
| | Monitor pH/C-900 |
| | Pump P-950 (sample pump) |
| | Software Unicorn Version 3.21 |
| Column: | Amersham Biosciences C 10/10 |
| Column material: | Q-Sepharose Fast Flow, Code no. 17-0510-01, Lot no. OD 06453 |
| Column volume: | 3 ml |
| Buffer A: | 20 mM Tris/HCl, pH 8.0, Lot-Nr. PL0746 |
| Buffer B: | 0.3M NaCl in 20 mM Tris/HCl, pH 8.0, Lot-Nr. PL0747 |
| Buffer C: | 1.5M NaCl in 20 mM Tris/HCl, pH 8.0, Lot-Nr. PL0748 |

Method

| Volume | Step | Buffer | Flow rate |
|---|---|---|---|
| 1 CV | Equilibration | 100% buffer A | 1.0 ml/min |
| 5-28 ml | Load sample | sample 1:10 in buffer A | 1.0 ml/min |
| 10 ml | Wash sample pump | 100% buffer A | 1.0 ml/min |
| 5 CV | Wash out unbound sample | 100% buffer A | 1.0 ml/min |
| | Start Fractionation | 100% buffer A | 1.0 ml/min |
| 6 CV | Elution, linear gradient | 0-100% buffer B | 0.8 ml/min |
| 2 CV | Elution, isocratic | 100% buffer B | 0.8 ml/min |
| 2 CV | Regeneration | 100% buffer C | 0.8 ml/min |
| 0.5 CV | Regeneration | 100% buffer B | 0.8 ml/min |
| | Stop Fractionation | 100% buffer B | 0.8 ml/min |
| 5 CV | Reequilibration | 100% buffer A | 1.0 ml/min |
| Detection: | 280 nm, 260 nm, 220 nm | | |
| | pH | | |
| | Conductivity | | |
| Fractionation: | 1 ml fractions | | |

14.4.3 Results

14.4.3.1 Sample According to Example 14

| | |
|---|---|
| sample composition: | 1 mg EP2001 (rhIFN-a2b) in 25 mM Na-phosphate, 0.13M Cl and 0.3 mM EDTA, pH 7.5 ± 0.2 |
| starting volume: | 0.5 ml, diluted 1:10 in buffer A = 5 ml |
| flow-through/wash | 9.3 ml |
| run date: | 2004 Sep. 29 |
| run no.: | QS24 D39 (see Table for example 14.4.4.1 |

14.4.3.2 Sample Accordino to Example 14.3.2 (Entry A)

| | |
|---|---|
| sample composition: | 2.5 mg EP2001 + 97.5 mg AldehydoHES10/0.4 (NZA256) 0.1M Na-acetate, 20 mM Na-cyanoborohydride, pH 5.0 |
| starting volume: | 2.5 ml, diluted 1:10 in buffer A = 25 ml |
| flow-through/wash: | 44 ml |
| run date: | 2004 Sep. 29 |
| run no.: | QS25 D56 (see Table for example 14.4.4.1) |

14.4.3.3 Sample According to Example 14.3.2 (Entry B)

| | |
|---|---|
| sample composition: | 2.5 mg EP2001 + 97.5 mg AldehydoHES10/0.7 (NZA235A) in 0.1M Na-acetate, 20 mM Na-cyanoborohydride, pH 5.0 |
| starting volume: | 2.5 ml, diluted 1:10 in buffer A = 25 ml |
| flow-through/wash: | 41 ml |
| run date: | 2004 Sep. 30 |
| run no.: | QS26 D57 (see Table for example 14.4.4.1) |

14.4.3.4 Sample According to Example 14.3.2 (Entry C)

| | |
|---|---|
| sample composition: | 2.5 mg EP2001 + 292 mg AldehydoHES30/0.4 (NZA328) in 0.1M Na-acetate, 20 mM Na-cyanoborohydride, pH 5.0 |
| starting volume: | 2.5 ml, diluted 1:10 in buffer A = 25 ml |
| flow-through/wash: | 42 ml |
| run date: | 2004 Sep. 30 |
| run no.: | QS27 D58 (see Table for example 14.4.4.1) |

14.4.3.5 Sample According to Example 14.3.2 (Entry D)

| | |
|---|---|
| sample composition: | 2.5 mg EP2001 + 292 mg AldehydoHES30/0.7 (NZA329) in 0.1M Na-acetate, 20 mM Na-cyanoborohydride, pH 5.0 |
| starting volume: | 2.5 ml, diluted 1:10 in buffer A = 25 ml |
| flow-through/wash: | 40 ml |
| run date: | 2004 Sep. 30 |
| run no.: | QS28 D59 (see Table for example 14.4.4.1) |

14.4.3.6 Sample According to Example 14.3.2 (Entry E)

| | |
|---|---|
| sample composition: | 2.5 mg EP2001 + 487 mg AldehydoHES50/0.4 (NZA303) in 0.1M Na-acetate, 20 mM Na-cyanoborohydride, pH 5.0 |
| starting volume: | 2.7 ml, diluted 1:10 in buffer A = 27 ml |
| flow-through/wash: | 50 ml |
| run date: | 2004 Sep. 30 |
| run no.: | QS29 D60 (see Table for example 14.4.4.1) |

14.4.3.7 Sample According to Example 14.3.2 (Entry F)

| | |
|---|---|
| sample composition: | 2.5 mg EP2001 + 487 mg AldehydoHES50/0.7 (NZA309) in 0.1M Na-acetate, 20 mM Na-cyanoborohydride, pH 5.0 |
| starting volume: | 2.6 ml, diluted 1:10 in buffer A = 26 ml |
| flow-through/wash: | 50 ml |
| run date: | 2004 Sep. 30 |
| run no.: | QS30 D61 (see Table for example 14.4.4.1) |

14.4.3.8 Sample According to Example 14.3.2 (Entry G)

| | |
|---|---|
| sample composition: | 1.7 mg EP2001 + 98 mg HES10/0.4 (Supramol Lot. 407B) in 0.1M Na-acetate, 20 mM Na-cyanoborohydride, pH 5.0 |
| starting volume: | 2.5 ml, diluted 1:10 in buffer A = 25 ml |
| flow-through/wash: | 42 ml |
| run date: | 2004 Oct. 01 |
| run no.: | QS31 D62 (see Table for example 14.4.4.1) |

14.4.4 Comparison of the Results
14.4.4.1 SDS-PAGE Analysis of IFN-Alpha Elution Peaks Table for Example 14.4.4.1: Comparison of the Peak Areas Detected at 280 nm During Q-Sepharose Chromatography of HESylated IFN-α

| Run no. | Calculated applied amount of unmodified IFN-α | Eluate Area (280 nm) [mAU × ml] | Eluate Area (280 nm)/ mg unmodified Protein [mAU × ml × mg−1] | Calculated yield total protein [mg] (HPLC-Quantification at 280 nm*) |
|---|---|---|---|---|
| QS-24 D39 | 1.0 mg | 961 | 961 | 0.42 |
| QS-25 D56 | 2.5 mg | 4370 | 1748 | 1.20 |
| QS-26 D57 | 2.5 mg | 5669 | 2268 | 1.64 |
| QS-27 D58 | 2.5 mg | 3350 | 1340 | 1.60 |
| QS-28 D59 | 2.5 mg | 2854 | 1142 | 1.54 |
| QS-29 D60 | 2.5 mg | 2255 | 902 | 1.52 |
| QS-30 D61 | 2.5 mg | 9278 | 3711 | 3.44 |
| QS-31 D62 | 1.7 mg | 1918 | 1128 | 1.40 |

*data of quantitative analysis derived from RP-HPLC-3

Example 15

Description of IFN Alpha Antiviral Activity Bioassay

Description of the Test Procedure: Antiviral activity of Interferon-alpha After pre-diluting the Test Items in cell culture medium, serial two-fold dilutions were prepared. In 96 well microtiter plates, diluted Interferon was added—in four-fold replicate per dilution—to freshly trypsinized MDBK cells (40.000 cells per well). The assays were incubated for 24 hours at 37° C. (total volume per well: 150 μL (example 15.1) or 175 μl (example 15.2, 15.3, 15.4, 15.5, 16.2, 16.3)).

Subsequently, 50 μL diluted VSV stock solution were added to each well (except for the positive control wells) resulting in a multiplicity of infection of 0.1.

The following controls were included in each assay: 12 wells that received virus plus cell culture medium instead of Interferon (negative control) and 12 wells that received cell culture medium instead of Interferon and virus (positive control).

The assays were incubated for 42 hours at 37° C. At the end of the incubation period the cell culture supernatant of each well was replaced with 50 μL of a solution of MTT (at least 2 mg/mL in cell culture medium). The cells were incubated for three hours. The purple formazan dye formed by the proliferating cells was solubilized by adding 100 μL solution of isopropanol/HCl (isopropanol with 40 mM HCl) to each well. Subsequently, the absorbance values of the solutions were measured at 570/630 nm in a microtiter plate reader.

The proliferative activity of MDBK cells grown in the presence of Interferon and VSV was calculated for each dilution of Interferon as follows:

$$\frac{\left(\begin{array}{c}\text{(Mean absorbance of four Interferon treated wells)} - \\ \text{(Mean absorbance of negative control)}\end{array}\right) * 100}{\text{(Mean absorbance of positive control)} - \text{(Mean absorbance of negative control)}}$$

The antiviral activity of Interferon-alpha was determined in four separate assays for each of the Test Items.

Example 15.1

Antiviral Activity of Intron® A Relative to NIH Standard

In all experiments, Intron® A (IFN-alpha 2b, Schering-Plough), calibrated against NIH-standard rhIFN-alpha 2a (NIAID, NIH, Bethesda, USA, Gxa01-901-535) was used as an internal lab reference. The NIH-standard had a specific activity of 9,000 IU/ml. The internal lab reference Intron® A had a specific activity of 8,487,000 IU/ml in the test as described in example 15.

Proliferative activity of Intron® A compared to NIH standard rhIFN-alpha 2a is shown in FIG. 33.

Example 15.2

Antiviral Activity of Mock Incubated IFN-HES Relative to Unmodified Starting Material As described in example 14.3.4 mock incubated IFN-alpha-HES (described in example 14.3.2, Entry G) was used as a reaction control. The antiviral activity of the material was compared to that of unmodified starting material to investigate the influence of the coupling and purification process on the bioactivity. Mock incubation did not affect the in vitro bioactivity of IFN-alpha.

Relative in vitro activity of mock incubated IFN-alpha-HES compared to unmodified IFN-alpha starting material is shown in FIG. 34.

Example 15.3

Antiviral Activity of IFN-Alpha-HES Conjugates Relative to Intron® A

In the assay system described in example 15, the conjugates (entries A, B, C, D, E from example 14.3.2 purified according to example 14.4) were tested compared to unmodified IFN-alpha starting material, Intron® A and Pegasys (Roche). The CPE50 concentration of the materials was calculated. All IFN-alpha-HES conjugates retained an antiviral activity which was substantially higher than that of Pegasys.

The relative in vitro activity of IFN-alpha-HES conjugates compared to unmodified IFN-alpha starting material, Intron® A and Pegasys is shown in FIG. 35.

Example 15.4

Antiviral Activity of IFN-Alpha-HES Conjugate Compared to Intron® A

In the assay system described in example 15, the IFN-alpha-HES conjugate of example 14.3.4 purified according to example 14.4 was tested compared to Intron® A. The CPE50 concentration of the materials was calculated. The IFN-alpha-HES conjugate retained high antiviral activity of approx. 25% compared to Intron® A.

The relative in vitro activity of IFN-alpha-HES conjugates compared to Intron® A is shown in FIG. 36.

Example 15.5

Antiviral Activity of IFN-Alpha-HES Conjugate Compared to Intron® A

In the assay system described in example 15, the IFN-alpha-HES conjugates of example 14.3.3, purified according to example 14.4 was tested compared to Intron® A and PegIntron®. The CPE50 concentration of the materials was calculated. The IFN-alpha-HES conjugates retained an antiviral activity of approx. 25% compared to Intron® A, which is on the same level as the in vitro activity of PegIntron.

The relative in vitro activity of IFN-alpha-HES conjugates compared to Intron® A is shown in FIG. 37.

Example 16

In vivo Bioactivity of IFN-Alpha-HES Conjugates (PK Study in Mice)

Example 16.1

Influence of Mouse Serum on Assay System as Described in Example 9

Dilutions of Interferon-alpha were prepared in cell culture medium (control) and in mouse serum (1:40 dilution and 1:80 dilution). The assay was performed as described in example 15.

The antiviral activity of Interferon-alpha was determined in two separate assays for the control, for mouse serum 1:40 diluted as well as for mouse serum 1:80 diluted. The results indicated that mouse serum at 1:40 dilution and 1:80 does not affect the bioassay for antiviral activity of Interferon-alpha.

Example 16.2

In vivo Study in Mice (I)

Antiviral activity of pooled serum was tested in the antiviral assay. Serum was collected from two mice (female BALB/c mice, aged 8 weeks) at each time, which were sacrificed 2 h, 4 h, 12 h, and 24 h post i.v.-injection of 30 μg/kg (based on the protein content) of IFN-alpha or the IFN-alpha-HES conjugate.

The serum samples were thawed and thoroughly homogenized by vortexing (and diluted). Serial two-fold dilutions were prepared in cell culture medium. A vial of Intron® A (diluted) was thawed and thoroughly homogenized by vortexing. Serial two-fold dilutions were prepared in cell culture medium.

The EC50-dilutions in the CPE-assay were determined from dose response curves of a 1:2 dilution series as described in example 15.

The half life of the materials was determined compared to unmodified starting material and Pegasys. The half life was calculated from a semi-logarithmic plot of the EC50-dilution vs. time post injection.

Antiviral activity was detected for (i) IFN-alpha-HES (example 14.3.2, entry B of the table), (ii) IFN-alpha-HES (example 14.3.2, entry D of the table), (iii) IFN-alpha-HES (example 14.3.4) up to 24 h. As can be seen from FIG. 38, half-life increased from (i) (approx. 3 h) over (ii) (approx 5 h) to (iii) (approx. 7 h).

For unmodified IFN-alpha, the antiviral activity of serum was too low to calculate a serum half-life. In *K. R. Reddy* et al. *Advanced Drug Delivery Reviews* 54 (2002) 571-586 a serum half-life of IFN-alpha in rats (i.v.) of 2 h was determined.

Example 16.3

In vivo Study in Mice (II)

Antiviral activity of pooled serum was tested in the antiviral assay. Serum was collected from two mice (female BALB/c mice, aged 8 weeks) at each time, which were sacrificed 2 h, 4 h, 12 h, and 24 h post i.v.-injection of 30 µg/kg (based on the protein content) of IFN-alpha or the IFN-alpha-HES conjugate.

The serum samples were thawed and thoroughly homogenized by vortexing (and diluted). Serial two-fold dilutions were prepared in cell culture medium. A vial of Intron® A (diluted) was thawed and thoroughly homogenized by vortexing. Serial two-fold dilutions were prepared in cell culture medium.

The EC50-dilutions in the CPE-assay were determined from dose response curves of a 1:2 dilution series as described in example 15.

The half life of the materials was determined compared to unmodified starting material and Pegasys. The half life was calculated from a semi-logarithmic plot of the EC50-dilution vs. time post injection.

Antiviral activity was detected for (i) PegIntron, (ii) IFN-alpha-HES (example 14.3.3.1) and (iii) IFN-alpha-HES (example 14.3.3.2) up to 24 h. As can be seen from FIG. 39, half life increased from (i) (approx. 3.6 h) to (ii) and (iii) (approx. 6.5 and 6.8 h).

Example 17

In vivo Bioactivity of IFN-Alpha-HES Conjugates (PK Study in Rabbits)

Example 17.1

Radioactive Labeling of IFN-Alpha and IFN-Alpha-HES Conjugates

The samples used for the PK study were labeled with $^{125}$I with the Chloramine T method. Chloramine T is reacted with iodide and an interhalogen species (I-Cl) is formed. The interhalogen reacts on the aromatic ring of Tyrosine and substitutes it in o-position.

Example 17.2

Reference Experiment: Labeling of Oxo-HES 50/0.4 with 125I

In a first experimental series under the given reaction conditions it was investigated whether trace amounts of iodine could be detected e.g. by iodine, polyiodine or polyiodide forming complexes with HES. In comparison, oxo-HES (Mw 42.1 kD, DS=0.41) and IFN-alpha-HES (example 14.3.2, entry E of table) were labeled under the same conditions and after the purification process, radioactivity in the samples was measured. According to literature amylopectine can form complexes with iodine, polyiodine or polyiodide when the helical structures have at least 11 anhydroglucose units.

Only in the IFN-alpha-HES sample, radioactivity was detected. This result proved that radioactivity was exclusively caused by covalent modification of Tyrosine residues in of IFN-alpha but not by potentially physically bound iodine, which was not removed in the purification process. Oxo-HES 50/0.4 (Mw 42.1 kD, DS=0.41) can be considered as negative control. Due to the high molecular weight and the low degree of substitution in this oxo-HES species, the longest helical structures would be expected if any are present and thus, in this case there would have been the highest risk of complexation of iodine.

Example 17.3

Labelling of Interferon-Alpha with Non-Radioactive Iodine ("Cold Iodination")

Interferon alpha was labeled with non-radioactive iodine in the same labelling and purification process as the IFN-alpha-HES-conjugates. In the antiviral assay antiviral activity was retained. However, no quantification was performed, because in the labelling and purification process the concentration was changed and could not be determined due to the small amount of material available.

Example 17.4

Radioactive Labeling of IFN-Alpha-HES Conjugates

Samples were labeled according to example 17.1 with radioactive $^{125}$I. The samples were IFN-alpha starting material, IFN-alpha-HES (example 14.3.2, entry D of table). The samples had a specific activity of 38 µCi/µg (IFN-alpha starting material), 41 µCi/µg (IFN-alpha-HES 30/0.7).

Example 17.5

In vivo PK Study in Rabbits

Example 17.5.1

Experimental Procedure

The test items were used as a dilution. A solution of 4 µCi/ml was prepared. Dilution buffer was PBS.

Four New Zealand White Rabbits HsdIf:NZW. Source Harlan Winkelmann GmbH, D-33178 Borchen, Sex: female; body weight at the commencement of the study: >2.5 kg. All animals have been applicated intraveneously with the radiolabelled test substances, receiving a volume of 1 ml/kg body weight, which is equivalent to a dosage of 4 µCi/kg body weight. Blood samples have been taken at defined time points. At each sampling point approx. 600 µl blood from the auricular vein of the animals was taken for further investigations.

For the blood sampling an intravenous indwelling catheter was layed under general anaesthesia (Ketamin/Rompun) into the auricular vein. Anaesthesia rested for the blood sampling point before application, for the application itself and the first three blood samplings after application (0.5 hours, 1 hour, and 2 hours). Catheters were let into animals for the further sampling points until they were excised by the animals themselfes. Further blood samplings were determined with a cannula through different areas of the auricular veins.

Further processing of the blood samples was performed after blood sampling. To determine the radiolabelled test item in the blood, the collected blood samples were processed according to a specific solubilization protocol. For this 250 µl of the blood samples were transferred to a new vial and an equal volume of Solvable™ was added. The samples were incubated for one hour at 50° C. in a shaking water bath. After the incubation time the samples were cooled to room temperature and 100 µl of EDTA-solution [100 mM] was added. Subsequent 300 µl of $H_2O_2$ [30%] was added and after shaking again the samples were incubated for one hour at 50° C. in a shaking water bath. Before further processing the samples were collected.

At the end of blood collecting and solubilization the samples were transferred to a 20 ml scintillation vial and 10 ml of the scintillation cocktail Ultima Gold™ was added. Until measurement of the isotop $^{125}I$ in a scintillation-counter (about 72 h after cocktail addition) the samples were stored in the dark at 2-8° C.

Prior to the processing and statistical analysis of the data the quench of the activity detection under the specific experimental conditions was determined. The regression coefficient ($r^2$=0.9970) is a measure of the fit to the line. The quench factor [pCi/cpm] was found to be 3.315938.

Results (see FIG. 40):

IFN-alpha-HES showed a distinct prolongation of half-life compared to the starting material. Beyond 24 h (approx. <1000 pCi/ml) the curve of the unmodified material leveled off and almost no decrease of activity was observed. The small standard deviation of the measured radioactivity for all samples proves the quality of the experiment.

The half-life was calculated from the concentration of IFN-alpha in the blood samples. For the evaluation shown in FIG. 41, only the data from blood samples taken between 4 and 24 h were considered. For the unmodified material a half-life of 7 h was calculated. With IFN-alpha-HES, a substantial increase of half-life was observed (approx. 33 h).

Data were evaluated statistically according to different compartment models as shown in the diagrams in FIG. 42*a*, and *b* (cut-out 0-12 h). In the one-compartment model, it is obvious, that the concentration of IFN-alpha rapidly drops during the first 2 hours after injection. For IFN-alpha-HES the half-life is clearly prolonged. Statistically calculated half-life was 0.26 h for IFN-alpha, 7.7 h for IFN-alpha-HES. According to the non-compartment model the statistical evaluation results in a half-life of 147 h for unmodified IFN-alpha (based on data 24-120 h), 42.7 h for IFN-alpha-HES (based on data 36-120 h). As described above the half-life of the unmodified IFN-alpha is substantially prolonged since the curve levels off beyond 24 h.

The half life of the two samples is summarized in the following table, based on the described models for the calculation.

Table of example 17.5.1

Half-Life of IFN-Alpha and IFN-Alpha-HES Calculated According to Different Models

|  | IFN-alpha starting material $t_{1/2}$ | IFN-alpha-HES $t_{1/2}$ |
|---|---|---|
| non compartment model | (147.0*) | 42.7** |
| one compartment model | 0.26 | 7.7 |
| Semi logarithmic plot (see FIG. 40, 4-24 h) | 7 | 33 |

*evaluated data 24-120 h,
**evaluated data 36-120 h

Example 18.1

Synthesis of Amino Functionalized Hydroxyethyl Starch

Oxo-HES (Mw=41,000 D, DS=0.76) was prepared by Supramol Parenteral Colloids GmbH, Rosbach-Rodheim, D; according to DE 196 28 705 A1.

To a solution of 0.51 g oxo-HES (19.15 µmol) in 2 ml dry dimethyl sulfoxide (DMSO, Acros Organics BVBA, Geel, B) was added dropwise under nitrogen 200 µl (19.9 mmol) 1,4-diaminobutan (Acros Organics BVBA, Geel, B) and the mixture was stirred for 24 h at 70° C. The reaction mixture was added to 20 ml cold acetone (0° C.). The resulting precipitate was separated by filtration, washed with 40 ml acetone and re-dissolved in 20 ml water. The solution was dialysed for one day against water (Snake-Skin dialysis tubing, 4-6 kD cut off, Perbio Science Deutschland GmbH, Bonn, D) and lyophilized. The yield was 80% (0.41 g) amino-HES.

The purification of the product was achieved by application to HiPrep 26/10 Desalting column (100 mm, Amersham Biosciences) using an ÄKTA explorer system (Amersham Biosciences). Therefore, the HiPrep 26/10 Desalting column is equilibrated with 0.1 M NaCl solution (10 ml/min) and the amino-HES in 0.1 M NaCl (5 mg/ml, volume of injection 10 ml) was applied. The pooled amino-HES fractions were applied to the HiPrep 26/10 Desalting column equilibrated with water (injection volume 10 ml). The pooled HES fractions were reapplied in the same conditions to the column. The pure product was lyophilized and the amine amount was determined by derivatisation with 2,4,6-trinitrobenzene sulfonic acid (TNBSA (Pierce), Instructions TNBSA product number 28997) and Boc-Lys-OH for the calibration. The amine amount was found to be 34.02 nmol/mg (92%)

Example 18.2

Synthesis of Iodoacetyl Functionalized Hydroxyethyl Starch

To a solution of 101.9 mg amino functionalized hydroxyethyl starch (amino-HESµmol as prepared in example 18.1) in 5 ml 0.1 M Na2CO3 (pH=8.3) was given 12.63 mg iodoacetic acid N-hydroxysuccinimide ester (44.65 µmol, Sigma, Taufkirchen, Germany). The mixture was stirred at room temperature in the dark under nitrogen for 15 h. 15 ml water was given into the aqueous solution and the purification of the product was achieved by application to HiPrep 26/10 Desalting column (Amersham Biosciences). Therefore, a column of HiPrep 26/10 Desalting (100 mm) is equilibrated with 0.1 M NaCl solution (10 ml/min) and the iodoacetyl functionalized hydroxyethyl starch was applied (injected volume 10 ml). The pooled iodoacetyl-HES fractions were applied to the HiPrep 26/10 Desalting column equilibrated with water and the pooled fraction were reapplied in the same conditions to the column. The pure product was lyophilized and the iodoacetyl amount was indirect determined by amine quantification with 2,4,6-trinitrobenzene sulfonic acid as described above. The amine amount was found to be 1.65 nmol/mg corresponding to an iodoacetyl amount from 32.37 nmol/mg (95%).

Example 18.3

Synthesis of MaleimidoHES from AminoHES of Example 18.1

25 mg of amino HES (prepared as described in example 18.1) with a calculated amino-content of ~29 nmolmg-1, were dissolved in 450 µl reaction buffer (0.1 M sodium phosphate, 150 mM NaCl, 5.0 M EDTA, pH 7.0). Separately 9 mg of N-[a-Maleimidoacetoxy]succinimide ester (AMAS, Aldrich, Sigma-Aldrich Chemie GmbH, Taufkirchen, D) were dissolved in 200 µl of dry DMSO (Acros Organics BVBA, Geel, B). The two solutions were pooled together.

The final solution was left under stirring for 100 min at 22° C. and for further 20 min at 40° C. The resulting solution was then diluted up to 5 ml and applied on a desalting column using an ÄKTA Explorer system (Amersham Biosciences) in order to eliminate the non-reacted AMAS, NHS and DMSO.

Therefore, a HiPrep 26/10 Desalting Column (100 mm, Amersham Biosciences) was equilibrated with the reaction buffer (0.1 M sodium phosphate, 150 mM sodium chloride, 5 mM EDTA, pH 7.0) and the maleimido-HES solution was injected (volume of injection 5 ml) and fractionated. The purification parameters were chosen as follow:

| Column: | HiPrep 26/10 Desalting |
|---|---|
| Flow rate: | 10 ml/min |
| Eluent: | 0.1M sodium phosphate buffer, 150 mM sodium chloride, 5 mM EDTA, pH = 7.0 |
| Sample volume: | 5.0 ml |
| Eluate fractionation: | 2.5 ml |
| Equilibration: | 0.5 column volumes |
| Length of elution: | 2.0 column volumes |

The pooled HES fractions (7 ml) were re-injected under the same conditions to ensure the absence of AMAS, NHS and DMSO in the final solution. The second purification yields 10 ml of pure MaleimidoHES ready for coupling with alpha1AT.

The eluted polymer was thereafter concentrated to a final volume of 250 µl in the same buffer.

Example 18.4a

Reduction of alpha1AT with DL-Dithiothreitol (DTT)

To a solution of alpha1AT solution (c (alpha1AT)=5.0 mg in 0.5 ml 0.1 M sodium phosphate buffer, 150 mM sodium chloride, pH 7.2, alpha1AT=rh alpha1AT provided by GTC Biotherapeutics Inc., Framingham, Mass., lot No. 080604A) was added 4 ml of the reaction buffer (0.1 M sodium phosphate buffer, 150 mM sodium chloride, 5 mM EDTA, pH=7.0) and 68.77 mg DTT (Sigma Taufkirchen, Germany).

The mixture was incubated at 20° C. for 2 h and the reduced protein was purified by size exclusion chromatography (SEC) using ÄKTA explorer system (Amersham Biosciences). Therefore, a HiPrep 26/10 Desalting Column (100 mm, Amersham Biosciences) was equilibrated with 0.1 M sodium phosphate buffer, 150 mM sodium chloride, 5 mM EDTA, pH=7.0 solution and the reduced protein solution was applied (volume of injection 4.5 ml) and fractionated. The purification parameters were chosen as outlined below:

| Column: | HiPrep 26/10 Desalting |
|---|---|
| Flow rate: | 10 ml/min |
| Eluent: | 0.1M sodium phosphate buffer, 150 mM sodium chloride, 5 mM EDTA, pH = 7.0 |
| Sample volume: | 4.5 ml |
| Eluate fractionation: | 2.5 ml |
| Equilibration: | 0.5 column volumes |
| Length of elution: | 2.0 column volumes |

The pooled protein fractions (8 ml) were re-injected in the same conditions to assure the absence of DTT in the protein solution. The second purification yields 10 ml of pure reduced α1AT solution with an approximate concentration of 0.5 mg/ml and was used for coupling with maleimido HES as described in Example 18.5.

Example 18.4b

Pre-Treatment of 1AT with Immobilized Tris-(2-carboxyethyl)-Phosphin-Hydrochlorid (TCEP) and Isolation of Thiol Containing Protein alpha1AT (GTC Biotherapeutics Inc., Framingham, Mass., lot No. 080604A) was freshly treated with immobilized TCEP (Pierce 77712, 2 ml gel slurry per mg protein) in order to reduce potential disulfide bonds. Immobilized TCEP was prepared as described by the manufacture using a buffer pH=7.0 (100 mM sodium phosphate, 150 mM sodium chloride and 5 mM EDTA). Reduction was performed according to the manufacturer's instructions.

The reduced protein was incubated with thiol-activated sepharose (Amersham Biosciences 71-7106-00; 0.15 g gel per mg protein) in order to bind thiol containing protein covalently. Unbound protein was washed out with a buffer containing 100 mM sodium phosphate, 150 mM sodium chloride and 5 mM EDTA, pH=7 until no protein was detectable in the eluat. For the proteine detection a BCA-assay was employed (Pierce). Protein bound to the column was released and eluted using a buffer pH=7.0 (100 mM sodium phosphate, 150 mM sodium chloride and 5 mM EDTA) containing 20 mM TCEP.

Example 18.5

Preparation of HES-Alpha1AT Conjugate from MaleimidoHES of Example 18.3 via Cysteine Coupling 725 nmol of MaleimidoHES (prepared as described in example 18.3) dissolved in 250 µl of reaction buffer (0.1 M sodium phosphate, 150 mM NaCl, pH 7.0) were added to 1540 µl of a 0.5 mgml-1 alpha1AT solution in the same buffer. The protein was pre-incubated with DTT as described in example T8/4a). The reaction was stirred at 22° C. for 18 h, then stopped by freezing under liquid nitrogen and stored at −80° C. The reaction mixture was analysed by gel electrophoresis (see FIG. 43).

Example 18.6

Preparation of HES-1AT Conjugate from IodoacetamidoHES of Example 18.2 via Cysteine Coupling 96 mg of IodoacetamideHES (prepared as described in example 18.2) with a calculated iodine content of ~16 nmolmg-1, were dissolved in 1.0 ml reaction buffer (1.0 M sodium carbonate, 2.0 mM EDTA, pH 8.3) and 2.5 ml distilled water. 500 µl of a 3 mgml-1 alpha1AT (pre-treated as described in example 18.4b) solution in 0.1 M sodium phosphate buffer, 150 mM NaCl (pH 7.0), were mixed with the polymer solution and finally 500 µl of a solution containing 7.2 mg of TCEP (Aldrich, Sigma-Aldrich Chemie GmbH, Taufkirchen, D) were added to yield a 5 mM final concentration of the reducing agent. The reaction was allowed to proceed under light exclusion and stirring, for 18 h at room temperature. Thereafter it was stopped by freezing under liquid nitrogen and stored at −80° C.

Example 18.7

Purification of HES-Alpha1AT Conjugate Prepared from IodoacetamidoHES of Example 18.2 via Cysteine Coupling Sample preparation: buffer exchange on a HiPrep 26/10 Desalting column (Amersham biosciences) in combination with the ÄKTA-Explorer chromatography system using 20 mM sodium phosphate, 20 mM sodium chloride, pH 8 as eluent.

Buffer exchange was performed with the crude reaction mixture (preparation as described in example T8/6, approximately 4 ml) using the following parameters:

| | |
|---|---|
| Column: | HiPrep 26/10 Desalting |
| Flow rate: | 10 ml/min |
| Eluent: | 20 mM sodium phosphate, 20 mM sodium chloride, pH 8 |
| Sample volume: | 10 ml |
| Eluate fractionation: | 2.5 ml |
| Equilibration: | 5 column volumes |
| Length of elution: | 2 column volumes |

Fractions from 6 to 16 ml were pooled. Excess of HES-derivatives were eliminated by IEC using the following parameters:

| | |
|---|---|
| Column: | HiTrap Q HP 1 ml |
| Flow rate: | 1 ml/min |
| Binding Buffer (BB): | 20 mM sodium phosphate, 20 mM sodium chloride, pH 8 |
| Elution Buffer (EB): | 20 mM sodium phosphate, 1M sodium chloride, pH 8 |
| Empty loop with: | 12 ml |
| Flow trough fractionation: | 2 ml |
| Eluate fractionation: | 1 ml |
| Start concentration EB: | 0% |
| Equilibration: | 5 column volumes |
| Wash out unbound sample: | 15 ml |
| Target concentration EB: | 15% |
| Length of gradient: | 50 ml |

Fractions from 43 to 73 ml were collected and concentrated to a final volume of 10 ml by ultracentrifugation. After desalting as described above (sample volume 10 ml, collected fractions contain the first 14 ml) a second IEC for separation of conjugate from unbound protein was performed using the following parameters:

| | |
|---|---|
| Column: | HiTrap Q HP 1 ml |
| Flow rate: | 1 ml/min |
| Binding Buffer (BB): | 20 mM sodium phosphate, 20 mM sodium chloride, pH 8 |
| Elution Buffer (EB): | 20 mM sodium phosphate, 1M sodium chloride, pH 8 |
| Empty loop with: | 15 ml |
| Flow trough fractionation: | 2 ml |
| Eluate fractionation: | 1 ml |
| Start concentration EB: | 0% |
| Equilibration: | 1 column volumes |
| Wash out unbound sample: | 2 ml |
| Gradient: | 5-15% |
| Length of gradient: | 100 ml |

The following fractions were collected and analysed by SDS-Page (see FIG. 44):

| |
|---|
| A: 26-32 ml |
| B: 37-45 ml |
| C: 55-65 m |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
                                -continued

<160> NUMBER OF SEQ ID NOS: 1

<210> SEQ ID NO 1
<211> LENGTH: 127
<212> TYPE: PRT
<213> ORGANISM: homo sapiens

<400> SEQUENCE: 1

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
            115                 120                 125
```

What is claimed is:

1. A conjugate comprising a protein and a polymer derivative, wherein the polymer is a hydroxyalkyl starch (HAS) and the protein is selected from the group consisting of IFN beta, GM-CSF, APC, tPA, A1AT, AT III, factor VII, factor VIII, and factor IX, said conjugate having a structure according to the formula

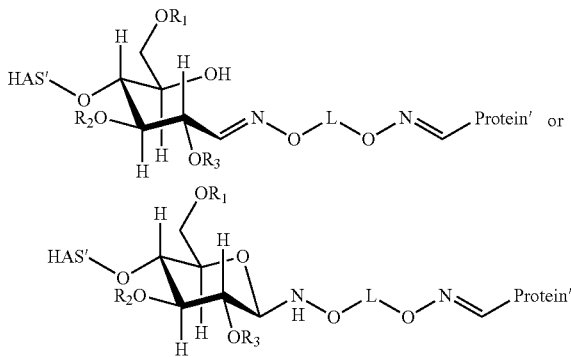

wherein $R_1$, $R_2$ and $R_3$ are independently hydrogen or a hydroxyalkyl group, or hydrogen or a hydroxyethyl group, wherein, in the conjugate, HAS is bonded at its non-oxidized reducing end to a bifunctional linking compound, and the bifunctional linking compound is bonded to an oxidized carbohydrate side chain or an oxidized N-terminal group of the protein, wherein HAS' is the remaining part of the starch molecule HAS, and wherein L is a substituted or unsubstituted, linear, branched and/or cyclic hydrocarbon residue, optionally comprising at least one heteroatom.

2. The conjugate of claim 1, wherein -L- is —[$(CR_aR_b)_m$ G]$_n$[$CR_cR_d$]$_o$— wherein $R_a$, $R_b$, $R_c$, and $R_d$ are independently hydrogen, alkyl, aryl, wherein G is selected from the group consisting of O and S, wherein m is 1, 2, 3 or 4, wherein the residues $R_a$ and $R_b$ may be the same or different in the m groups $CR_aR_b$;

wherein n is 0 to 20;

wherein o is 0 to 20, wherein the residues $R_c$ and $R_d$ may be the same or different in the o groups $CR_cR_d$; and wherein n and o are not 0 at the same time.

3. The conjugate of claim 2, wherein $R_a$, $R_b$, $R_c$, and $R_d$ are hydrogen, m is 2, n is 1, and o is 2.

4. The conjugate of claim 1, wherein the hydroxyalkyl starch is hydroxyethyl starch.

5. The conjugate of claim 4, wherein the hydroxyethyl starch has a molecular weight of from 2 to 200 kD.

6. A pharmaceutical composition comprising one or more conjugates of claim 1 and a pharmaceutically acceptable diluent, adjuvant, or carrier, wherein the protein is IFN beta.

7. The conjugate of claim 1, wherein the protein is IFN beta.

8. The conjugate of claim 1, wherein the protein is GM-CSF.

9. The conjugate of claim 1, wherein the protein is APC.

10. The conjugate of claim 1, wherein the protein is tPA.

11. The conjugate of claim 1, wherein the protein is A1AT.

12. The conjugate of claim 1, wherein the protein is AT III.

13. The conjugate of claim 1, wherein the protein is Factor VII.

14. The conjugate of claim 1, wherein the protein is Factor VIII.

15. The conjugate of claim 1, wherein the protein is Factor IX.

16. A pharmaceutical composition comprising the conjugate of claim 1, wherein the protein is GM-CSF.

17. A pharmaceutical composition comprising one or more conjugates of claim 1 and a pharmaceutically acceptable diluent, adjuvant, or carrier, wherein the protein is APC.

18. A pharmaceutical composition comprising one or more conjugates of claim 1 and a pharmaceutically acceptable diluent, adjuvant, or carrier, wherein the protein is tPA.

19. A pharmaceutical composition comprising one or more conjugates of claim 1 and a pharmaceutically acceptable diluent, adjuvant, or carrier, wherein the protein is A1AT.

20. A pharmaceutical composition comprising one or more conjugates of claim 1 and a pharmaceutically acceptable diluent, adjuvant, or carrier, wherein the protein is AT III.

21. A pharmaceutical composition comprising one or more conjugates of claim 1 and a pharmaceutically acceptable diluent, adjuvant, or carrier, wherein the protein is Factor VII.

22. A pharmaceutical composition comprising one or more conjugates of claim 1 and a pharmaceutically acceptable diluent, adjuvant, or carrier, wherein the protein is Factor VIII.

23. A pharmaceutical composition comprising one or more conjugates of claim 1 and a pharmaceutically acceptable diluent, adjuvant, or carrier, wherein the protein is Factor IX.

24. A method comprising administering the conjugate of claim 1 to a human or animal in need thereof, wherein the human or animal is in need of treatment for multiple sclerosis, and wherein the protein is IFN beta.

25. A method comprising administering the conjugate of claim 1 to a human or animal in need thereof, wherein the human or animal is in need of treatment for thrombosis, thromboembolism or occlusive arterial diseases, and wherein the protein is APC.

26. A method comprising administering the conjugate of claim 1 to a human or animal in need thereof, wherein the human or animal is in need of treatment for myocardial infarction, thrombosis, thromboembolism or occlusive arterial disease, and wherein the protein is tPA.

27. A method comprising administering the conjugate of claim 1 to a human or animal in need thereof, wherein the human or animal is in need of treatment for emphysema, cystic fibrosis, atopic dermatitis, or bronchitis, and wherein the protein is A1AT.

28. A method comprising administering the conjugate of claim 1 to a human or animal in need thereof, wherein the human or animal is in need of treatment for veno-occlusive disease, disseminated intravascular coagulation, or sepsis, and wherein the protein is AT III.

29. A method comprising administering the conjugate of claim 1 to a human or animal in need thereof, wherein the human or animal is in need of treatment for hemophilia A, and wherein the protein is Factor VIII.

* * * * *